(12) United States Patent
Markosyan et al.

(10) Patent No.: US 11,653,679 B2
(45) Date of Patent: May 23, 2023

(54) HIGH-PURITY STEVIOL GLYCOSIDES

(71) Applicant: PureCircle Sdn Bhd, Kuala Lumpur (MY)

(72) Inventors: Avetik Markosyan, Yerevan (AM); Indra Prakash, Alpharetta, GA (US); Cyrille Jarrin, Muret (FR); Aurelien Badie, Labege (FR); Robert Ter Halle, Baziege (FR); Cynthia Curran, Atlanta, GA (US); Daniel Auriol, Roques (FR)

(73) Assignee: PURECIRCLE SDN BHD, Kuala Lumpur (MY)

( * ) Notice: Subject to any disclaimer, the term of this patent is extended or adjusted under 35 U.S.C. 154(b) by 1108 days.

(21) Appl. No.: 15/512,711

(22) PCT Filed: Aug. 21, 2015

(86) PCT No.: PCT/US2015/046354
§ 371 (c)(1),
(2) Date: Sep. 27, 2017

(87) PCT Pub. No.: WO2016/043926
PCT Pub. Date: Mar. 24, 2016

(65) Prior Publication Data
US 2017/0303565 A1    Oct. 26, 2017

Related U.S. Application Data

(63) Continuation-in-part of application No. PCT/US2015/045906, filed on Aug. 19, 2015.

(60) Provisional application No. 62/061,359, filed on Oct. 8, 2014, provisional application No. 62/062,288, filed on Oct. 10, 2014, provisional application No. 62/064,630, filed on Oct. 16, 2014, provisional application No. 62/082,446, filed on Nov. 20, 2014, provisional application No. 62/097,387, filed on Dec. 29, 2014, provisional application No. 62/185,964, filed on Jun. 29, 2015, provisional application No. 62/118,132, filed on Feb. 19, 2015, provisional application No. 62/052,544, filed on Sep. 19, 2014.

(51) Int. Cl.
| | |
|---|---|
| *A23L 2/60* | (2006.01) |
| *A23L 27/30* | (2016.01) |
| *C07H 1/06* | (2006.01) |
| *C07H 15/256* | (2006.01) |
| *C12P 19/18* | (2006.01) |
| *C12P 19/56* | (2006.01) |

(52) U.S. Cl.
CPC .............. *A23L 2/60* (2013.01); *A23L 27/36* (2016.08); *C07H 1/06* (2013.01); *C07H 15/256* (2013.01); *C12P 19/18* (2013.01); *C12P 19/56* (2013.01); *C12Y 204/01* (2013.01); *C12Y 302/01021* (2013.01); *A23V 2002/00* (2013.01); *Y02P 20/582* (2015.11)

(58) Field of Classification Search
CPC ... A23L 2/60; C07H 1/06; C12P 19/18; C12P 19/56; C12Y 204/01; C12Y 302/01021; Y02P 20/582; A23V 2002/00
See application file for complete search history.

(56) References Cited

U.S. PATENT DOCUMENTS

| | | | |
|---|---|---|---|
| 9,243,273 B2 | 1/2016 | Markosyan et al. | |
| 9,562,251 B2 | 2/2017 | Kishore et al. | |
| 9,752,174 B2 * | 9/2017 | Markosyan | A24B 15/10 |
| 2014/0271996 A1 | 9/2014 | Prakash et al. | |
| 2014/0357588 A1 * | 12/2014 | Markosyan | A24B 15/302 |
| | | | 514/34 |

FOREIGN PATENT DOCUMENTS

| | | |
|---|---|---|
| CN | 103179850 | 6/2013 |
| CN | 103974628 | 8/2014 |
| WO | 2010038911 | 4/2010 |
| WO | 2013022989 | 2/2013 |
| WO | 2013102793 A2 | 7/2013 |
| WO | 2013110673 A1 † | 8/2013 |
| WO | WO 2013/176738 A9 * | 11/2013 |
| WO | WO 2013176738 A9 * | 11/2013 |
| WO | 2014122227 A1 † | 8/2014 |
| WO | 2014/146135 | 9/2014 |
| WO | 2014146089 | 9/2014 |

(Continued)

OTHER PUBLICATIONS

Yang et al. Base substitution mutations in uridine-diphosphate-dependent glycosyltransferase 76G1 of Stevia rebaudiana causes the low levels of rebaudioside A: Mutations in UGT76G1, a key gene of steviol glycosides synthesis. Plant Physiology and Biochemistry 80 (2014): 220-225, Epub Apr. 23, 2014.*

(Continued)

*Primary Examiner* — Iqbal H Chowdhury

(57) ABSTRACT

Methods of preparing highly purified steviol glycosides, particularly rebaudiosides A, D and M are described. The methods include utilizing recombinant microorganisms for converting various staring compositions to target steviol glycosides. In addition, novel steviol glycosides reb D2, reb M2, and reb I are disclosed, as are methods of preparing the same. The highly purified rebaudiosides are useful as non-caloric sweetener in edible and chewable compositions such as any beverages, confectioneries, bakery products, cookies, and chewing gums.

5 Claims, 88 Drawing Sheets
Specification includes a Sequence Listing.

(56) References Cited

FOREIGN PATENT DOCUMENTS

| WO | WO-2014-193934 A1 | * | 12/2014 |
| --- | --- | --- | --- |
| WO | 2015171555 A1 | † | 11/2015 |
| WO | 2017218888 A1 | | 12/2017 |
| WO | 2018031955 A2 | | 2/2018 |
| WO | 2018164747 A1 | | 9/2018 |
| WO | 2019006244 A1 | | 1/2019 |

OTHER PUBLICATIONS

Dian Spakman, How to broaden the applicability of the high potency sweeteners steviol glycosides: from enzymatic glycosylation to recombinant production. University of Groningen, GBB, p. 1-21, 2014.*

Okamoto et al. Purification and Some Properties of a pGlucosidase from Flavobacterium johnsonae. Biosci. Biotechnol. Biochem. 64(2): 333-340, 2000.*

Whisstock et al. Quaterly Reviews of Biophysics, 2003, "Prediction of protein function from protein sequence and structure", 36(3): 307-340.*

Witkowski et al. Conversion of a beta-ketoacyl synthase to a malonyl decarboxylase by replacement of the active-site cysteine with glutamine, Biochemistry. Sep. 7, 1999;38(36):11643-50.*

Noguchi et al. cDNA cloning of glycosyltransferases from Chinese wolfberry (*Lycium barbarum* L.) fruits and enzymatic synthesis of a catechin glucoside using a recombinant enzyme (UGT73A10). Journal of Molecular Catalysis B: Enzymatic 55 (2008) 84-92.*

Prakash, I et al. "Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia rebaudiana Morita" Biomolecules, vol. 4, Mar. 31, 2014, pp. 374-389; p. 385, paragraph [5].

Masaya Ohta et al, "Characterization of Novel Steviol Glycosides from Leaves of Stevia rebaudiana Morita", Oyo Toshitsu Kagaku—Journal of Applied Glycoscience., JP, (Aug. 17, 2010), vol. 57, No. 3, doi:10.5458/jag.57.199, ISSN 1340-3494, pp. 199-209, XP055121080 [X] 13 * p. 204; table 4 * [Y] 14-17.

* cited by examiner
† cited by third party

SEQUENCE LISTING

<160> NUMBER OF SEQ ID NOS: 13

<210> SEQ ID NO 1
<211> LENGTH: 1397
<212> TYPE: DNA
<213> ORGANISM: Stevia rebaudiana

<400> SEQUENCE: 1

```
ccatggccca tatggaaaac aaaaccgaaa ccaccgttcg tcgtcgtcgc cgtattattc      60
tgtttccggt tccgtttcag ggtcatatta atccgattct gcagctggca aatgtgctgt     120
atagcaaagg ttttagcatt accatttttc ataccaattt taacaaaccg aaaaccagca     180
attatccgca ttttaccttt cgctttattc tggataatga tccgcaggat gaacgcatta     240
gcaatctgcc gacacatggt ccgctggcag gtatgcgtat tccgattatt aacgaacatg     300
gtgcagatga actgcgtcgt gaactggaac tgctgatgct ggcaagcgaa gaagatgaag     360
aagttagctg tctgattacc gatgcactgt ggtattttgc acagagcgtt gcagatagcc     420
tgaatctgcg tcgtctggtt ctgatgacca gcagcctgtt taactttcat gcacatgtta     480
gcctgccgca gtttgatgaa ctgggttatc tggatccgga tgataaaacc cgtctggaag     540
aacaggcaag cggttttccg atgctgaaag tgaaagatat caaaagcgcc tatagcaatt     600
ggcagattct gaaagaaatt ctgggcaaaa tgattaaaca gaccaaagca agcagcggtg     660
ttatttggaa tagctttaaa gaactggaag aaagcgaact ggaaaccgtg attcgtgaaa     720
ttccggcacc gagctttctg attccgctgc cgaaacatct gaccgcaagc agcagcagcc     780
tgctggatca tgatcgtacc gtttttcagt ggctggatca gcagcctccg agcagcgttc     840
tgtatgttag ctttggtagc accagcgaag ttgatgaaaa agatttttctg gaaattgccc     900 gtggtctggt tgatagcaaa cagagctttc tgtgggttgt tcgtccgggt tttgttaaag     960
gtagcacctg ggttgaaccg ctgccggatg ttttctggg tgaacgtggt cgtattgtta    1020
aatgggttcc gcagcaagaa gttctggcac acggcgcaat tggtgcattt tggacccata    1080
gcggttggaa tagcaccctg gaaagcgttt gtgaaggtgt tccgatgatt tttagcgatt    1140
ttggtctgga tcagccgctg aatgcacgtt atatgagtga tgttctgaaa gtgggtgtgt    1200
atctggaaaa tggttgggaa cgtggtgaaa ttgcaaatgc aattcgtcgt gttatggtgg    1260
```

```
atgaagaagg tgaatatatt cgtcagaatg cccgtgttct gaaacagaaa gcagatgtta      1320
gcctgatgaa aggtggtagc agctatgaaa gcctggaaag tctggttagc tatattagca      1380
gcctgtaata actcgag                                                      1397

<210> SEQ ID NO 2
<211> LENGTH: 1442
<212> TYPE: DNA
<213> ORGANISM: Stevia rebaudiana

<400> SEQUENCE: 2
ccatggcaca tatggcaacc agcgatagca ttgttgatga tcgtaaacag ctgcatgttg        60
caacctttcc gtggctggca tttggtcata ttctgccgta tctgcagctg agcaaactga       120
ttgcagaaaa aggtcataaa gtgagctttc tgagcaccac ccgtaatatt cagcgtctga       180
gcagccatat tagtccgctg attaatgttg ttcagctgac cctgcctcgt gttcaagaac       240
tgccggaaga tgccgaagca accaccgatg ttcatccgga agatattccg tatctgaaaa       300
aagcaagtga tggtctgcag ccggaagtta cccgttttct ggaacagcat agtccggatt       360
ggatcatcta tgattatacc cattattggc tgccgagcat tgcagcaagc ctgggtatta       420
gccgtgcaca ttttagcgtt accaccccgt gggcaattgc atatatgggt ccgagcgcag       480
atgcaatgat taatggtagt gatggtcgta ccaccgttga agatctgacc acccctccga       540
aatggtttcc gtttccgacc aaagtttgtt ggcgtaaaca tgatctggca cgtctggttc       600
cgtataaagc accgggtatt agtgatggtt atcgtatggg tctggttctg aaaggtagcg       660
attgtctgct gagcaaatgc tatcatgaat ttggcaccca gtggctgccg ctgctggaaa       720
ccctgcatca ggttccggtt gttccggtgg gtctgctgcc tccggaagtt ccgggtgatg       780
aaaaagatga aacctgggtt agcatcaaaa atggctgga tggtaaacag aaaggtagcg       840
tggtttatgt tgcactgggt agcgaagttc tggttagcca gaccgaagtt gttgaactgg       900
cactgggtct ggaactgagc ggtctgccgt ttgtttgggc atatcgtaaa ccgaaaggtc       960
cggcaaaaag cgatagcgtt gaactgccgg atggttttgt tgaacgtacc cgtgatcgtg      1020
gtctggtttg gaccagctgg gcacctcagc tgcgtattct gagccatgaa agcgtttgtg      1080
gttttctgac ccattgtggt agcggtagca ttgtggaagg tctgatgttt ggtcatccgc      1140
tgattatgct gccgatttt ggtgatcagc cgctgaatgc acgtctgctg aagataaac      1200 aggttggtat tgaaattccg cgtaatgaag aagatggttg cctgaccaaa gaaagcgttg      1260
cacgtagcct gcgtagcgtt gttgttgaaa agaaggcga atctataaa gccaatgcac      1320 gtgaactgag caaaatctat aatgatacca agtggaaaa agaatatgtg agccagttcg      1380
tggattatct ggaaaaaaac acccgtgcag ttgccattga tcacgaaagc taatgactcg      1440
ag                                                                      1442

<210> SEQ ID NO 3
<211> LENGTH: 472
<212> TYPE: PRT
<213> ORGANISM: Oryza sativa

<400> SEQUENCE: 3

Met Asp Asp Ala His Ser Ser Gln Ser Pro Leu His Val Val Ile Phe
1               5                   10                  15

Pro Trp Leu Ala Phe Gly His Leu Leu Pro Cys Leu Asp Leu Ala Glu
            20                  25                  30
```

```
Arg Leu Ala Ala Arg Gly His Arg Val Ser Phe Val Ser Thr Pro Arg
             35                  40                  45

Asn Leu Ala Arg Leu Pro Pro Val Arg Pro Glu Leu Ala Glu Leu Val
 50                  55                  60

Asp Leu Val Ala Leu Pro Leu Pro Arg Val Asp Gly Leu Pro Asp Gly
 65                  70                  75                  80

Ala Glu Ala Thr Ser Asp Val Pro Phe Asp Lys Phe Glu Leu His Arg
                 85                  90                  95

Lys Ala Phe Asp Gly Leu Ala Ala Pro Phe Ser Ala Phe Leu Asp Thr
            100                 105                 110

Ala Cys Ala Gly Gly Lys Arg Pro Asp Trp Val Leu Ala Asp Leu Met
            115                 120                 125

His His Trp Val Ala Leu Ala Ser Gln Glu Arg Gly Val Pro Cys Ala
        130                 135                 140

Met Ile Leu Pro Cys Ser Ala Ala Val Val Ala Ser Ser Ala Pro Pro
145                 150                 155                 160

Thr Glu Ser Ser Ala Asp Gln Arg Glu Ala Ile Val Arg Ser Met Gly
                165                 170                 175

Thr Ala Ala Pro Ser Phe Glu Ala Lys Arg Ala Thr Glu Glu Phe Ala
            180                 185                 190

Thr Glu Gly Ala Ser Gly Val Ser Ile Met Thr Arg Tyr Ser Leu Thr
        195                 200                 205

Leu Gln Arg Ser Lys Leu Val Ala Met Arg Ser Cys Pro Glu Leu Glu
    210                 215                 220

Pro Gly Ala Phe Thr Ile Leu Thr Arg Phe Tyr Gly Lys Pro Val Val
225                 230                 235                 240

Pro Phe Gly Leu Leu Pro Pro Arg Pro Asp Gly Ala Arg Gly Val Ser
                245                 250                 255

Lys Asn Gly Lys His Asp Ala Ile Met Gln Trp Leu Asp Ala Gln Pro
            260                 265                 270

Ala Lys Ser Val Val Tyr Val Ala Leu Gly Ser Glu Ala Pro Met Ser
        275                 280                 285

Ala Asp Leu Leu Arg Glu Leu Ala His Gly Leu Asp Leu Ala Gly Thr
    290                 295                 300

Arg Phe Leu Trp Ala Met Arg Lys Pro Ala Gly Val Asp Ala Asp Ser
305                 310                 315                 320

Val Leu Pro Ala Gly Phe Leu Gly Arg Thr Gly Glu Arg Gly Leu Val
                325                 330                 335

Thr Thr Arg Trp Ala Pro Gln Val Ser Ile Leu Ala His Ala Ala Val
            340                 345                 350

Cys Ala Phe Leu Thr His Cys Gly Trp Gly Ser Val Val Glu Gly Leu
        355                 360                 365

Gln Phe Gly His Pro Leu Ile Met Leu Pro Ile Leu Gly Asp Gln Gly
    370                 375                 380

Pro Asn Ala Arg Ile Leu Glu Gly Arg Lys Leu Gly Val Ala Val Pro
385                 390                 395                 400

Arg Asn Asp Glu Asp Gly Ser Phe Asp Arg Gly Val Ala Gly Ala
                405                 410                 415

Val Arg Ala Val Val Glu Glu Gly Lys Thr Phe Phe Ala Asn
            420                 425                 430

Ala Arg Lys Leu Gln Glu Ile Val Ala Asp Arg Glu Arg Glu Arg
        435                 440                 445

Cys Ile Asp Glu Phe Val Gln His Leu Thr Ser Trp Asn Glu Leu Lys
```

```
                450             455             460
Asn Asn Ser Asp Gly Gln Tyr Pro
465                 470

<210> SEQ ID NO 4
<211> LENGTH: 502
<212> TYPE: PRT
<213> ORGANISM: Avena strigosa

<400> SEQUENCE: 4

Met Ala Val Lys Asp Glu Gln Gln Ser Pro Leu His Ile Leu Leu Phe
1               5                   10                  15

Pro Phe Leu Ala Pro Gly His Leu Ile Pro Ile Ala Asp Met Ala Ala
            20                  25                  30

Leu Phe Ala Ser Arg Gly Val Arg Cys Thr Ile Leu Thr Thr Pro Val
        35                  40                  45

Asn Ala Ala Ile Ile Arg Ser Ala Val Asp Arg Ala Asn Asp Ala Phe
    50                  55                  60

Arg Gly Ser Asp Cys Pro Ala Ile Asp Ile Ser Val Val Pro Phe Pro
65                  70                  75                  80

Asp Val Gly Leu Pro Pro Gly Val Glu Asn Gly Asn Ala Leu Thr Ser
                85                  90                  95

Pro Ala Asp Arg Leu Lys Phe Phe Gln Ala Val Ala Glu Leu Arg Glu
            100                 105                 110

Pro Phe Asp Arg Phe Leu Ala Asp Asn His Pro Asp Ala Val Val Ser
        115                 120                 125

Asp Ser Phe Phe His Trp Ser Thr Asp Ala Ala Ala Glu His Gly Val
    130                 135                 140

Pro Arg Leu Gly Phe Leu Gly Ser Ser Met Phe Ala Gly Ser Cys Asn
145                 150                 155                 160

Glu Ser Thr Leu His Asn Asn Pro Leu Glu Thr Ala Ala Asp Asp Pro
                165                 170                 175

Asp Ala Leu Val Ser Leu Pro Gly Leu Pro His Arg Val Glu Leu Arg
            180                 185                 190

Arg Ser Gln Met Met Asp Pro Lys Lys Arg Pro Asp His Trp Ala Leu
        195                 200                 205

Leu Glu Ser Val Asn Ala Ala Asp Gln Lys Ser Phe Gly Glu Val Phe
    210                 215                 220

Asn Ser Phe His Glu Leu Glu Pro Asp Tyr Val Glu His Tyr Gln Thr
225                 230                 235                 240

Thr Leu Gly Arg Arg Thr Trp Leu Val Gly Pro Val Ala Leu Ala Ser
                245                 250                 255

Lys Asp Met Ala Gly Arg Gly Ser Thr Ser Ala Arg Ser Pro Asp Ala
            260                 265                 270

Asp Ser Cys Leu Arg Trp Leu Asp Thr Lys Gln Pro Gly Ser Val Val
        275                 280                 285

Tyr Val Ser Phe Gly Thr Leu Ile Arg Phe Ser Pro Ala Glu Leu His
    290                 295                 300

Glu Leu Ala Arg Gly Leu Asp Leu Ser Gly Lys Asn Phe Val Trp Val
305                 310                 315                 320

Leu Gly Arg Ala Gly Pro Asp Ser Ser Glu Trp Met Pro Gln Gly Phe
                325                 330                 335

Ala Asp Leu Ile Thr Pro Arg Gly Asp Arg Gly Phe Ile Arg Gly
            340                 345                 350
```

```
Trp Ala Pro Gln Met Leu Ile Leu Asn His Arg Ala Leu Gly Gly Phe
            355                 360                 365

Val Thr His Cys Gly Trp Asn Ser Thr Leu Glu Ser Val Ser Ala Gly
    370                 375                 380

Val Pro Met Val Thr Trp Pro Arg Phe Ala Asp Gln Phe Gln Asn Glu
385                 390                 395                 400

Lys Leu Ile Val Glu Val Leu Lys Val Gly Val Ser Ile Gly Ala Lys
                405                 410                 415

Asp Tyr Gly Ser Gly Ile Glu Asn His Asp Val Ile Arg Gly Glu Val
            420                 425                 430

Ile Ala Glu Ser Ile Gly Lys Leu Met Gly Ser Ser Glu Glu Ser Asp
        435                 440                 445

Ala Ile Gln Arg Lys Ala Lys Asp Leu Gly Ala Glu Ala Arg Ser Ala
    450                 455                 460

Val Glu Asn Gly Gly Ser Ser Tyr Asn Asp Val Gly Arg Leu Met Asp
465                 470                 475                 480

Glu Leu Met Ala Arg Arg Ser Val Lys Val Gly Asp Ile Ile
                485                 490                 495

Pro Thr Asn Asp Gly Leu
            500

<210> SEQ ID NO 5
<211> LENGTH: 470
<212> TYPE: PRT
<213> ORGANISM: Solanum lycopersicum

<400> SEQUENCE: 5

Met Ser Pro Lys Leu His Lys Glu Leu Phe His Ser Leu Tyr Lys
1               5                   10                  15

Lys Thr Arg Ser Asn His Thr Met Ala Thr Leu Lys Val Leu Met Phe
            20                  25                  30

Pro Phe Leu Ala Tyr Gly His Ile Ser Pro Tyr Leu Asn Val Ala Lys
        35                  40                  45

Lys Leu Ala Asp Arg Gly Phe Leu Ile Tyr Phe Cys Ser Thr Pro Ile
    50                  55                  60

Asn Leu Lys Ser Thr Ile Glu Lys Ile Pro Glu Lys Tyr Ala Asp Ser
65                  70                  75                  80

Ile His Leu Ile Glu Leu His Leu Pro Glu Leu Pro Gln Leu Pro Pro
                85                  90                  95

His Tyr His Thr Thr Asn Gly Leu Pro Pro Asn Leu Asn Gln Val Leu
            100                 105                 110

Gln Lys Ala Leu Lys Met Ser Lys Pro Asn Phe Ser Lys Ile Leu Gln
        115                 120                 125

Asn Leu Lys Pro Asp Leu Val Ile Tyr Asp Ile Leu Gln Arg Trp Ala
    130                 135                 140

Lys His Val Ala Asn Glu Gln Asn Ile Pro Ala Val Lys Leu Leu Thr
145                 150                 155                 160

Ser Gly Ala Ala Val Phe Ser Tyr Phe Phe Asn Val Leu Lys Lys Pro
                165                 170                 175

Gly Val Glu Phe Pro Phe Pro Gly Ile Tyr Leu Arg Lys Ile Glu Gln
            180                 185                 190

Val Arg Leu Ser Glu Met Met Ser Lys Ser Asp Lys Glu Lys Glu Leu
        195                 200                 205

Glu Asp Asp Asp Asp Asp Asp Leu Leu Val Asp Gly Asn Met Gln
    210                 215                 220
```

```
Ile Met Leu Met Ser Thr Ser Arg Thr Ile Glu Ala Lys Tyr Ile Asp
225                 230                 235                 240

Phe Cys Thr Ala Leu Thr Asn Trp Lys Val Val Pro Val Gly Pro Pro
                245                 250                 255

Val Gln Asp Leu Ile Thr Asn Asp Val Asp Asp Met Glu Leu Ile Asp
            260                 265                 270

Trp Leu Gly Thr Lys Asp Glu Asn Ser Thr Val Phe Val Ser Phe Gly
        275                 280                 285

Ser Glu Tyr Phe Leu Ser Lys Glu Asp Met Glu Glu Val Ala Phe Ala
    290                 295                 300

Leu Glu Leu Ser Asn Val Asn Phe Ile Trp Val Ala Arg Phe Pro Lys
305                 310                 315                 320

Gly Glu Glu Arg Asn Leu Glu Asp Ala Leu Pro Lys Gly Phe Leu Glu
                325                 330                 335

Arg Ile Gly Glu Arg Gly Arg Val Leu Asp Lys Phe Ala Pro Gln Pro
            340                 345                 350

Arg Ile Leu Asn His Pro Ser Thr Gly Gly Phe Ile Ser His Cys Gly
        355                 360                 365

Trp Asn Ser Ala Met Glu Ser Ile Asp Phe Gly Val Pro Ile Ile Ala
    370                 375                 380

Met Pro Met His Leu Asp Gln Pro Met Asn Ala Arg Leu Ile Val Glu
385                 390                 395                 400

Leu Gly Val Ala Val Glu Ile Val Arg Asp Asp Gly Lys Ile His
                405                 410                 415

Arg Gly Glu Ile Ala Glu Thr Leu Lys Gly Val Ile Thr Gly Lys Thr
            420                 425                 430

Gly Glu Lys Leu Arg Ala Lys Val Arg Asp Ile Ser Lys Asn Leu Lys
        435                 440                 445

Thr Ile Arg Asp Glu Glu Met Asp Ala Ala Glu Glu Leu Ile Gln
    450                 455                 460

Leu Cys Arg Asn Gly Asn
465             470

<210> SEQ ID NO 6
<211> LENGTH: 464
<212> TYPE: PRT
<213> ORGANISM: Oryza sativa

<400> SEQUENCE: 6

Met His Val Val Met Leu Pro Trp Leu Ala Phe Gly His Ile Leu Pro
1               5                   10                  15

Phe Ala Glu Phe Ala Lys Arg Val Ala Arg Gln Gly His Arg Val Thr
                20                  25                  30

Leu Phe Ser Thr Pro Arg Asn Thr Arg Arg Leu Ile Asp Val Pro Pro
            35                  40                  45

Ser Leu Ala Gly Arg Ile Arg Val Val Asp Ile Pro Leu Pro Arg Val
        50                  55                  60

Glu His Leu Pro Glu His Ala Glu Ala Thr Ile Asp Leu Pro Ser Asn
65                  70                  75                  80

Asp Leu Arg Pro Tyr Leu Arg Arg Ala Tyr Asp Glu Ala Phe Ser Arg
                85                  90                  95

Glu Leu Ser Arg Leu Leu Gln Glu Thr Gly Pro Ser Arg Pro Asp Trp
            100                 105                 110

Val Leu Ala Asp Tyr Ala Ala Tyr Trp Ala Pro Ala Ala Ala Ser Arg
```

```
            115                 120                 125
His Gly Val Pro Cys Ala Phe Leu Ser Leu Phe Gly Ala Ala Leu
    130                 135                 140

Cys Phe Phe Gly Pro Ala Glu Thr Leu Gln Gly Arg Gly Pro Tyr Ala
145                 150                 155                 160

Lys Thr Glu Pro Ala His Leu Thr Ala Val Pro Glu Tyr Val Pro Phe
                    165                 170                 175

Pro Thr Thr Val Ala Phe Arg Gly Asn Glu Ala Arg Glu Leu Phe Lys
                180                 185                 190

Pro Ser Leu Ile Pro Asp Glu Ser Gly Val Ser Glu Ser Tyr Arg Phe
            195                 200                 205

Ser Gln Ser Ile Glu Gly Cys Gln Leu Val Ala Val Arg Ser Asn Gln
        210                 215                 220

Glu Phe Glu Pro Glu Trp Leu Glu Leu Leu Gly Glu Leu Tyr Gln Lys
225                 230                 235                 240

Pro Val Ile Pro Ile Gly Met Phe Pro Pro Pro Pro Gln Asp Val
                    245                 250                 255

Ala Gly His Glu Glu Thr Leu Arg Trp Leu Asp Arg Gln Glu Pro Asn
                260                 265                 270

Ser Val Val Tyr Ala Ala Phe Gly Ser Glu Val Lys Leu Thr Ala Glu
            275                 280                 285

Gln Leu Gln Arg Ile Ala Leu Gly Leu Glu Ala Ser Glu Leu Pro Phe
        290                 295                 300

Ile Trp Ala Phe Arg Ala Pro Pro Asp Ala Gly Asp Gly Asp Gly Leu
305                 310                 315                 320

Pro Gly Gly Phe Lys Glu Arg Val Asn Gly Arg Gly Val Val Cys Arg
                    325                 330                 335

Gly Trp Val Pro Gln Val Lys Phe Leu Ala His Ala Ser Val Gly Gly
                340                 345                 350

Phe Leu Thr His Ala Gly Trp Asn Ser Ile Ala Glu Gly Leu Ala Asn
            355                 360                 365

Gly Val Arg Leu Val Leu Leu Pro Leu Met Phe Glu Gln Gly Leu Asn
        370                 375                 380

Ala Arg Gln Leu Ala Glu Lys Val Ala Val Glu Val Ala Arg Asp
385                 390                 395                 400

Glu Asp Asp Gly Ser Phe Ala Ala Asn Asp Ile Val Asp Ala Leu Arg
                    405                 410                 415

Arg Val Met Val Gly Glu Glu Gly Asp Glu Phe Gly Val Lys Val Lys
                420                 425                 430

Glu Leu Ala Lys Val Phe Gly Asp Asp Glu Val Asn Asp Arg Tyr Val
            435                 440                 445

Arg Asp Phe Leu Lys Cys Leu Ser Glu Tyr Lys Met Gln Arg Gln Gly
        450                 455                 460

<210> SEQ ID NO 7
<211> LENGTH: 515
<212> TYPE: PRT
<213> ORGANISM: Arabidopsis lyrata

<400> SEQUENCE: 7

Met Asp Asp Lys Lys Glu Glu Val Met His Ile Ala Met Phe Pro Trp
1               5                   10                  15

Leu Ala Met Gly His Leu Leu Pro Phe Leu Arg Leu Ser Lys Leu Leu
                20                  25                  30
```

```
Ala Gln Lys Gly His Lys Ile Ser Phe Ile Ser Thr Pro Arg Asn Ile
            35                  40                  45
Leu Arg Leu Pro Lys Leu Pro Ser Asn Leu Ser Ser Ile Thr Phe
 50                  55                  60
Val Ser Phe Pro Leu Pro Ser Ile Ser Gly Leu Pro Pro Ser Ser Glu
 65                  70                  75                  80
Ser Ser Met Asp Val Pro Tyr Asn Lys Gln Gln Ser Leu Lys Ala Ala
                 85                  90                  95
Phe Asp Leu Leu Gln Pro Pro Leu Thr Glu Phe Leu Arg Leu Ser Ser
            100                 105                 110
Pro Asp Trp Ile Ile Tyr Asp Tyr Ala Ser His Trp Leu Pro Ser Ile
            115                 120                 125
Ala Lys Glu Leu Gly Ile Ser Lys Ala Phe Phe Ser Leu Phe Asn Ala
    130                 135                 140
Ala Thr Leu Cys Phe Met Gly Pro Ser Ser Ser Leu Ile Glu Glu Ser
145                 150                 155                 160
Arg Ser Thr Pro Glu Asp Phe Thr Val Val Pro Pro Trp Val Pro Phe
                165                 170                 175
Lys Ser Thr Ile Val Phe Arg Tyr His Glu Val Ser Arg Tyr Val Glu
            180                 185                 190
Lys Thr Asp Glu Asp Val Thr Gly Val Ser Asp Ser Val Arg Phe Gly
            195                 200                 205
Tyr Thr Ile Asp Gly Ser Asp Ala Val Phe Val Arg Ser Cys Pro Glu
    210                 215                 220
Phe Glu Pro Glu Trp Phe Ser Leu Leu Gln Asp Leu Tyr Arg Lys Pro
225                 230                 235                 240
Val Phe Pro Ile Gly Phe Leu Pro Pro Val Ile Glu Asp Asp Asp
                245                 250                 255
Asp Thr Thr Trp Val Arg Ile Lys Glu Trp Leu Asp Lys Gln Arg Val
            260                 265                 270
Asn Ser Val Val Tyr Val Ser Leu Gly Thr Glu Ala Ser Leu Arg Arg
    275                 280                 285
Glu Glu Leu Thr Glu Leu Ala Leu Gly Leu Glu Lys Ser Glu Thr Pro
290                 295                 300
Phe Phe Trp Val Leu Arg Asn Glu Pro Gln Ile Pro Asp Gly Phe Glu
305                 310                 315                 320
Glu Arg Val Lys Gly Arg Gly Met Val His Val Gly Trp Val Pro Gln
                325                 330                 335
Val Lys Ile Leu Ser His Glu Ser Val Gly Gly Phe Leu Thr His Cys
            340                 345                 350
Gly Trp Asn Ser Val Val Glu Gly Ile Gly Phe Gly Lys Val Pro Ile
            355                 360                 365
Phe Leu Pro Val Leu Asn Glu Gln Gly Leu Asn Thr Arg Leu Leu Gln
370                 375                 380
Gly Lys Gly Leu Gly Val Glu Val Leu Arg Asp Glu Arg Asp Gly Ser
385                 390                 395                 400
Phe Gly Ser Asp Ser Val Ala Asp Ser Val Arg Leu Val Met Ile Asp
                405                 410                 415
Asp Ala Gly Glu Glu Ile Arg Glu Lys Val Lys Leu Met Lys Gly Leu
            420                 425                 430
Phe Gly Asn Met Asp Glu Asn Ile Arg Tyr Val Asp Glu Leu Val Gly
            435                 440                 445
Phe Met Arg Asn Asp Glu Ser Ser Gln Leu Lys Glu Glu Glu Glu Glu
```

```
            450                 455                 460
Asp Asp Cys Ser Asp Asp Gln Ser Ser Glu Val Ser Ser Glu Thr Asp
465                 470                 475                 480

Glu Lys Glu Leu Asn Leu Asp Leu Lys Glu Lys Arg Arg Ile Ser
                485                 490                 495

Val Tyr Lys Ser Leu Ser Ser Glu Phe Asp Asp Tyr Val Ala Asn Glu
                500                 505                 510

Lys Met Gly
        515

<210> SEQ ID NO 8
<211> LENGTH: 772
<212> TYPE: PRT
<213> ORGANISM: Oryza sativa

<400> SEQUENCE: 8

Met His Val Val Ile Cys Pro Leu Leu Ala Phe Gly His Leu Leu Pro
1               5                   10                  15

Cys Leu Asp Leu Ala Gln Arg Leu Ala Cys Gly His Arg Val Ser Phe
                20                  25                  30

Val Ser Thr Pro Arg Asn Ile Ser Arg Leu Pro Pro Val Arg Pro Ser
            35                  40                  45

Leu Ala Pro Leu Val Ser Phe Val Ala Leu Pro Leu Pro Arg Val Glu
        50                  55                  60

Gly Leu Pro Asn Gly Ala Glu Ser Thr His Asn Val Pro His Asp Arg
65                  70                  75                  80

Pro Asp Met Val Glu Leu His Leu Arg Ala Phe Asp Gly Leu Ala Ala
                85                  90                  95

Pro Phe Ser Glu Phe Leu Gly Thr Ala Cys Ala Asp Trp Val Met Pro
            100                 105                 110

Thr Ser Ser Ala Pro Arg Gln Thr Leu Ser Ser Asn Ile His Arg Asn
        115                 120                 125

Ser Ser Arg Pro Gly Thr Pro Ala Pro Ser Gly Arg Leu Leu Cys Pro
    130                 135                 140

Ile Thr Pro His Ser Asn Thr Leu Glu Arg Ala Ala Glu Lys Leu Val
145                 150                 155                 160

Arg Ser Ser Arg Gln Asn Ala Arg Ala Arg Ser Leu Leu Ala Phe Thr
                165                 170                 175

Ser Pro Pro Leu Pro Tyr Arg Asp Val Phe Arg Ser Leu Leu Gly Leu
            180                 185                 190

Gln Met Gly Arg Lys Gln Leu Asn Ile Ala His Glu Thr Asn Gly Arg
        195                 200                 205

Arg Thr Gly Thr Leu Pro Leu Asn Leu Cys Arg Trp Met Trp Lys Gln
    210                 215                 220

Arg Arg Cys Gly Lys Leu Arg Pro Ser Asp Val Glu Phe Asn Thr Ser
225                 230                 235                 240

Arg Ser Asn Glu Ala Ile Ser Pro Ile Gly Ala Ser Leu Val Asn Leu
                245                 250                 255

Gln Ser Ile Gln Ser Pro Asn Pro Arg Ala Val Leu Pro Ile Ala Ser
            260                 265                 270

Ser Gly Val Arg Ala Val Phe Ile Gly Arg Ala Arg Thr Ser Thr Pro
        275                 280                 285

Thr Pro Pro His Ala Lys Pro Ala Arg Ser Ala Ala Pro Arg Ala His
    290                 295                 300
```

```
Arg Pro Pro Ser Ser Val Met Asp Ser Gly Tyr Ser Ser Ser Tyr Ala
305                 310                 315                 320

Ala Ala Ala Gly Met His Val Val Ile Cys Pro Trp Leu Ala Phe Gly
            325                 330                 335

His Leu Leu Pro Cys Leu Asp Leu Ala Gln Arg Leu Ala Ser Arg Gly
            340                 345                 350

His Arg Val Ser Phe Val Ser Thr Pro Arg Asn Ile Ser Arg Leu Pro
            355                 360                 365

Pro Val Arg Pro Ala Leu Ala Pro Leu Val Ala Phe Val Ala Leu Pro
        370                 375                 380

Leu Pro Arg Val Glu Gly Leu Pro Asp Gly Ala Glu Ser Thr Asn Asp
385                 390                 395                 400

Val Pro His Asp Arg Pro Asp Met Val Glu Leu His Arg Arg Ala Phe
                405                 410                 415

Asp Gly Leu Ala Ala Pro Phe Ser Glu Phe Leu Gly Thr Ala Cys Ala
                420                 425                 430

Asp Trp Val Ile Val Asp Val Phe His His Trp Ala Ala Ala Ala Ala
            435                 440                 445

Leu Glu His Lys Val Pro Cys Ala Met Met Leu Leu Gly Ser Ala His
450                 455                 460

Met Ile Ala Ser Ile Ala Asp Arg Arg Leu Glu Arg Ala Glu Thr Glu
465                 470                 475                 480

Ser Pro Ala Ala Ala Gly Gln Gly Arg Pro Ala Ala Pro Thr Phe
                485                 490                 495

Glu Val Ala Arg Met Lys Leu Ile Arg Thr Lys Gly Ser Ser Gly Met
            500                 505                 510

Ser Leu Ala Glu Arg Phe Ser Leu Thr Leu Ser Arg Ser Ser Leu Val
            515                 520                 525

Val Gly Arg Ser Cys Val Glu Phe Glu Pro Glu Thr Val Pro Leu Leu
        530                 535                 540

Ser Thr Leu Arg Gly Lys Pro Ile Thr Phe Leu Gly Leu Met Pro Pro
545                 550                 555                 560

Leu His Glu Gly Arg Arg Glu Asp Gly Glu Asp Ala Thr Val Arg Trp
                565                 570                 575

Leu Asp Ala Gln Pro Ala Lys Ser Val Val Tyr Val Ala Leu Gly Ser
            580                 585                 590

Glu Val Pro Leu Gly Val Glu Lys Val His Glu Leu Ala Leu Gly Leu
        595                 600                 605

Glu Leu Ala Gly Thr Arg Phe Leu Trp Ala Leu Arg Lys Pro Thr Gly
    610                 615                 620

Val Ser Asp Ala Asp Leu Leu Pro Ala Gly Phe Glu Glu Arg Thr Arg
625                 630                 635                 640

Gly Arg Gly Val Val Ala Thr Arg Trp Val Pro Gln Met Ser Ile Leu
            645                 650                 655

Ala His Ala Ala Val Gly Ala Phe Leu Thr His Cys Gly Trp Asn Ser
            660                 665                 670

Thr Ile Glu Gly Leu Met Phe Gly His Pro Leu Ile Met Leu Pro Ile
    675                 680                 685

Phe Gly Asp Gln Gly Pro Asn Ala Arg Leu Ile Glu Ala Lys Asn Ala
        690                 695                 700

Gly Leu Gln Val Ala Arg Asn Asp Gly Asp Gly Ser Phe Asp Arg Glu
705                 710                 715                 720

Gly Val Ala Ala Ala Ile Arg Ala Val Ala Val Glu Glu Glu Ser Ser
```

```
                725                 730                 735
Lys Val Phe Gln Ala Lys Ala Lys Leu Gln Glu Ile Val Ala Asp
            740                 745                 750
Met Ala Cys His Glu Arg Tyr Ile Asp Gly Phe Ile Gln Gln Leu Arg
            755                 760                 765
Ser Tyr Lys Asp
    770

<210> SEQ ID NO 9
<211> LENGTH: 442
<212> TYPE: PRT
<213> ORGANISM: Solanum lycopersicum

<400> SEQUENCE: 9

Met Ala Thr Asn Leu Arg Val Leu Met Phe Pro Trp Leu Ala Tyr Gly
1               5                   10                  15
His Ile Ser Pro Phe Leu Asn Ile Ala Lys Gln Leu Ala Asp Arg Gly
                20                  25                  30
Phe Leu Ile Tyr Leu Cys Ser Thr Arg Ile Asn Leu Glu Ser Ile Ile
            35                  40                  45
Lys Lys Ile Pro Glu Lys Tyr Ala Asp Ser Ile His Leu Ile Glu Leu
50                  55                  60
Gln Leu Pro Glu Leu Pro Glu Leu Pro Pro His Tyr His Thr Thr Asn
65                  70                  75                  80
Gly Leu Pro Pro His Leu Asn Pro Thr Leu His Lys Ala Leu Lys Met
                85                  90                  95
Ser Lys Pro Asn Phe Ser Arg Ile Leu Gln Asn Leu Lys Pro Asp Leu
                100                 105                 110
Leu Ile Tyr Asp Val Leu Gln Pro Trp Ala Glu His Val Ala Asn Glu
            115                 120                 125
Gln Asn Ile Pro Ala Gly Lys Leu Leu Thr Ser Cys Ala Ala Val Phe
130                 135                 140
Ser Tyr Phe Phe Ser Phe Arg Lys Asn Pro Gly Val Glu Phe Pro Phe
145                 150                 155                 160
Pro Ala Ile His Leu Pro Glu Val Glu Lys Val Lys Ile Arg Glu Ile
                165                 170                 175
Leu Ala Lys Glu Pro Glu Glu Gly Gly Arg Leu Asp Glu Gly Asn Lys
            180                 185                 190
Gln Met Met Leu Met Cys Thr Ser Arg Thr Ile Glu Ala Lys Tyr Ile
        195                 200                 205
Asp Tyr Cys Thr Glu Leu Cys Asn Trp Lys Val Val Pro Val Gly Pro
210                 215                 220
Pro Phe Gln Asp Leu Ile Thr Asn Asp Ala Asp Asn Lys Glu Leu Ile
225                 230                 235                 240
Asp Trp Leu Gly Thr Lys His Glu Asn Ser Thr Val Phe Val Ser Phe
                245                 250                 255
Gly Ser Glu Tyr Phe Leu Ser Lys Glu Asp Met Glu Glu Val Ala Phe
            260                 265                 270
Ala Leu Glu Leu Ser Asn Val Asn Phe Ile Trp Val Ala Arg Phe Pro
        275                 280                 285
Lys Gly Glu Glu Arg Asn Leu Glu Asp Ala Leu Pro Lys Gly Phe Leu
    290                 295                 300
Glu Arg Ile Gly Glu Arg Gly Arg Val Leu Asp Lys Phe Ala Pro Gln
305                 310                 315                 320
```

```
Pro Arg Ile Leu Asn His Pro Ser Thr Gly Phe Ile Ser His Cys
            325                 330                 335

Gly Trp Asn Ser Ala Met Glu Ser Ile Asp Phe Gly Val Pro Ile Ile
            340                 345                 350

Ala Met Pro Ile His Asn Asp Gln Pro Ile Asn Ala Lys Leu Met Val
            355                 360                 365

Glu Leu Gly Val Ala Val Glu Ile Val Arg Asp Asp Gly Lys Ile
            370                 375                 380

His Arg Gly Glu Ile Ala Glu Thr Leu Lys Ser Val Val Thr Gly Glu
385                 390                 395                 400

Thr Gly Glu Ile Leu Arg Ala Lys Val Arg Glu Ile Ser Lys Asn Leu
            405                 410                 415

Lys Ser Ile Arg Asp Glu Glu Met Asp Ala Val Ala Glu Glu Leu Ile
            420                 425                 430

Gln Leu Cys Arg Asn Ser Asn Lys Ser Lys
            435                 440
```

<210> SEQ ID NO 10
<211> LENGTH: 454
<212> TYPE: PRT
<213> ORGANISM: Escherichia coli

<400> SEQUENCE: 10

```
Met Gly Thr Glu Val Thr Val His Lys Asn Thr Leu Arg Val Leu Met
1               5                   10                  15

Phe Pro Trp Leu Ala Tyr Gly His Ile Ser Pro Phe Leu Asn Val Ala
                20                  25                  30

Lys Lys Leu Val Asp Arg Gly Phe Leu Ile Tyr Leu Cys Ser Thr Ala
            35                  40                  45

Ile Asn Leu Lys Ser Thr Ile Lys Lys Ile Pro Glu Lys Tyr Ser Asp
        50                  55                  60

Ser Ile Gln Leu Ile Glu Leu His Leu Pro Glu Leu Pro Glu Leu Pro
65                  70                  75                  80

Pro His Tyr His Thr Thr Asn Gly Leu Pro Pro His Leu Asn His Thr
                85                  90                  95

Leu Gln Lys Ala Leu Lys Met Ser Lys Pro Asn Phe Ser Lys Ile Leu
            100                 105                 110

Gln Asn Leu Lys Pro Asp Leu Val Ile Tyr Asp Leu Leu Gln Gln Trp
        115                 120                 125

Ala Glu Gly Val Ala Asn Glu Gln Asn Ile Pro Ala Val Lys Leu Leu
130                 135                 140

Thr Ser Gly Ala Ala Val Leu Ser Tyr Phe Phe Asn Leu Val Lys Lys
145                 150                 155                 160

Pro Gly Val Glu Phe Pro Phe Pro Ala Ile Tyr Leu Arg Lys Asn Glu
                165                 170                 175

Leu Glu Lys Met Ser Glu Leu Leu Ala Gln Ser Ala Lys Asp Lys Glu
            180                 185                 190

Pro Asp Gly Val Asp Pro Phe Ala Asp Gly Asn Met Gln Val Met Leu
        195                 200                 205

Met Ser Thr Ser Arg Ile Ile Glu Ala Lys Tyr Ile Asp Tyr Phe Ser
210                 215                 220

Gly Leu Ser Asn Trp Lys Val Val Pro Val Gly Pro Pro Val Gln Asp
225                 230                 235                 240

Pro Ile Ala Asp Asp Ala Asp Glu Met Glu Leu Ile Asp Trp Leu Gly
                245                 250                 255
```

```
Lys Lys Asp Glu Asn Ser Thr Val Phe Val Ser Phe Gly Ser Glu Tyr
            260                 265                 270

Phe Leu Ser Lys Glu Asp Arg Glu Ile Ala Phe Gly Leu Glu Leu
    275                 280                 285

Ser Asn Val Asn Phe Ile Trp Val Ala Arg Phe Pro Lys Gly Glu Glu
290                 295                 300

Gln Asn Leu Glu Asp Ala Leu Pro Lys Gly Phe Leu Glu Arg Ile Gly
305                 310                 315                 320

Asp Arg Gly Arg Val Leu Asp Lys Phe Ala Pro Gln Pro Arg Ile Leu
                325                 330                 335

Asn His Pro Ser Thr Gly Gly Phe Ile Ser His Cys Gly Trp Asn Ser
            340                 345                 350

Val Met Glu Ser Val Asp Phe Gly Val Pro Ile Ile Ala Met Pro Ile
            355                 360                 365

His Leu Asp Gln Pro Met Asn Ala Arg Leu Ile Val Glu Leu Gly Val
        370                 375                 380

Ala Val Glu Ile Val Arg Asp Asp Tyr Gly Lys Ile His Arg Glu Glu
385                 390                 395                 400

Ile Ala Glu Ile Leu Lys Asp Val Ile Ala Gly Lys Ser Gly Glu Asn
                405                 410                 415

Leu Lys Ala Lys Met Arg Asp Ile Ser Lys Asn Leu Lys Ser Ile Arg
            420                 425                 430

Asp Glu Glu Met Asp Thr Ala Ala Glu Glu Leu Ile Gln Leu Cys Lys
            435                 440                 445

Asn Ser Pro Lys Leu Lys
        450

<210> SEQ ID NO 11
<211> LENGTH: 458
<212> TYPE: PRT
<213> ORGANISM: Stevia rebaudiana

<400> SEQUENCE: 11

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
```

165                 170                 175
Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
            195                 200                 205

Lys Gln Thr Lys Ala Ser Ser Gly Val Ile Trp Asn Ser Phe Lys Glu
            210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
            245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
            275                 280                 285

Glu Lys Asp Phe Leu Glu Ile Ala Arg Gly Leu Val Asp Ser Lys Gln
            290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
            325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
            370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
            450                 455

<210> SEQ ID NO 12
<211> LENGTH: 470
<212> TYPE: PRT
<213> ORGANISM: Solanum lycopersicum

<400> SEQUENCE: 12

Met Ser Pro Lys Leu His Lys Glu Leu Phe Phe His Ser Leu Tyr Lys
1               5                   10                  15

Lys Thr Arg Ser Asn His Thr Met Ala Thr Leu Lys Val Leu Met Phe
            20                  25                  30

Pro Phe Leu Ala Tyr Gly His Ile Ser Pro Tyr Leu Asn Val Ala Lys
            35                  40                  45

Lys Leu Ala Asp Arg Gly Phe Leu Ile Tyr Phe Cys Ser Thr Pro Ile
            50                  55                  60

Asn Leu Lys Ser Thr Ile Glu Lys Ile Pro Glu Lys Tyr Ala Asp Ser
65                  70                  75                  80

Ile His Leu Ile Glu Leu His Leu Pro Glu Leu Pro Gln Leu Pro Pro
            85                  90                  95

His Tyr His Thr Thr Asn Gly Leu Pro Pro Asn Leu Asn Gln Val Leu
            100                 105                 110

Gln Lys Ala Leu Lys Met Ser Lys Pro Asn Phe Ser Lys Ile Leu Gln
            115                 120                 125

Asn Leu Lys Pro Asp Leu Val Ile Tyr Asp Ile Leu Gln Arg Trp Ala
130                 135                 140

Lys His Val Ala Asn Glu Gln Asn Ile Pro Ala Val Lys Leu Leu Thr
145                 150                 155                 160

Ser Gly Ala Ala Val Phe Ser Tyr Phe Phe Asn Val Leu Lys Lys Pro
                    165                 170                 175

Gly Val Glu Phe Pro Phe Pro Gly Ile Tyr Leu Arg Lys Ile Glu Gln
            180                 185                 190

Val Arg Leu Ser Glu Met Met Ser Lys Ser Asp Lys Glu Lys Glu Leu
            195                 200                 205

Glu Asp Asp Asp Asp Asp Asp Leu Leu Val Asp Gly Asn Met Gln
            210                 215                 220

Ile Met Leu Met Ser Thr Ser Arg Thr Ile Glu Ala Lys Tyr Ile Asp
225                 230                 235                 240

Phe Cys Thr Ala Leu Thr Asn Trp Lys Val Val Pro Val Gly Pro Pro
                    245                 250                 255

Val Gln Asp Leu Ile Thr Asn Asp Val Asp Asp Met Glu Leu Ile Asp
            260                 265                 270

Trp Leu Gly Thr Lys Asp Glu Asn Ser Thr Val Phe Val Ser Phe Gly
            275                 280                 285

Ser Glu Tyr Phe Leu Ser Lys Glu Asp Met Glu Glu Val Ala Phe Ala
            290                 295                 300

Leu Glu Leu Ser Asn Val Asn Phe Ile Trp Val Ala Arg Phe Pro Lys
305                 310                 315                 320

Gly Glu Glu Arg Asn Leu Glu Asp Ala Leu Pro Lys Gly Phe Leu Glu
                    325                 330                 335

Arg Ile Gly Glu Arg Gly Arg Val Leu Asp Lys Phe Ala Pro Gln Pro
            340                 345                 350

Arg Ile Leu Asn His Pro Ser Thr Gly Gly Phe Ile Ser His Cys Gly
            355                 360                 365

Trp Asn Ser Ala Met Glu Ser Ile Asp Phe Gly Val Pro Ile Ile Ala
            370                 375                 380

Met Pro Met His Leu Asp Gln Pro Met Asn Ala Arg Leu Ile Val Glu
385                 390                 395                 400

Leu Gly Val Ala Val Glu Ile Val Arg Asp Asp Asp Gly Lys Ile His
                    405                 410                 415

Arg Gly Glu Ile Ala Glu Thr Leu Lys Gly Val Ile Thr Gly Lys Thr
            420                 425                 430

Gly Glu Lys Leu Arg Ala Lys Val Arg Asp Ile Ser Lys Asn Leu Lys
            435                 440                 445

Thr Ile Arg Asp Glu Glu Met Asp Ala Ala Ala Glu Glu Leu Ile Gln
450                 455                 460

Leu Cys Arg Asn Gly Asn
465                 470

<210> SEQ ID NO 13
<211> LENGTH: 808
<212> TYPE: PRT

<213> ORGANISM: Arabidopsis thaliana

<400> SEQUENCE: 13

```
Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
            20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu
50                  55                  60

Glu Gly Gly Pro Phe Phe Asp Leu Leu Lys Ser Thr Gln Glu Ala Ile
65                  70                  75                  80

Val Leu Pro Pro Trp Val Ala Leu Ala Val Arg Pro Arg Pro Gly Val
            85                  90                  95

Trp Glu Tyr Leu Arg Val Asn Leu His Ala Leu Val Val Glu Glu Leu
        100                 105                 110

Gln Pro Ala Glu Phe Leu His Phe Lys Glu Glu Leu Val Asp Gly Val
    115                 120                 125

Lys Asn Gly Asn Phe Thr Leu Glu Leu Asp Phe Glu Pro Phe Asn Ala
130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
            165                 170                 175

Leu Leu Pro Leu Leu Lys Phe Leu Arg Leu His Ser His Gln Gly Lys
        180                 185                 190

Asn Leu Met Leu Ser Glu Lys Ile Gln Asn Leu Asn Thr Leu Gln His
    195                 200                 205

Thr Leu Arg Lys Ala Glu Glu Tyr Leu Ala Glu Leu Lys Ser Glu Thr
210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
            245                 250                 255

Leu Asp Leu Leu Glu Ala Pro Asp Pro Cys Thr Leu Glu Thr Phe Leu
        260                 265                 270

Gly Arg Val Pro Met Val Phe Asn Val Val Ile Leu Ser Pro His Gly
    275                 280                 285

Tyr Phe Ala Gln Asp Asn Val Leu Gly Tyr Pro Asp Thr Gly Gly Gln
290                 295                 300

Val Val Tyr Ile Leu Asp Gln Val Arg Ala Leu Glu Ile Glu Met Leu
305                 310                 315                 320

Gln Arg Ile Lys Gln Gln Gly Leu Asn Ile Lys Pro Arg Ile Leu Ile
            325                 330                 335

Leu Thr Arg Leu Leu Pro Asp Ala Val Gly Thr Thr Cys Gly Glu Arg
        340                 345                 350

Leu Glu Arg Val Tyr Asp Ser Glu Tyr Cys Asp Ile Leu Arg Val Pro
    355                 360                 365

Phe Arg Thr Glu Lys Gly Ile Val Arg Lys Trp Ile Ser Arg Phe Glu
370                 375                 380

Val Trp Pro Tyr Leu Glu Thr Tyr Thr Glu Asp Ala Ala Val Glu Leu
385                 390                 395                 400
```

```
Ser Lys Glu Leu Asn Gly Lys Pro Asp Leu Ile Ile Gly Asn Tyr Ser
                405                 410                 415

Asp Gly Asn Leu Val Ala Ser Leu Leu Ala His Lys Leu Gly Val Thr
            420                 425                 430

Gln Cys Thr Ile Ala His Ala Leu Glu Lys Thr Lys Tyr Pro Asp Ser
        435                 440                 445

Asp Ile Tyr Trp Lys Lys Leu Asp Asp Lys Tyr His Phe Ser Cys Gln
450                 455                 460

Phe Thr Ala Asp Ile Phe Ala Met Asn His Thr Asp Phe Ile Ile Thr
465                 470                 475                 480

Ser Thr Phe Gln Glu Ile Ala Gly Ser Lys Glu Thr Val Gly Gln Tyr
                485                 490                 495

Glu Ser His Thr Ala Phe Thr Leu Pro Gly Leu Tyr Arg Val Val His
                500                 505                 510

Gly Ile Asp Val Phe Asp Pro Lys Phe Asn Ile Val Ser Pro Gly Ala
            515                 520                 525

Asp Met Ser Ile Tyr Phe Pro Tyr Thr Glu Glu Lys Arg Arg Leu Thr
            530                 535                 540

Lys Phe His Ser Glu Ile Glu Glu Leu Leu Tyr Ser Asp Val Glu Asn
545                 550                 555                 560

Lys Glu His Leu Cys Val Leu Lys Asp Lys Lys Pro Ile Leu Phe
                565                 570                 575

Thr Met Ala Arg Leu Asp Arg Val Lys Asn Leu Ser Gly Leu Val Glu
            580                 585                 590

Trp Tyr Gly Lys Asn Thr Arg Leu Arg Glu Leu Ala Asn Leu Val Val
            595                 600                 605

Val Gly Gly Asp Arg Arg Lys Glu Ser Lys Asp Asn Glu Glu Lys Ala
        610                 615                 620

Glu Met Lys Lys Met Tyr Asp Leu Ile Glu Glu Tyr Lys Leu Asn Gly
625                 630                 635                 640

Gln Phe Arg Trp Ile Ser Ser Gln Met Asp Arg Val Arg Asn Gly Glu
                645                 650                 655

Leu Tyr Arg Tyr Ile Cys Asp Thr Lys Gly Ala Phe Val Gln Pro Ala
                660                 665                 670

Leu Tyr Glu Ala Phe Gly Leu Thr Val Val Glu Ala Met Thr Cys Gly
            675                 680                 685

Leu Pro Thr Phe Ala Thr Cys Lys Gly Gly Pro Ala Glu Ile Ile Val
            690                 695                 700

His Gly Lys Ser Gly Phe His Ile Asp Pro Tyr His Gly Asp Gln Ala
705                 710                 715                 720

Ala Asp Thr Leu Ala Asp Phe Phe Thr Lys Cys Lys Glu Asp Pro Ser
                725                 730                 735

His Trp Asp Glu Ile Ser Lys Gly Gly Leu Gln Arg Ile Glu Glu Lys
            740                 745                 750

Tyr Thr Trp Gln Ile Tyr Ser Gln Arg Leu Leu Thr Leu Thr Gly Val
            755                 760                 765

Tyr Gly Phe Trp Lys His Val Ser Asn Leu Asp Arg Leu Glu Ala Arg
        770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
                805
```

HIGH-PURITY STEVIOL GLYCOSIDES

CROSS REFERENCE TO RELATED APPLICATIONS

This application is a Section 371 national phase of international Patent Application No. PCT/US2015/046354, filed on Aug. 21, 2015, which is a continuation-in-part of International Patent Application No. PCT/US 2015/045906, filed on Aug. 19, 2015, and which also claims priority to U.S. Provisional Application No. 62/061,359, filed on Oct. 8, 2014, U.S. Provisional Application No. 62/062,288, filed on Oct. 10, 2014, U.S. Provisional Application No. 62/064,630, filed on Oct. 16, 2014, U.S. Provisional Application No. 62/208,446, filed on Nov. 20, 2014, U.S. Provisional Application No. 62/097,387, filed on Dec. 29, 2014, U.S. Provisional Application No. 62/185,964, filed on Jun. 29, 2015, U.S. Provisional Application No. 62/118,132, filed on Feb. 19, 2015, and U.S. Provisional Application No. 62/052,544, filed on Sep. 19, 2014, each of which is incorporated by reference herein in its entirety.

JOINT RESEARCH AGREEMENT

The present disclosure was made by or on behalf of the below listed parties to a joint research agreement. The joint research agreement was in effect on or before the date the present disclosure was made and the present disclosure was made as a result of activities undertaken within the scope of the joint research agreement. The parties to the joint research agreement are 1) PURECIRCLE SDN BHD and 2) THE COCA-COLA COMPANY.

TECHNICAL FIELD

The present invention relates to a biocatalytic process for preparing compositions comprising steviol glycosides, including highly purified steviol glycoside compositions. The present invention also relates to novel steviol glycosides, methods for isolation of the same and uses for the novel steviol glycosides.

BACKGROUND OF THE INVENTION

High intensity sweeteners possess a sweetness level that is many times greater than the sweetness level of sucrose. They are essentially non-caloric and are commonly used in diet and reduced-calorie products, including foods and beverages. High intensity sweeteners do not elicit a glycemic response, making them suitable for use in products targeted to diabetics and others interested in controlling for their intake of carbohydrates.

Steviol glycosides are a class of compounds found in the leaves of *Stevia rebaudiana* Bertoni, a perennial shrub of the Asteraceae (Compositae) family native to certain regions of South America. They are characterized structurally by a single base, steviol, differing by the presence of carbohydrate residues at positions C13 and C19. They accumulate in *Stevia* leaves, composing approximately 10%-20% of the total dry weight. On a dry weight basis, the four major glycosides found in the leaves of *Stevia* typically include stevioside (9.1%), rebaudioside A (3.8%), rebaudioside C (0.6-1.0%) and dulcoside A (0.3%). Other known steviol glycosides include rebaudioside B, C, D, E, F and M, steviolbioside and rubusoside.

Although methods are known for preparing steviol glycosides from *Stevia rebaudiana*, many of these methods are unsuitable for use commercially.

Accordingly, there remains a need for simple, efficient, and economical methods for preparing compositions comprising steviol glycosides, including highly purified steviol glycoside compositions.

Additionally, there remains a need for novel steviol glycosides and methods of preparing and isolating the same.

SUMMARY OF THE INVENTION

The present invention provides a biocatalytic process for preparing a composition comprising a target steviol glycoside by contacting a starting composition comprising an organic substrate with a microorganism and/or biocatalyst, thereby producing a composition comprising a target steviol glycoside.

The starting composition comprises an organic compound. In one embodiment, the starting composition is selected from the group consisting of polyols and various carbohydrates.

The target steviol glycoside can be any steviol glycoside. In one embodiment, the target steviol glycoside is steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N, rebaudioside O or a synthetic steviol glycoside.

In one embodiment, the target steviol glycoside is stevioside.

In another embodiment, the target steviol glycoside is rebaudioside A.

In still another embodiment, the target steviol glycoside is rebaudioside D.

In yet another embodiment, the target steviol glycoside is rebaudioside M.

The microorganism can be any microorganism comprising at least one biocatalyst suitable for converting the starting composition to target steviol glycosides.

The biocatalysts can be located on the surface and/or inside the microorganism.

The biocatalysts include the steviol biosynthesis enzymes and UDP-glycosyltransferases (UGTs), or their variants, having greater than 75% amino-acid sequence identity.

In one embodiment the steviol biosynthesis enzymes include mevalonate (MVA) pathway enzymes.

In another embodiment the steviol biosynthesis enzymes include non-mevalonate 2-C-methyl-D-erythritol-4-phosphate pathway (MEP/DOXP) enzymes.

In one embodiment the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase etc.

The UDP-glucosyltransferase can be any UDP-glucosyltransferase capable of adding at least one glucose unit to the steviol and or steviol glycoside substrate to provide the target steviol glycoside.

The microorganism may be any suitable microorganism. In one embodiment, the microorganism may be, for example, *E. coli, Saccharomyces* sp., *Aspergillus* sp., *Pichia* sp., *Bacillus* sp., *Yarrowia* sp. etc. In another embodiment, the UDP-glucosyltransferases are synthesized.

In one embodiment, the UDP-glucosyltransferase is selected from group including UGT74G1, UGT85C2, UGT76G1, UGT91D2 or their variants, having greater than 75% amino-acid sequence identity.

In one embodiment, the UDP-glucosyltransferase is any UDP-glucosyltransferase capable of adding at least one glucose unit to rubusoside to form stevioside. In a particular embodiment, the UDP-glucosyltransferase is UGT91D2 or UGT91D2 variant, having greater than 75% amino-acid sequence identity with UGT91D2.

In one embodiment, the UDP-glucosyltransferase is any UDP-glucosyltransferase capable of adding at least one glucose unit to stevioside to form rebaudioside A. In a particular embodiment, the UDP-glucosyltransferase is UGT76G1 or UGT76G1 variant, having greater than 75% amino-acid sequence identity with UGT76G1.

In another embodiment, the UDP-glucosyltransferase is any UDP-glucosyltransferase capable of adding at least one glucose unit to rebaudioside A to form rebaudioside D. In a particular embodiment, the UDP-glucosyltransferase is UGT91D2 or UGT91D2 variant, having greater than 75% amino-acid sequence identity with UGT91D2.

In yet another embodiment, the UDP-glucosyltransferase is any UDP-glucosyltransferase capable of adding at least one glucose unit to rebaudioside D to form rebaudioside M. In a particular embodiment, the UDP-glucosyltransferase is UGT76G1 or UGT76G1 variant, having greater than 75% amino-acid sequence identity with UGT76G1.

In yet another embodiment, the UDP-glucosyltransferase is any UDP-glucosyltransferase capable of adding at least one glucose unit to rebaudioside I to form rebaudioside M. In a particular embodiment, the UDP-glucosyltransferase is UGTSL or UGTSL variant, having greater than 75% amino-acid sequence identity with UGTSL.

In yet another embodiment, the UDP-glucosyltransferase is any UDP-glucosyltransferase capable of adding at least two glucose units to rebaudioside E to form rebaudioside M. In a particular embodiment, the UDP-glucosyltransferase is UGT76G1 or UGT76G1 variant, having greater than 75% amino-acid sequence identity with UGT76G1.

Optionally, the method of the present invention further comprises recycling UDP to provide UDP-glucose. In one embodiment, the method comprises recycling UDP by providing a recycling catalyst and a recycling substrate, such that the biotransformation of the steviol glycoside substrate to the target steviol glycoside is carried out using catalytic amounts of UDP-glucosyltransferase and UDP-glucose (FIG. 3).

In one embodiment, the recycling catalyst is sucrose synthase.

In one embodiment, the recycling substrate is sucrose.

Optionally, the method of the present invention further comprises purifying the composition comprising the target steviol glycoside. The composition comprising the target steviol glycoside can be purified by any suitable method, such as, for example, crystallization, separation by membranes, centrifugation, extraction, chromatographic separation or a combination of such methods.

In one embodiment, purification produces a composition comprising greater than about 80% by weight of the target steviol glycoside on an anhydrous basis. In another embodiment, purification produces a composition comprising greater than about 90% by weight of the target steviol glycoside. In particular embodiments, the composition comprises greater than about 95% by weight of the target steviol glycoside.

The target steviol glycoside can be in any polymorphic or amorphous form, including hydrates, solvates, anhydrous or combinations thereof.

The present invention also provides consumable products comprising compositions prepared by the disclosed methods. Suitable consumer products include, but are not limited to, food, beverages, pharmaceutical compositions, tobacco products, nutraceutical compositions, oral hygiene compositions, and cosmetic compositions.

The present invention also provides novel steviol glycosides reb D2 and reb M2, which are isomers of reb D and reb M, respectively. In one embodiment, isolated and purified reb D2 is provided. In another embodiment, isolated and purified reb M2 is provided. Reb D2 and reb M2 may also be present in any consumable products disclosed herein. In a particular embodiment, beverages comprising reb D2 and/or reb M2 are provided.

Methods of preparing reb D2 and reb M2 are also provided herein. Both are formed during the biotransformation of reb A to reb D. Reb M2 is believed to form from biotransformation of reb D2 in situ.

Methods of selective hydrolysis of 1,6-β-glucosidic linkages in reb D2 and/or reb M2, by enzyme with β-1,6-glucosidase activity, are also provided herein.

In one embodiment for selective hydrolysis of 1,6-β-glucosidic linkages in reb D2 and/or reb M2, at least one enzyme is selected from the group including, glycosidase (NC-IUBMB EC 3.2.1), glucosidase, glucanase, Isolase (011410; National Enzyme Company, USA), Aromase (GLY0151441; Amano Enzyme, Japan), naringinase (NAH0550102; Amano Enzyme, Japan), cellulase (e.g. Cellulase from *Trichoderma reesei* ATCC 26921; Sigma C2730), cellobiase (e.g. Cellobiase from *Aspergillus niger*, Sigma C6105), Viscozyme L (Sigma V2010), etc.

In one embodiment, the present invention is a method for the preparation of a composition comprising reb D2 comprising: (a) contacting a starting composition comprising reb A with an enzyme capable of transforming reb A to reb D2, UDP-glucose, and optionally UDP-glucose recycling enzymes, to produce a composition comprising reb D2, and (b) isolating the composition comprising reb D2.

In another embodiment, the present invention is a method for the preparation of a composition comprising reb M comprising (a) contacting a starting composition comprising reb D with an enzyme capable of transforming reb D to reb M, UDP-glucose, and optionally UDP-glucose recycling enzymes, to produce a composition comprising reb M, and (b) and isolating the composition comprising reb M.

A further embodiment, the present invention is a method for the preparation of a composition comprising reb M comprising (a) contacting a starting composition comprising reb A with an enzyme capable of transforming reb A to reb D, UDP-glucose, and optionally UDP-glucose recycling enzymes, to produce a composition comprising reb D, (b) optionally, isolating the composition comprising reb D, (c) contacting the composition comprising reb D with an enzyme capable of transforming reb D to reb A UDP-glucose, and optionally UDP-glucose recycling enzymes to produce a composition comprising reb M, and (d) isolating the composition comprising reb M.

The composition can be further purified to provide reb D or reb M with purities greater than about 95% by weight on a dry basis.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION

Figure 1:
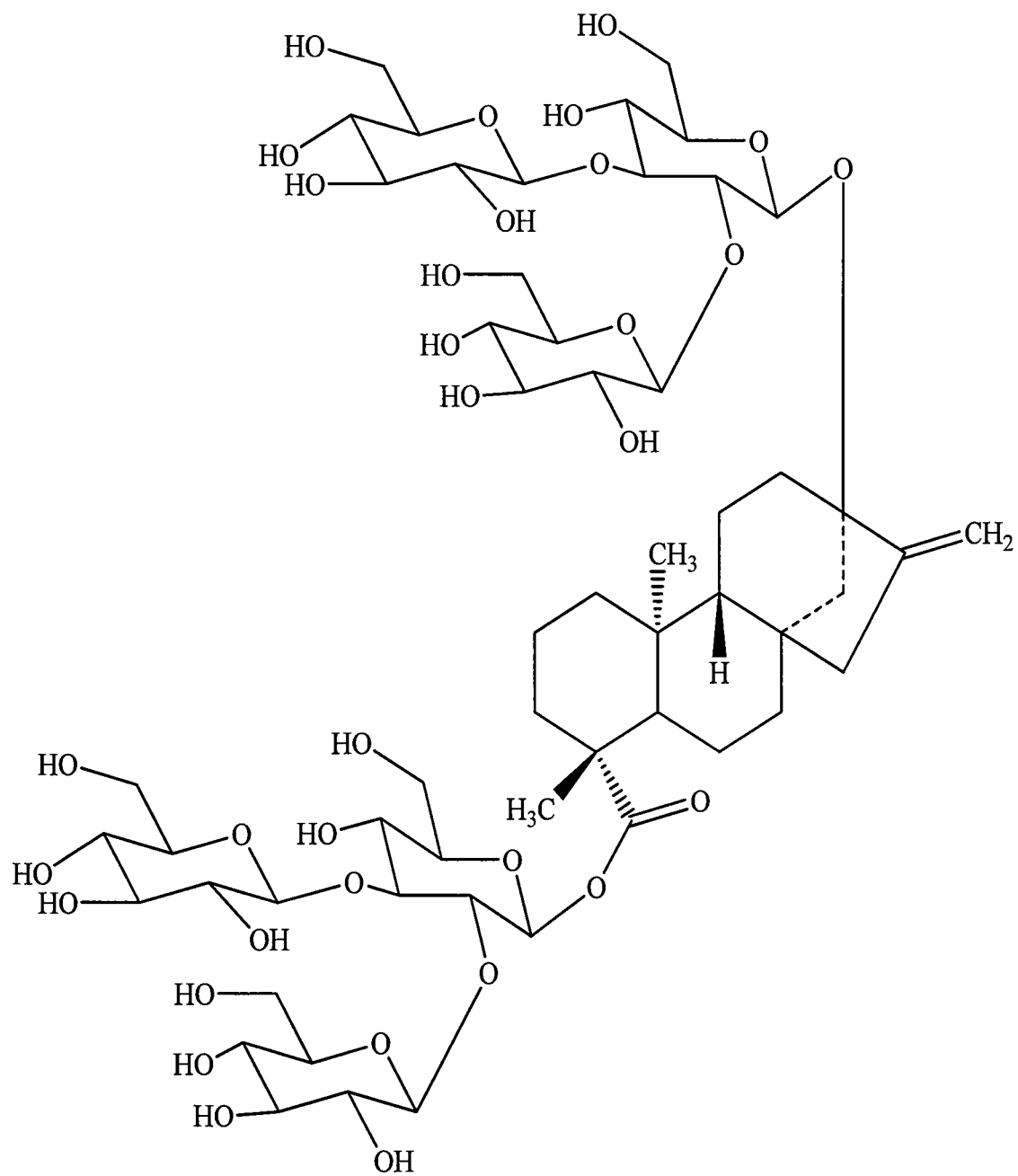
FIG. 1 shows the structure of reb M.
Figure 2:
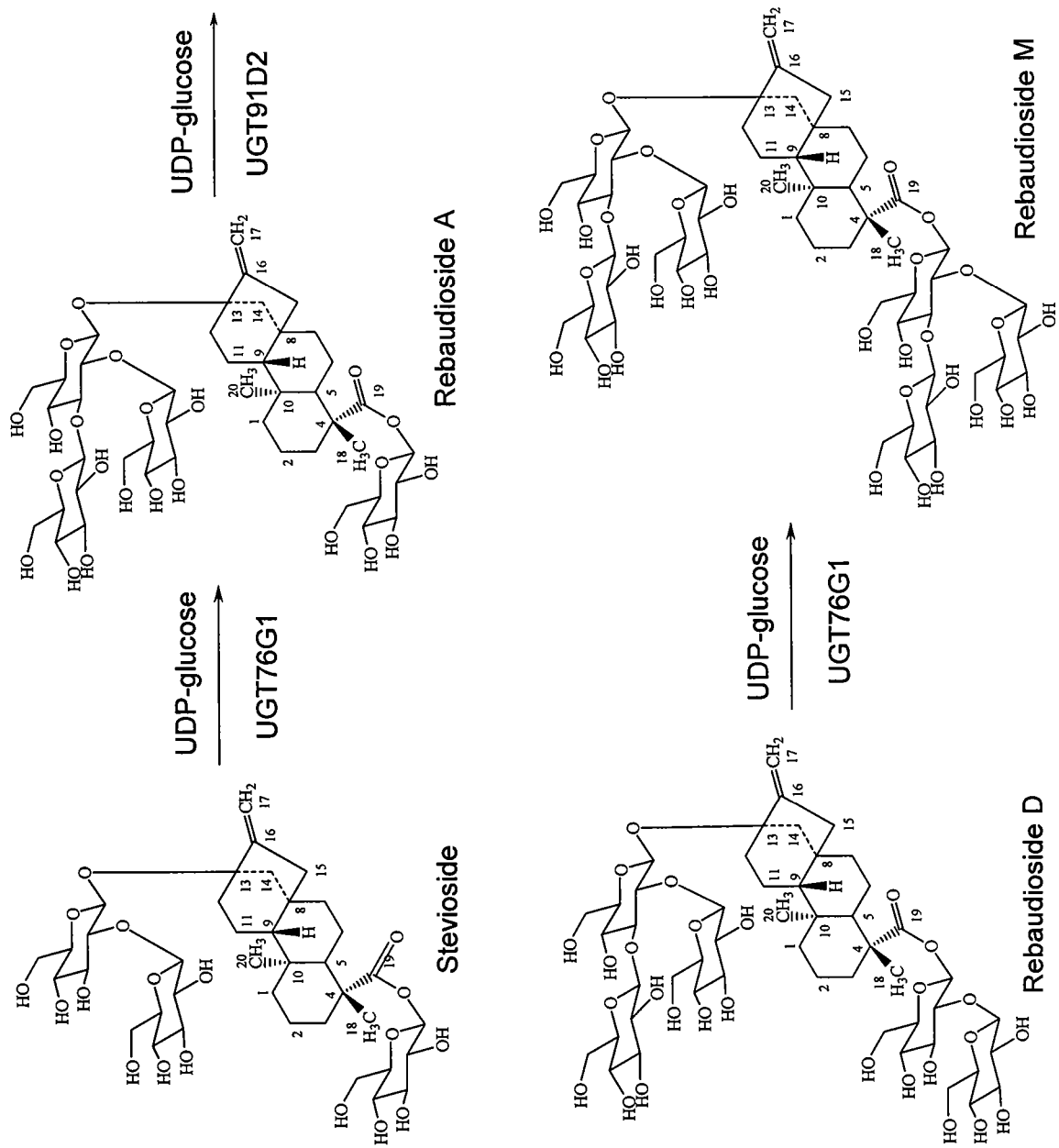
FIG. 2 shows the biocatalytic production of reb M from stevioside.

The present invention provides a biocatalytic process for preparing a composition comprising a target steviol glycoside by contacting a starting composition comprising an organic substrate with a microorganism, thereby producing a composition comprising a target steviol glycoside.

One object of the invention is to provide an efficient biocatalytic method for preparing steviol glycosides, particularly stevioside, reb E, reb A, reb D, reb D2, reb M, and reb M2 from various starting compositions.

As used herein, "biocatalysis" or "biocatalytic" refers to the use of natural or genetically engineered biocatalysts, such as cells, protein enzymes, to perform single or multiple step chemical transformations on organic compounds. Biocatalysis include fermentation, biosynthesis and biotransformation processes. Both, isolated enzyme and whole-cell biocatalysis methods are known in the art. Biocatalyst protein enzymes can be naturally occurring or recombinant proteins.

All sequences listed herein, including any nucleic acid or amino acid sequences, include variants having >75%, >80%, >90%, >95%, >96%, >97%, >98%, or >99% sequence identity to the nucleic acid or amino acid sequences described herein.

As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside D, rebaudioside M2, rebaudioside D2, rebaudioside N, rebaudioside O, synthetic steviol glycosides, e.g. enzymatically glucosylated steviol glycosides and combinations thereof.

Chemical structures of steviol and its glycosides

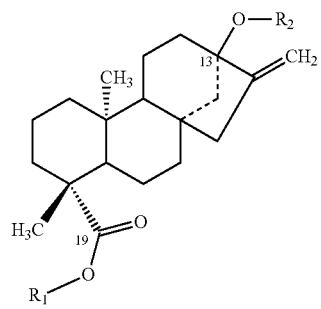

| Compound | $R_1$ | $R_2$ |
|---|---|---|
| Steviol | H | H |
| Steviolmonoside | H | β—Glc |
| Steviol monoglucosyl ester | β—Glc | H |
| Rubusoside | β—Glc | β—Glc |
| Steviolbioside | H | β—Glc—β—Glc(2→1) |
| Stevioside | β—Glc | β—Glc—β—Glc(2→1) |
| Rebaudioside A | β—Glc | β—Glc—β—Glc(2→1)<br>    |<br>β—Glc(3→1) |
| Rebaudioside D | β—Glc—β—Glc(2→1) | β—Glc—β—Glc(2→1)<br>    |<br>β—Glc(3→1) |
| Rebaudioside E | β—Glc—β—Glc(2→1) | β—Glc—β—Glc(2→1) |

-continued

| Compound | $R_1$ | $R_2$ |
|---|---|---|
| Rebaudioside M | β—Glc—β—Glc(2→1)<br>\|<br>β—Glc(3→1) | β—Glc—β—Glc(2→1)<br>\|<br>β—Glc(3→1) |

(Glc = glucose)

Starting Composition

As used herein, "starting composition" refers to any composition (generally an aqueous solution) containing one or more organic compound comprising at least one carbon atom.

In one embodiment, the starting composition is selected from the group consisting of polyols and various carbohydrates.

The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced.

The term "carbohydrate" refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

The starting composition may be synthetic or purified (partially or entirely), commercially available or prepared.

In one embodiment, the starting composition is glycerol.

In another embodiment, the starting composition is glucose.

In still another embodiment, the starting composition is sucrose.

In yet another embodiment, the starting composition is starch.

In another embodiment, the starting composition is maltodextrin.

In another embodiment, the starting composition is steviol glycoside(s).

The organic compound(s) of starting composition serve as a substrate(s) for the production of the target steviol glycoside(s), as described herein.

Target Steviol Glycoside

The target steviol glycoside of the present method can be any steviol glycoside that can be prepared by the process disclosed herein. In one embodiment, the target steviol glycoside is selected from the group consisting of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N or rebaudioside O, or other glycoside of steviol.

In one embodiment, the target steviol glycoside is stevioside. In another embodiment, the target steviol glycoside is reb A. In still another embodiment, the target steviol glycoside is reb E. In yet another embodiment, the target steviol glycoside is reb D. In yet another embodiment, the target steviol glycoside is reb D2. In a further embodiment, the target steviol glycoside is reb M. In a still further another embodiment, the target steviol glycoside is reb M2.

The target steviol glycoside can be in any polymorphic or amorphous form, including hydrates, solvates, anhydrous or combinations thereof.

In one embodiment, the present invention is a biocatalytic process for the production of reb D.

In yet another embodiment, the present invention is a biocatalytic process for the production of reb D2.

In still another embodiment, the present invention is a biocatalytic process for the production of reb M.

In a further embodiment, the present invention is a biocatalytic process for the production of reb M2.

In one embodiment, the present invention is a biocatalytic process for the production of reb I.

In yet another embodiment, the present invention is a biocatalytic process for the production of reb E.

Optionally, the method of the present invention further comprises separating the target steviol glycoside from the starting composition. The target steviol glycoside can be separated by any suitable method, such as, for example, crystallization, separation by membranes, centrifugation, extraction, chromatographic separation or a combination of such methods.

In particular embodiments, the process described herein results in a highly purified target steviol glycoside composition. The term "highly purified", as used herein, refers to a composition having greater than about 80% by weight of the target steviol glycoside on an anhydrous basis. In one embodiment, the highly purified target steviol glycoside composition contains greater than about 90% by weight of the target steviol glycoside on an anhydrous basis, such as, for example, greater than about 91%, greater than about 92%, greater than about 93%, greater than about 94%, greater than about 95%, greater than about 96%, greater than about 97%, greater than about 98% or greater than about 99% target steviol glycoside content on a dry basis.

In one embodiment, when the target steviol glycoside is reb M, the process described herein provides a composition having greater than about 90% reb M content by weight on a dry basis. In another particular embodiment, when the target steviol glycoside is reb M, the process described herein provides a composition comprising greater than about 95% reb M content by weight on a dry basis.

In another embodiment, when the target steviol glycoside is reb M2, the process described herein provides a composition having greater than about 90% reb M2 content by weight on a dry basis. In another particular embodiment, when the target steviol glycoside is reb M2, the process described herein provides a composition comprising greater than about 95% reb M2 content by weight on a dry basis.

In yet another embodiment, when the target steviol glycoside is reb D, the process described herein provides a composition greater than about 90% reb D content by weight on a dry basis. In another particular embodiment, when the target steviol glycoside is reb D, the process described herein provides a composition comprising greater than about 95% reb D content by weight on a dry basis.

In still another embodiment, when the target steviol glycoside is reb D2, the process described herein provides a composition greater than about 90% reb D2 content by weight on a dry basis. In another particular embodiment, when the target steviol glycoside is reb D2, the process described herein provides a composition comprising greater than about 95% reb D2 content by weight on a dry basis.

In a further embodiment, when the target steviol glycoside is reb A, the process described herein provides a composition comprising greater than about 90% reb A content by weight on a dry basis. In another particular embodiment, when the target steviol glycoside is reb A, the process described herein provides a composition comprising greater than about 95% reb A content by weight on a dry basis.

In a still further embodiment, when the target steviol glycoside is reb E, the process described herein provides a composition comprising greater than about 90% reb E content by weight on a dry basis. In another particular embodiment, when the target steviol glycoside is reb E, the process described herein provides a composition comprising greater than about 95% reb E content by weight on a dry basis.

In one embodiment, when the target steviol glycoside is reb I, the process described herein provides a composition comprising greater than about 90% reb I content by weight on a dry basis. In another particular embodiment, when the target steviol glycoside is reb I, the process described herein provides a composition comprising greater than about 95% reb I content by weight on a dry basis.

In yet a further embodiment, when the target steviol glycoside is stevioside, the process described herein provides a composition comprising greater than about 90% stevioside content by weight on a dry basis. In another particular embodiment, when the target steviol glycoside is stevioside, the process described herein provides a composition comprising greater than about 95% stevioside content by weight on a dry basis.

Microorganism

In one embodiment of present invention, a microorganism is contacted with the starting composition to produce a composition comprising the target steviol glycoside. The microorganism can be any microorganism possessing biocatalysts suitable for converting the starting composition to the target steviol glycoside. These biocatalysts are encoded within the microorganism's genome.

In one embodiment the microorganism may be, for example, *E. coli, Saccharomyces* sp., *Aspergillus* sp., *Pichia* sp., *Bacillus* sp., *Yarrowia* sp. etc.

The biocatalysts can be located on the surface and/or inside the cell of the microorganism.

The biocatalysts can be separated from the microorganism and used for conversion of starting composition to target steviol glycoside(s). The separation can be achieved by any means known to art, including but not limited to lysis of microbial cells, centrifugation, filtration.

The biocatalysts can be excreted from the microorganism (extracellular enzymes) and used for conversion of starting composition to target steviol glycoside(s).

In one embodiment, the biocatalysts are steviol biosynthesis enzymes and UDP-glycosyltransferases (UGTs), or their variants, having greater than 75% amino-acid sequence identity.

The steviol biosynthesis can be any steviol biosynthesis enzyme, or its variant, having greater than 75% amino-acid sequence identity.

In one embodiment the steviol biosynthesis enzymes include mevalonate (MVA) pathway enzymes, or their variants, having greater than 75% amino-acid sequence identity.

In another embodiment the steviol biosynthesis enzymes include non-mevalonate 2-C-methyl-D-erythritol-4-phosphate pathway (MEP/DOXP) enzymes, or their variants, having greater than 75% amino-acid sequence identity.

In one embodiment, the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase, etc., or their variants, having greater than 75% amino-acid sequence identity.

The UDP-glucosyltransferase can be any UDP-glucosyltransferase capable of adding at least one glucose unit to the steviol and or steviol glycoside substrate to provide the target steviol glycoside.

In one embodiment, the microorganism is free. In another embodiment, the microorganism is immobilized. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

In one embodiment the microorganism is in aqueous medium, comprising water, and various components selected form group including carbon sources, energy sources, nitrogen sources, microelements, vitamins, nucleosides, nucleoside phosphates, nucleoside diphosphates, nucleoside triphosphates, organic and inorganic salts, organic and mineral acids, bases etc. Carbon sources include glycerol, glucose, carbon dioxide, carbonates, bicarbonates. Nitrogen sources can include nitrates, nitrites, amino acids, peptides, peptones, or proteins.

In a particular embodiment, the medium comprises buffer. Suitable buffers include, but are not limited to, PIPES buffer, acetate buffer and phosphate buffer. In a particular embodiment, the medium comprises phosphate buffer.

In one embodiment, the medium can also include an organic solvent.

In one embodiment, the UDP-glucosyltransferase is any UDP-glucosyltransferase capable of adding at least one glucose unit to rubusoside, thereby producing stevioside. The UDP-glucosyltransferase may be, for example, UGT91D2 or UGT91D2 variant, having greater than 75% amino-acid sequence identity with UGT91D2.

In another embodiment, the UDP-glucosyltransferase is any UDP-glucosyltransferase capable of adding at least one glucose unit to rubusoside, thereby producing rebaudioside E. The UDP-glucosyltransferase may be, for example, UGTSL2 or UGTSL2 variant, having greater than 75% amino-acid sequence identity with UGTSL2.

In still another embodiment, the UDP-glucosyltransferase is any UDP-glucosyltransferase capable of adding at least one glucose unit to rebaudioside E, thereby producing rebaudioside D. The UDP-glucosyltransferase may be, for example, UGT76G1 or UGT76G1 variant, having greater than 75% amino-acid sequence identity with UGT76G1.

In yet embodiment, the UDP-glucosyltransferase is any UDP-glucosyltransferase capable of adding at least one glucose unit to stevioside, thereby producing rebaudioside A. The UDP-glucosyltransferase may be, for example, UGT76G1 or UGT76G1 variant, having greater than 75% amino-acid sequence identity with UGT76G1.

In a further embodiment, the UDP-glucosyltransferase is any UDP-glucosyltransferase capable of adding at least one glucose unit to rebaudioside A, thereby producing rebaudioside D and/or rebaudioside D2 and/or rebaudioside M2. The UDP-glucosyltransferase may be, for example, UGT91D2 or UGTSL2 or their variant, having greater than 75% amino-acid sequence identity with UGT91D2 or UGTSL2.

In yet another embodiment, the UDP-glucosyltransferase is any UDP-glucosyltransferase capable of adding at least one glucose unit to rebaudioside I to form rebaudioside M. In a particular embodiment, the UDP-glucosyltransferase is UGTSL or UGTSL variant, having greater than 75% amino-acid sequence identity with UGTSL.

In yet another embodiment, the UDP-glucosyltransferase is any UDP-glucosyltransferase capable of adding at least two glucose units to rebaudioside E to form rebaudioside M. In a particular embodiment, the UDP-glucosyltransferase is UGT76G1 or UGT76G1 variant, having greater than 75% amino-acid sequence identity with UGT76G1.

In another embodiment, the UDP-glucosyltransferase capable of adding at least one glucose unit to produce target steviol glycoside, has greater than 75% amino-acid sequence identity with at least one enzyme selected from the following listing of GenInfo identifier numbers, preferably from the group presented in Table 1, and more preferably the group presented in Table 2.

| | | | | | |
|---:|---:|---:|---:|---:|---:|
| 397567 | 30680413 | 115480946 | 147798902 | 218193594 | 225443294 |
| 454245 | 32816174 | 116310259 | 147811764 | 218193942 | 225444853 |
| 1359905 | 32816178 | 116310985 | 147827151 | 219885307 | 225449296 |
| 1685003 | 34393978 | 116788066 | 147836230 | 222615927 | 225449700 |
| 1685005 | 37993665 | 116788606 | 147839909 | 222619587 | 225454338 |
| 2191136 | 37993671 | 116789315 | 147846163 | 222623142 | 225454340 |
| 2501497 | 37993675 | 119394507 | 147855977 | 222625633 | 225454342 |
| 2911049 | 39104603 | 119640480 | 148905778 | 222625635 | 225454473 |
| 4218003 | 41469414 | 122209731 | 148905999 | 222636620 | 225454475 |
| 4314356 | 41469452 | 125526997 | 148906835 | 222636621 | 225458362 |
| 13492674 | 42566366 | 125534279 | 148907340 | 222636628 | 225461551 |
| 13492676 | 42570280 | 125534461 | 148908935 | 222636629 | 225461556 |
| 15217773 | 42572855 | 125540090 | 148909182 | 224053242 | 225461558 |
| 15217796 | 44890129 | 125541516 | 148909920 | 224053386 | 225469538 |
| 15223396 | 46806235 | 125545408 | 148910082 | 224055535 | 225469540 |
| 15223589 | 50284482 | 125547340 | 148910154 | 224056138 | 226316457 |
| 15227766 | 51090402 | 125547520 | 148910612 | 224056160 | 226492603 |
| 15230017 | 51090594 | 125554547 | 148910769 | 224067918 | 226494221 |
| 15231757 | 52839682 | 125557592 | 156138791 | 224072747 | 226495389 |
| 15234056 | 56550539 | 125557593 | 156138797 | 224080189 | 226495945 |
| 15234195 | 62734263 | 125557608 | 156138799 | 224091845 | 226502400 |

-continued

| | | | | | |
|---|---|---|---|---|---|
| 15234196 | 62857204 | 125559566 | 156138803 | 224094703 | 226507980 |
| 15238503 | 62857206 | 125563266 | 165972256 | 224100653 | 226531147 |
| 15239523 | 62857210 | 125571055 | 168016721 | 224100657 | 226532094 |
| 15239525 | 62857212 | 125579728 | 171674071 | 224101569 | 238477377 |
| 15239543 | 75265643 | 125588307 | 171906258 | 224103105 | 240254512 |
| 15239937 | 75285934 | 125589492 | 183013901 | 224103633 | 242032615 |
| 15240305 | 75288884 | 125599469 | 183013903 | 224103637 | 242032621 |
| 15240534 | 77550661 | 125601477 | 186478321 | 224109218 | 242038423 |
| 15982889 | 77556148 | 126635837 | 187373030 | 224114583 | 242043290 |
| 18086351 | 82791223 | 126635845 | 187373042 | 224116284 | 242044836 |
| 18418378 | 83778990 | 126635847 | 190692175 | 224120552 | 242051252 |
| 18418380 | 89953335 | 126635863 | 194701936 | 224121288 | 242056217 |
| 18418382 | 110741436 | 126635867 | 195620060 | 224121296 | 242056219 |
| 19743740 | 110743955 | 126635883 | 209954691 | 224121300 | 242056663 |
| 19911201 | 115438196 | 126635887 | 209954719 | 224130358 | 242059339 |
| 20149064 | 115438785 | 133874210 | 209954725 | 224140703 | 242059341 |
| 20260654 | 115441237 | 133874212 | 209954733 | 224143404 | 242060922 |
| 21435782 | 115454819 | 145358033 | 210063105 | 224143406 | 242067411 |
| 21553613 | 115456047 | 147772508 | 210063107 | 224144306 | 242067413 |
| 21593514 | 115457492 | 147776893 | 212275846 | 224285244 | 242076258 |
| 22759895 | 115459312 | 147776894 | 216296854 | 225431707 | 242076396 |
| 23955910 | 115464719 | 147776895 | 217074506 | 225435532 | 242084750 |
| 26452040 | 115471069 | 147786916 | 218185693 | 225436321 | 242091005 |
| 28393204 | 115471071 | 147798900 | 218187075 | 225440041 | 242095206 |
| 30679796 | 115474009 | 147798901 | 218189427 | 225441116 | 242345159 |
| 242345161 | 297724601 | 326492035 | 356523945 | 357140904 | 359486938 |
| 255536859 | 297725463 | 326493430 | 356523957 | 357165849 | 359487055 |
| 255538228 | 297728331 | 326500410 | 356523959 | 357165852 | 359488135 |
| 255541676 | 297738632 | 326506816 | 356523961 | 357168415 | 359488708 |
| 255547075 | 297745347 | 326507826 | 356523963 | 357437837 | 359493630 |
| 255552620 | 297745348 | 326508394 | 356524387 | 357442755 | 359493632 |
| 255552622 | 297795735 | 326509445 | 356524403 | 357442757 | 359493634 |
| 255555343 | 297796253 | 326511261 | 356527181 | 357445729 | 359493636 |
| 255555361 | 297796257 | 326511866 | 356533209 | 357445731 | 359493815 |
| 255555363 | 297796261 | 326512412 | 356533852 | 357445733 | 359495856 |
| 255555365 | 297797587 | 326517673 | 356534718 | 357446799 | 359495858 |
| 255555369 | 297798502 | 326518800 | 356535480 | 357446805 | 359495869 |
| 255555373 | 297799226 | 326521124 | 356542996 | 357452779 | 359495871 |
| 255555377 | 297805988 | 326525567 | 356543136 | 357452781 | 359497638 |
| 255556812 | 297807499 | 326525957 | 356543932 | 357452783 | 359807261 |
| 255556818 | 297809125 | 326526607 | 356549841 | 357452787 | 374256637 |
| 255563008 | 297809127 | 326527141 | 356549843 | 357452789 | 377655465 |
| 255564074 | 297811403 | 326530093 | 356554358 | 357452791 | 378405177 |
| 255564531 | 297820040 | 326534036 | 356554360 | 357452797 | 378829085 |
| 255572878 | 297821483 | 326534312 | 356558606 | 357452799 | 387135070 |
| 255577901 | 297825217 | 332071132 | 356560333 | 357470367 | 387135072 |
| 255583249 | 297832276 | 339715876 | 356560599 | 357472193 | 387135078 |
| 255583253 | 297832280 | 342306012 | 356560749 | 357472195 | 387135092 |
| 255583255 | 297832518 | 342306016 | 356566018 | 357474295 | 387135094 |
| 255585664 | 297832520 | 343457675 | 356566169 | 357474493 | 387135098 |
| 255585666 | 297840825 | 343457677 | 356566173 | 357474497 | 387135100 |
| 255634688 | 297840827 | 350534960 | 356567761 | 357474499 | 387135134 |
| 255644801 | 297847402 | 356498085 | 356574704 | 357490035 | 387135136 |
| 255645821 | 297849372 | 356499771 | 356576401 | 357493567 | 387135174 |
| 255647456 | 300078590 | 356499777 | 356577660 | 357497139 | 387135176 |
| 255648275 | 300669727 | 356499779 | 357114993 | 357497581 | 387135184 |
| 260279126 | 302142947 | 356501328 | 357115447 | 357497671 | 387135186 |
| 260279128 | 302142948 | 356502523 | 357115451 | 357500579 | 387135188 |
| 261343326 | 302142950 | 356503180 | 357115453 | 357504663 | 387135190 |
| 283132367 | 302142951 | 356503184 | 357116080 | 357504691 | 387135192 |
| 283362112 | 302765302 | 356503295 | 357116928 | 357504699 | 387135194 |
| 289188052 | 302796334 | 356504436 | 357117461 | 357504707 | 387135282 |
| 295841350 | 302811470 | 356504523 | 357117463 | 357505859 | 387135284 |
| 296088529 | 302821107 | 356504765 | 357117829 | 357510851 | 387135294 |
| 296090415 | 302821679 | 356511113 | 357117839 | 357516975 | 387135298 |
| 296090524 | 319759260 | 356515120 | 357125059 | 359477003 | 387135300 |
| 296090526 | 319759266 | 356517088 | 357126015 | 359477998 | 387135302 |
| 297599503 | 320148814 | 356520732 | 357134488 | 359478043 | 387135304 |
| 297601531 | 326489963 | 356522586 | 357135657 | 359478286 | 387135312 |
| 297611791 | 326490273 | 356522588 | 357138503 | 359484299 | 387135314 |
| 297722841 | 326491131 | 356522590 | 357139683 | 359486936 | 387135316 |
| 387135318 | 449440433 | 460376293 | 460413408 | 462423864 | 475546199 |
| 387135320 | 449445896 | 460378310 | 460416351 | 470101924 | 475556485 |
| 387135322 | 449446454 | 460380744 | 462394387 | 470102280 | 475559699 |
| 387135324 | 449447657 | 460381726 | 462394433 | 470102858 | 475578293 |
| 387135326 | 449449002 | 460382093 | 462394557 | 470104211 | 475591753 |
| 387135328 | 449449004 | 460382095 | 462395646 | 470104264 | 475593742 |
| 388493506 | 449449006 | 460382754 | 462395678 | 470104266 | 475612072 |
| 388495496 | 449451379 | 460384935 | 462396388 | 470106317 | 475622476 |

-continued

| | | | | | |
|---|---|---|---|---|---|
| 388498446 | 449451589 | 460384937 | 462396389 | 470106357 | 475622507 |
| 388499220 | 449451591 | 460385076 | 462396419 | 470115448 | 475623787 |
| 388502176 | 449451593 | 460385872 | 462396542 | 470130404 | 482550481 |
| 388517521 | 449453712 | 460386018 | 462397507 | 470131550 | 482550499 |
| 388519407 | 449453714 | 460389217 | 462399998 | 470136482 | 482550740 |
| 388521413 | 449453716 | 460394872 | 462400798 | 470136484 | 482550999 |
| 388827901 | 449453732 | 460396139 | 462401217 | 470136488 | 482552352 |
| 388827903 | 449457075 | 460397862 | 462402118 | 470136492 | 482554970 |
| 388827907 | 449467555 | 460397864 | 462402237 | 470137933 | 482555336 |
| 388827909 | 449468742 | 460398541 | 462402284 | 470137937 | 482555478 |
| 388827913 | 449495638 | 460403139 | 462402416 | 470140422 | 482556454 |
| 393887637 | 449495736 | 460403141 | 462404228 | 470140426 | 482557289 |
| 393887646 | 449499880 | 460403143 | 462406358 | 470140908 | 482558462 |
| 393887649 | 449502786 | 460403145 | 462408262 | 470141232 | 482558508 |
| 393990627 | 449503471 | 460405998 | 462409325 | 470142008 | 482558547 |
| 397746860 | 449503473 | 460407578 | 462409359 | 470142010 | 482561055 |
| 397789318 | 449515857 | 460407590 | 462409777 | 470142012 | 482561555 |
| 413924864 | 449518643 | 460409128 | 462411467 | 470143607 | 482562795 |
| 414590349 | 449519559 | 460409134 | 462414311 | 470143939 | 482562850 |
| 414590661 | 449522783 | 460409136 | 462414416 | 470145404 | 482565074 |
| 414591157 | 449524530 | 460409459 | 462414476 | 473923244 | 482566269 |
| 414879558 | 449524591 | 460409461 | 462415526 | 474114354 | 482566296 |
| 414879559 | 449528823 | 460409463 | 462415603 | 474143634 | 482566307 |
| 414879560 | 449528825 | 460409465 | 462415731 | 474202268 | 482568689 |
| 414888074 | 449534021 | 460409467 | 462416307 | 474299266 | 482570049 |
| 431812559 | 460365546 | 460410124 | 462416920 | 474363119 | 482570572 |
| 449432064 | 460366882 | 460410126 | 462416922 | 474366157 | 482575121 |
| 449432066 | 460369823 | 460410128 | 462416923 | 474429346 | |
| 449433069 | 460369829 | 460410130 | 462416924 | 475432777 | |
| 449436944 | 460369831 | 460410132 | 462417401 | 475473002 | |
| 449438665 | 460369833 | 460410134 | 462419769 | 475489790 | |
| 449438667 | 460370755 | 460410213 | 462420317 | 475511330 | |
| 449440431 | 460374714 | 460411200 | 462423366 | 475516200 | |

TABLE 1

| GI number | Accession | Origin |
|---|---|---|
| 190692175 | ACE87855.1 | *Stevia rebaudiana* |
| 41469452 | AAS07253.1 | *Oryza sativa* |
| 62857204 | BAD95881.1 | *Ipomoea nil* |
| 62857206 | BAD95882.1 | *Ipomoea purperea* |
| 56650539 | BAD77944.1 | *Bellis perennis* |
| 115454819 | NP_001051010.1 | *Oryza sativa* Japonica Group |
| 115459312 | NP_001053256.1 | *Oryza sativa* Japonica Group |
| 115471069 | NP_001059133.1 | *Oryza sativa* Japonica Group |
| 115471071 | NP_001059134.1 | *Oryza sativa* Japonica Group |
| 116310985 | CAH67920.1 | *Oryza sativa* Indica Group |
| 116788066 | ABK24743.1 | *Picea sitchensis* |
| 122209731 | Q2V6J9.1 | *Fragaria × ananassa* |
| 125534461 | EAY81009.1 | *Oryza sativa* Indica Group |
| 125559566 | EAZ05102.1 | *Oryza sativa* Indica Group |
| 125588307 | EAZ28971.1 | *Oryza sativa* Japonica Group |
| 148907340 | ABR16806.1 | *Picea sitchensis* |
| 148910082 | ABR18123.1 | *Picea sitchensis* |
| 148910612 | ABR18376.1 | *Picea sitchensis* |
| 15234195 | NP_194486.1 | *Arabidopsis thaliana* |
| 15239523 | NP_200210.1 | *Arabidopsis thaliana* |
| 15239937 | NP_196793.1 | *Arabidopsis thaliana* |
| 1685005 | AAB36653.1 | *Nicotiana tabacum* |
| 183013903 | ACC38471.1 | *Medicago truncatula* |
| 186478321 | NP_172511.3 | *Arabidopsis thaliana* |
| 187373030 | ACD03249.1 | *Avena strigosa* |
| 194701936 | ACF85052.1 | *Zea mays* |
| 19743740 | AAL92461.1 | *Solanum lycopersicum* |
| 212275846 | NP_001131009.1 | *Zea mays* |
| 222619587 | EEE55719.1 | *Oryza sativa* Japonica Group |
| 224055535 | XP_002298527.1 | *Populus trichocarpa* |
| 224101569 | XP_002334266.1 | *Populus trichocarpa* |
| 224120552 | XP_002318358.1 | *Populus trichocarpa* |
| 224121288 | XP_002330790.1 | *Populus trichocarpa* |
| 225444853 | XP_002281094 | *Vitis vinifera* |
| 225454342 | XP_002275850.1 | *Vitis vinifera* |
| 225454475 | XP_002280923.1 | *Vitis vinifera* |
| 225461556 | XP_002285222 | *Vitis vinifera* |
| 225469540 | XP_002270294.1 | *Vitis vinifera* |
| 226495389 | NP_001148083.1 | *Zea mays* |

TABLE 1-continued

| GI number | Accession | Origin |
|---|---|---|
| 226502400 | NP_001147674.1 | *Zea mays* |
| 238477377 | ACR43489.1 | *Triticum aestivum* |
| 240254512 | NP_565540.4 | *Arabidopsis thaliana* |
| 2501497 | Q43716.1 | *Petunia × hybrida* |
| 255555369 | XP_002518721.1 | *Ricinus communis* |
| 26452040 | BAC43110.1 | *Arabidopsis thaliana* |
| 296088529 | CBI37520.3 | *Vitis vinifera* |
| 297611791 | NP_001067852.2 | *Oryza sativa* Japonica Group |
| 297795735 | XP_002865752.1 | *Arabidopsis lyrata* subsp. *lyrata* |
| 297798502 | XP_002867135.1 | *Arabidopsis lyrata* subsp. *lyrata* |
| 297820040 | XP_002877903.1 | *Arabidopsis lyrata* subsp. *lyrata* |
| 297832276 | XP_002884020.1 | *Arabidopsis lyrata* subsp. *lyrata* |
| 302821107 | XP_002992218.1 | *Selaginella moellendorffii* |
| 30680413 | NP_179446.2 | *Arabidopsis thaliana* |
| 319759266 | ADV71369.1 | *Pueraria montana* var. *lobata* |
| 326507826 | BAJ86656.1 | *Hordeum vulgare* subsp. *Vulgare* |
| 343457675 | AEM37036.1 | *Brassica rapa* subsp. *oleifera* |
| 350534960 | NP_001234680.1 | *Solanum lycopersicum* |
| 356501328 | XP_003519477.1 | *Glycine max* |
| 356522586 | XP_003529927.1 | *Glycine max* |
| 356535480 | XP_003536273.1 | *Glycine max* |
| 357445733 | XP_003593144.1 | *Medicago truncatula* |
| 357452783 | XP_003596668.1 | *Medicago truncatula* |
| 357474493 | XP_003607531.1 | *Medicago truncatula* |
| 357500579 | XP_003620578.1 | *Medicago truncatula* |
| 357504691 | XP_003622634.1 | *Medicago truncatula* |
| 359477998 | XP_003632051.1 | *Vitis vinifera* |
| 359487055 | XP_002271587 | *Vitis vinifera* |
| 359495869 | XP_003635104.1 | *Vitis vinifera* |
| 387135134 | AFJ52948.1 | *Linum usitatissimum* |
| 387135176 | AFJ52969.1 | *Linum usitatissimum* |
| 387135192 | AFJ52977.1 | *Linum usitatissimum* |
| 387135282 | AFJ53022.1 | *Linum usitatissimum* |
| 387135302 | AFJ53032.1 | *Linum usitatissimum* |
| 387135312 | AFJ53037.1 | *Linum usitatissimum* |
| 388519407 | AFK47765.1 | *Medicago truncatula* |
| 393887646 | AFN26668.1 | *Barbarea vulgaris* subsp. *arcuata* |
| 414888074 | DAA64088.1 | *Zea mays* |
| 42572855 | NP_974524.1 | *Arabidopsis thaliana* |

TABLE 1-continued

| GI number | Accession | Origin |
|---|---|---|
| 449440433 | XP_004137989.1 | Cucumis sativus |
| 449446454 | XP_004140986.1 | Cucumis sativus |
| 449449004 | XP_004142255.1 | Cucumis sativus |
| 449451593 | XP_004143546.1 | Cucumis sativus |
| 449515857 | XP_004164964.1 | Cucumis sativus |
| 460382095 | XP_004236775.1 | Solanum lycopersicum |
| 460409128 | XP_004249992.1 | Solanum lycopersicum |
| 460409461 | XP_004250157.1 | Solanum lycopersicum |
| 460409465 | XP_004250159.1 | Solanum lycopersicum |
| 462396388 | EMJ02187.1 | Prunus persica |
| 462402118 | EMJ07675.1 | Prunus persica |
| 462409359 | EMJ14693.1 | Prunus persica |
| 462416923 | EMJ21660.1 | Prunus persica |
| 46806235 | BAD17459.1 | Oryza sativa Japonica Group |
| 470104266 | XP_004288529.1 | Fragaria vesca subsp. vesca |
| 470142008 | XP_004306714.1 | Fragaria vesca subsp. vesca |
| 475432777 | EMT01232.1 | Aegilops tauschii |
| 51090402 | BAD35324.1 | Oryza sativa Japonica Group |

TABLE 2

| GI number | Accession | Origin |
|---|---|---|
| 460409128 | XP.004249992.1 | Solanum lycopersicum |
| 460386018 | XP.004238697.1 | Solanum lycopersicum |
| 460409134 | XP.004249995.1 | Solanum lycopersicum |
| 460410132 | XP.004250485.1 | Solanum lycopersicum |
| 460410130 | XP.004250484.1 | Solanum lycopersicum |
| 460410128 | XP.004250483.1 | Solanum lycopersicum |
| 460378310 | XP.004234916.1 | Solanum lycopersicum |
| 209954733 | BAG80557.1 | Lycium barbarum |
| 209954725 | BAG80553.1 | Lycium barbarum |

In yet another embodiment, the UDP-glucosyltransferase is any UDP-glucosyltransferase capable of adding at least one glucose unit to rebaudioside D to form rebaudioside M and/or rebaudioside M2. The UDP-glucosyltransferase may be, for example, UGT76G1 or UGT76G1 variant, having greater than 75% amino-acid sequence identity with UGT76G1.

Figure 3:
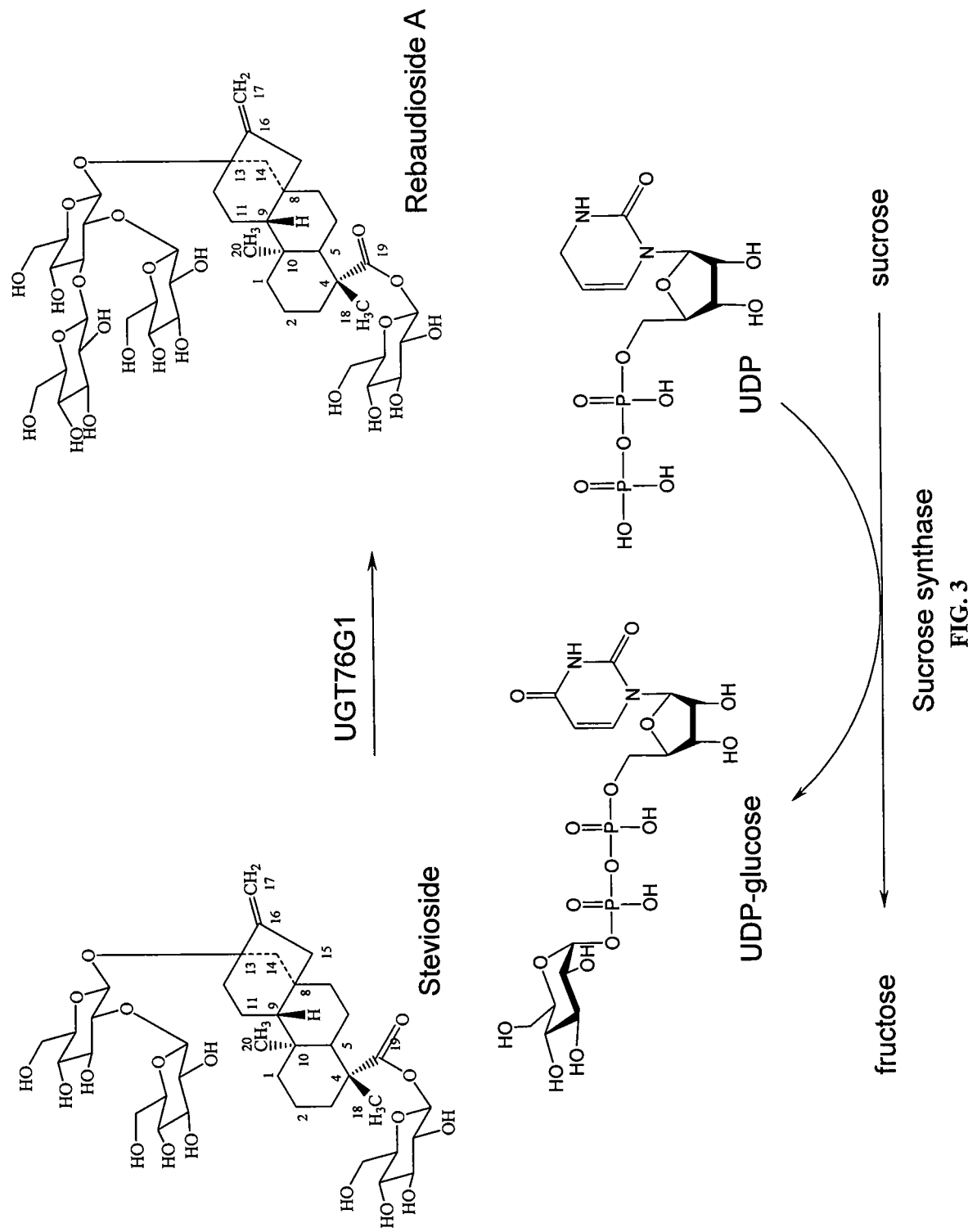
FIG. 3 shows the biocatalytic production of reb A from stevioside using the enzyme UGT76G1 and concomitant recycling of UDP to UDP glucose via sucrose synthase.

Optionally, the method of the present invention further comprises recycling UDP to provide UDP-glucose. In one embodiment, the method comprises recycling UDP by providing a recycling catalyst, i.e., a biocatalyst capable of UDP-glucose overproduction, and a recycling substrate, such that the conversion of the substrate steviol glycoside to the target steviol glycoside is carried out using catalytic amounts of UDP-glucosyltransferase and UDP-glucose (FIG. 3).

In one embodiment, the UDP-glucose recycling catalyst is sucrose synthase.

In one embodiment, the recycling substrate is sucrose.

Optionally, the method of the present invention further comprises hydrolysis of 1,6-β-glucosidic linkages in reb D2 and/or reb M2. In one embodiment, the method comprises hydrolysis of 1,6-β-glucosidic linkages in reb D2 and/or reb M2 by providing a β-glucosidase.

In one embodiment β-glucosidase is provided together with UDP-recycling biocatalyst and UGTs to minimize the content of reb D2 and/or reb M2 in final reaction mixture and maximize the yield of reb M.

In a particular embodiment to minimize the content of reb D2 and/or reb M2 in final reaction mixture and maximize the yield of reb M, β-glucosidase is provided together with UDP-recycling biocatalyst, UGT76G1 and UGTSL2, or their variants having greater than 75% amino-acid sequence identity with UGT76G1 or UGTSL2.

The target steviol glycoside is optionally purified from the resulting composition. Purification of the target steviol glycoside from the reaction medium can be achieved by any suitable method to provide a highly purified target steviol glycoside composition. Suitable methods include crystallization, separation by membranes, centrifugation, extraction (liquid or solid phase), chromatographic separation, HPLC (preparative or analytical) or a combination of such methods.

Compounds and Methods

The present invention also provides isolated and highly purified reb D2. Reb D2 is an isomer of reb D and has the following structure:

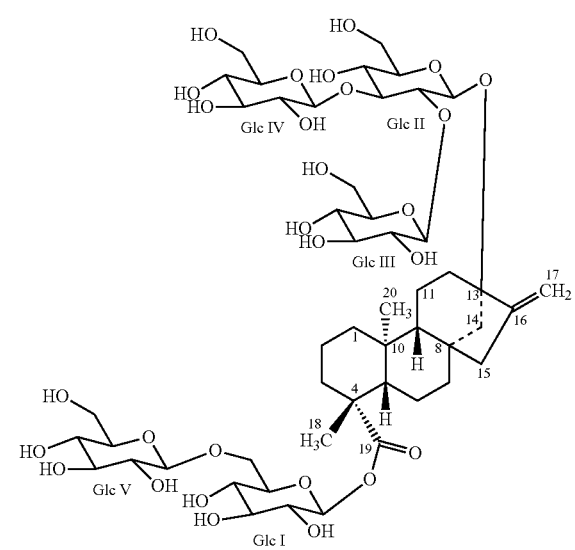

13-[(2-O-β-D-glucopyranosyl-3-O-β-D-glucopyranosyl-β-D-glucopyranosyl)oxy] ent-kaur-16-en-19-oic acid-[(6-O-β-D-glucopyranosyl-β-D-glucopyranosyl) ester]

In another embodiment, the present invention provides reb D2 having a purity greater than about 95% by weight on an anhydrous basis, such as, for example, greater than about 96% by weight, greater than about 97% by weight, greater than about 98% by weight or greater than about 99% by weight.

In still another embodiment, the present invention provides reb D2 having a purity greater than about 95% by weight in a steviol glycoside mixture, such as, for example, greater than about 96% by weight, greater than about 97% by weight, greater than about 98% by weight or greater than about 99% by weight.

The present invention also provides compositions comprising reb D2.

In one embodiment, the present invention provides a method for preparing reb D2 comprising:
a. contacting a starting composition comprising reb A with an enzyme capable of transforming reb A to reb D2, UDP-glucose, and optionally UDP-glucose recycling enzymes, to produce a composition comprising reb D2; and
b. isolating the composition comprising reb D2.

In some embodiments, the enzyme capable of transforming reb A to reb D2 is a UDP-glucosyltransferase, such as, for example, UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11.

The enzyme capable of transforming reb A to reb D2 can be immobilized or provided in the form of a recombinant microorganism.

In one embodiment, the enzyme is immobilized. In another embodiment, the enzyme is provided in the form of a recombinant microorganism.

In one embodiment, the microorganism is free. In another embodiment, the microorganism is immobilized. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

Suitable microorganisms include, but are not limited to, *E. coli*, *Saccharomyces* sp., *Aspergillus* sp., *Pichia* sp., *Bacillus* sp., *Yarrowia* sp.

In one embodiment the microorganism is in an aqueous medium, comprising water, and various components selected form group including carbon sources, energy sources, nitrogen sources, microelements, vitamins, nucleosides, nucleoside phosphates, nucleoside diphosphates, nucleoside triphosphates, organic and inorganic salts, organic and mineral acids, bases etc. Carbon sources include glycerol, glucose, carbon dioxide, carbonates, bicarbonates. Nitrogen sources can include nitrates, nitrites, amino acids, peptides, peptones, or proteins.

In a particular embodiment, the medium comprises buffer. Suitable buffers include, but are not limited to, PIPES buffer, acetate buffer and phosphate buffer. In a particular embodiment, the medium comprises phosphate buffer.

In one embodiment the medium can also include an organic solvent.

In a particular embodiment, the enzyme is a UDP-glucosyltransferase capable of transforming reb A to reb D2 and is contained in *E. coli*.

In a more particular embodiment, the enzyme is selected from UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11 and is contained in *E. coli*.

In a still more particular embodiment, the enzyme is UGTSL2 and is contained in *E. coli*.

Isolation of reb D2 from the reaction medium can be achieved by any suitable method to provide a composition comprising reb D2. Suitable methods include, but are not limited to, lysis, crystallization, separation by membranes, centrifugation, extraction (liquid or solid phase), chromatographic separation, HPLC (preparative or analytical) or a combination of such methods. In a particular embodiment, isolation can be achieved by lysis and centrifugation.

In some embodiments, isolation may result in a reb D2 purity less than about 95% by weight on an anhydrous basis, and the composition may contain, e.g., steviol glycosides and/or residual reaction products. The composition comprising reb D2 can be further purified to provide highly purified reb D2, i.e. reb D2 having a purity greater than about 95% by weight on an anhydrous basis. In some embodiments, the compositions comprising reb D2 can be further purified to provide reb D2 having a purity greater than about 96%, greater than about 97%, greater than about 98% or greater than about 99% by weight on an anhydrous basis.

Purification can be affected by any means known to one of skill in the art including, but not limited to, crystallization, separation by membranes, centrifugation, extraction (liquid or solid phase), chromatographic separation, HPLC (preparative or analytical) or a combination of such methods. In a particular embodiment, HPLC is used to purify reb D2. In a more particular embodiment, semi-preparative HPLC is used to purify reb D2.

For example, a two-step semi-preparative HPLC purification can be used. The first step utilizes a C18 column with a mobile phase containing A (25% MeCN in water) and B (30% MeCN in water) with the following gradient:

| Time (min) | % A | % B |
|---|---|---|
| 0.0-5.0 | 100 | 0 |
| 20 | 20 | 80 |
| 25 | 20 | 80 |
| 30 | 100 | 0 |

The secondary step utilizes the same column and conditions, but with only an isocratic mobile phase: 20% MeCN in water.

Those of skill in the art will recognize that the particular column, mobile phases, injection volumes and other HPLC parameters can vary.

In one embodiment, the present invention provides isolated and highly purified reb M2. Reb M2 is an isomer of reb M and has the following structure:

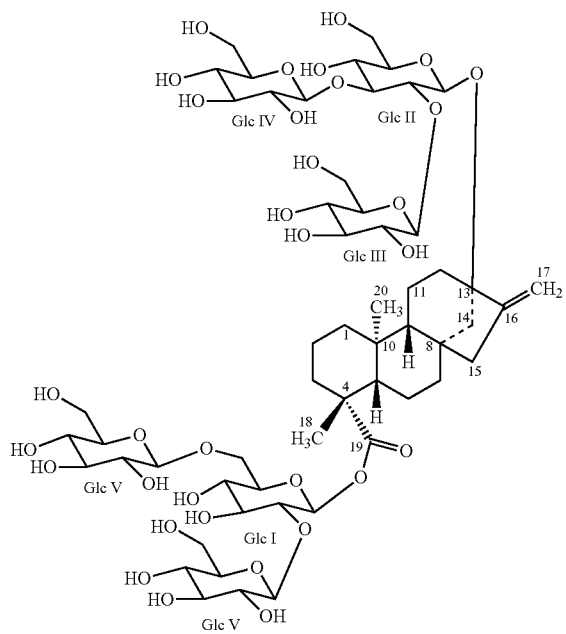

13-[(2-O-β-D-glucopyranosyl-3-O-β-D-glucopyranosyl-β-D-glucopyranosyl)oxy] ent-kaur-16-en-19-oic acid-[(2-O-β-D-glucopyranosyl-6-O-β-D-glucopyranosyl-β-D-glucopyranosyl) ester]

In another embodiment, the present invention provides reb M2 having a purity greater than about 95% by weight on an anhydrous basis, such as, for example, greater than about 96% by weight, greater than about 97% by weight, greater than about 98% by weight or greater than about 99% by weight.

In still another embodiment, the present invention provides reb M2 having a purity greater than about 95% by weight in a steviol glycoside mixture, such as, for example, greater than about 96% by weight, greater than about 97% by weight, greater than about 98% by weight or greater than about 99% by weight.

In yet another embodiment, the present invention provides reb M2 having a purity greater than about 95% by weight in a *stevia* extract, such as, for example, greater than about 96% by weight, greater than about 97% by weight, greater than about 98% by weight or greater than about 99% by weight.

The present invention also provides compositions comprising reb M2.

It has been found that reb M2 is produced during biotransformation of reb A to reb D. As noted above, biotransformation of reb A to reb D also produces reb D2. Accordingly, in one embodiment, the present invention provides a method for preparing reb M2 comprising:
  a. contacting a starting composition comprising reb A and/or reb D2 with an enzyme capable of transforming reb A and/or reb D2 to reb M2, UDP-glucose, and optionally UDP-glucose recycling enzymes to produce a composition comprising reb M2; and
  b. isolating a composition comprising reb M2.

Not wishing to be bound by theory, it is currently believed that the pathway begins with transformation of reb A to reb D2, followed by transformation of reb D2 to reb M2. Accordingly, In one embodiment, the present invention provides a method for preparing reb M2 comprising:
  a. contacting a starting composition comprising reb D2 with an enzyme capable of transforming reb D2 to reb M2, UDP-glucose, and optionally UDP-glucose recycling enzymes to produce a composition comprising reb M2; and
  b. isolating a composition comprising reb M2.

In yet another embodiment, a method for preparing reb M2 comprises:
  a. contacting a starting composition comprising reb A with an enzyme capable of transforming reb A to reb D2, UDP-glucose, and optionally UDP-glucose recycling enzymes to produce a composition comprising reb D2;
  b. optionally, isolating a composition comprising reb D2;
  c. contacting the composition comprising reb D2 with an enzyme capable of transforming reb D2 to reb M2, UDP-glucose, and optionally UDP-glucose recycling enzymes to produce a composition comprising reb M2; and
  d. isolating a composition comprising reb M2.

The enzyme can be a UDP-glucosyltransferase, such as, for example, UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11.

The enzyme can be immobilized or in a recombinant microorganism.

In one embodiment, the enzyme is immobilized. In another embodiment, the enzyme is in a recombinant microorganism.

In one embodiment, the microorganism is free. In another embodiment, the microorganism is immobilized. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

Suitable microorganisms include, but are not limited to, *E. coli, Saccharomyces* sp., *Aspergillus* sp., *Pichia* sp., *Bacillus* sp., *Yarrowia* sp.

In one embodiment the microorganism is in aqueous medium, comprising water, and various components selected form group including carbon sources, energy sources, nitrogen sources, microelements, vitamins, nucleosides, nucleoside phosphates, nucleoside diphosphates, nucleoside triphosphates, organic and inorganic salts, organic and mineral acids, bases etc. Carbon sources include glycerol, glucose, carbon dioxide, carbonates, bicarbonates. Nitrogen sources can include nitrates, nitrites, amino acids, peptides, peptones, or proteins.

In a particular embodiment, the medium comprises buffer. Suitable buffers include, but are not limited to, PIPES buffer, acetate buffer and phosphate buffer. In a particular embodiment, the medium comprises phosphate buffer.

In one embodiment the medium can also include an organic solvent.

In a particular embodiment, the enzyme is a UDP-glucosyltransferase capable of transforming reb A and/or reb D2 to reb M2 and is contained in *E. coli*.

In a more particular embodiment, the enzyme is selected from UGT91D2, UGTSL, UGTSL_Sc, UGTSL2 (GI No. 460410132 version XP_004250485.1), GI No. 460409128 (UGTSL) version XP_004249992.1, GI No. 115454819 version NP 001051010.1, GI No. 187373030, version ACD03249.1. GI No. 222619587 version EEE55719.1, GI No. 297795735 version XP_002865752.1 or EUGT11 and is contained in *E. coli*.

In a still more particular embodiment, the enzyme is UGTSL2 and is contained in *E. coli*.

Isolation of reb M2 from the reaction medium can be achieved by any suitable method to provide a composition comprising reb M2. Suitable methods include, but are not limited to, lysis, crystallization, separation by membranes, centrifugation, extraction (liquid or solid phase), chromatographic separation, HPLC (preparative or analytical) or a combination of such methods. In a particular embodiment, isolation can be achieved by lysis and centrifugation.

In some embodiments, isolation may result in a reb M2 purity less than about 95% by weight on an anhydrous basis, and the composition may contain, e.g., steviol glycosides and/or residual reaction products.

The composition comprising reb M2 can be further purified to provide highly purified reb M2, i.e. reb M2 having a purity greater than about 95% by weight on an anhydrous basis. In some embodiments, the compositions comprising reb M2 can be further purified to provide reb M2 having a purity greater than about 96%, greater than about 97%, greater than about 98% or greater than about 99% by weight on an anhydrous basis.

Purification can be affected by any means known to one of skill in the art including, but not limited to, crystallization, separation by membranes, centrifugation, extraction (liquid or solid phase), chromatographic separation, HPLC (preparative or analytical) or a combination of such methods. In a particular embodiment, HPLC is used to purify reb M2. In a more particular embodiment, semi-preparative HPLC is used to purify reb M2.

For example, a two-step semi-preparative HPLC purification can be used. The first step utilizes a C18 column with a mobile phase containing A (25% MeCN in water) and B (30% MeCN in water) with the following gradient:

| Time (min) | % A | % B |
|---|---|---|
| 0.0-5.0 | 100 | 0 |
| 20 | 20 | 80 |
| 25 | 20 | 80 |
| 30 | 100 | 0 |

The secondary step utilizes the same column and conditions, but with only an isocratic mobile phase: 20% MeCN in water.

Those of skill in the art will recognize that the particular column, mobile phases, injection volumes and other HPLC parameters can vary.

Purified steviol glycosides, prepared in accordance with the present invention, may be used in a variety of consumable products including, but not limited to, foods, beverages, pharmaceutical compositions, tobacco products, nutraceutical compositions, oral hygiene compositions, and cosmetic compositions.

Figure 4:
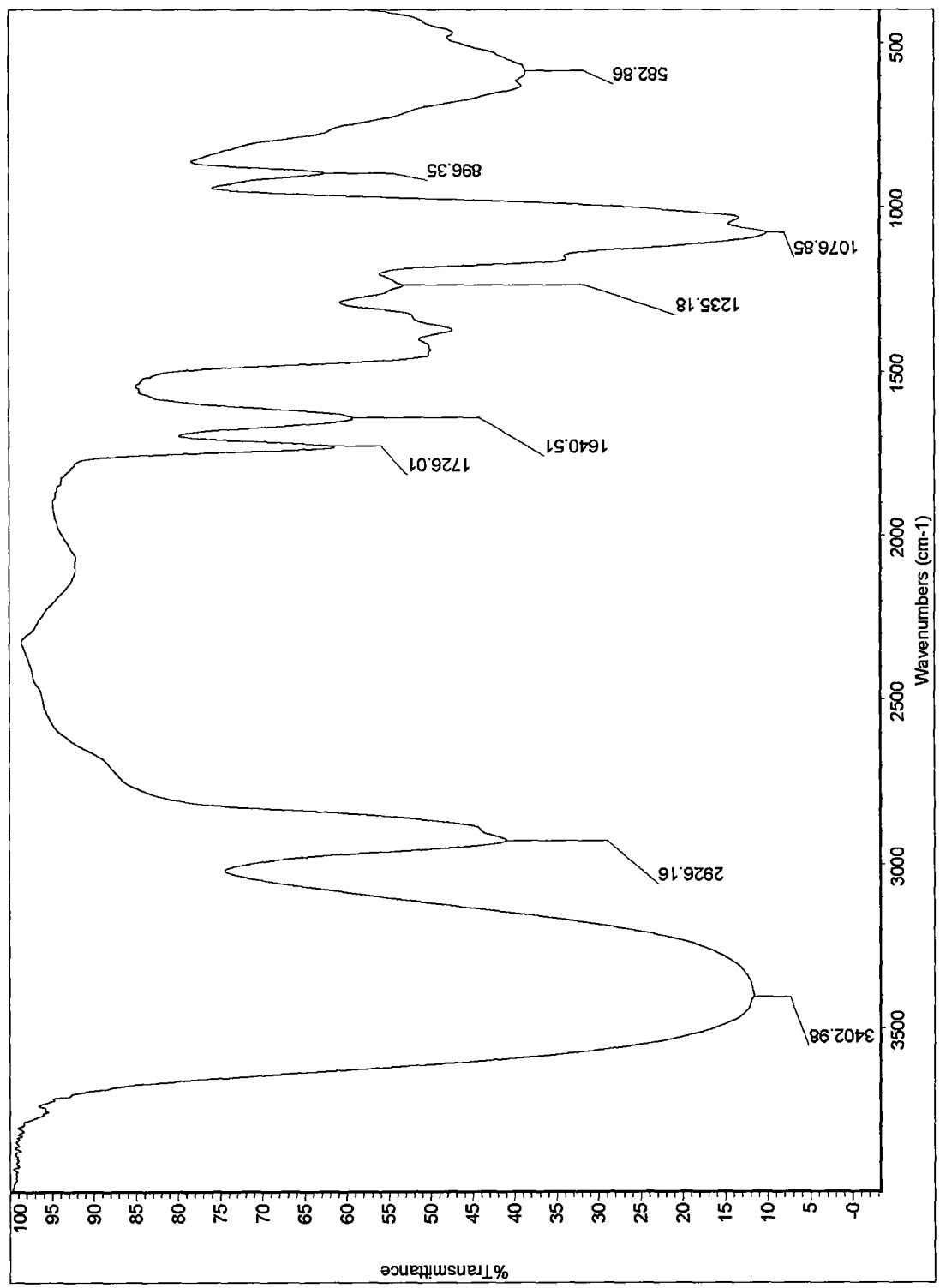
FIG. 4 shows the IR spectrum of reb M.

The high purity reb M obtained in this invention, having a molecular weight of 1291.29, a molecular formula of $C_{56}H_{90}O_{33}$, CAS registry number 1220616-44-3, and the structure presented in FIG. 1, is in the form of a white and odorless powder. The compound is about 200 times sweeter than sugar when compared to a 10% sucrose solution. The infrared absorption spectrum is shown in FIG. 4.

Other properties of the pure reb M compound include a melting point of 249-250° C., and a specific rotation of $[\alpha]_D^{25}$ –19.0° in 50% ethanol (C=1.0). The solubility of reb M in water is around 0.3%, and increases with an increase in temperature.

Reb M is soluble in diluted solutions of methanol, ethanol, n-propanol, and isopropanol. However, it is insoluble in acetone, benzene, chloroform, and ether.

Reb M obtained in accordance with the present invention is heat and pH-stable.

Highly purified target glycoside(s) particularly, reb D, reb D2, reb M and/or reb M2 obtained according to this invention can be used "as-is" or in combination with other sweeteners, flavors and food ingredients.

Non-limiting examples of flavors include lime, lemon, orange, fruit, banana, grape, pear, pineapple, mango, bitter almond, cola, cinnamon, sugar, cotton candy and vanilla flavors.

Non-limiting examples of other food ingredients include flavors, acidulants, organic and amino acids, coloring agents, bulking agents, modified starches, gums, texturizers, preservatives, antioxidants, emulsifiers, stabilizers, thickeners and gelling agents.

Highly purified target glycoside(s) particularly, reb D, reb D2, reb M and/or reb M2 obtained according to this invention can be prepared in various polymorphic forms, including but not limited to hydrates, solvates, anhydrous, amorphous forms and/or mixtures thereof.

Highly purified target steviol glycoside(s), particularly, reb D, reb D2, reb M and/or reb M2 obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc.

Highly purified target steviol glycoside(s), particularly, reb D, reb D2, reb M and/or reb M2 as a sweetening compound may be employed as the sole sweetener, or it may be used together with other naturally occurring high intensity sweeteners such as stevioside, reb A, reb B, reb C, reb D, reb E, reb F, steviolbioside, dulcoside A, rubusoside, mogrosides, brazzein, neohesperidin dihydrochalcone, glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyl lin, phlorizin, trilobatin, di hydroflavon ol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, mogroside V, siamenoside and others.

In a particular embodiment, reb D2 and/or reb M2 can be used together in a sweetener composition comprising a compound selected from the group consisting of reb A, reb B, reb D, NSF-02, Mogroside V, erythritol and combinations thereof.

Highly purified target steviol glycoside(s), particularly, reb D, reb D2, reb M and/or reb M2 may also be used in combination with synthetic high intensity sweeteners such as sucralose, potassium acesulfame, aspartame, alitame, saccharin, neohesperidin dihydrochalcone, cyclamate, neotame, dulcin, suosan advantame, salts thereof, and the like.

Moreover, highly purified target steviol glycoside(s), particularly, reb D, reb D2, reb M and/or reb M2 can be used in combination with natural sweetener suppressors such as gymnemic acid, hodulcin, ziziphin, lactisole, and others. Reb D, reb D2, reb M and/or reb M2 may also be combined with various umami taste enhancers. Reb D, reb D2, reb M and/or reb M2 can be mixed with umami tasting and sweet amino acids such as glutamate, aspartic acid, glycine, alanine, threonine, proline, serine, glutamate, lysine and tryptophan.

Highly purified target steviol glycoside(s), particularly, reb D, reb D2, reb M can be used in combination with one or more additive selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

Highly purified target steviol glycoside(s), particularly, reb D, reb D2, reb M and/or reb M2 may be combined with polyols or sugar alcohols. The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced which do not adversely affect the taste of the sweetener composition.

Highly purified target steviol glycoside(s), particularly, reb D, reb D2, reb M and/or reb M2 may be combined with reduced calorie sweeteners such as D-tagatose, L-sugars, L-sorbose, L-arabinose, and others.

Highly purified target steviol glycoside(s), particularly, reb D, reb D2, reb M and/or reb M2 may also be combined with various carbohydrates. The term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, Psicose, turanose, allose, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

Highly purified target steviol glycoside(s), particularly, reb D, reb D2, reb M and/or reb M2 obtained according to this invention can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory. Exemplary functional ingredients are provided in WO2013/096420, the contents of which is hereby incorporated by reference.

Highly purified target steviol glycoside(s), particularly, reb D, reb D2, reb M and/or reb M2 obtained according to this invention may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, highly purified target steviol glycoside(s), particularly, reb D, reb D2, reb M and/or reb M2 can be used as a sweetener not only for drinks, foodstuffs, and other products dedicated for human consumption, but also in animal feed and fodder with improved characteristics.

Examples of consumable products in which highly purified target steviol glycoside(s), particularly, reb D, reb D2, reb M and/or reb M2 may be used as a sweetening compound include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others. In principle it can have unlimited applications.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

Moreover, the highly purified target steviol glycoside(s), particularly, reb D, reb D2, reb M and/or reb M2 obtained in this invention may be used in dry or liquid forms. In one embodiment, a tabletop sweetener comprising reb D2 is provided. In another embodiment, a tabletop sweetener comprising reb M2 is provided.

The highly purified target steviol glycoside can be added before or after heat treatment of food products. The amount of the highly purified target steviol glycoside(s), particularly, reb D, reb D2, reb M and/or reb M2 depends on the purpose of usage. As discussed above, it can be added alone or in combination with other compounds.

The present invention is also directed to sweetness enhancement in beverages using reb D2. The present invention is also directed to sweetness enhancement in beverages containing reb M2. Accordingly, the present invention provides a beverage comprising a sweetener and reb D2 and/or reb M2 as a sweetness enhancer, wherein reb D2 and/or reb M2 is present in a concentration at or below their respective sweetness recognition thresholds.

As used herein, the term "sweetness enhancer" refers to a compound capable of enhancing or intensifying the perception of sweet taste in a composition, such as a beverage. The term "sweetness enhancer" is synonymous with the terms "sweet taste potentiator," "sweetness potentiator," "sweetness amplifier," and "sweetness intensifier."

The term "sweetness recognition threshold concentration," as generally used herein, is the lowest known concentration of a sweet compound that is perceivable by the human sense of taste, typically around 1.0% sucrose equivalence (1.0% SE). Generally, the sweetness enhancers may enhance or potentiate the sweet taste of sweeteners without providing any noticeable sweet taste by themselves when present at or below the sweetness recognition threshold concentration of a given sweetness enhancer; however, the sweetness enhancers may themselves provide sweet taste at concentrations above their sweetness recognition threshold concentration. The sweetness recognition threshold concentration is specific for a particular enhancer and can vary based on the beverage matrix. The sweetness recognition threshold concentration can be easily determined by taste testing increasing concentrations of a given enhancer until greater than 1.0% sucrose equivalence in a given beverage matrix is detected. The concentration that provides about 1.0% sucrose equivalence is considered the sweetness recognition threshold.

In some embodiments, sweetener is present in the beverage in an amount from about 0.5% to about 12% by weight, such as, for example, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight, about 9.0% by weight, about 9.5% by weight, about 10.0% by weight, about 10.5% by weight, about 11.0% by weight, about 11.5% by weight or about 12.0% by weight.

In a particular embodiment, the sweetener is present in the beverage in an amount from about 0.5% of about 10%, such as for example, from about 2% to about 8%, from about 3% to about 7% or from about 4% to about 6% by weight. In a particular embodiment, the sweetener is present in the beverage in an amount from about 0.5% to about 8% by weight. In another particular embodiment, the sweetener is present in the beverage in an amount from about 2% to about 8% by weight.

In one embodiment, the sweetener is a traditional caloric sweetener. Suitable sweeteners include, but are not limited to, sucrose, fructose, glucose, high fructose corn syrup and high fructose starch syrup.

In another embodiment, the sweetener is erythritol.

In still another embodiment, the sweetener is a rare sugar. Suitable rare sugars include, but are not limited to, D-allose, D-psicose, L-ribose, D-tagatose, L-glucose, L-fucose, L-arbinose, D-turanose, D-leucrose and combinations thereof.

It is contemplated that a sweetener can be used alone, or in combination with other sweeteners.

In one embodiment, the rare sugar is D-allose. In a more particular embodiment, D-allose is present in the beverage in an amount of about 0.5% to about 10% by weight, such as, for example, from about 2% to about 8%.

In another embodiment, the rare sugar is D-psicose. In a more particular embodiment, D-psicose is present in the beverage in an amount of about 0.5% to about 10% by weight, such as, for example, from about 2% to about 8%.

In still another embodiment, the rare sugar is D-ribose. In a more particular embodiment, D-ribose is present in the beverage in an amount of about 0.5% to about 10% by weight, such as, for example, from about 2% to about 8%.

In yet another embodiment, the rare sugar is D-tagatose. In a more particular embodiment, D-tagatose is present in the beverage in an amount of about 0.5% to about 10% by weight, such as, for example, from about 2% to about 8%.

In a further embodiment, the rare sugar is L-glucose. In a more particular embodiment, L-glucose is present in the beverage in an amount of about 0.5% to about 10% by weight, such as, for example, from about 2% to about 8%.

In one embodiment, the rare sugar is L-fucose. In a more particular embodiment, L-fucose is present in the beverage in an amount of about 0.5% to about 10% by weight, such as, for example, from about 2% to about 8%.

In another embodiment, the rare sugar is L-arabinose. In a more particular embodiment, L-arabinose is present in the beverage in an amount of about 0.5% to about 10% by weight, such as, for example, from about 2% to about 8%.

In yet another embodiment, the rare sugar is D-turanose. In a more particular embodiment, D-turanose is present in the beverage in an amount of about 0.5% to about 10% by weight, such as, for example, from about 2% to about 8%.

In yet another embodiment, the rare sugar is D-leucrose. In a more particular embodiment, D-leucrose is present in the beverage in an amount of about 0.5% to about 10% by weight, such as, for example, from about 2% to about 8%.

The addition of the sweetness enhancer at a concentration at or below its sweetness recognition threshold increases the detected sucrose equivalence of the beverage comprising the sweetener and the sweetness enhancer compared to a corresponding beverage in the absence of the sweetness enhancer. Moreover, sweetness can be increased by an amount more than the detectable sweetness of a solution containing the same concentration of the at least one sweetness enhancer in the absence of any sweetener.

Accordingly, the present invention also provides a method for enhancing the sweetness of a beverage comprising a sweetener comprising providing a beverage comprising a sweetener and adding a sweetness enhancer selected from reb D2, reb M2 or a combination thereof, wherein reb D2 and reb M2 are present in a concentration at or below their sweetness recognition thresholds.

Addition of reb D2 and/or reb M2 in a concentration at or below the sweetness recognition threshold to a beverage containing a sweetener may increase the detected sucrose equivalence from about 1.0% to about 5.0%, such as, for example, about 1.0%, about 1.5%, about 2.0%, about 2.5%, about 3.0%, about 3.5%, about 4.0%, about 4.5% or about 5.0%.

The following examples illustrate preferred embodiments of the invention for the preparation of highly purified target steviol glycoside(s), particularly, reb D, reb D2, reb M and/or reb M2. It will be understood that the invention is not limited to the materials, proportions, conditions and procedures set forth in the examples, which are only illustrative.

Example 1

In-Vivo Production of UGT76G1

NcoI and NdeI restriction sites were added to the original nucleic sequence as described in Genbank accession no. AAR06912.1. After codon optimization the following nucleic sequence was obtained (SEQ ID NO:1):

```
CCATGGCCCATATGGAAAACAAAACCGAAACCACCGTTCGTCGTCGTCGC
CGTATTATTCTGTTTCCGGTTCCGTTTCAGGGTCATATTAATCCGATTCT
GCAGCTGGCAAATGTGCTGTATAGCAAAGGTTTTAGCATTACCATTTTTC
ATACCAATTTTAACAAACCGAAAACCAGCAATTATCCGCATTTTACCTTT
CGCTTTATTCTGGATAATGATCCGCAGGATGAACGCATTAGCAATCTGCC
GACACATGGTCCGCTGGCAGGTATGCGTATTCCGATTATTAACGAACATG
GTGCAGATGAACTGCGTCGTGAACTGGAACTGCTGATGCTGGCAAGCGAA
GAAGATGAAGAAGTTAGCTGTCTGATTACCGATGCACTGTGGTATTTTGC
ACAGAGCGTTGCAGATAGCCTGAATCTGCGTCGTCTGGTTCTGATGACCA
GCAGCCTGTTTAACTTTCATGCACATGTTAGCCTGCCGCAGTTTGATGAA
CTGGGTTATCTGGATCCGGATGATAAAACCCGTCTGGAAGAACAGGCAAG
CGGTTTTCCGATGCTGAAAGTGAAAGATATCAAAAGCGCCTATAGCAATT
GGCAGATTCTGAAAGAAATTCTGGGCAAAATGATTAAACAGACCAAAGCA
AGCAGCGGTGTTATTTGGAATAGCTTTAAAGAACTGGAAGAAAGCGAACT
GGAAACCGTGATTCGTGAAATTCCGGCACCGAGCTTTCTGATTCCGCTGC
CGAAACATCTGACCGCAAGCAGCAGCAGCCTGCTGGATCATGATCGTACC
GTTTTTCAGTGGCTGGATCAGCAGCCTCCGAGCAGCGTTCTGTATGTTAG
CTTTGGTAGCACCAGCGAAGTTGATGAAAAGATTTTCTGGAAATTGCCC
GTGGTCTGGTTGATAGCAAACAGAGCTTTCTGTGGGTTGTTCGTCCGGGT
TTTGTTAAAGGTAGCACCTGGGTTGAACCGCTGCCGGATGGTTTTCTGGG
TGAACGTGGTCGTATTGTTAAATGGGTTCCGCAGCAAGAAGTTCTGGCAC
ACGGCGCAATTGGTGCATTTTGGACCCATAGCGGTTGGAATAGCACCCTG
GAAAGCGTTTGTGAAGGTGTTCCGATGATTTTTAGCGATTTTGGTCTGGA
TCAGCCGCTGAATGCACGTTATATGAGTGATGTTCTGAAAGTGGGTGTGT
ATCTGGAAAATGGTTGGGAACGTGGTGAAATTGCAAATGCAATTCGTCGT
GTTATGGTGGATGAAGAAGGTGAATATATTCGTCAGAATGCCCGTGTTCT
GAAACAGAAAGCAGATGTTAGCCTGATGAAAGGTGGTAGCAGCTATGAAA
GCCTGGAAAGTCTGGTTAGCTATATTAGCAGCCTGTAATAACTCGAG
```

After synthesis of the gene and subcloning into pET30A+ vector using NdeI and XhoI cloning sites, the UGT76G1_pET30a+ plasmid was introduced in *E. coli* Bl21(DE3) and *E. coli* EC100 by electroporation. The obtained cells were grown in petri-dishes in the presence of Kanamycin and suitable colonies were selected and allowed to grow in liquid LB medium (erlenmeyer flasks). Glycerol was added to the suspension as cryoprotectant and 400 μL aliquots were stored at −20° C. and at −80° C.

The storage aliquots of *E. coli* BL21(DE3) containing the pET30A+_UGT76G1 plasmid were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycin). This culture was allowed to shake at 135 rpm at 30° C. for 8 h.

The production medium contained 60 g/L of overnight express instant TB medium (Novagen), 10 g/L of glycerol and 50 mg/L of Kanamycin. The medium was allowed to stir at 20° C. while taking samples to measure the OD and pH. The cultures gave significant growth and a good OD was obtained. After 40 h, the cells were harvested by centrifugation and frozen to yield 12.7 g of cell wet weight.

Lysis was performed by addition of Bugbuster Master mix (Novagen) and the lysate was recovered by centrifugation and kept frozen. Activity tests were performed with thawed lysate.

Example 2

In-Vitro Production of UGT76G1

The S30 T7 High Yield Protein expression system kit from Promega was used. 4 μg of UGT76G1_pET30a+ plasmid from *E. coli* EC100 was mixed with 80 μL of S30 premix plus and 72 μL of S30 T7 extract was added. Nuclease-free water was added in order to obtain a total volume of 200 μL and the resulting solution was incubated for 2 h at 30° C. 180 μL was used in the catalytic test reaction.

Example 3

In-Vitro Production of UGT91D2

NcoI and NdeI restriction sites were added to the original nucleic sequence as described in Genbank accession no. ACE87855.1. After codon optimization the following nucleic sequence was obtained (SEQ ID NO:2):

```
CCATGGCACATATGGCAACCAGCGATAGCATTGTTGATGATCGTAAACAG
CTGCATGTTGCAACCTTTCCGTGGCTGGCATTTGGTCATATTCTGCCGTA
TCTGCAGCTGAGCAAACTGATTGCAGAAAAAGGTCATAAAGTGAGCTTTC
TGAGCACCACCCGTAATATTCAGCGTCTGAGCAGCCATATTAGTCCGCTG
ATTAATGTTGTTCAGCTGACCCTGCCTCGTGTTCAAGAACTGCCGGAAGA
TGCCGAAGCAACCACCGATGTTCATCCGGAAGATATTCCGTATCTGAAAA
AAGCAAGTGATGGTCTGCAGCCGGAAGTTACCCGTTTTCTGGAACAGCAT
AGTCCGGATTGGATCATCTATGATTATACCCATTATTGGCTGCCGAGCAT
```

-continued

```
TGCAGCAAGCCTGGGTATTAGCCGTGCACATTTTAGCGTTACCACCCCGT

GGGCAATTGCATATATGGGTCCGAGCGCAGATGCAATGATTAATGGTAGT

GATGGTCGTACCACCGTTGAAGATCTGACCACCCCTCCGAAATGGTTTCC

GTTTCCGACCAAAGTTTGTTGGCGTAAACATGATCTGGCACGTCTGGTTC

CGTATAAAGCACCGGGTATTAGTGATGGTTATCGTATGGGTCTGGTTCTG

AAAGGTAGCGATTGTCTGCTGAGCAAATGCTATCATGAATTTGGCACCCA

GTGGCTGCCGCTGCTGGAAACCCTGCATCAGGTTCCGGTTGTTCCGGTGG

GTCTGCTGCCTCCGGAAGTTCCGGGTGATGAAAAAGATGAAACCTGGGTT

AGCATCAAAAAATGGCTGGATGGTAAACAGAAAGGTAGCGTGGTTTATGT

TGCACTGGGTAGCGAAGTTCTGGTTAGCCAGACCGAAGTTGTTGAACTGG

CACTGGGTCTGGAACTGAGCGGTCTGCCGTTTGTTTGGGCATATCGTAAA

CCGAAAGGTCCGGCAAAAAGCGATAGCGTTGAACTGCCGGATGGTTTTGT

TGAACGTACCCGTGATCGTGGTCTGGTTTGGACCAGCTGGGCACCTCAGC

TGCGTATTCTGAGCCATGAAAGCGTTTGTGGTTTTCTGACCCATTGTGGT

AGCGGTAGCATTGTGGAAGGTCTGATGTTTGGTCATCCGCTGATTATGCT

GCCGATTTTTGGTGATCAGCCGCTGAATGCACGTCTGCTGGAAGATAAAC

AGGTTGGTATTGAAATTCCGCGTAATGAAGAAGATGGTTGCCTGACCAAA

GAAAGCGTTGCACGTAGCCTGCGTAGCGTTGTTGTTGAAAAAGAAGGCGA

AATCTATAAAGCCAATGCACGTGAACTGAGCAAAATCTATAATGATACCA

AAGTGGAAAAAGAATATGTGAGCCAGTTCGTGGATTATCTGGAAAAAAAC

ACCCGTGCAGTTGCCATTGATCACGAAAGCTAATGACTCGAG
```

After synthesis of the gene and subcloning into pET30A+ vector using NcoI and XhoI cloning sites, the UGT91D2_pET30a+ plasmid was introduced into *E. coli* EC100 by electroporation. The obtained cells were grown in the presence of Kanamycin and suitable colonies were selected and allowed to grow in liquid LB medium (erlenmeyer flasks). Glycerol was added to the suspension as cryoprotectant and 400 µL aliquots were stored at −20° C. and at −80° C.

The S30 T7 High Yield Protein expression system kit from Promega was used for the in-vitro synthesis of the protein.

4 µg of UGT91D2_pET30a+ plasmid was mixed with 80 µL of S30 premix plus and 72 µL of S30 T7 extract was added. Nuclease-free water was added in order to obtain a total volume of 200 µL and the resulting solution was incubated for 2 h at 30° C. 5 µL was used for SDS-page analysis while the remaining 45 µL was used in the catalytic test reaction.

Example 4

Catalytic Reaction with In-Vivo Produced UGT76G1

Figure 51:
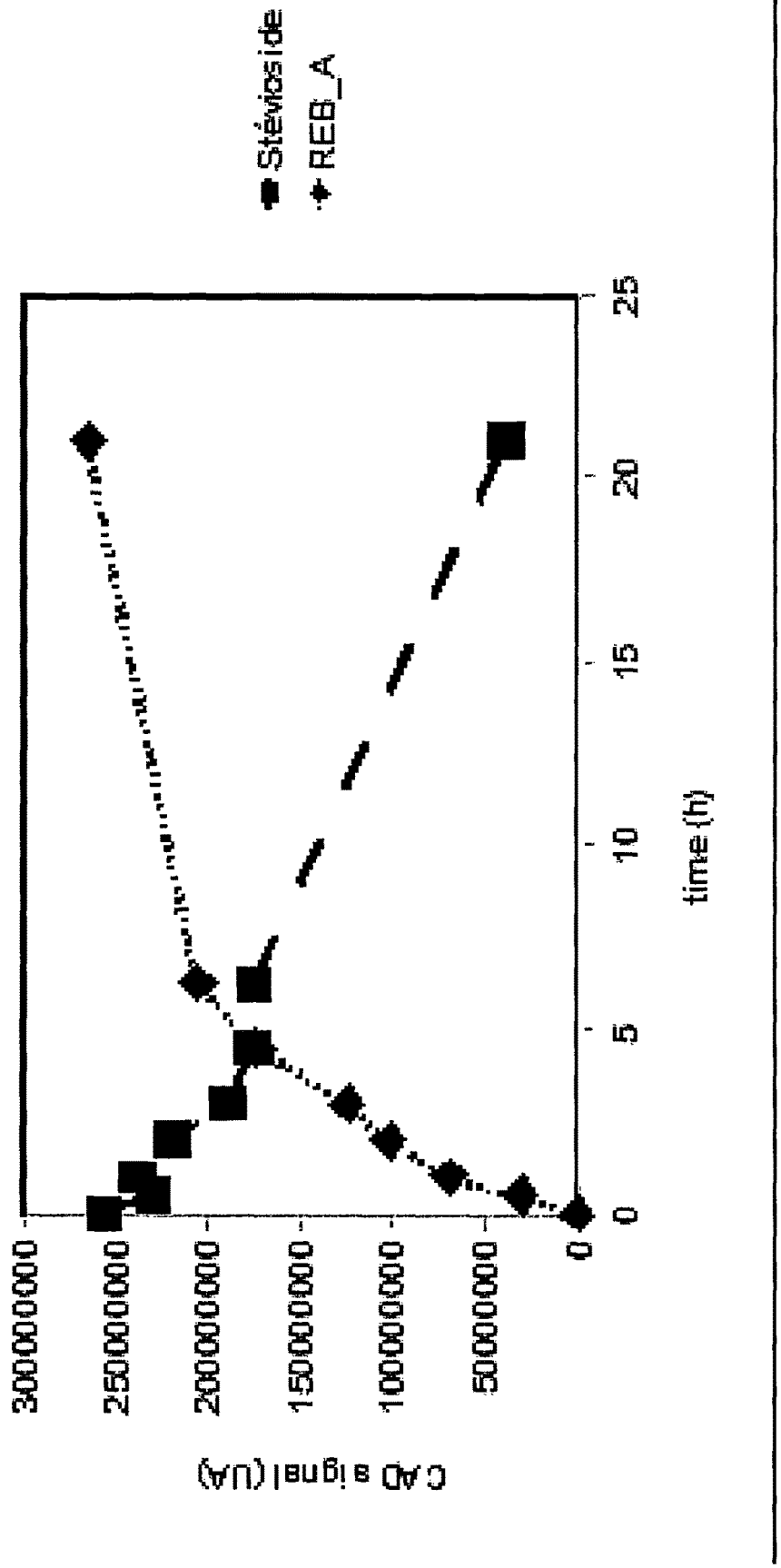
FIG. 51 shows an HPLC (CAD) graph showing conversion of stevioside to rebaudioside A.

The total volume of the reaction was 5.0 mL with the following composition: 50 mM sodium phosphate buffer pH 7.2, 3 mM $MgCl_2$, 2.5 mM UDP-glucose, 0.5 mM Stevioside and 500 µl, of UGT76G1 thawed lysate. The reactions were run at 30° C. on an orbitary shaker at 135 rpm. For each sample, 460 µL of the reaction mixture was quenched with 40 µL of 2N $H_2SO_4$ and 420 µL of methanol/water (6/4). The samples were immediately centrifuged and kept at 10° C. before analysis by HPLC (CAD). HPLC indicated almost complete conversion of stevioside to rebaudioside A, as shown in FIG. 51.

Example 5

Catalytic Reaction with In-Vitro Produced UGT91D2

The total volume of the reaction was 0.5 mL with the following composition: 50 mM sodium phosphate buffer pH 7.2, 3 mM $MgCl_2$, 3.8 mM UDP-glucose, 0.1 mM Rebaudioside A and 180 µL of in-vitro produced UGT91D2. The reactions were run at 30° C. on an orbitary shaker at 135 rpm. For each sample, 450 µl of reaction mixture was quenched with 45 µL of 2N $H_2SO_4$ and 405 µL of 60% MeOH. After centrifugation, the supernatant was analyzed by HPLC (CAD). HPLC indicated a 4.7% conversion of rebaudioside A to rebaudioside D after 120 h.

Example 6

Catalytic Reaction with In-Vitro Produced UGT76G1

Figure 52:
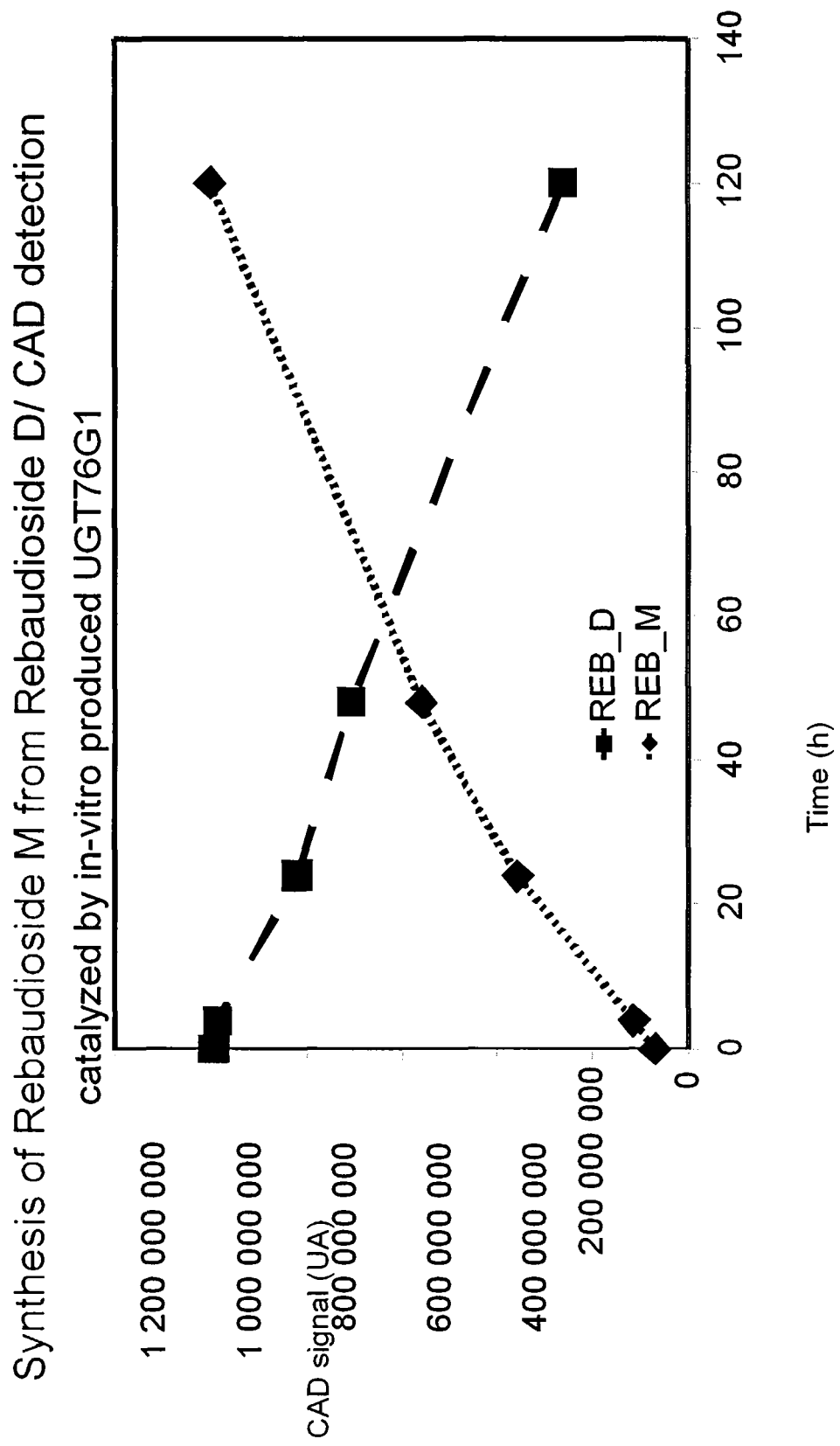
FIG. 52 shows an HPLC (CAD) graph showing conversion of rebaudioside D to rebaudioside M.
Figure 53A:
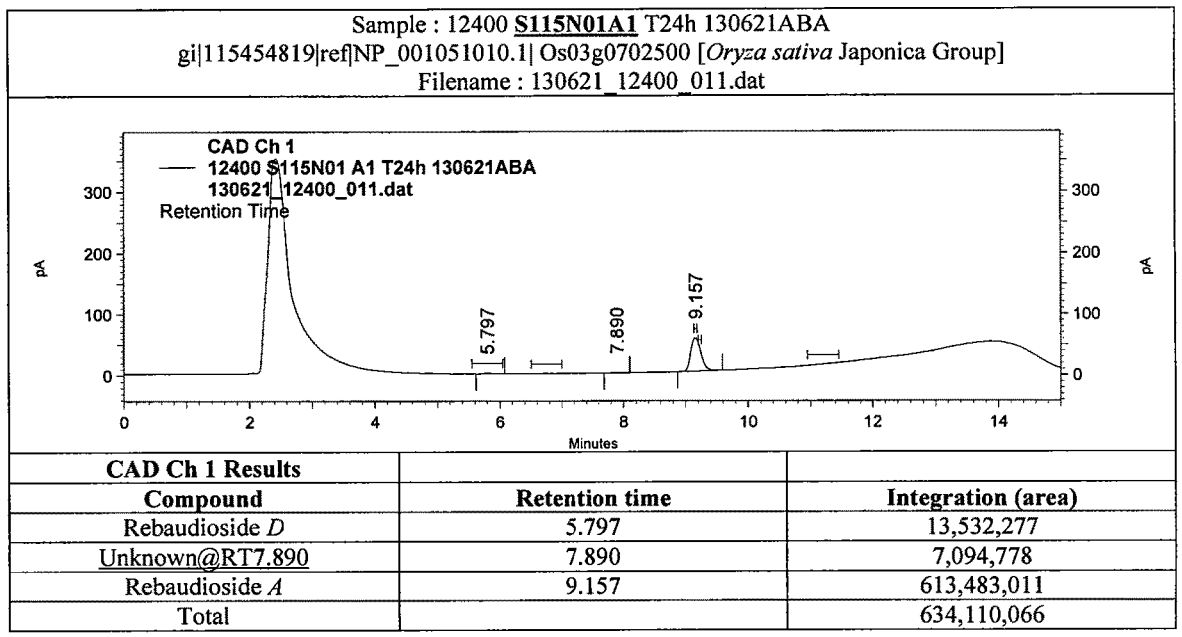
FIG. 53a-e show HPLC chromatograms showing HPLC assay results for Example 20.
Figure 53B:
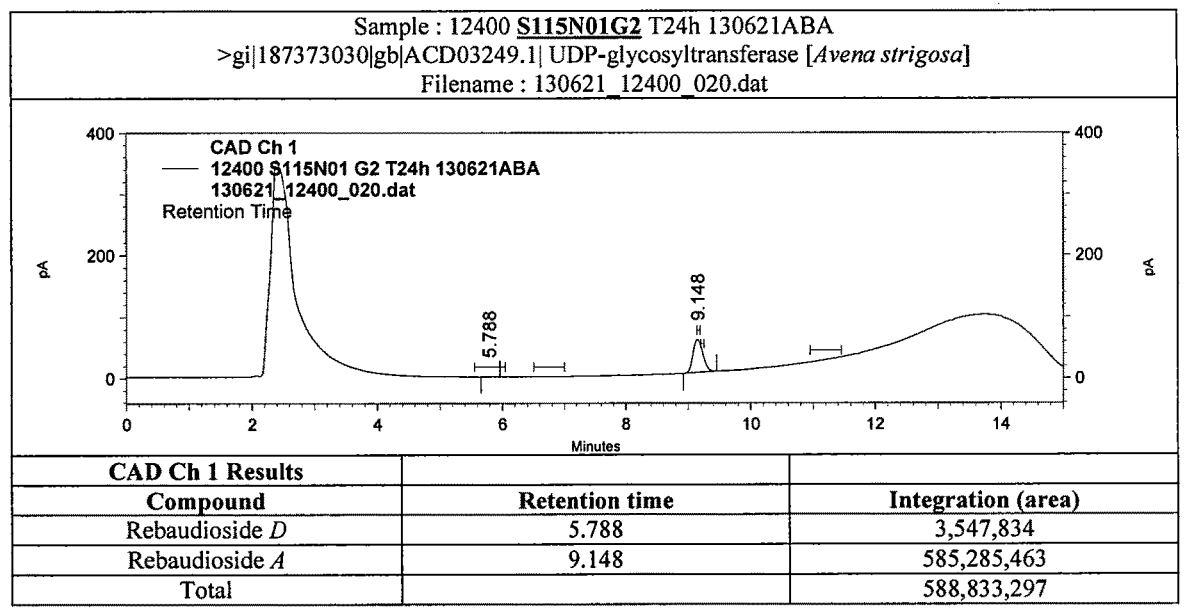
Figure 53C:
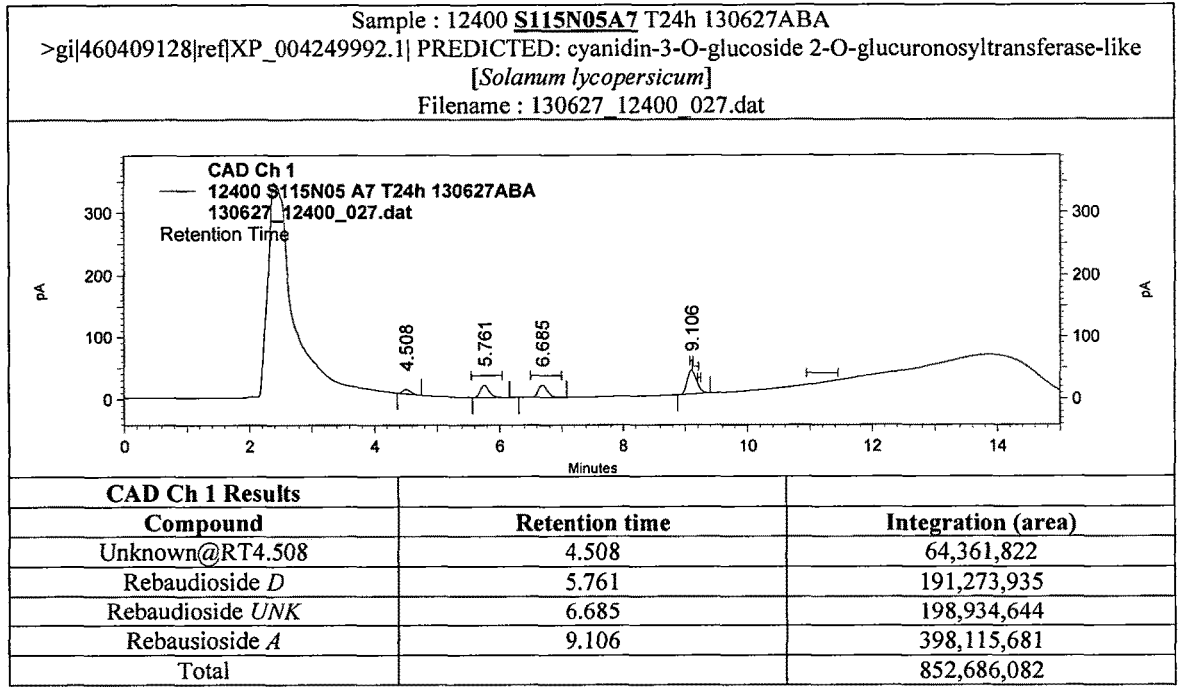
Figure 53D:
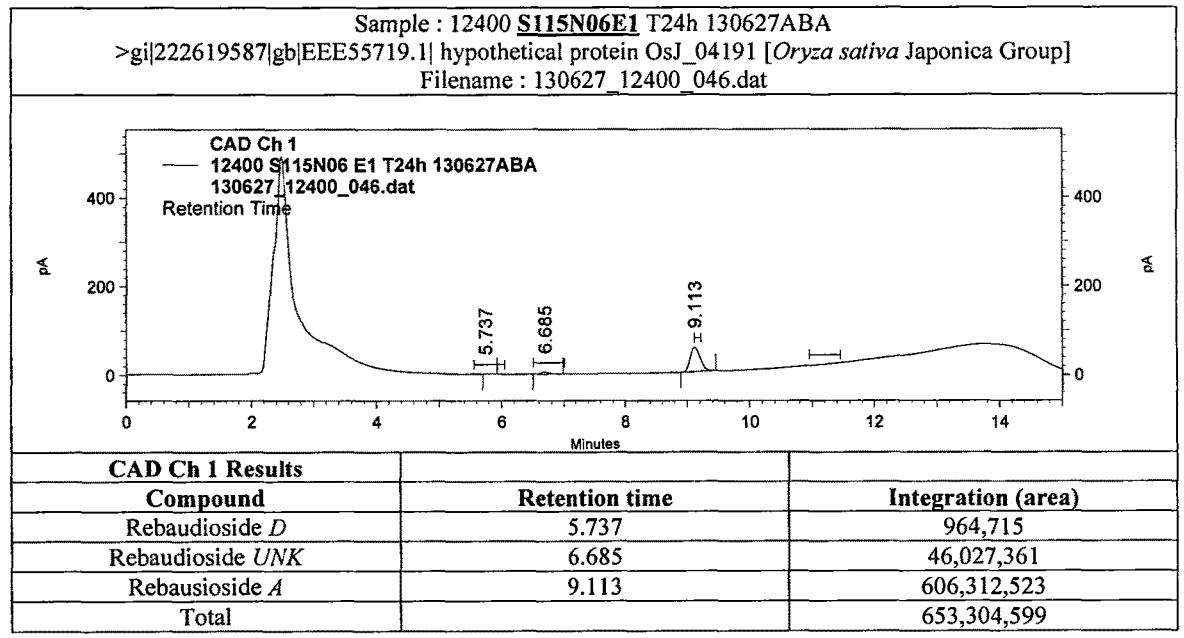
Figure 53E:
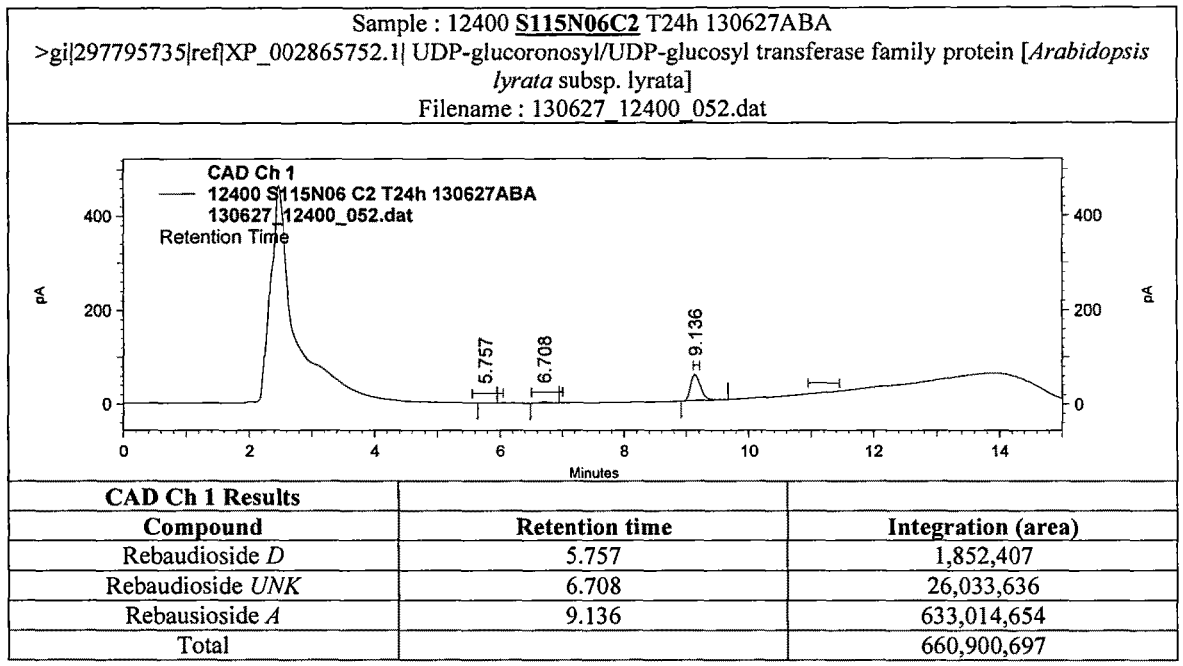

The total volume of the reaction was 2 mL with the following composition: 50 mM sodium phosphate buffer pH 7.2, 3 mM $MgCl_2$, 3.8 mM UDP-glucose, 0.5 mM Rebaudioside D and 180 µL of in-vitro produced UGT76G1. The reactions were run at 30° C. on an orbitary shaker at 135 rpm. For each sample, 400 µL of reaction mixture was quenched with 40 µL of 2N $H_2SO_4$ and 360 µL of 60% MeOH. After centrifugation, the supernatant was analyzed by HPLC (CAD). HPLC indicated 80% conversion of rebaudioside D to rebaudioside M after 120 h as shown in FIG. 52.

For examples 7 to 12, the following abbreviations were used:

LBGKP medium: 20 g/L Luria Broth Lennox; 50 mM PIPES buffer pH 7.00; 50 mM Phosphate buffer pH 7.00; 2.5 g/L glucose and 50 mg/L of Kanamycin or Ampicillin LB medium: (20 g/L Luria Broth Lennox)

Example 7

Preparation and Activity of UGT76G1 Prepared by pET30a+ Plasmid and BL21 (DE3) Expression Strain The pET30a+_UGT76G1 plasmid was transformed into BL21(DE3) expression strain (Lucigen E. Cloni® EXPRESS Electrocompetent Cells). The obtained cells were grown on LB Agar medium in petri-dishes in the presence of Kanamycin. Suitable colonies were selected and allowed to grow in liquid LBGKP medium containing Kanamycin. Glycerol was added and 400 µL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 20° C. while taking samples to measure the OD (600 nm) and pH. After 40 h, the cells were harvested by centrifugation and frozen. The obtained cell wet weight was 10.58 g.

3.24 g of obtained pellet was lysed by addition of 8.1 mL of "Bugbuster Master mix" (Novagen, reference 71456) and 3.5 mL of water. The lysate was recovered by centrifugation and kept frozen.

Example 8

Preparation and Activity of UGT76G1 Prepared by pET30a+ Plasmid and Tuner (DE3) Expression Strain The pET30a+_UGT76G1 plasmid was transformed into Tuner (DE3) expression strain (Novagen Tune™ (DE3)

Competent cells) by heat shock treatment. The obtained cells were grown on LB Agar medium in petri-dishes in the presence of Kanamycin. Suitable colonies were selected and allowed to grow in liquid LBGKP medium containing Kanamycin). Glycerol was added and 400 μL aliquots were stored at −20° C. and at −80° C.

A storage aliquot was thawed and added to 100 mL of LB medium containing 50 mg/L of Kanamycin. This culture allowed to shake at 30° C. for 15 h. 4.4 mL of this culture was used to inoculate 200 mL of production medium containing LB. This medium was allowed to stir at 37° C. until an OD (600 nm) of 0.9 was obtained, after which 400 μL of a 100 mM IPTG solution was added and the medium was allowed to stir at 30° C. for 4 h. The cells were harvested by centrifugation and frozen. The obtained cell wet weight was 1.38 g.

The obtained pellet was lysed by addition of 4.9 mL of "Bugbuster Master mix" (Novagen, reference 71456) and 2.1 mL of water. The lysate was recovered by centrifugation and kept frozen.

Example 9

Preparation and Activity of UGT76G1 Prepared by pMAL Plasmid and BL21 Expression Strain After subcloning the synthetic UGT76G1 gene into the pMAL plasmid using NdeI and Sal1 cloning sites, the pMAL_UGT76G1 plasmid was transformed into BL21 expression strain (New England Biolabs BL21 Competent E. coli) by heat shock treatment. The obtained cells were grown on LB Agar medium in petri-dishes in the presence of Ampicillin. Suitable colonies were selected and allowed to grow in liquid LBGKP medium containing Ampicillin). Glycerol was added and 400 μL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. while taking samples to measure the OD and pH. After 40 h, the cells were harvested by centrifugation and frozen. The obtained cell wet weight was 5.86 g.

2.74 g of obtained pellet was lysed by addition of 9.6 mL of "Bugbuster Master Mix" (Novagen, reference 71456) and 4.1 mL of water. The lysate was recovered by centrifugation and kept frozen.

Example 10

Preparation and Activity of UGT76G1 Prepared by pMAL Plasmid and ArcticExpress Expression Strain The pMAL_UGT76G1 plasmid was transformed into ArticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing of Ampicillin and Geneticin. Glycerol was added and 400 μL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 12° C. while taking samples to measure the OD (600 nm) and pH. After 68 h, the cells were harvested by centrifugation and frozen. The obtained cell wet weight was 8.96 g.

2.47 g of the obtained pellet was lysed by addition of 8.73 mL of "Bugbuster Master Mix" (Novagen, reference 71456) and 3.79 mL of water. The lysate was recovered by centrifugation and kept frozen.

Example 11

Preparation and Activity of UGT76G1 Prepared by pCOLDIII Plasmid and ArcticExpress Expression Strain After subcloning the synthetic UGT76G1 gene into the pCOLDIII plasmid using NdeI and XhoI cloning sites, the pCOLDIII_UGT76G1 plasmid was transformed into ArcticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing Ampicillin and Geneticin. Glycerol was added and 400 μL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 12° C. while taking samples to measure the OD (600 nm) and pH. After 63 h, the cells were harvested by centrifugation and frozen. The obtained cell wet weight was 6.54 g.

2.81 g of the obtained pellet was lysed by addition of 9.8 mL of "Bugbuster Master Mix" (Novagen, reference 71456) and 4.2 mL of water. The lysate was recovered by centrifugation and kept frozen.

Example 12

Preparation and Activity of UGT76G1 Prepared by pCOLDIII Plasmid and Origami2 (DE3) Expression Strain The pCOLDIII_UGT76G1 plasmid was transformed into Origami2 (DE3) expression strain (Novagen Origami™2 (DE3) Competent Cells) by heat shock treatment. The obtained cells were grown on LB Agar medium in petri-dishes in the presence of Ampicillin. Suitable colonies were selected and allowed to grow in liquid LBGKP medium containing Ampicillin. Glycerol was added and 400 μL aliquots were stored at −20° C. and at −80° C.

A storage aliquot was thawed and added to 30 mL of LBGKP medium (containing Ampicillin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 12° C. while taking samples to measure the OD (600 nm) and pH. After 68 h, the cells were harvested by centrifugation and frozen. The obtained cell wet weight was 2.53 g.

1.71 g of the obtained pellet was lysed by addition of 6.0 mL of "Bugbuster Master mix" (Novagen, reference 71456) and 1.9 mL of water. The lysate was recovered by centrifugation and kept frozen.

Example 13

Determination of Activity

Activity tests were performed on a 5 mL scale with 500 µL of thawed lysate for the transformation of Stevioside to Rebaudioside A and Rebaudioside D to Rebaudioside M using 0.5 mM of substrate, 2.5 mM of UDP-Glucose and 3 mM $MgCl_2$ in 50 mM Sodium Phosphate buffer at pH 7.2. Samples were taken and analyzed by HPLC. The results for the different preparations of UGT76G1 are summarized in the following table.

|  |  |  | Transformation activity* | |
| --- | --- | --- | --- | --- |
| Example | Plasmid | Expression strain | Stevioside to Rebaudioside A | Rebaudioside D to Rebaudioside M |
| 7 | pET30a+ | BL21 (DE3) | 29 U mL$^{-1}$ | 0.31 U mL$^{-1}$ |
| 8 | pET30a+ | Tuner (DE3) | 33 U mL$^{-1}$ | 0.40 U mL$^{-1}$ |
| 9 | pMAL | BL21 | 20 U mL$^{-1}$ | 0.15 U mL$^{-1}$ |
| 10 | pMAL | ArcticExpress | 15 U mL$^{-1}$ | 0.25 U mL$^{-1}$ |
| 11 | pCOLDIII | ArcticExpress | 15 U mL$^{-1}$ | 0.11 U mL$^{-1}$ |
| 12 | pCOLDIII | Origami2 (DE3) | 37 U mL$^{-1}$ | 0.20 U mL$^{-1}$ |

*Note
The activities for the transformation of Stevioside and Rebaudioside M are mentioned per mL of lysate. 1 U will transform 1 µmol of substance in 1 hour at 30° C. and pH 7.2

Example 14

50 mL Scale Reaction for the Transformation of Rebaudioside D to Rebaudioside M 5 mL of the lysate of Example 12 was used to transform Rebaudioside D to Rebaudioside M on a 50 mL scale. The reaction medium consisted of 50 mM Sodium Phosphate buffer pH 7.2, 3 mM of $MgCl_2$, 2.5 mM of UDP-Glucose and 0.5 mM of Rebaudioside D. After allowing the reaction to be shaken at 30° C. for 90 h. 50 mL of ethanol was added and the resulting mixture was allowed to stir at −20° C. for 1 h. After centrifugation at 5000 g for 10 min. the supernatant was purified via ultrafiltration (Vivaflow MWCO 30000). 78 mL of permeate was obtained and the 9 mL of retentate was diluted with 9 mL of ethanol and resubjected to Ultrafiltration (Vivaflow MWCO 30000). Another 14 mL of filtrate was obtained, which was combined with the first permeate. The combined permeates were concentrated under reduced pressure at 30° C. until 32 mL of a clear solution was obtained.

Figure 5:
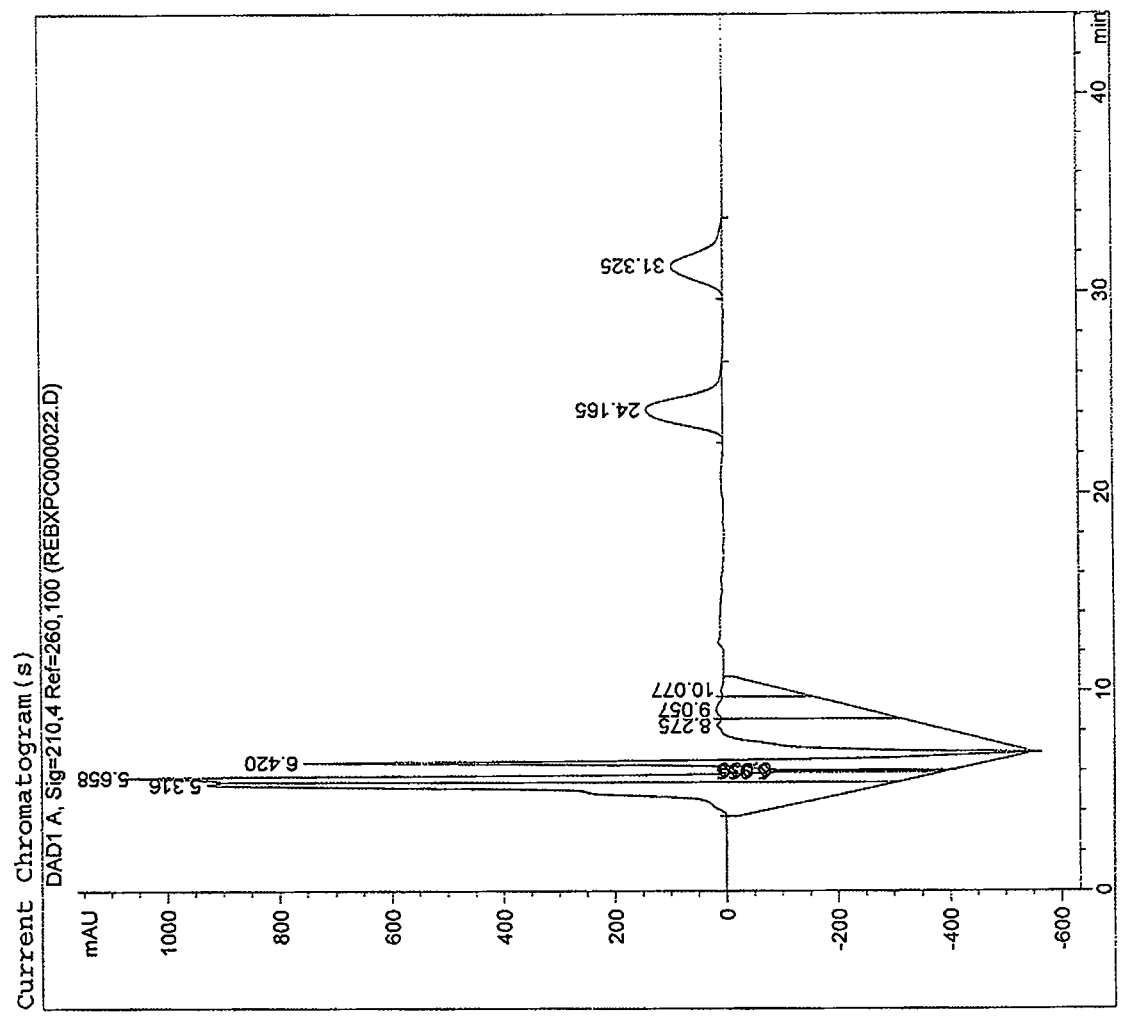
FIG. 5. shows the HPLC chromatogram of the product of the biocatalytic production of reb M from reb D, as detailed in Example 14. The peak with retention time of 24.165 minutes corresponds to unreacted reb D. The peak with retention time of 31.325 minutes corresponds to reb M.

The HPLC trace of the product mixture is shown in FIG. 5. HPLC was carried out on an Agilent 1200 series equipped with a binary pump, auto sampler, and thermostat column compartment. The method was isocratic, with a mobile phase composed of 70% water (0.1% formic acid): 30% acetonitrile. The flow rate was 0.1 µL/min. The column used was Phenomenex Prodigy 5µ ODS (3) 100 A; 250×2 mm. The column temperature was maintained at 40° C. The injection volume was 20-40 µl.

Example 15

Preparation of UGT91D2 Using pMAL Plasmid and BL21 Expression Strain

After subcloning the synthetic UGT91D2 gene into the pMAL plasmid using NdeI and Sal1 cloning sites, the pMAL_UGT91D2 plasmid was transformed into BL21 expression strain (New England Biolabs BL21 Competent *E. coli*) by heat shock treatment. The obtained cells were grown on LB Agar medium in petri-dishes in the presence of Ampicillin. Suitable colonies were selected and allowed to grow in liquid LBGKP medium containing Ampicillin). Glycerol was added and 400 µL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. while taking samples to measure the OD and pH. After 40 h, the cells were harvested by centrifugation and frozen. The obtained cell wet weight is 12.32 g.

2.18 g of obtained pellet was lysed by addition of 7.7 mL of "Bugbuster Master Mix" (Novagen, reference 71456) and 3.2 mL of water. The lysate was recovered by centrifugation and used directly for activity testing.

Example 16

Preparation of UGT91D2 Using pMAL Plasmid and ArcticExpress Expression Strain

The pMAL_UGT91D2 plasmid was transformed into ArcticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing Ampicillin and Geneticin. Glycerol was added and 400 µL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. for 16 h. followed by another 50 h. at 12° C. while taking samples to measure the OD (600 nm) and pH. The cells were harvested by centrifugation and frozen. The obtained cell wet weight is 15.77 g.

2.57 g of the obtained pellet was lysed by addition of 9.0 mL of "Bugbuster Master Mix" (Novagen, reference 71456) and 3.8 mL of water. The lysate was recovered by centrifugation and used directly for activity testing.

Example 17

Preparation of UGT91D2 Using pET30a+ Plasmid and Tuner (DE3) Expression Strain

The pET30a+_UGT91D2 plasmid was transformed into Tuner (DE3) expression strain (Novagen Tuner™ (DE3) Competent cells) by heat shock treatment. The obtained cells were grown on LB Agar medium in petri-dishes in the presence of Kanamycin. Suitable colonies were selected and allowed to grow in liquid LBGKP medium (containing Kanamycin). Glycerol was added and 400 µL aliquots were stored at −20° C. and at −80° C.

A storage aliquot was thawed and added to 100 mL of LB medium containing 50 mg/L of Kanamycin. This culture allowed to shake at 30° C. for 15 h. 6.2 mL of this culture was used to inoculate 500 mL of production medium containing LB. This medium was allowed to stir at 37° C. until an OD (600 nm) of 0.9 was obtained after which 500 µL of a 100 mM IPTG solution was added (IPTG concentration in medium is 100 µM) and the medium was allowed to stir at 30° C. for 4 h, the cells were harvested by centrifugation and frozen. The obtained cell wet weight is 4.02 g.

1.92 g of the obtained pellet was lysed by addition of 6.8 mL of "Bugbuster Master mix" (Novagen, reference 71456) and 2.8 mL of water. The lysate was recovered by centrifugation and tested directly for activity.

Example 18

Preparation of UGT91D2 Using pET30a+ Plasmid and ArcticExpress Expression Strain The pET30a+_UGT91D2 plasmid was transformed into ArcticExpress (DE3) expression strain (Agilent ArcticExpress competent cells) by heat shock treatment. The obtained cells were grown on LB Agar medium in petri-dishes in the presence of Kanamycin and Geneticin. Suitable colonies were selected and allowed to grow in liquid LBGKP medium containing of Kanamycin and Geneticin. Glycerol was added and 400 µL aliquots were stored at −20° C. and at −80° C.

A storage aliquot was thawed and added to 30 mL of LBGKP medium (containing Kanamycin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. for 16 h. followed by another 50 h. at 12° C. while taking samples to measure the OD (600 nm) and pH. After 60 h, the cells were harvested by centrifugation and frozen. The obtained cell wet weight is 16.07 g.

3.24 g of the obtained pellet was lysed by addition of 11.4 mL of "Bugbuster Master Mix" (Novagen, reference 71456) and 4.8 mL of water. The lysate was recovered by centrifugation and used directly for activity testing.

Example 19

Determination of Activity of In-Vivo Preparations of UGT91D2

Activity tests were performed at 5 mL scale with 1000 µL of lysate for the transformation of Rubusoside to Stevioside using 0.5 mM of substrate, 2.5 mM of UDP-Glucose and 3 mM $MgCl_2$ in 50 mM Sodium Phosphate buffer at pH 7.2. Samples were taken and analyzed by HPLC. The results for the different preparations of UGT91D2 are summarized in the following table.

| Example | Plasmid | Expression strain | Transformation activity* Rubusoside to Stevioside |
|---|---|---|---|
| 15 | pMAL | BL21 | 9 mU mL$^{-1}$ |
| 16 | pMAL | ArcticExpress | 60 mU mL$^{-1}$ |
| 17 | pET30a+ | Tuner (DE3) | 28 mU mL$^{-1}$ |
| 18 | pET30a+ | ArcticExpress (DE3) | 21 mU mL$^{-1}$ |

*Note:
The activities are mentioned per mL of lysate. 1 U will transform 1 µmol of substrate in 1 hour at 30° C. and pH 7.2

Example 20

Other Enzymes for Rebaudioside A to Rebaudioside D Conversion

The following genes of UDP-glucosyltransferases were identified from public databases, synthesized by DNA2.0 and subsequently subcloned in pET30a+ vector.

| Microplate | Position | Gene Name | Internal reference | Conversion RebA to RebD |
|---|---|---|---|---|
| C908201 | A1 | gi115454819_NP_001051010.1 | S115N01 A1 | Active |
| C908201 | G2 | gi187373030_ACD03249.1 | S115N01 G2 | Active |
| C908201 | A7 | gi460409128_XP_004249992.1 | S115N05 A7 | Active |
| C912666 | E1 | gi222619587_EEE55719.1 | S115N06 E1 | Active |
| C912666 | C2 | gi297795735_XP_002865752.1 | S115N06 C2 | Active |

The aminoacid sequences are as follows:

\>gi|115454819|ref|NP_001051010.1|Os03g0702500 [*Oryza sativa* Japonica Group]

SEQ ID NO:3:

MDDAHSSQSPLHVVIFPWLAFGHLLPCLDLAERLAARGHRVSFVSTPRNL

ARLPPVRPELAELVDLVALPLPRVDGLPDGAEATSDVPFDKFELHRKAFD

GLAAPFSAFLDTACAGGKRPDWVLADLMHHWVALASQERGVPCAMILPCS

AAVVASSAPPTESSADQREAIVRSMGTAAPSFEAKRATEEFATEGASGVS

IMTRYSLTLQRSKLVAMRSCPELEPGAFTILTRFYGKPVVPFGLLPPRPD

GARGVSKNGKHDAIMQWLDAQPAKSVVYVALGSEAPMSADLLRELAHGLD

LAGTRFLWAMRKPAGVDADSVLPAGFLGRTGERGLVTTRWAPQVSILAHA

AVCAFLTHCGWGSVVEGLQFGHPLIMLPILGDQGPNARILEGRKLGVAVP

RNDEDGSFDRGGVAGAVRAVVVEEEGKTFFANARKLQEIVADREREERCI

DEFVQHLTSWNELKNNSDGQYP

\>gi|187373030|gb|ACD03249.1|UDP-glycosyltransferase [*Avena strigosa*]

SEQ ID NO:4:

MAVKDEQQSPLHILLFPFLAPGHLIPIADMAALFASRGVRCTILTTPVNA

AIIRSAVDRANDAFRGSDCPAIDISVVPFPDVGLPPGVENGNALTSPADR

LKFFQAVAELREPFDRFLADNHPDAVVSDSFFHWSTDAAAEHGVPRLGFL

GSSMFAGSCNESTLHNNPLETAADDPDALVSLPGLPHRVELRRSQMMDPK

KRPDHWALLESVNAADQKSFGEVFNSFHELEPDYVEHYQTTLGRRTWLVG

PVALASKDMAGRGSTSARSPDADSCLRWLDTKQPGSVVYVSFGTLIRFSP

AELHELARGLDLSGKNFVWVLGRAGPDSSEWMPQGFADLITPRGDRGFII

RGWAPQMLILNHRALGGFVTHCGWNSTLESVSAGVPMVTWPRFADQFQNE

KLIVEVLKVGVSIGAKDYGSGIENHDVIRGEVIAESIGKLMGSSEESDAI

QRKAKDLGAEARSAVENGGSSYNDVGRLMDELMARRSSVKVGEDIIPTND

GL

>gi|460409128|ref|XP_004249992.1| PREDICTED: cyanidin-3-O-glucoside 2-O-glucuronosyltransferase-like [*Solanum lycopersicum*]
SEQ ID NO:5:

MSPKLHKELFFHSLYKKTRSNHTMATLKVLMFPFLAYGHISPYLNVAKKL

ADRGFLIYFCSTPINLKSTIEKIPEKYADSIHLIELHLPELPQLPPHYHT

TNGLPPNLNQVLQKALKMSKPNFSKILQNLKPDLVIYDILQRWAKHVANE

QNIPAVKLLTSGAAVFSYFFNVLKKPGVEFPFPGIYLRKIEQVRLSEMMS

KSDKEKELEDDDDDDLLVDGNMQIMLMSTSRTIEAKYIDFCTALTNWKV

VPVGPPVQDLITNDVDDMELIDWLGTKDENSTVFVSFGSEYFLSKEDMEE

VAFALELSNVNFIWVARFPKGEERNLEDALPKGFLERIGERGRVLDKFAP

QPRILNHPSTGGFISHCGWNSAMESIDFGVPIIAMPMHLDQPMNARLIVE

LGVAVEIVRDDDGKIHRGEIAETLKGVITGKTGEKLRAKVRDISKNLKTI

RDEEMDAAAEELIQLCRNGN

>gi|222619587|gb|EEE55719.1| hypothetical protein OsJ_04191 [*Oryza sativa* Japonica Group]
SEQ ID NO:6:

MHVVMLPWLAFGHILPFAEFAKRVARQGHRVTLFSTPRNTRRLIDVPPSL

AGRIRVVDIPLPRVEHLPEHAEATIDLPSNDLRPYLRRAYDEAFSRELSR

LLQETGPSRPDWVLADYAAYWAPAAASRHGVPCAFLSLFGAAALCFFGPA

ETLQGRGPYAKTEPAHLTAVPEYVPFPTTVAFRGNEARELFKPSLIPDES

GVSESYRFSQSIEGCQLVAVRSNQEFEPEWLELLGELYQKPVIPIGMFPP

PPPQDVAGHEETLRWLDRQEPNSVVYAAFGSEVKLTAEQLQRIALGLEAS

ELPFIWAFRAPPDAGDGDGLPGGFKERVNGRGVVCRGWVPQVKFLAHASV

GGFLTHAGWNSIAEGLANGVRLVLLPLMFEQGLNARQLAEKKVAVEVARD

EDDGSFAANDIVDALRRVMVGEEGDEFGVKVKELAKVFGDDEVNDRYVRD

FLKCLSEYKMQRQG

>gi|297795735|ref|XP_002865752.1| UDP-glucoronosyl/UDP-glucosyl transferase family protein [*Arabidopsis lyrata* subsp. *lyrata*]
SEQ ID NO:7:

MDDKKEEVMHIAMFPWLAMGHLLPFLRLSKLLAQKGHKISFISTPRNILR

LPKLPSNLSSSITFVSFPLPSISGLPPSSESSMDVPYNKQQSLKAAFDLL

QPPLTEFLRLSSPDWIIYDYASHWLPSIAKELGISKAFFSLFNAATLCFM

GPSSSLIEESRSTPEDFTVVPPWVPFKSTIVFRYHEVSRYVEKTDEDVTG

VSDSVRFGYTIDGSDAVFVRSCPEFEPEWFSLLQDLYRKPVFPIGFLPPV

IEDDDDDTTWVRIKEWLDKQRVNSVVYVSLGTEASLRREELTELALGLEK

SETPFFWVLRNEPQIPDGFEERVKGRGMVHVGWVPQVKILSHESVGGFLT

HCGWNSVVEGIGFGKVPIFLPVLNEQGLNTRLLQGKGLGVEVLRDERDGS

FGSDSVADSVRLVMIDDAGEEIREKVKLMKGLFGNMDENIRYVDELVGFM

RNDESSQLKEEEEEDDCSDDQSSEVSSETDEKELNLDLKEEKRRISVYKS

LSSEFDDYVANEKMG

The tested plasmids were received in a microtiterplate containing a plasmid as freeze-dried solid in each separate well.

Suspension of Plasmids.

To each well was added 24 µL of ultra-pure sterile water and the microtiter plate was shaken for 30 minutes at Room Temperature. Subsequently, the plate was incubated at 4° C. for 1 hour. The content of each well were further mixed by pipetting up and down. The plasmid quantification was performed by Qubit2.0 analysis using 1 µL of suspension. Determined quantities of plasmids were:

| Microtiter plate | Position | Internal reference | [Plasmid] ng/µL |
|---|---|---|---|
| C908201 | A1 | S115N01 A1 | 32.8 |
| C908201 | G2 | S115N01 G2 | 41.0 |
| C908201 | A7 | S115N05 A7 | 56.6 |
| C912666 | E1 | S115N06 E1 | 64.0 |
| C912666 | C2 | S115N06 C2 | 31.4 |

Transformation of Competent Cells with Plasmids.

Aliquots of chemically competent EC100 cells were taken from freezer at −80° C. and stored on ice. The cells were allowed to thaw on ice for 10 minutes. 10 µL of a dilution of above described plasmid solution was added to a sterile microtube of 1.5 mL (in order to transform each cell with 50 pg of DNA) and stored on ice. 100 µL of chemically competent cells was added to each microtube. After incubation of the chemically competent cells plasmid mixtures on ice for 20 min a thermal shock of 30 seconds at 42° C. was performed.

Further incubation was performed on ice for 2 minutes. To each microtube 300 µL of SOC medium was added and the resulting mixture was transferred to a sterile 15 mL tube. After incubate for 1 hour at 37° C. while shaking at 135 rpm, the mixture is spread on solid Luria Broth medium containing Kanamycin 50 µg/mL. The petri-dishes are allowed to incubate for 16 hours at 37° C.

Preparation of Stock Solutions in Glycerol and Purification of Plasmids.

To a 50 mL sterile Falcon Tube 10 mL of Luria Broth medium containing 50 µg/mL of Kanamycin was added. The medium was seeded with an isolated colony from the above described Petri dish and the cultures were allowed to incubate for 16 hours at 37° C. while shaking at 135 rpm.

To sterile microtube of 1.5 mL containing 300 µL of a 60% sterile glycerol solution, 600 µL of the culture was added. The stock solution was stored at −80° C.

The remainder of the culture was centrifuged at 5,525 g for 10 minutes at 10° C. and after removal of the supernatant, the pellet was stored on ice. The produced plasmids were purified according to the Qiagen Qiaprep Spin Miniprep kit (ref: 27106) and the plasmid yield was measured at 260 nm. The plasmid solution was stored at 4° C. Plasmid quantities were determined as follows:

| Microtiter plate | Position | Internal reference of test | [Plasmid] ng/µL |
|---|---|---|---|
| C908201 | A1 | S115N01 A1 | 115.7 |
| C908201 | G2 | S115N01 G2 | 120.4 |
| C908201 | A7 | S115N05 A7 | 293.8 |
| C912666 | E1 | S115N06 E1 | 126.1 |
| C912666 | C2 | S115N06 C2 | 98.8 |

In-Vitro Expression of Enzymes.

18 µL of plasmid solution (containing approximately 1.5 µg of plasmid) was used for in-vitro expression according to the Promega S30 T7 High-Yield Protein Expression System (ref: L1110) kit. The expression medium was produced as follows:

|  | S30 Premix Plus | T7 S30 Extract | Total |
|---|---|---|---|
| Trials | 30 µL | 27 µL | 57 µL |
| reference | 20 µL | 18 µL | 38 µL |

The prepared expression medium mix was added to the plasmid solution and the solution was allowed to incubate at 30° C. for 3 hours while mixing the mixture every 45 minutes. 5 µL of the mixture was frozen whereas the remainder was used for the catalytic test for the conversion of Rebaudioside A to Rebaudioside D.

Catalytic Test for Transformation of Rebaudioside A to Rebaudioside D.

430 µL of a reaction mixture containing 0.5 mM Rebaudioside A, 3 mM $MgCl_2$, 50 mM phosphate buffer (pH7.2) and 2.5 mM UDP-glucose was added to a 1.5 mL sterile microtube. 52 µl of the enzyme expression medium was added and the resulting mixture was allowed to react at 30° C. for 24 hours. 125 µL samples were taken after 2 hours, 16 hours and 24 hours and added to a 115 µL of 60% methanol and 10 µL of 2 N $H_2SO_4$. The quenched sample was centrifuged at 18,000 g for 2 minutes at RT. 200 µL was transferred to an HPLC vial and analyzed.

HPLC Analysis

The HPLC assay was performed as follows:

Apparatus

| Equipment | Supplier | Reference | Lot# |
|---|---|---|---|
| Elite | Hitachi | L-2130 | NA |
| Photodiode Array | Hitachi | L-2455 | NA |
| Corona CAD detector | ESA | 70-6186A | CO-2044 |
| Injector 100 µL | Hitachi |  | NA |
| Column Synergy 4 u Hydro-RP 80A (250 × 4.60 mm) | Phenomenex | 00G-4375-E0 | 588582-12 |

Instrument Conditions

| Column Temperature | 55° C. |
| Detection | UV 205 nm; bw 400 nm CAD detection |
| Analysis duration | 15 min |
| Injected volume | 10 µL |
| Flow rate | 1 mL/min |

Mobile Phase Gradient Program

| Time (min) | % Water containing 0.04% acetic acid | % methanol |
|---|---|---|
| 0 | 40 | 60 |
| 8 | 25 | 75 |
| 10 | 25 | 75 |
| 11 | 40 | 60 |
| 15 | 40 | 60 |

The HPLC assay results are provided below and shown in FIGS. 53a-e:

| Internal reference | Steviol glycoside conversion in reaction mixture (% area) | | |
|---|---|---|---|
|  | Reb D | Reb UNK | Reb A |
| S115N01 A1 | 2.1 | ND | 96.7 |
| S115N01 G2 | 0.6 | ND | 99.4 |
| S115N05 A7 | 22.4 | 23.3 | 46.7 |
| S115N06 E1 | 0.14 | 7.0 | 92.8 |
| S115N06 C2 | 0.28 | 3.9 | 95.8 |

The enzyme S115N05 A7 had the highest activity for Reb A to Reb D conversion (ca. 22.4%)

At least three enzymes produced a significant amount of an unknown glycoside (marked as Reb UNK; later identified as reb D2) along with reb D.

Example 21

Activity of In-Vitro Produced EUGT11

EUGT11 gene as was described in the Patent application WO/2013/022989A2 was synthesized by DNA2.0 and subsequently subcloned in pET30a+ vector.

| Microplate | Position | GI number | Version | Internal reference | Conversion RebA to RebD |
|---|---|---|---|---|---|
| C912666 | G4 | 41469452 | AAS07253.1 | S115N08 G4 | Active |

The amino-acid sequence is as follows:
>gi|41469452|gb|AAS07253.1| putative UDP-glucoronosyl and UDP-glucosyl transferase [*Oryza sativa* Japonica Group] EUGT11 enzyme from patent application WO/2013/022989A2

SEQ ID NO:8:

MHVVICPLLAFGHLLPCLDLAQRLACGHRVSFVSTPRNISRLPPVRPSLA

PLVSFVALPLPRVEGLPNGAESTHNVPHDRPDMVELHLRAFDGLAAPFSE

FLGTACADWVMPTSSAPRQTLSSNIHRNSSRPGTPAPSGRLLCPITPHSN

TLERAAEKLVRSSRQNARARSLLAFTSPPLPYRDVFRSLLGLQMGRKQLN

IAHETNGRRTGTLPLNLCRWMWKQRRCGKLRPSDVEFNTSRSNEAISPIG

ASLVNLQSIQSPNPRAVLPIASSGVRAVFIGRARTSTPTPPHAKPARSAA

PRAHRPPSSVMDSGYSSSYAAAAGMHVVICPWLAFGHLLPCLDLAQRLAS

RGHRVSFVSTPRNISRLPPVRPALAPLVAFVALPLPRVEGLPDGAESTND

VPHDRPDMVELHRRAFDGLAAPFSEFLGTACADWVIVDVFHHWAAAAALE

HKVPCAMMLLGSAHMIASIADRRLERAETESPAAAGQGRPAAAPTFEVAR

MKLIRTKGSSGMSLAERFSLTLSRSSLVVGRSCVEFEPETVPLLSTLRGK

PITFLGLMPPLHEGRREDGEDATVRWLDAQPAKSVVYVALGSEVPLGVEK

VHELALGLELAGTRFLWALRKPTGVSDADLLPAGFEERTRGRGVVATRWV

PQMSILAHAAVGAFLTHCGWNSTIEGLMFGHPLIMLPIFGDQGPNARLIE

AKNAGLQVARNDGDGSFDREGVAAAIRAVAVEEESSKVFQAKAKKLQEIV

ADMACHERYIDGFIQQLRSYKD

The tested plasmid was received in a microtiterplate containing a plasmid as freeze-dried solid in a separate well.

Suspension of Plasmid

To the well was added 24 μL of ultra-pure sterile water and the microtiter plate was shaken for 30 minutes at Room Temperature. Subsequently, the plate was incubated at 4° C. for 1 hour. The content of the well was further mixed by pipetting up and down. The plasmid quantification was performed by Qubit2.0 analysis using 1 μL of suspension. Plasmid quantity was determined as follows:

| Microtiter plate | Position | Internal reference of test | [Plasmid] ng/μL |
|---|---|---|---|
| C912666 | G4 | S115N08 G4 | 19.2 |

Transformation of Competent Cells with Plasmid.

An aliquot of chemically competent EC100 cells was taken from freezer at −80° C. and stored on ice. The cells were allowed to thaw on ice for 10 minutes. 10 μL of a dilution of above described plasmid solution was added to a sterile microtube of 1.5 mL (in order to transform each cell with 50 pg of DNA) and stored on ice. 100 μL of chemically competent cells was added to the microtube. After incubation of the chemically competent cells/plasmid mixture on ice for 20 min a thermal shock of 30 seconds at 42° C. was performed.

Further incubation was performed on ice for 2 minutes. To the microtube 300 μL of SOC medium was added and the resulting mixture was transferred to a sterile 15 mL tube. After incubate for 1 hour at 37° C. while shaking at 135 rpm, the mixture is spread on solid Luria Broth medium containing Kanamycin 50 μg/mL. The Petri dish is allowed to incubate for 16 hours at 37° C.

Preparation of Stock Solutions in Glycerol and Purification of Plasmid.

To a 50 mL sterile Falcon Tube 10 mL of Luria Broth medium containing 50 μg/mL of Kanamycin was added. The medium was seeded with an isolated colony from the above described Petri dish and the cultures were allowed to incubate for 16 hours at 37° C. while shaking at 135 rpm.

To sterile microtube of 1.5 mL containing 300 μL of a 60% sterile glycerol solution, 600 μL of the culture was added. The stock solution was stored at −80° C.

The remainder of the culture was centrifuged at 5,525 g for 10 minutes at 10° C. and after removal of the supernatant, the pellet was stored on ice. The produced plasmids were purified according to the Qiagen Qiaprep Spin Miniprep kit (ref: 27106) and the plasmid yield was measured at 260 nm. The plasmid solution was stored at 4° C. Plasmid quantity was determined as follows:

| Microtiter plate | Position | Internal reference of test | [Plasmid] ng/μL |
|---|---|---|---|
| C912666 | G4 | S115N08 G4 | 38.4 |

In-Vitro Expression of EUGT11.

18 μL of a diluted plasmid solution (containing approximately 1.5 μg of plasmid) was used for in-vitro expression according to the Promega S30 T7 High-Yield Protein Expression System (ref: L1110) kit. The expression medium was produced as follows:

| | S30 Premix Plus | T7 S30 Extract | DNA template | Total |
|---|---|---|---|---|
| Trials | 30 μL | 27 μL | 18 μL (~1.5 μg) | 75 μL |
| reference | 20 μL | 18 μL | 12 μL (~1.0 μg) | 50 μL |

The prepared expression medium mix was added to the plasmid solution and the solution was allowed to incubate at 30° C. for 3 hours while mixing the mixture every 45 minutes. 5 μL of the mixture was frozen whereas the remainder was used for the catalytic test for the conversion of Rebaudioside A to Rebaudioside D.

Catalytic Test for Transformation of Rebaudioside A to Rebaudioside D.

430 μL of a reaction mixture containing 0.5 mM Rebaudioside A, 3 mM $MgCl_2$, 50 mM phosphate buffer (pH7.2) and 2.5 mM UDP-glucose was added to a 1.5 mL sterile microtube. 52 μL of the enzyme expression medium was added and the resulting mixture was allowed to react at 30° C. for 24 hours. 125 μL samples were taken after 2 hours, 16 hours and 24 hours and added to a 115 μL of 60% methanol and 10 μL of 2 N $H_2SO_4$. The quenched sample was centrifuged at 18,000 g for 2 minutes at RT. 200 μL was transferred to HPLC vial and analyzed.

HPLC Analysis.

The HPLC assay was performed as described in EXAMPLE 20.

Figure 54:
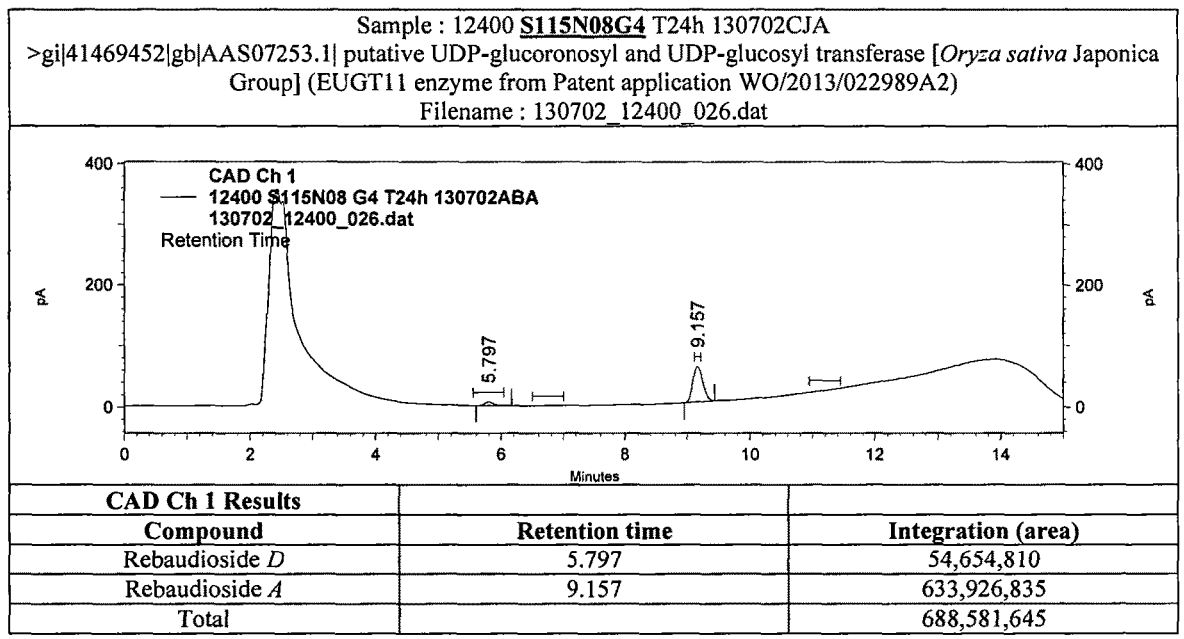
FIG. 54 shows an HPLC chromatogram showing the HPLC assay results for Example 21.
Figure 55A:
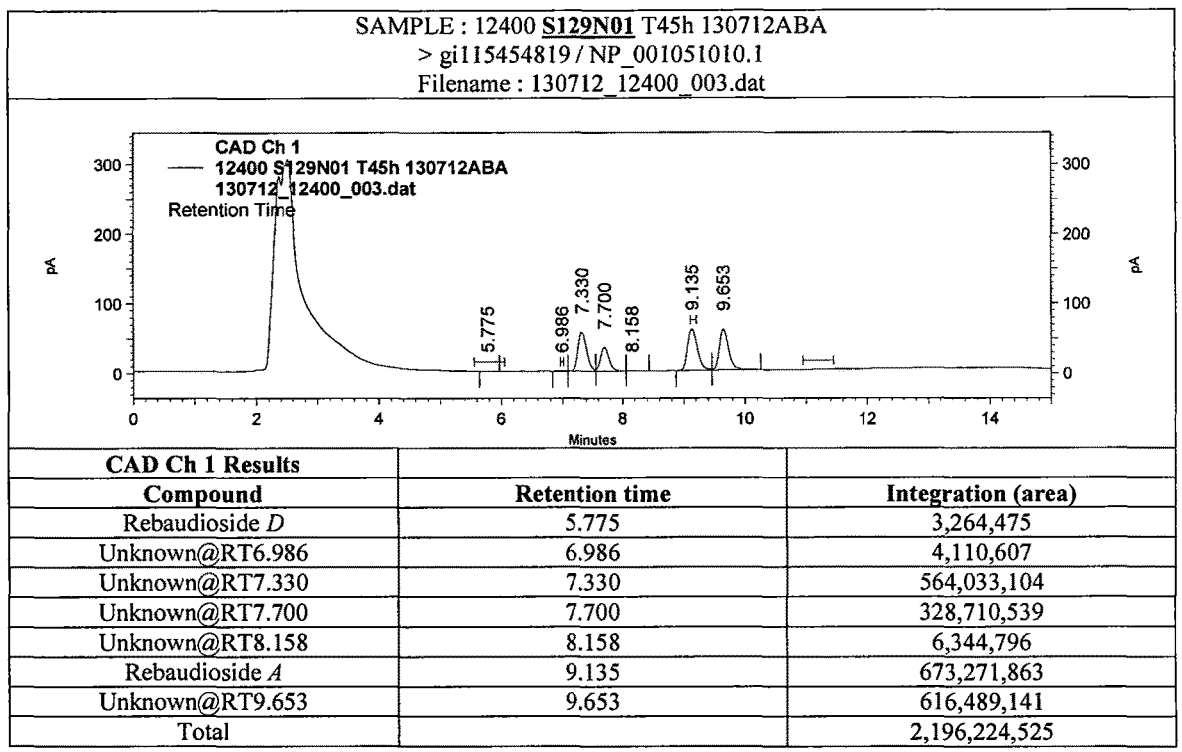
FIG. 55a-e show HPLC chromatograms showing the HPLC assay results for Example 22.
Figure 55B:
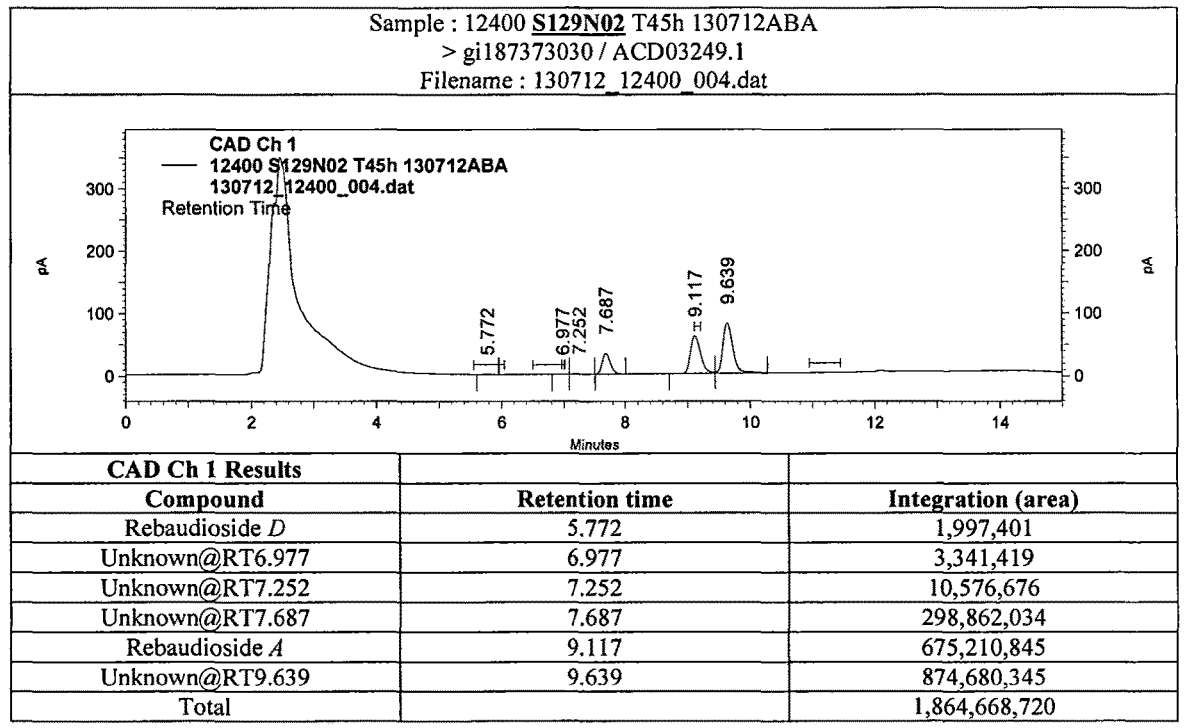
Figure 55C:
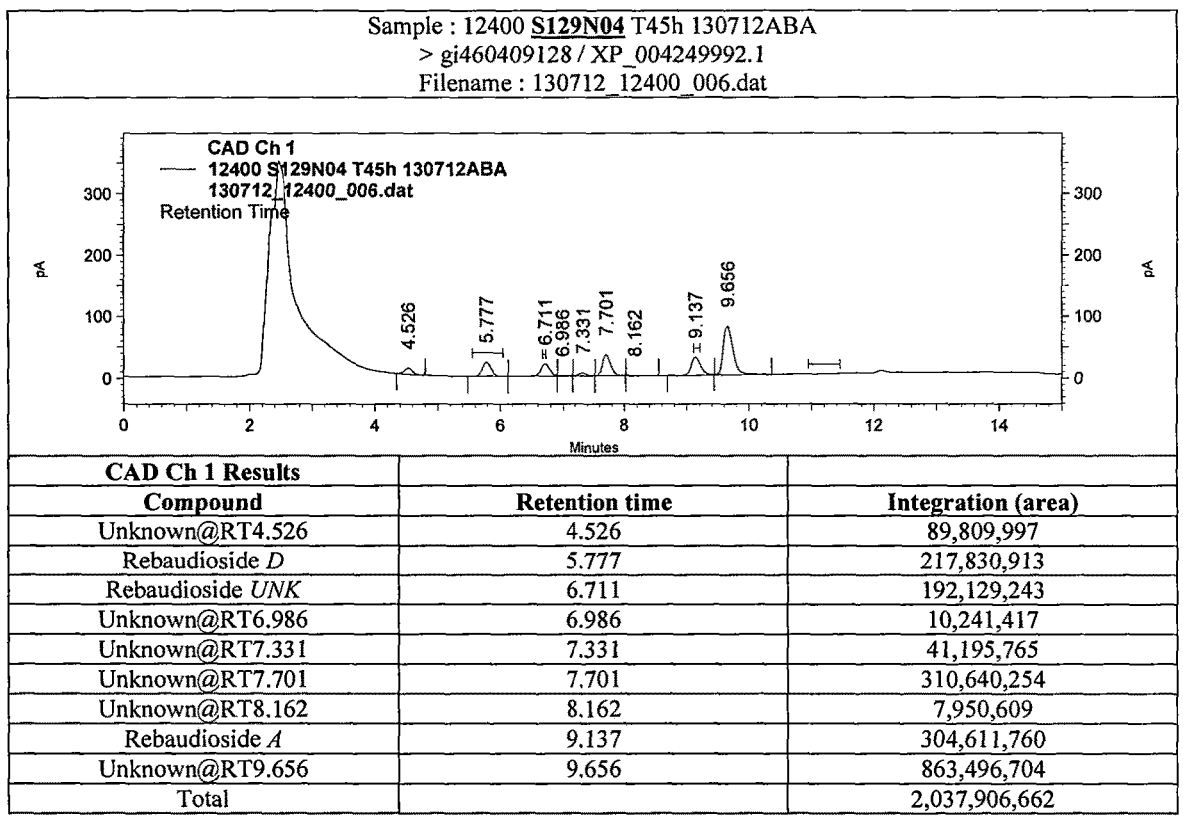
Figure 55D:
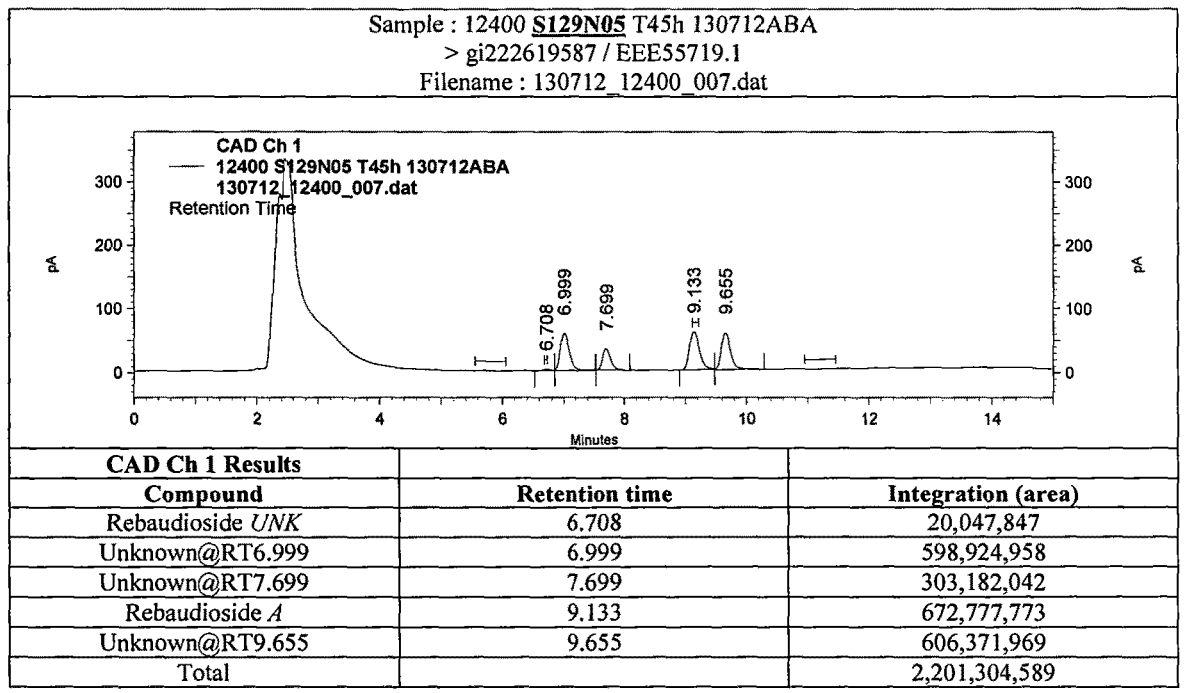
Figure 55E:
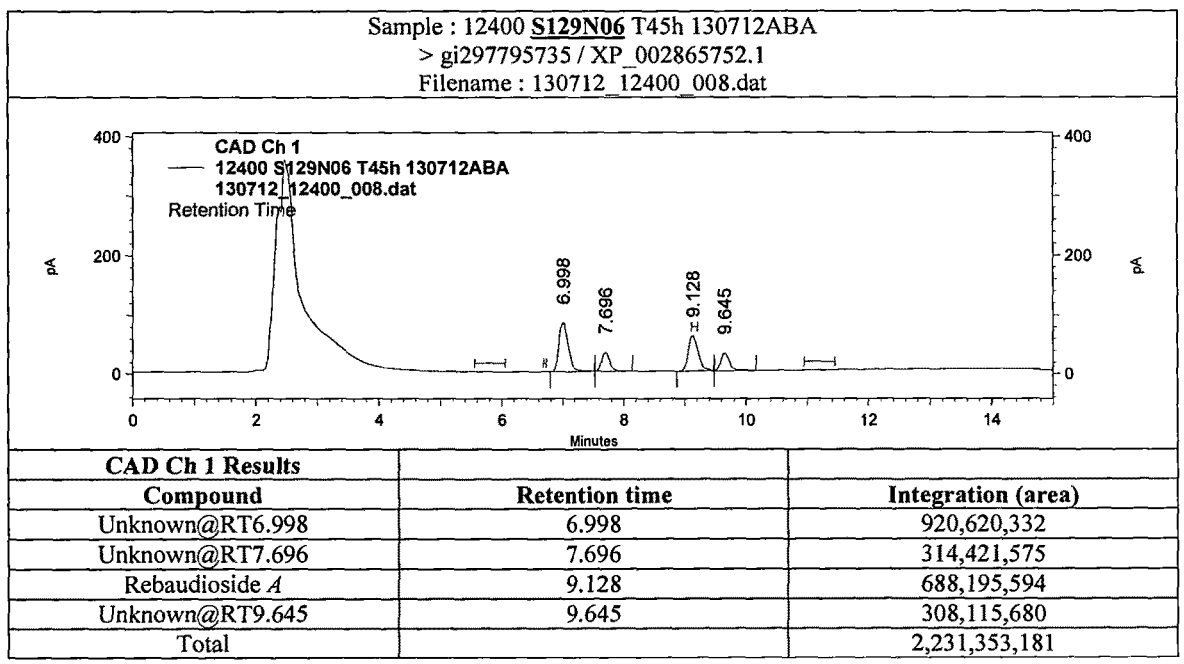
Figure 56A:
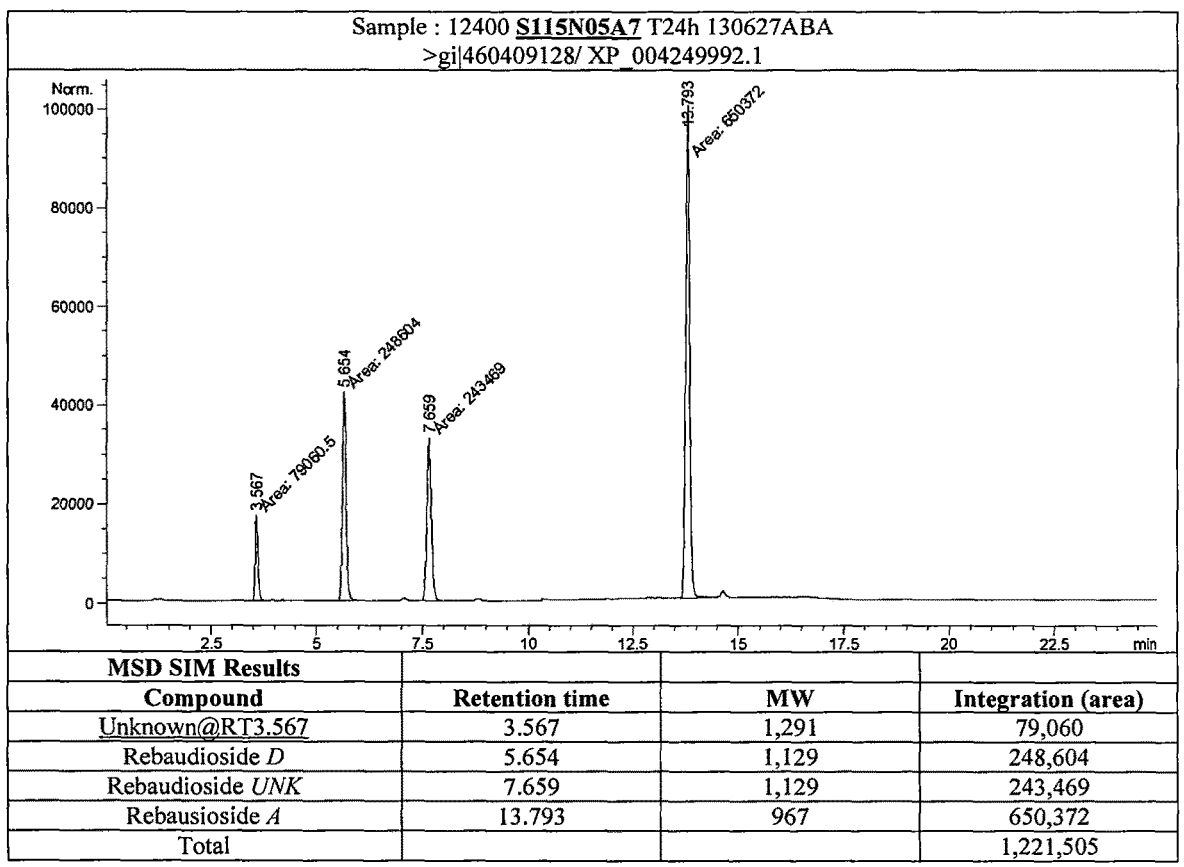
FIG. 56a-b show HPLC chromatograms showing the HPLC assay results for Example 23.
Figure 56B:
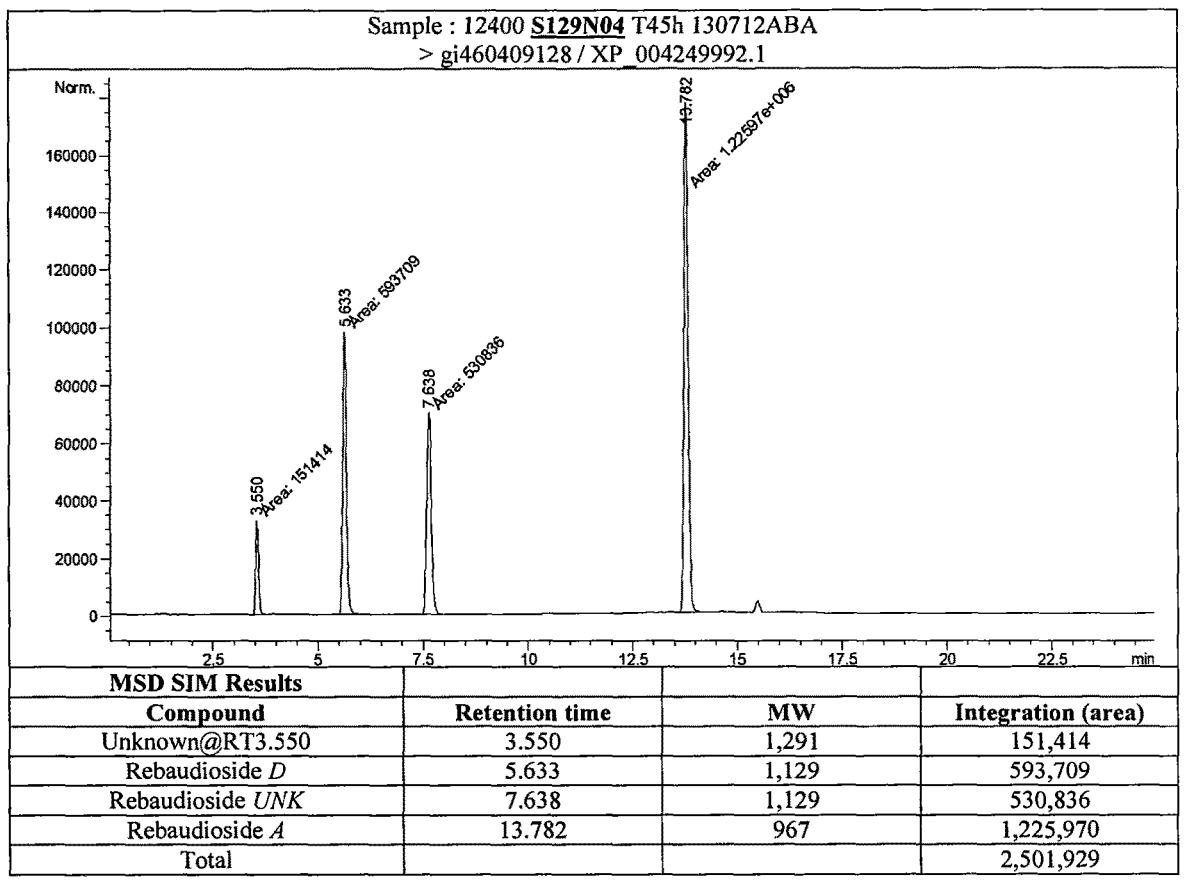

The HPLC assay results are shown in FIG. 54.

Example 22

In-Vivo Production of Enzymes

The enzymes described in EXAMPLE 20 were produced in vivo.

The pET30A+ vector containing the gene corresponding to the enzyme was introduced in E. coli BL21(DE3) by heat shock. The obtained cells were grown in Petri dishes in the presence of Kanamycin and suitable colonies were selected and allowed to grow in liquid LB medium (Erlenmeyer flasks). Glycerol was added to the suspension as cryoprotector and 400 μL aliquots were stored at −20° C. and at −80° C.

The storage aliquots of E. coli BL21(DE3) containing the pET30A+_UGT plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake at 135 rpm at 30° C. for 8 hrs.

The production medium contained 60 g/L of overnight express instant TB medium (Novagen), 10 g/L of glycerol and 50 mg/L of Kanamycine. The preculture was added to 400 mL of this medium and the solution was allowed to stir at 20° C. while taking samples to measure the OD and pH. The cultures gave significant growth and a good OD was obtained. After 40 hrs, the cells were harvested by centrifugation and frozen. The following yields of cell wet weights (CWW) are mentioned below.

| GI number | Version | CWW |
|---|---|---|
| 115454819 | NP_001051010.1 | 9.2 g |
| 187373030 | ACD03249.1 | 7.4 g |
| 460409128 | XP_004249992.1 | 6.8 g |
| 222619587 | EEE55719.1 | 7.5 g |
| 297795735 | XP_002865752.1 | 8.8 g |

Lysis was performed by addition of Bugbuster Master mix (Novagen) and the lysate was recovered by centrifugation and used fresh.

Determination of Activity.

Activity tests were performed at 5 mL scale with 1,000 µL of thawed lysate for the transformation of Rebaudioside A using 0.5 mM of substrate, 2.5 mM of UDP-Glucose and 3 mM $MgCl_2$ in 50 mM Sodium Phosphate buffer at pH 7.2. Samples were taken and analyzed by HPLC.

HPLC Analysis.

The HPLC assay was performed as described in EXAMPLE 20.

The results for the different enzymes are provided below and shown in FIGS. 55a-e.

| GI Number | Version | Conversion after 45 hrs. | Reb D selectivity |
|---|---|---|---|
| 115454819 | NP_001051010.1 | 1.1% | 100% |
| 187373030 | ACD03249.1 | 0.8% | 100% |
| 460409128 | XP_004249992.1 | 62.1% | 43.6% |
| 222619587 | EEE55719.1 | 2.9% | Reb D Not detected |
| 297795735 | XP_002865752.1 | 0.0% | Reb D Not detected |

Example 23

Identification of Glycosides

The reaction mixtures representing GI No. 460409128, particularly the sample "12400 S115N05A7 T24h 130627ABA" of EXAMPLE 20 (hereinafter S115N05A7), and the sample "12400 S129N04 T45h 130712ABA" of EXAMPLE 22 (hereinafter S129N04) were additionally assayed by LC-MS to identify the unknown glycosides. An Agilent 1200 series HPLC system, equipped with binary pump (G1312B), autosampler (G1367D), thermostatted column compartment (G1316B), DAD detector (G1315C), connected with Agilent 6110A MSD, and interfaced with "LC/MSD Chemstation" software, was used.

Instrument Conditions

| Column | Phenomenex Kinetex 2.6u C18 100 A, 4.6 mm × 150 mm, 2.6 µm |
|---|---|
| Column Temperature | 55° C. |
| Detection | DAD at 210 nm bw 360 nm |
| | MSD (Scan and SIM mode) |
| | Mode: ES-API, Negative Polarity |
| | Drying gas flow: 13.0 L/min |
| | Nebulizer pressure: 30 psig |
| | Drying gas temperature: 270° C. |
| Analysis duration | 25 min |
| Injected volume | 2 µL |
| Flow rate | 1 mL/min |

Mobile Phase Gradient Program

| Time (min) | A (%): Formic acid 0.1% | B (%): Acetonitrile |
|---|---|---|
| 0 | 75 | 25 |
| 8.5 | 75 | 25 |
| 10.0 | 71 | 29 |
| 16.5 | 70 | 30 |

The compound observed on LCMS system at 3.5 min, corresponds to compound "Unknown@4.508" in sample "S115N05A7" (EXAMPLE 20), and compound "Unknown@RT4.526" in sample "S129N04" (EXAMPLE 22). The LCMS data suggests that this compound has six glucosidic residues ($C_{56}H_{90}O_{33}$) in its structure, and was found to be an isomer form of reb M, namely reb M2 (see Example 40 for discussion).

Whereas the compound observed on LCMS system at 7.6 min, corresponds to compound "reb UNK" in sample "S115N05A7" (EXAMPLE 20), and compound "reb UNK" in sample "S129N04" (EXAMPLE 22), The LCMS data suggests that "reb UNK" has five glucosidic residues ($C_{50}H_{80}O_{28}$) in its structure, and was found to be an isomer form of reb D, namely reb D2 (see Example 39 for discussion). The ratio of these compounds and the LCMS chromatograms are provided below.

| | Steviol glycoside conversion in reaction mixture (% area) | | | |
|---|---|---|---|---|
| Sample | Unknown@RT3.5 | Reb D | Reb UNK | Reb A |
| S115N05A7 | 6.47 | 20.35 | 19.93 | 53.24 |
| S129N04 | 6.05 | 23.73 | 21.22 | 49.00 |

Example 24

Identification of Glycosides

The reaction mixture representing GI No. 460409128, particularly the sample "12400 S129N04 T45h 130712ABA" of EXAMPLE 22 (hereinafter S129N04) were additionally assayed by LC-MS along with *Stevia rebaudiana* Bertoni leaf extract "MLD1" produced by PureCircle Sdn Bhd (Malaysia) to determine the occurrence of S129N04 glycosides in nature.

Figure 57A:
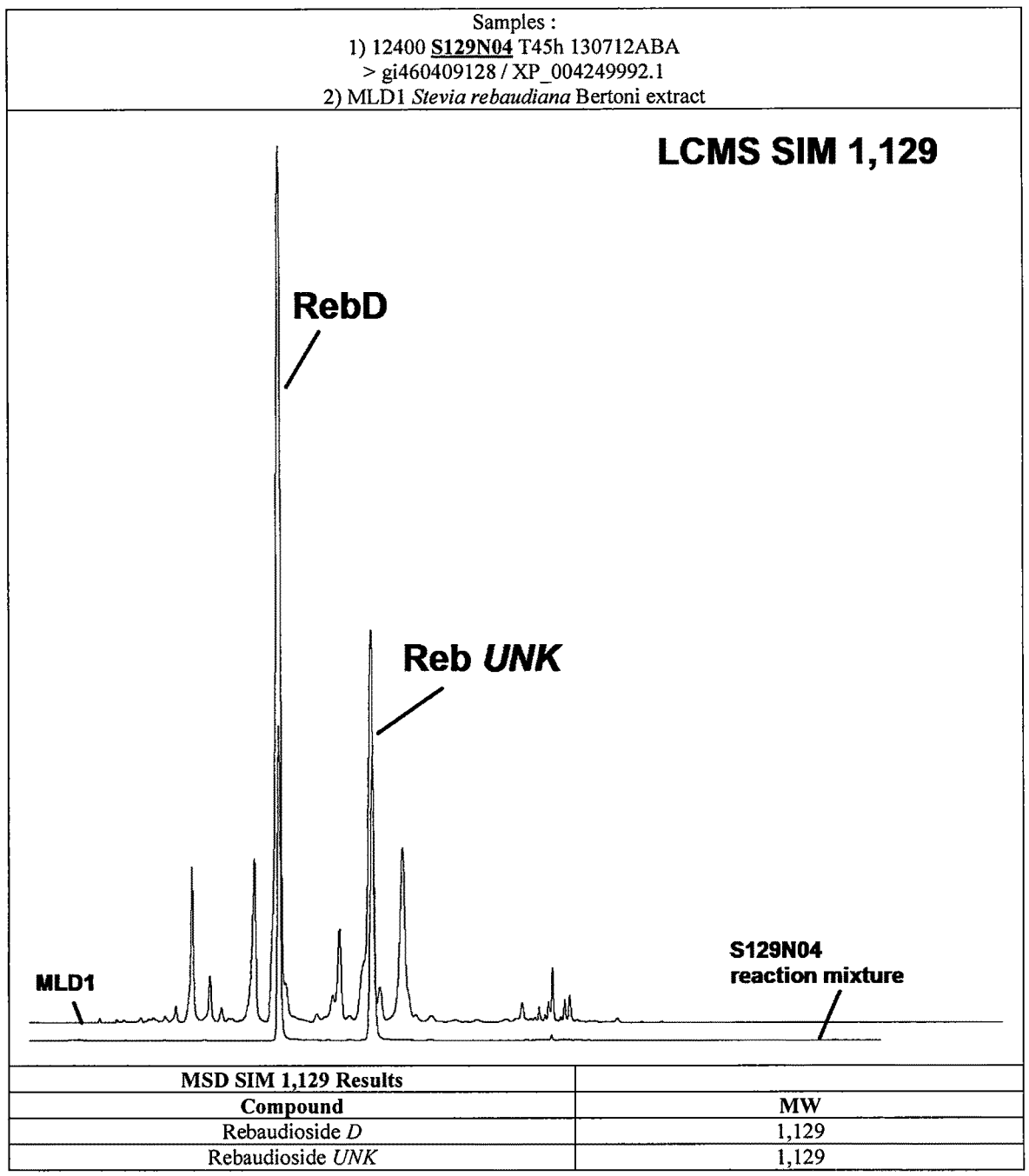
FIG. 57a-b show LC-MS spectrograms showing the LC-MS assay results for Example 24.
Figure 57B:
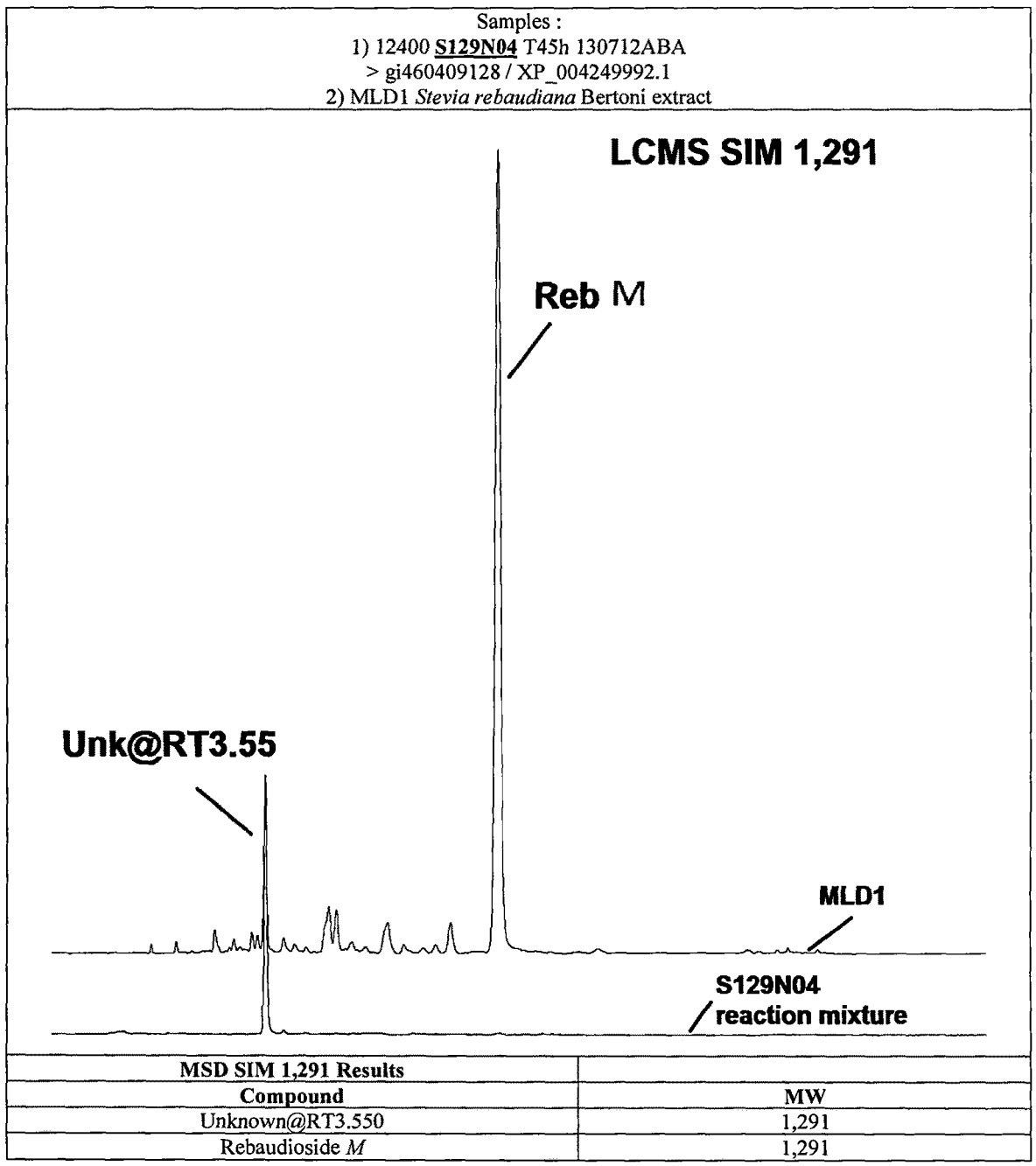

The assays in FIGS. 57a-b show that the compound observed on LCMS system at 3.5 min, in EXAMPLE 23 ($C_{56}H_{90}O_{33}$; later confirmed as reb M2), and the compound observed on LCMS system at 7.6 min, in EXAMPLE 23 ($C_{50}H_{80}O_{28}$; reb UNK; later confirmed as reb D2) occur in the extract of *Stevia rebaudiana* Bertoni plant.

Example 25

Conversion of Rebaudioside E to Rebaudioside D

Figure 58:
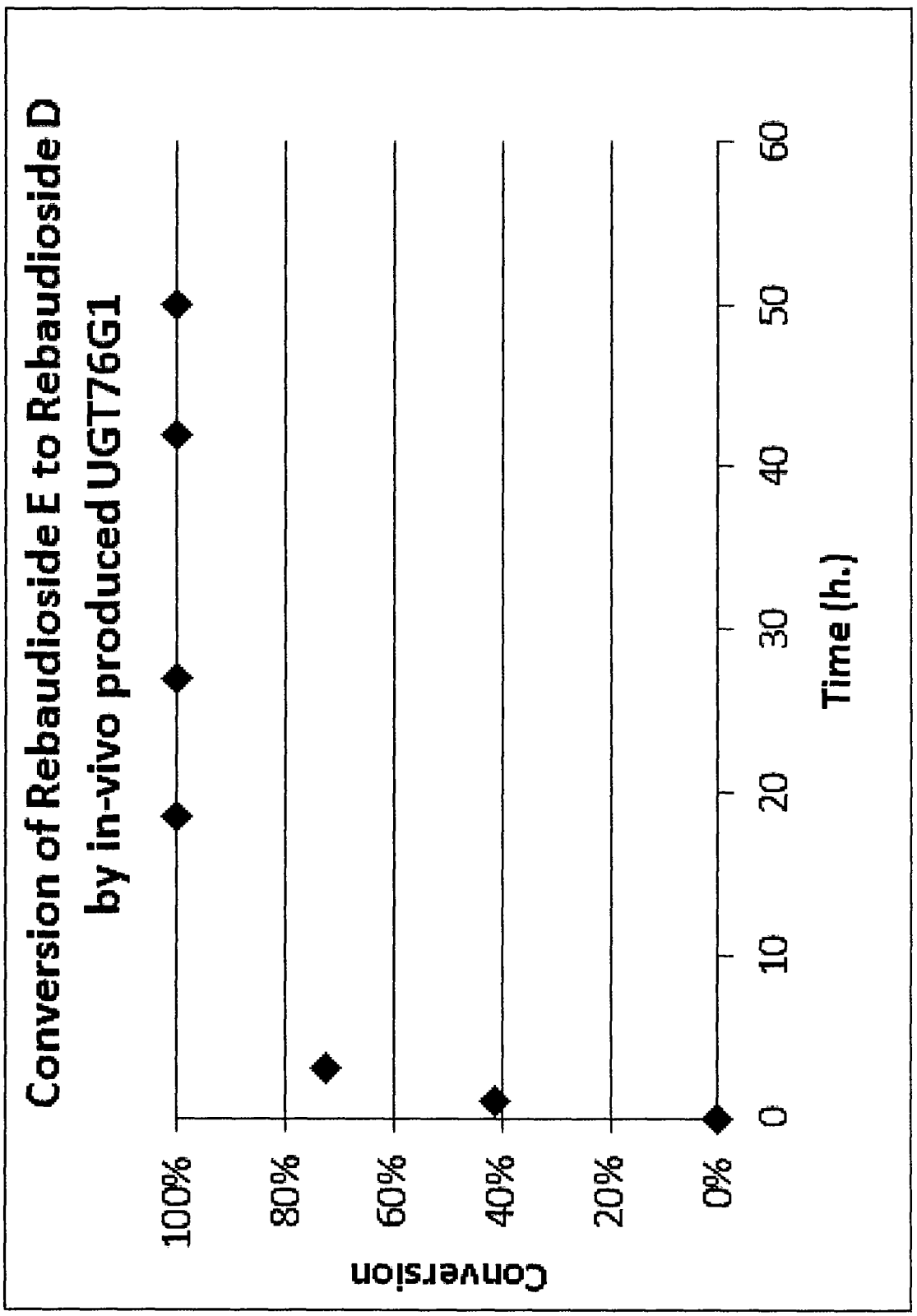
FIG. 58 shows a graph showing the reaction profile for Example 25.

The total volume of the reaction was 5.0 mL with the following composition: 100 mM potassium phosphate buffer pH 7.5, 3 mM $MgCl_2$, 2.5 mM UDP-glucose, 0.5 mM Rebaudioside E and 500 µL of UGT76G1 thawed lysate (UGT76G1 gene was cloned in pET30a+ vector and expressed in *E. coli* BL21 (DE3)). The reactions were run at 30° C. on an orbitary shaker at 135 rpm. For sampling 300 µL of the reaction mixture was quenched with 30 µL of 2N $H_2SO_4$ and 270 µL of methanol/water (6/4). The samples were immediately centrifuged and kept at 10° C. before analysis by HPLC (CAD detection). The reaction profile shown in FIG. 58 was obtained corresponding to a complete conversion of Rebaudioside E to Rebaudioside D.

Example 26

Directed Evolution of UGT76G1 for the Conversion of Rebaudioside D to Rebaudioside M Starting from the amino acid sequence of UGT76G1, as is described in Genbank (AAR06912.1), different mutations at various amino acid positions were identified that could alter the activity of the enzyme for the transformation of Rebaudioside D (Reb to Rebaudioside M (Reb M). This list of mutations, designed by DNA2.0 ProteinGPS™ strategy, was subsequently used to synthesize 96 variant genes that contained 3, 4 or 5 of these mutations that were codon-optimized for expression in *E. coli*. The genes were subcloned in the pET30a+ plasmid and used for transformation of *E. coli* BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of *E. coli* BL21(DE3) containing the pET30a+_UGT76G1var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 135 rpm at 30° C. for 8 h.

3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm; 1 cm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 µL of fresh lysate that was added to a solution of Rebaudioside D (final concentration 0.5 mM), $MgCl_2$ (final concentration 3 mM) and UDP-Glucose (final concentration 2.5 mM) in 50 mM phosphate buffer pH 7.2.

The reaction was allowed to run at 30° C. and samples were taken after 2, 4, 7 and 24 h. to determine conversion and initial rate by HPLC (CAD detection) using the analytical method that was described above for the transformation of Rebaudioside D to Rebaudioside M. The results are depicted in the following table.

| Clone | Mutations* | conversion Reb D to Reb M after 24 h (%) | initial rate (Reb M area/min) |
|---|---|---|---|
| UGT76G1var1 | E224A_F314S_R334K | 51.8 | 5.5E+07 |
| UGT76G1var2 | S274G_T284I_L379G | 49.3 | 4.7E+07 |
| UGT76G1var3 | I295T_S357C_V366I | 9.6 | 1.6E+06 |
| UGT76G1var4 | E224D_E231A_F265I | 14.7 | 8.6E+06 |
| UGT76G1var5 | F22Y_I373L_P382M | 3.5 | 2.3E+06 |
| UGT76G1var6 | Q266S_S357N_I373L | 0.5 | 1.8E+06 |
| UGT76G1var7 | F22L_I43V_A239V | 0.2 | −6.0E+04 |
| UGT76G1var8 | E224A_Q266S_Q342E | 0.5 | 2.3E+04 |
| UGT76G1var9 | E231A_D301N_G348P | 52.0 | 4.9E+07 |
| UGT76G1var10 | A33G_L246F_Q342E | 0.3 | −7.7E+02 |
| UGT76G1var11 | F22L_A33G_V310I | 0.4 | 3.8E+04 |
| UGT76G1var12 | L243P_K303G_A352G | 0.5 | 8.7E+04 |
| UGT76G1var13 | L243A_S357C_A385T | 0.2 | −3.3E+04 |
| UGT76G1var14 | A239I_F265I_V396F | 5.3 | 1.5E+06 |
| UGT76G1var15 | F41L_L246F_Q425E | 5.6 | 1.5E+06 |
| UGT76G1var16 | F265I_P272A_I335V | 18.6 | 5.8E+06 |
| UGT76G1var17 | F265L_Q266E_Q342K | 0.7 | 7.2E+05 |
| UGT76G1var18 | L243P_S274G_N409R | 1.9 | 5.0E+05 |
| UGT76G1var19 | E224D_E229A_Q432E | 10.5 | 5.5E+06 |
| UGT76G1var20 | S375M_K393G_Y397E | 1.8 | 1.9E+06 |
| UGT76G1var21 | A239V_V300A_K303G | 41.9 | 3.3E+07 |
| UGT76G1var22 | E231A_V310I_R334K | 34.4 | 2.4E+07 |
| UGT76G1var23 | T263S_G348P_A352G | 47.8 | 4.1E+07 |
| UGT76G1var24 | A239I_P272A_Q425E | 31.0 | 2.1E+07 |
| UGT76G1var25 | T284L_Q342K_Y397Q | 0.9 | 6.3E+04 |
| UGT76G1var26 | S241I_F265L_F377C | 1.8 | 7.5E+05 |
| UGT76G1var27 | A239I_L379A_V394I | 29.0 | 1.5E+07 |
| UGT76G1var28 | L243A_S274G_P382M | 6.1 | 2.4E+06 |
| UGT76G1var29 | F22Y_V279I_N409R | 41.0 | 2.9E+07 |
| UGT76G1var30 | I43V_E224A_S241I | 13.6 | 5.6E+06 |
| UGT76G1var31 | E224D_L243P_V300A | 0.4 | 2.4E+05 |
| UGT76G1var32 | A239V_L243A_S375M | 0.0 | −4.4E+04 |
| UGT76G1var33 | A33G_R334H_Y397Q | 1.0 | 7.5E+06 |
| UGT76G1var34 | I43V_T284I_I295T | 3.4 | 1.5E+06 |
| UGT76G1var35 | T284L_F314S_S357N | 0.5 | 1.8E+05 |
| UGT76G1var36 | F265L_L379A_V396F | 20.0 | 8.8E+06 |
| UGT76G1var37 | E229A_L379G_I407V | 39.1 | 2.8E+07 |
| UGT76G1var38 | F41L_I295M_F377C | 8.2 | 3.7E+06 |
| UGT76G1var39 | F22Y_F41L_V366I | 7.2 | 3.3E+06 |
| UGT76G1var40 | T263S_Q266E_S375R | 47.6 | 3.3E+07 |
| UGT76G1var41 | L246F_A385T_K393G | 0.8 | 1.4E+06 |
| UGT76G1var42 | T263S_Q266S_R334H | 34.6 | 2.2E+07 |
| UGT76G1var43 | S241I_P272A_V279I | 19.9 | 9.4E+06 |
| UGT76G1var44 | I335V_S375R_I407V | 35.3 | 2.3E+07 |
| UGT76G1var45 | V279I_D301N_S389E | 38.6 | 2.3E+07 |
| UGT76G1var46 | F22L_Q266E_I295M | 0.6 | 9.8E+05 |
| UGT76G1var47 | E229A_T284I_S389E | 4.8 | 2.7E+06 |
| UGT76G1var48 | V394I_Y397E_Q432E | 47.6 | 3.8E+07 |
| UGT76G1var49 | F41L_Q266E_T284I_Y397Q | 2.6 | 1.1E+06 |
| UGT76G1var50 | F22Y_V310I_S375M_F377C | 1.9 | 7.9E+05 |
| UGT76G1var51 | K303G_S357C_S389E_V396F | 18.7 | 9.5E+06 |
| UGT76G1var52 | D301N_I373L_F377C_I407V | 12.9 | 4.6E+06 |
| UGT76G1var53 | R334K_A352G_P382M_S389E | 9.3 | 4.1E+06 |

| Clone | Mutations* | conversion Reb D to Reb M after 24 h (%) | initial rate (Reb M area/min) |
|---|---|---|---|
| UGT76G1var54 | E229A_T284L_R334K_Q342E | 0.7 | 4.3E+05 |
| UGT76G1var55 | I295M_Q342E_V366I_N409R | 1.0 | 2.2E+05 |
| UGT76G1var56 | L246F_A352G_S357N_Q432E | 0.4 | 4.1E+04 |
| UGT76G1var57 | S241I_T263S_L379G_A385T | 0.8 | 1.5E+05 |
| UGT76G1var58 | S357C_S375M_N409R_Q425E | 7.5 | 2.2E+06 |
| UGT76G1var59 | I335V_K393G_V394I_Y397Q | 33.0 | 2.7E+07 |
| UGT76G1var60 | E231A_L243A_V279I_S357N | 0.5 | 9.5E+04 |
| UGT76G1var61 | I43V_F265I_Q266S_L379A | 6.4 | 2.0E+06 |
| UGT76G1var62 | L243P_P272A_V394I_V396F | 0.1 | 3.4E+04 |
| UGT76G1var63 | F314S_R334H_Q342K_L379G | 3.4 | 1.2E+06 |
| UGT76G1var64 | F22L_A239I_R334H_I407V | 0.3 | 3.1E+04 |
| UGT76G1var65 | A33G_A239V_P382M_Q425E | 1.2 | 3.3E+05 |
| UGT76G1var66 | F265L_V310I_V366I_A385T | 0.8 | 3.7E+05 |
| UGT76G1var67 | E224D_F314S_S375R_Y397E | −2.1 | −5.6E+05 |
| UGT76G1var68 | Q342K_G348P_I373L_Y397E | −1.4 | −1.1E+05 |
| UGT76G1var69 | S274G_I295T_I335V_L379A | 24.7 | 8.3E+06 |
| UGT76G1var70 | E224A_I295T_V300A_G348P | 24.0 | 8.4E+06 |
| UGT76G1var71 | I295M_V300A_K393G_Q432E | 42.9 | 2.1E+07 |
| UGT76G1var72 | T284L_D301N_K303G_S375R | 19.2 | 9.1E+06 |
| UGT76G1var73 | F22Y_D301N_R334H_Q342E_V396F | 0.8 | 8.7E+05 |
| UGT76G1var74 | I295T_I373L_S375R_Y397Q_Q432E | 0.6 | 9.6E+04 |
| UGT76G1var75 | F41L_A239I_Q266S_S375M_P382M | 0.8 | −1.3E+05 |
| UGT76G1var76 | F22Y_A239I_L246F_I295M_R334K | 2.6 | 7.2E+05 |
| UGT76G1var77 | A239V_F265I_I295T_D301N_K393G | 1.9 | 4.4E+05 |
| UGT76G1var78 | V279I_V300A_V310I_I335V_S357C | 3.2 | 8.2E+05 |
| UGT76G1var79 | E224D_T284I_V366I_I373L_K393G | 8.5 | 3.8E+06 |
| UGT76G1var80 | L243P_L379A_S389E_Q425E_Q432E | 1.0 | 2.1E+05 |
| UGT76G1var81 | A33G_T263S_S274G_V279I_Y397E | 15.0 | 6.5E+06 |
| UGT76G1var82 | E224D_L243A_F265L_R334H_A352G | 1.1 | 2.5E+05 |
| UGT76G1var83 | I43V_Q342E_S357N_S375R_L379G | 0.5 | 4.3E+04 |
| UGT76G1var84 | F22L_Q266S_F314S_A352G_S357C | 1.2 | 2.3E+05 |
| UGT76G1var85 | T284L_G348P_F377C_P382M_N409R | 1.8 | 4.0E+05 |
| UGT76G1var86 | E224A_T284L_V396F_Y397E_I407V | 1.6 | 3.8E+05 |
| UGT76G1var87 | S241I_L243A_V300A_F314S_N409R | 35.7 | 2.1E+07 |
| UGT76G1var88 | A239V_T284I_V310I_Q342K_L379A | 1.6 | 3.8E+05 |
| UGT76G1var89 | F41L_E229A_E231A_F265L_P272A | 1.2 | 2.1E+05 |
| UGT76G1var90 | E231A_S241I_S274G_Y397Q_Q425E | 34.5 | 1.9E+07 |
| UGT76G1var91 | E224A_L246F_T263S_F265I_Q342K | 1.2 | 2.3E+05 |
| UGT76G1var92 | K303G_S357N_V366I_V394I_I407V | 1.6 | 3.6E+05 |
| UGT76G1var93 | I43V_Q266E_S375M_S389E_V394I | 1.8 | 4.5E+05 |
| UGT76G1var94 | Q266E_P272A_R334K_G348P_L379G | 72.0 | 7.9E+07 |
| UGT76G1var95 | A33G_I295M_K303G_I335V_A385T | −1.3 | −1.7E+05 |
| UGT76G1var96 | F22L_E229A_L243P_F377C_A385T | 1.2 | 2.7E+05 |

*Mutations are noted as follows: original amino acid-position-new amino acid: For example the mutation of an alanine at position 33 to a glycine is noted as A33G.

Example 27

In-Vivo Production of UGTSL2

UGTSL2 (GI_460410132/XP_004250485.1) amino acid sequence (SEQ ID NO:9):

MATNLRVLMFPWLAYGHISPFLNIAKQLADRGFLIYLCSTRINLESIIKK

IPEKYADSIHLIELQLPELPELPPHYHTTNGLPPHLNPTLHKALKMSKPN

FSRILQNLKPDLLIYDVLQPWAEHVANEQNIPAGKLLTSCAAVFSYFFSF

RKNPGVEFPFPAIHLPEVEKVKIREILAKEPEEGGRLDEGNKQMMLMCTS

RTIEAKYIDYCTELCNWKVVPVGPPFQDLITNDADNKELIDWLGTKHENS

TVFVSFGSEYFLSKEDMEEVAFALELSNVNFIWVARFPKGEERNLEDALP

KGFLERIGERGRVLDKFAPQPRILNHPSTGGFISHCGWNSAMESIDFGVP

IIAMPIHNDQPINAKLMVELGVAVEIVRDDDGKIHRGEIAETLKSVVTGE

TGEILRAKVREISKNLKSIRDEEMDAVAEELIQLCRNSNKSK

The pET30A+ vector containing the UGTSL2 gene was introduced in E. coli Bl21(DE3) by heat shock. The obtained cells were grown in petri-dishes in the presence of Kanamycin and suitable colonies were selected and allowed to grow in liquid LB medium (erlenmeyer flasks). Glycerol was added to the suspension as cryoprotecteur and 400 μl aliquots were stored at −20° C. and at −80° C.

The storage aliquots of E. coli BL21(DE3) containing the pET30A+_UGTSL2 plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycin). This culture was allowed to shake at 135 rpm at 30° C. for 8 h.

The production medium contained 60 g/L of overnight express instant TB medium (Novagen), 10 g/L of glycerol and 50 mg/L of Kanamycin. The preculture was added to 200 mL of this medium and the solution was allowed to stir at 20° C. while taking samples to measure the OD and pH. The culture gave significant growth and a good OD was obtained. After 40 h, the cells were harvested by centrifugation and frozen to obtain 6.22 g of cell wet weight.

Lysis was performed on 1.4 g of cells by addition of Bugbuster Master mix (Novagen) and the lysate was recovered by centrifugation and used fresh.

Example 28

Determination of Activity for Stevioside to Rebaudioside E Conversion with UGTSL and UGTSL2

UGTSL was prepared according to EXAMPLE 22, and UGTSL2 was prepared according to EXAMPLE 27.

Activity tests were performed at 3 mL scale with 600 μL of lysate for the transformation of Stevioside using 0.5 mM of substrate, 2.5 mM of UDP-Glucose and 3 mM MgCl$_2$ in 50 mM Sodium Phosphate buffer at pH 7.2. Samples were taken and analyzed by HPLC. HPLC Analysis. The HPLC assay was performed as described in EXAMPLE 20.

Figure 59A:
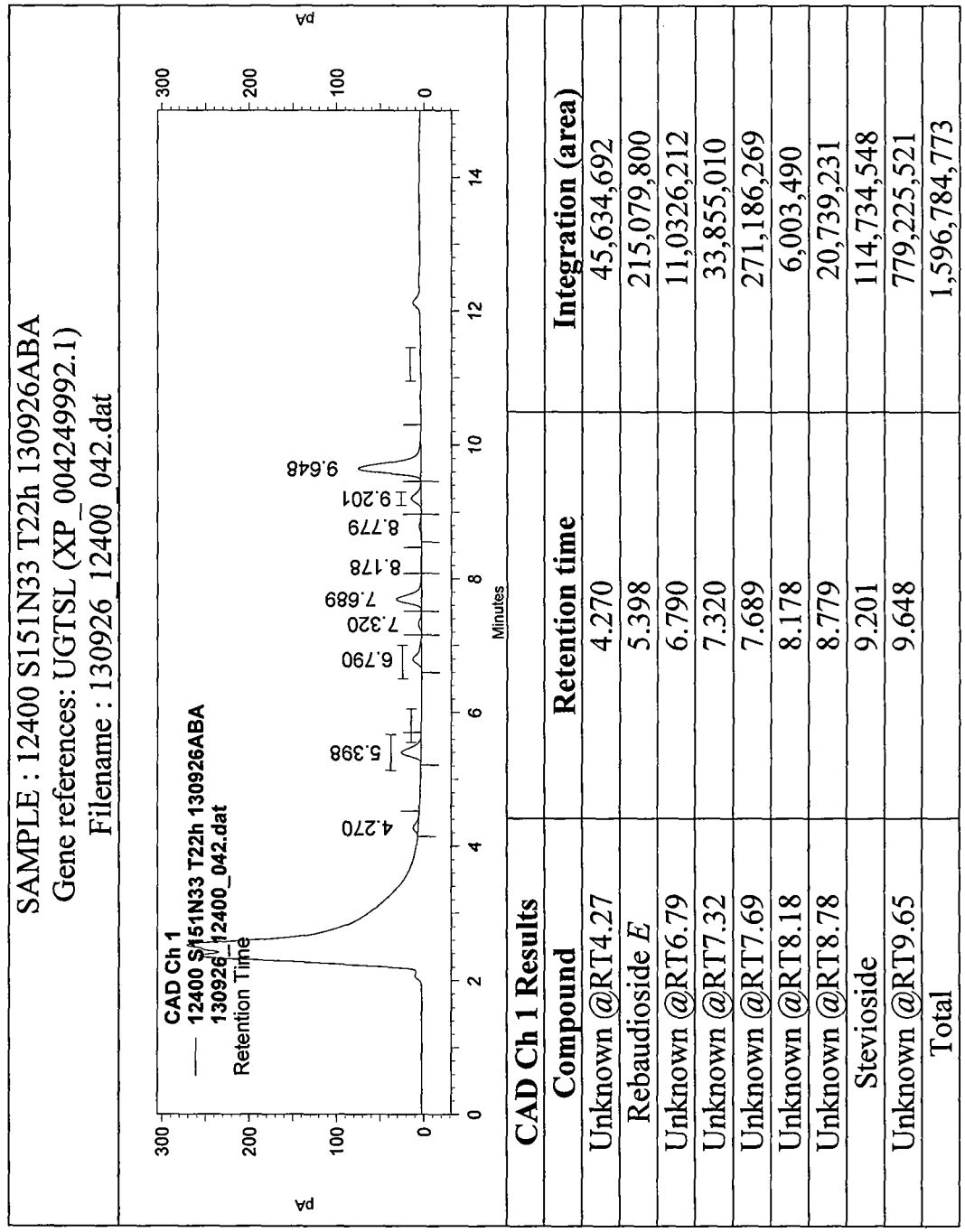
FIG. 59a-b show HPLC chromatograms showing the HPLC assay results for Example 28.
Figure 59B:
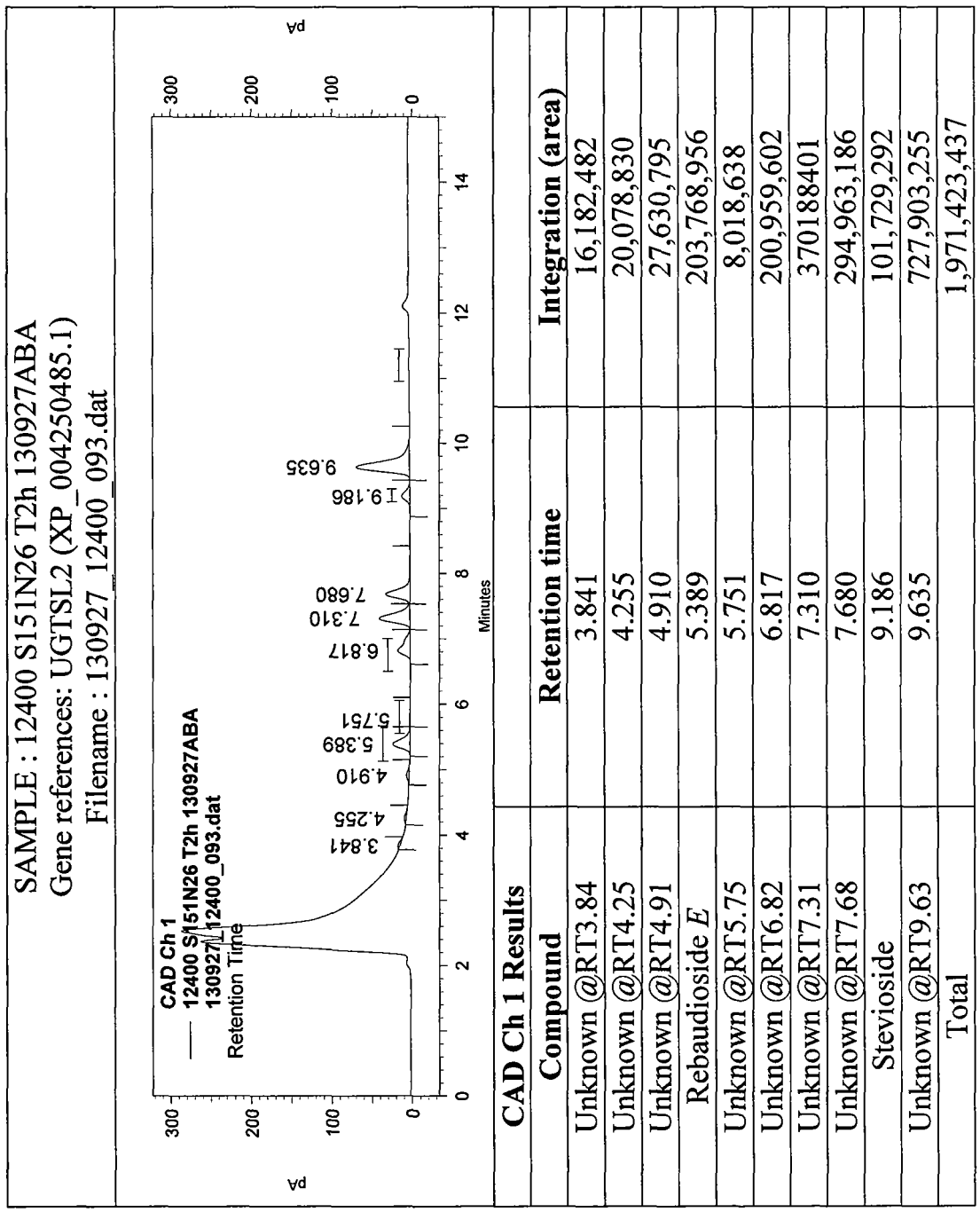

The results for the different enzymes and the corresponding chromatograms are provided below and shown in FIGS. 59a-b

| Enzyme internal reference | GI Number | Version | Stevioside conv.[1] (reaction time) | Rebaudioside E formation[1] |
|---|---|---|---|---|
| UGTSL | 460409128 | XP_004249992.1 | 74% (22 h.) | 46% |
| UGTSL2 | 460410132 | XP_004250485.1 | 77% (2 h.) | 50% |

Note:
[1]Based on initial concentration of Stevioside

Example 29

Determination of Activity for Rubusoside to Rebaudioside E Conversion with UGTSL and UGTSL2

UGTSL was prepared according to EXAMPLE 22, and UGTSL2 was prepared according to EXAMPLE 27.

Activity tests were performed at 3 mL scale with 600 μL of lysate for the transformation of Rubusoside using 0.5 mM of substrate, 2.5 mM of UDP-Glucose and 3 mM MgCl$_2$ in 50 mM Sodium Phosphate buffer at pH 7.2. Samples were taken and analyzed by HPLC. The HPLC assay was performed as described in EXAMPLE 20.

Figure 60A:
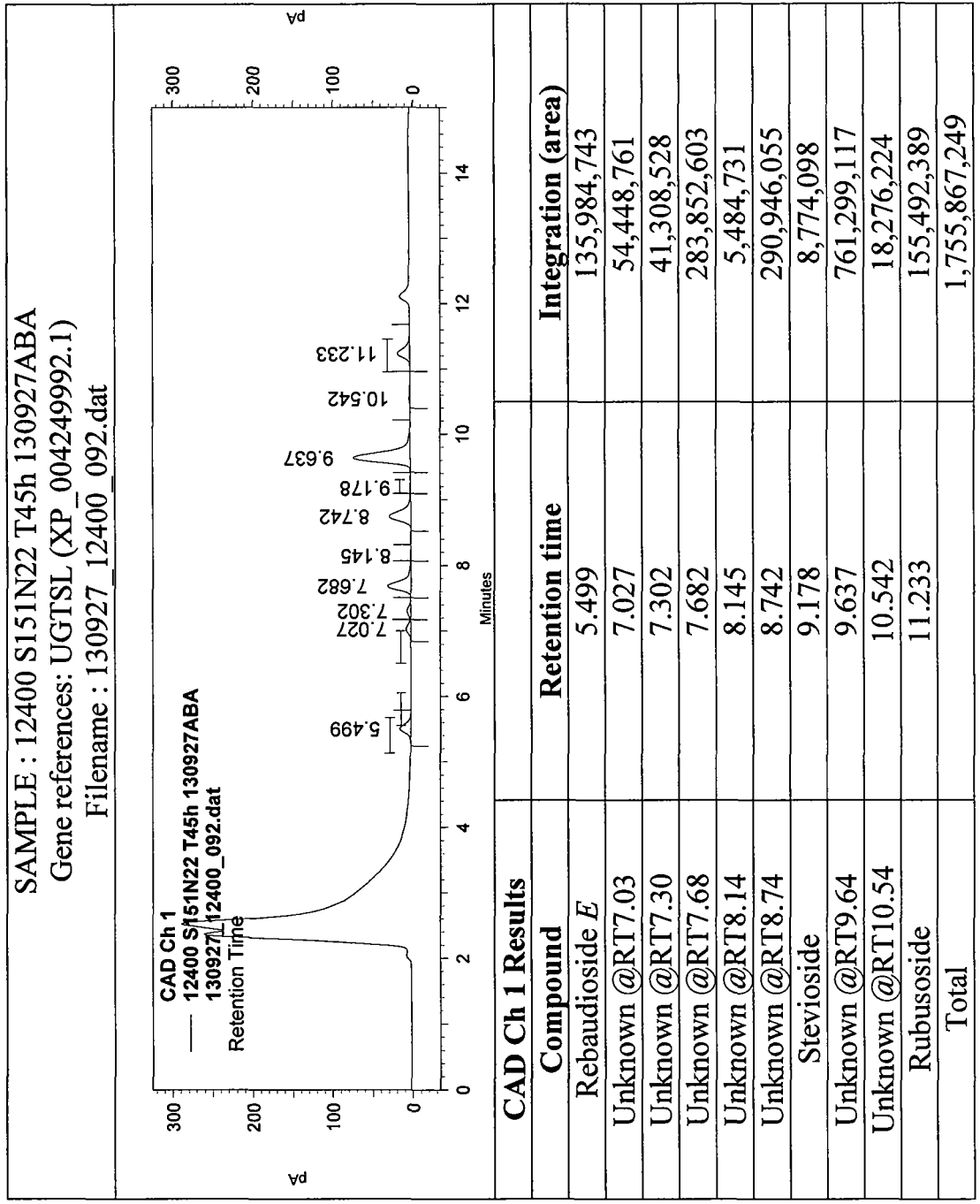
FIG. 60a-b show HPLC chromatograms showing the HPLC assay results for Example 29.
Figure 60B:
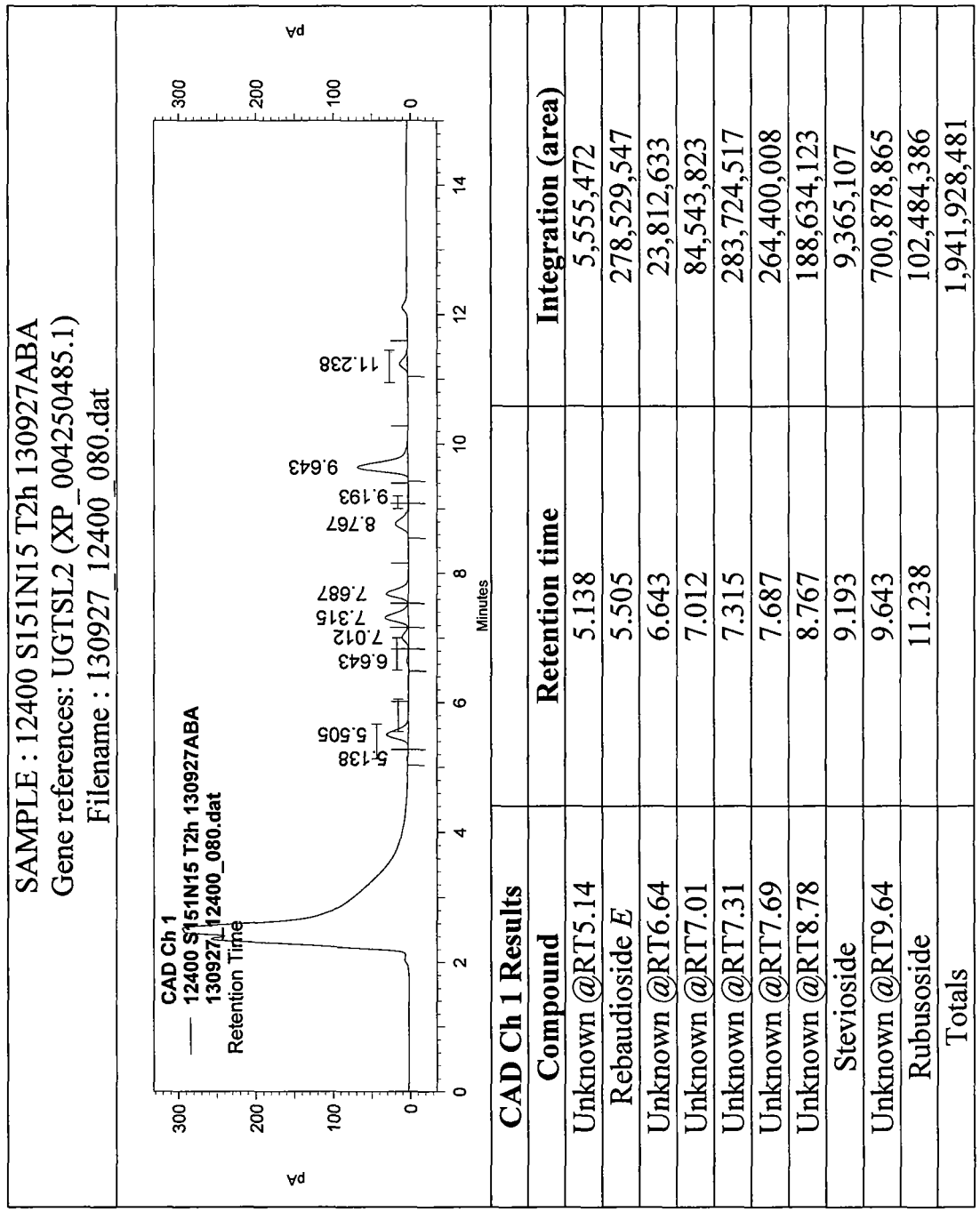

The results for the different enzymes and the corresponding chromatograms are provided below and shown in FIGS. 60a-b.

| Enzyme internal reference | GI Number | Version | Rubusoside conv.[1] (reactiontime) | Rebaudioside E formation[1] |
|---|---|---|---|---|
| UGTSL | 460409128 | XP_004249992.1 | 70% (45 h.) | 27% |
| UGTSL2 | 460410132 | XP_004250485.1 | 80% (2 h.) | 55% |

Note:
[1]Based on initial concentration of Rubusoside

Example 30

Determination of Activity for Rebaudioside A to Rebaudioside D Conversion with UGTSL2

UGTSL2 was prepared according to EXAMPLE 27.

Activity tests were performed at 3 mL scale with 60 μL of lysate for the transformation of Rebaudioside A using 0.5 mM of substrate, 2.5 mM of UDP-Glucose and 3 mM MgCl$_2$ in 50 mM Sodium Phosphate buffer at pH 7.2. Samples were taken and analyzed by HPLC. The HPLC assay was performed as described in EXAMPLE 20.

Figure 61:
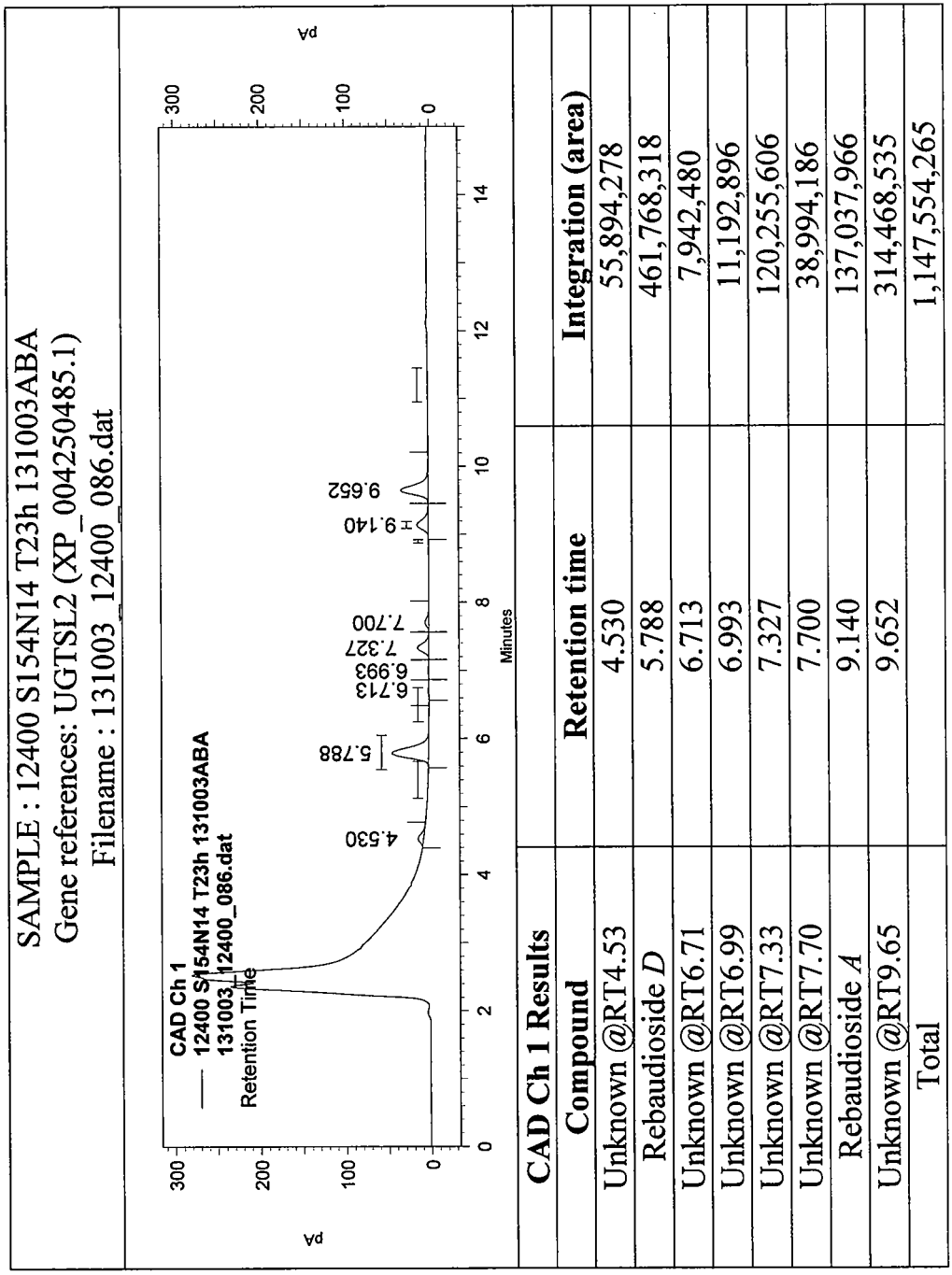
FIG. 61 shows an HPLC chromatogram showing the HPLC assay results for Example 30.

The result after 23 h. of reaction and the corresponding chromatogram is provided below and shown in FIG. 61.

| Enzyme internal reference | GI Number | Version | Rebaudioside A conv.[1] (reaction time) | Rebaudioside D formation[1] |
|---|---|---|---|---|
| UGTSL2 | 460410132 | XP_004250485.1 | 78% (23 h.) | 75% |

Note:
[1]Based on initial concentration of Rebaudioside A

Example 31

Identification of Glycosides

The reaction mixtures prepared according to EXAMPLE 30 and incubated for 45 hrs was analyzed by LC-MS, along with *Stevia rebaudiana* Bertoni leaf extract "MLD1" produced by PureCircle Sdn Bhd (Malaysia), to determine the occurrence of formed glycosides in nature.

An Agilent 1200 series HPLC system, equipped with binary pump (G1312B), autosampler (G1367D), thermostatted column compartment (G1316B), DAD detector (G1315C), connected with Agilent 6110A MSD, and interfaced with "LC/MSD Chemstation" software, was used.

Instrument Conditions

| Column | Phenomenex Prodigy 3u C18 100 A, 4.6 mm × 250 mm, 3 μm |
|---|---|
| Column Temperature | 55° C. |
| Detection | DAD at 210 nm bw 360 nm |
| | MSD (Scan and SIM mode) |
| | Mode: ES-API, Negative Polarity |
| | Drying gas flow: 13.0 L/min |
| | Nebulizer pressure: 30 psig |
| | Drying gas temperature: 270° C. |
| Analysis duration | 75 min |
| Injected volume | 10 μL |
| Flow rate | 0.5 mL/min |

Mobile Phase Gradient Program

| Time (min) | A (%): Formic acid 0.1% | B (%): Acetonitrile |
|---|---|---|
| 0 | 75 | 25 |
| 30 | 75 | 25 |
| 33 | 68 | 32 |
| 75 | 68 | 32 |

Figure 62:
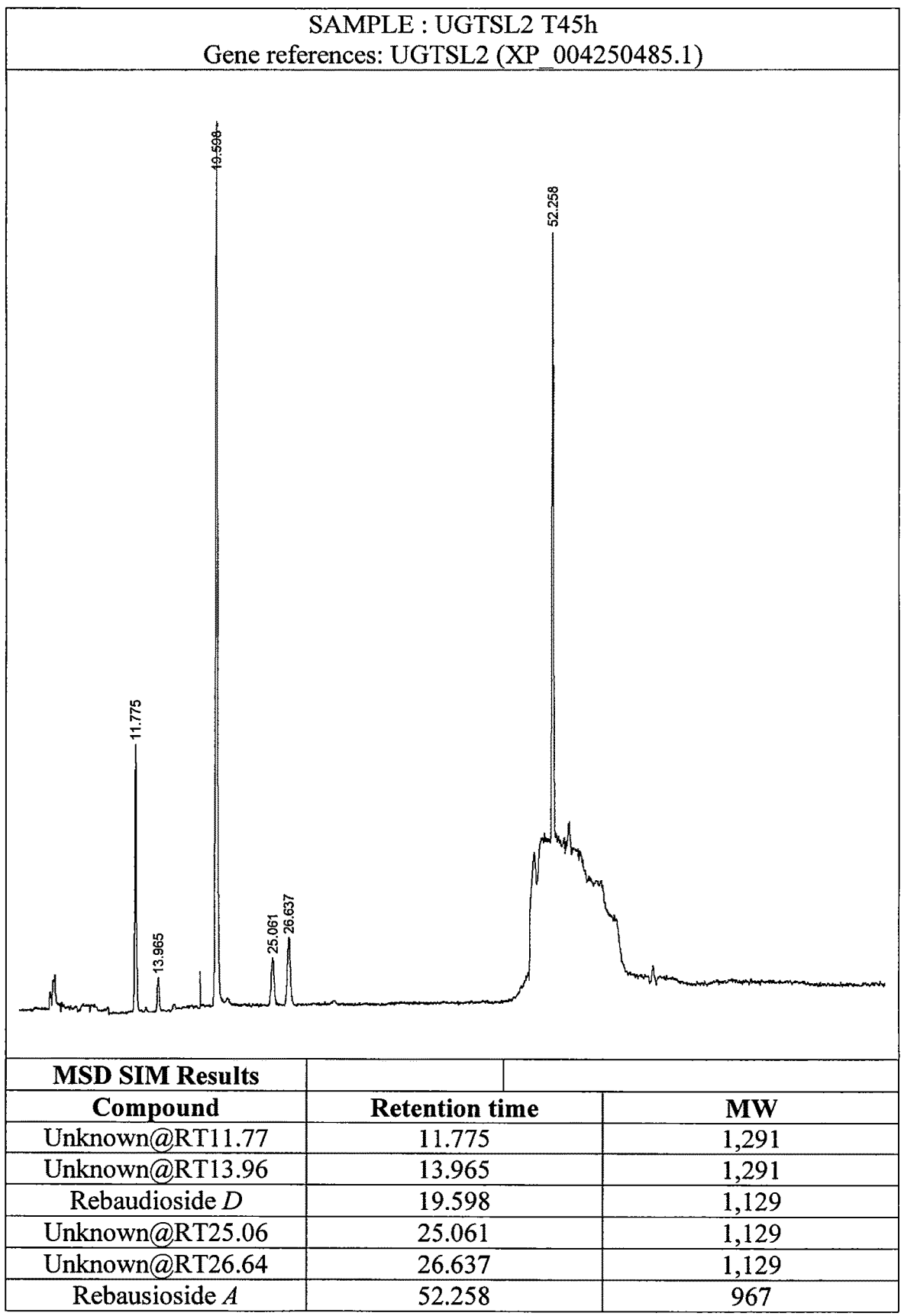
FIG. 62 shows an LS-MS spectrogram showing the LS-MS assay results for Example 31.

The assay shown in FIG. 62 shows that the compound observed on LC-MS system at 11.77 min is the same as the compound at 3.5 min, in EXAMPLE 23 ($C_{56}H_{90}O_{33}$; later confirmed as reb M2), and the compound observed at 26.64 min is the same as the compound at 7.6 min, in EXAMPLE 23 ($C_{50}H_{80}O_{28}$; reb UNK; later confirmed as reb D2). Other isomers of reb X were observed at 13.96 min and also another isomer form of reb D was observed at 25.06 min. All observed compounds occurred in the extract of *Stevia rebaudiana* Bertoni plant.

Example 32

In Vivo Preparation and Activity Determination of UGTLB

UGTLB (GI_209954733/BAG80557.1) amino acid sequence (SEQ ID NO:10):

MGTEVTVHKNTLRVLMFPWLAYGHISPFLNVAKKLVDRGFLIYLCSTAI

NLKSTIKKIPEKYSDSIQLIELHLPELPELPPHYHTTNGLPPHLNHTLQ

KALKMSKPNFSKILQNLKPDLVIYDLLQQWAEGVANEQNIPAVKLLTSG

AAVLSYFFNLVKKPGVEFPFPAIYLRKNELEKMSELLAQSAKDKEPDGV

DPFADGNMQVMLMSTSRIIEAKYIDYFSGLSNWKVVPVGPPVQDPIADD

ADEMELIDWLGKKDENSTVFVSFGSEYFLSKEDREEIAFGLELSNVNFI

WVARFPKGEEQNLEDALPKGFLERIGDRGRVLDKFAPQPRILNHPSTGG

FISHCGWNSVMESVDFGVPIIAMPIHLDQPMNARLIVELGVAVEIVRDD

YGKIHREEIAEILKDVIAGKSGENLKAKMRDISKNLKSIRDEEMDTAAE

ELIQLCKNSPKLK

The pET30A+ vector containing the UGTLB gene was introduced in *E. coli* Bl21(DE3) by heat shock. The obtained cells were grown in petri-dishes in the presence of Kanamycin and suitable colonies were selected and allowed to grow in liquid LB medium (erlenmeyer flasks). Glycerol was added to the suspension as cryoprotecteur and 400 μL aliquots were stored at −20° C. and at −80° C.

The storage aliquots of *E. coli* BL21(DE3) containing the pET30A+_UGTLB plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake at 135 rpm at 30° C. for 8 h.

The production medium contained 60 g/L of overnight express instant TB medium (Novagen), 10 g/L of glycerol and 50 mg/L of Kanamycine. The preculture was added to 200 mL of this medium and the solution was allowed to stir at 20° C. while taking samples to measure the OD and pH. The culture gave significant growth and a good OD was obtained. After 40 h, the cells were harvested by centrifugation and frozen to obtain 5.7 g of cell wet weight.

Lysis was performed on 1.2 g of cells by addition of 6 mL Bugbuster Master mix (Novagen) and the lysate was recovered by centrifugation and used fresh.

Figure 63A:
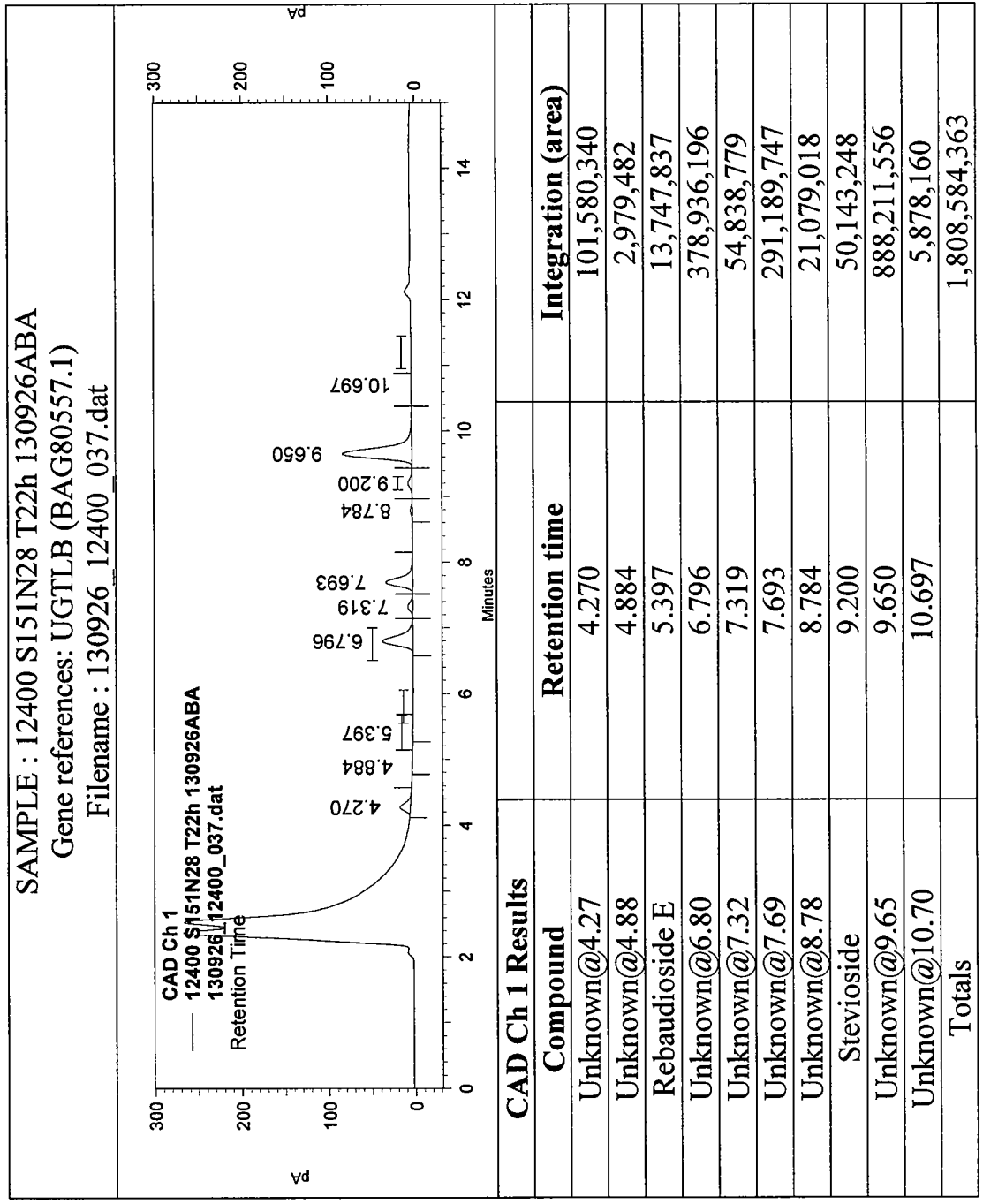
FIG. 63a-c show HPLC chromatograms showing the HPLC assay results for Example 32.

Determination of Activity for Stevioside to Rebaudioside E Conversion with UGTLB Activity tests were performed at 3 mL scale with 600 μL of lysate for the transformation of Stevioside using 0.5 mM of substrate, 2.5 mM of UDP-Glucose and 3 mM $MgCl_2$ in 50 mM Sodium Phosphate buffer at pH 7.2. Samples were taken and analyzed by HPLC. The corresponding chromatograms are depicted in FIG. 63a.

| Enzyme internal reference | GI Number | Version | Stevioside conv.[1] (reaction time) | Rebaudioside E formation[1] |
|---|---|---|---|---|
| UGTLB | 209954733 | BAG80557.1 | 89% (22 h.) | 3% |

Note:
[1]Based on initial concentration of Stevioside

Figure 63B:
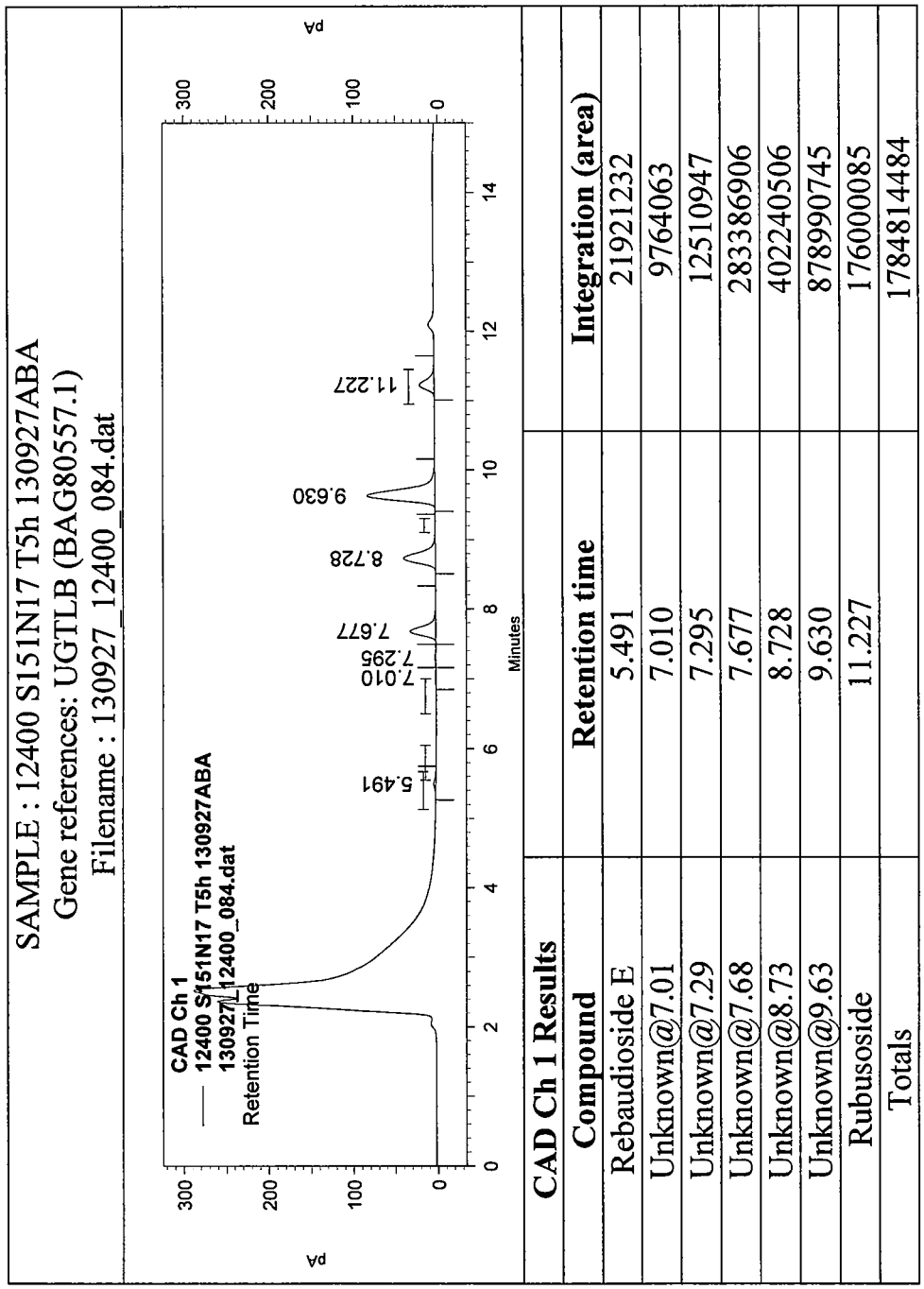

Determination of Activity for Rubusoside to Rebaudioside E Conversion with UGTLB Activity tests were performed at 3 mL scale with 600 μL of lysate for the transformation of Rubusoside using 0.5 mM of substrate, 2.5 mM of UDP-Glucose and 3 mM $MgCl_2$ in 50 mM Sodium Phosphate buffer at pH 7.2. Samples were taken and analyzed by HPLC. The corresponding chromatograms are depicted in FIG. 63b.

| Enzyme internal reference | GI Number | Version | Rubusoside conv.[1] (reaction time) | Rebaudioside E formation[1] |
|---|---|---|---|---|
| UGTLB | 209954733 | BAG80557.1 | 65% (5 h.) | 4% |

Note:
[1]Based on initial concentration of Rubusoside

Figure 63C:
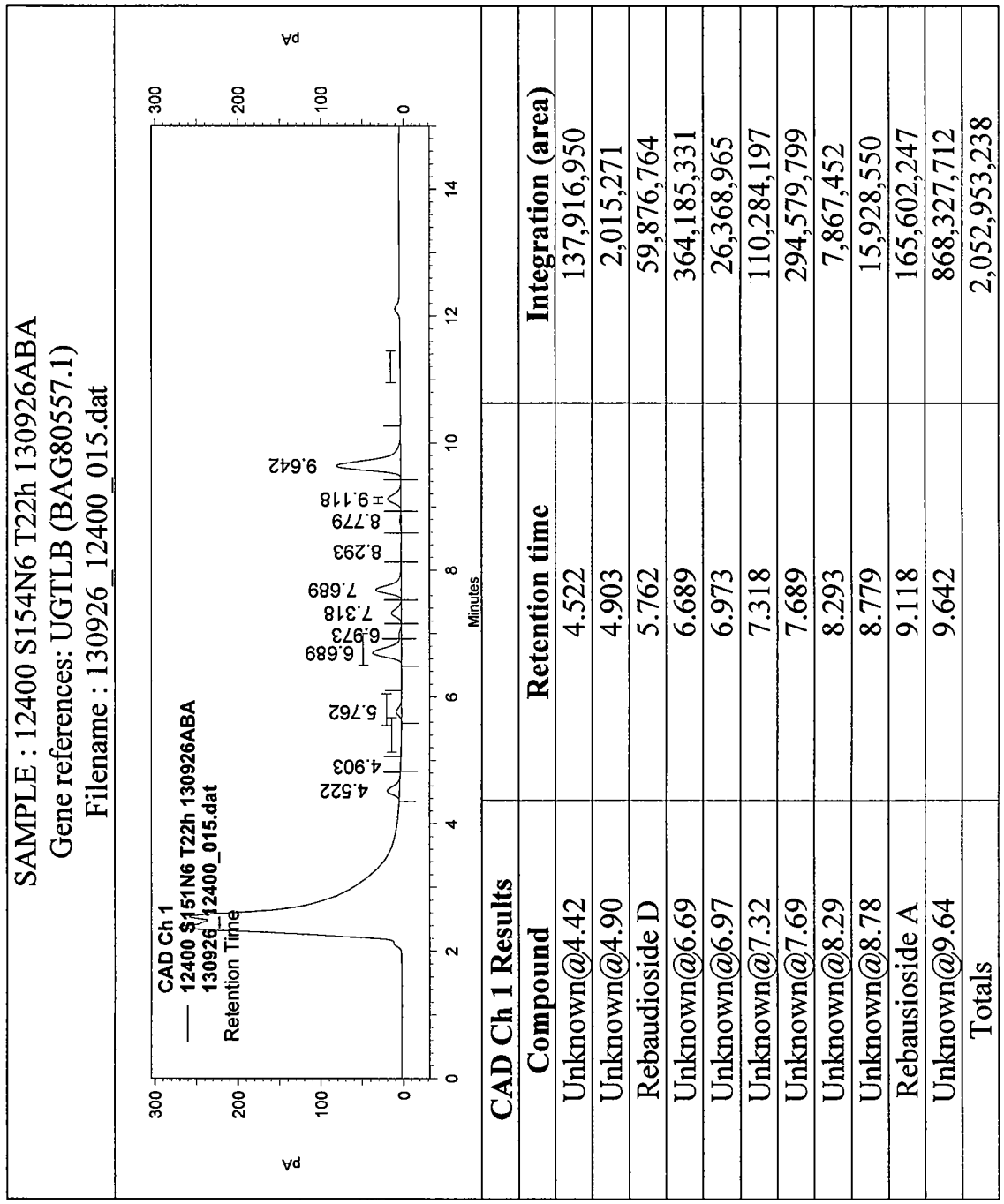

Determination of Activity for Rebaudioside A to Rebaudioside D Conversion with UGTLB Activity tests were performed at 3 mL scale with 600 μL of lysate for the transformation of Rebaudioside A using 0.5 mM of substrate, 2.5 mM of UDP-Glucose and 3 mM MgCl$_2$ in 50 mM Sodium Phosphate buffer at pH 7.2. Samples were taken and analyzed by HPLC. The corresponding chromatogram after 23 h. of reaction is depicted in FIG. 63*c*.

| Enzyme internal reference | GI Number | Version | Rebaudioside A conv.[1] (reaction time) | Rebaudioside D formation[1] |
|---|---|---|---|---|
| UGTLB | 209954733 | BAG80557.1 | 72% (22 h.) | 10% |

Note:
[1]Based on initial concentration of Rebaudioside A

Example 33

Determination of Reaction Products for Rubusoside and Stevioside Conversion with UGTSL, UGTSL2, and UGTLB Conversion of stevioside with UGTSL and UGTSL2 was conducted in similar manner to Example 28, and the conversion of rubusoside with UGTSL and UGTSL2 was conducted similarly to Example 29. Conversions of rubusoside and stevioside with UGTLB was conducted similarly to Example 32.

The reaction mixtures were analyzed by LCMS to determine all reaction products.

Rubusoside Conversion Products have same Molecular Weight as Reb E. Since these compounds have same molecular weight with Reb A and Reb E it can be assumed that these novel steviol glycosides are isomers of Reb A (Reb E).

Example 34

In Vivo Production of UGT76G1 in *S. cerevisiae*
UGT76G1 [*Stevia rebaudiana*] (gi_37993653/gb_AAR06912.1)
SEQ ID NO:11:

MENKTETTVRRRRRIILFPVPFQGHINPILQLANVLYSKGFSITIFHTNF

NKPKTSNYPHFTFRFILDNDPQDERISNLPTHGPLAGMRIPIINEHGADE

LRRELELLMLASEEDEEVSCLITDALWYFAQSVADSLNLRRLVLMTSSLF

NFHAHVSLPQFDELGYLDPDDKTRLEEQASGFPMLKVKDIKSAYSNWQIL

KEILGKMIKQTKASSGVIWNSFKELEESELETVIREIPAPSFLIPLPKHL

TASSSSLLDHDRTVFQWLDQQPPSSVLYVSFGSTSEVDEKDFLEIARGLV

DSKQSFLWVVRPGFVKGSTWVEPLPDGFLGERGRIVKWVPQQEVLAHGAI

GAFWTHSGWNSTLESVCEGVPMIFSDFGLDQPLNARYMSDVLKVGVYLEN

GWERGEIANAIRRVMVDEEGEYIRQNARVLKQKADVSLMKGGSSYESLES

LVSYISSL

The above mentioned amino acid sequence was codon optimized for expression in *S. cerevisiae*. Furthermore the yeast consensus sequence AACACA was added before the

| Sample ID | UGT (reaction time) | LC-MS, peak area ratio (%) | | | | | |
|---|---|---|---|---|---|---|---|
| | | Rub | Stev | REb E | Reb D | Unknown peak #1 (MW804) RT 30.70 min | Unknown peak #2 (MW804) RT 49.50 min | Unknown peak #3 (MW804) RT 50.40 min |
| S151N15 | UGTSL2 (2 hrs) | 3.54 | 2.12 | 52.88 | 6.73 | 12.02 | 9.94 | 12.77 |
| S151N17 | UGTLB (5 hrs) | 13.49 | ND | 9.21 | 1.29 | 4.07 | 66.67 | 5.27 |
| S151N22 | UGTSL (45 hrs) | 7.82 | 2.37 | 35.88 | 3.45 | 20.38 | 27.75 | 2.35 |

Stevioside Conversion Products

| Sample ID | UGT (reaction time) | LC-MS, peak area ratio (%) | | | | | |
|---|---|---|---|---|---|---|---|
| | | Stev | Reb E | Reb D | Unknown peak #1 (MW966) RT = 22.60 min | Unknown peak #2 (MW966) RT = 26.50 min | Unknown peak #3 (MW966) RT = 29.50 min |
| S151N26 | UGTSL2 (2 hrs) | 20.01 | 42.56 | 1.70 | 4.48 | 5.56 | 25.70 |
| S151N28 | UGTLB (2 hrs) | 43.11 | 3.12 | ND | ND | 53.78 | ND |
| S151N33 | UGTSL (22 hrs) | 25.24 | 49.68 | 0.54 | 3.97 | 20.56 | ND |

It can be seen that amongst Rubusoside conversion products, besides Stevioside, Reb E and Reb D, there are at least 3 additional compounds with Molecular Weight of 804. The retention time of these compounds do not match with Reb B which is known to have same Molecular Weight as Stevioside. Since these compounds have same molecular weight with Stevioside it can be assumed that these novel steviol glycosides are isomers of Stevioside. On the other hand amongst Stevioside conversion products, besides Reb E and Reb D, there are at least 3 additional compounds with Molecular Weight of 966. The retention time of these compounds do not match with Reb A which is known to ATG start codon. The synthetic gene was subcloned in the pYES2 vector using Hind III and Xba I restriction sites. The pYES2_UGT76G1_Sc vector was used to transform chemically competent *S. cerevisiae* INVSc1 cells (Invitrogen).

The cells were grown on a solid synthetic minimal medium containing 2% glucose lacking Uracil and a single colony was picked and allowed to grow in liquid synthetic minimal medium lacking Uracil (SC-U containing 2% glucose). After centrifugation, the cells were suspended with SC-U (containing 2% glucose) and 60% glycerol/water. Aliquots were stored at −80° C. and one aliquot was used to start a culture in SC-U (containing 2% glucose) for 43 h at 30° C. Part of this culture was centrifuged and suspended in induction medium (SC-U containing 2% galactose) for 19h30 at 30° C.

Cells were obtained by centrifugation and lysis with five volumes of CelLytic™ Y Cell Lysis Reagent (Sigma). The lysates were used directly for activity testing (UGT76G1_Sc).

Example 35

Figure 64:
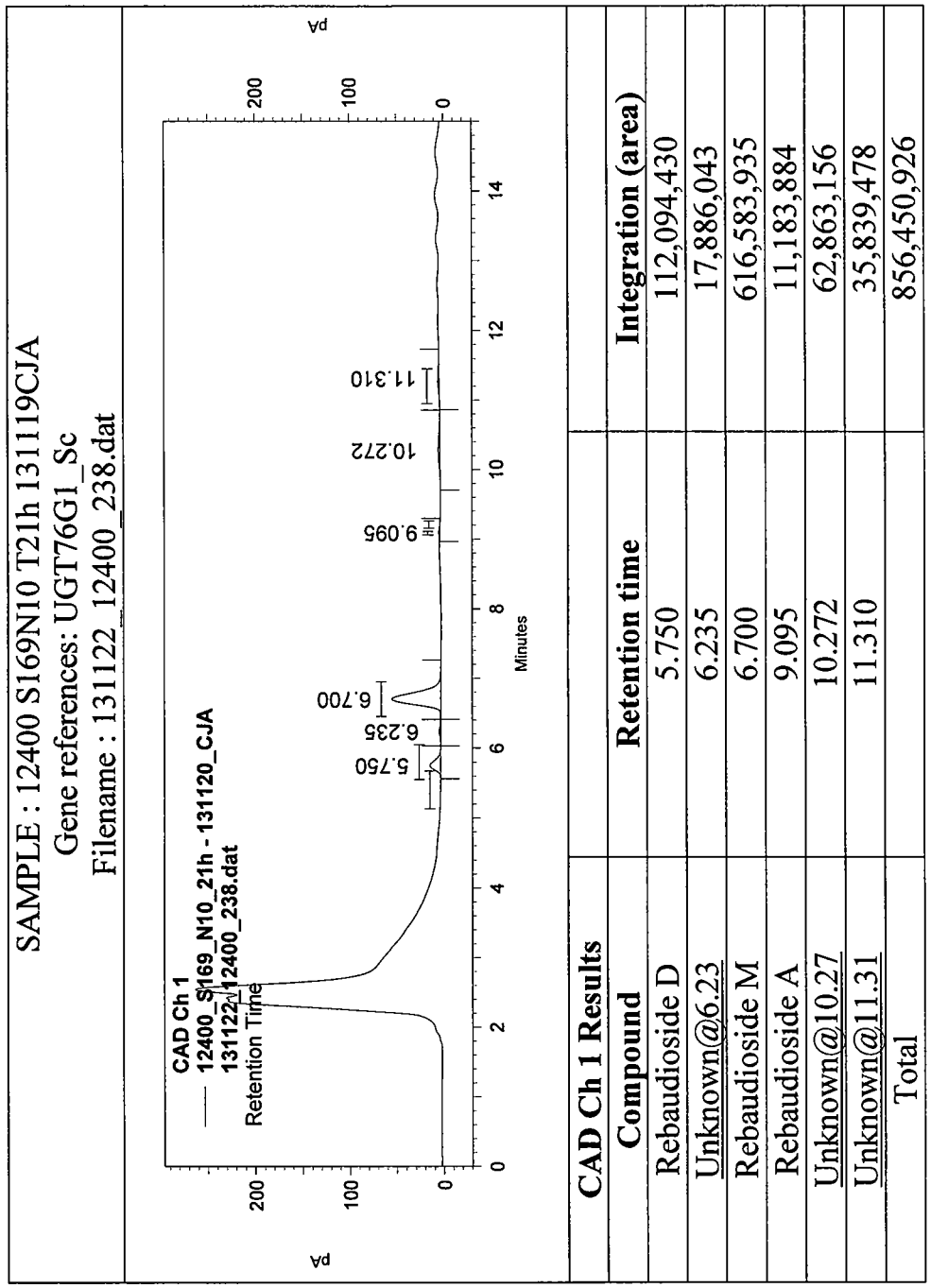
FIG. 64 shows an HPLC chromatogram showing the HPLC assay results for Example 35.

Determination of Activity of UGT76G1_Sc for the Conversion of Rebaudioside D to Rebaudioside M UGT76G1_Sc was prepared according to EXAMPLE 34. Activity tests were performed at 2 mL scale with 200 μL of lysate for the transformation of Rebaudioside D using 0.5 mM of substrate, 2.5 mM of UDP-Glucose and 3 mM $MgCl_2$ in 50 mM Sodium Phosphate buffer at pH 7.2. Samples were taken and analyzed by HPLC. The corresponding chromatogram is depicted in FIG. 64.

| Enzyme internal reference | Rebaudioside D conv.[1] (reaction time) | Rebaudioside M selectivity[1] |
|---|---|---|
| UGT76G1_Sc | 85% (21 h.) | 100% |

Note:
[1]Based on initial concentration of Rebaudioside D

Example 36

In Vivo Production of UGTSL in *S. cerevisiae*

UGTSL [*Solanum lycopersicum*] (gi_460409128/XP_004249992.1
SEQ ID NO:12:

MSPKLHKELFFHSLYKKTRSNHTMATLKVLMFPPFLAYGHISPYLNVAKKL

ADRGFLIYFCSTPINLKSTIEKIPEKYADSIHLIELHLPELPQLPPHYHT

TNGLPPNLNQVLQKALKMSKPNFSKILQNLKPDLVIYDILQRWAKHVANE

QNIPAVKLLTSGAAVFSYFFNVLKKPGVEFPFPGIYLRKIEQVRLSEMMS

KSDKEKELEDDDDDDDLLVDGNMQIMLMSTSRTIEAKYIDFCTALTNWKV

VPVGPPVQDLITNDVDDMELIDWLGTKDENSTVFVSFGSEYFLSKEDMEE

VAFALELSNVNFIWVARFPKGEERNLEDALPKGFLERIGERGRVLDKFAP

QPRILNHPSTGGFISHCGWNSAMESIDFGVPIIAMPMHLDQPMNARLIVE

LGVAVEIVRDDDGKIHRGEIAETLKGVITGKTGEKLRAKVRDISKNLKTI

RDEEMDAAAEELIQLCRNGN

The above mentioned amino acid sequence was codon optimized for expression in *S. cerevisiae*. Furthermore the yeast consensus sequence AACACA was added before the ATG start codon. The synthetic gene was subcloned in the pYES2 vector using Hind III and Xba I restriction sites. The pYES2_UGTSL_Sc vector was used to transform chemically competent *S. cerevisiae* INVSc1 cells (Invitrogen).

The cells were grown on a solid synthetic minimal medium containing 2% glucose, lacking Uracil and a single colony was picked and allowed to grow in liquid synthetic minimal medium lacking Uracil (SC-U containing 2% glucose). After centrifugation, the cells were suspended with SC-U (containing 2% glucose) and 60% glycerol/water. Aliquots were stored at −80° C. and one aliquot was used to start a culture in SC-U (containing 2% glucose) for 43 h at 30° C. Part of this culture was centrifuged and suspended in induction medium (SC-U containing 2% galactose) for 19h30 at 30° C. Cells were obtained by centrifugation and lysis with five volumes of CelLytic™ Y Cell Lysis Reagent (Sigma). The lysates were used directly for activity testing (UGTSL_Sc).

Example 37

Figure 65:
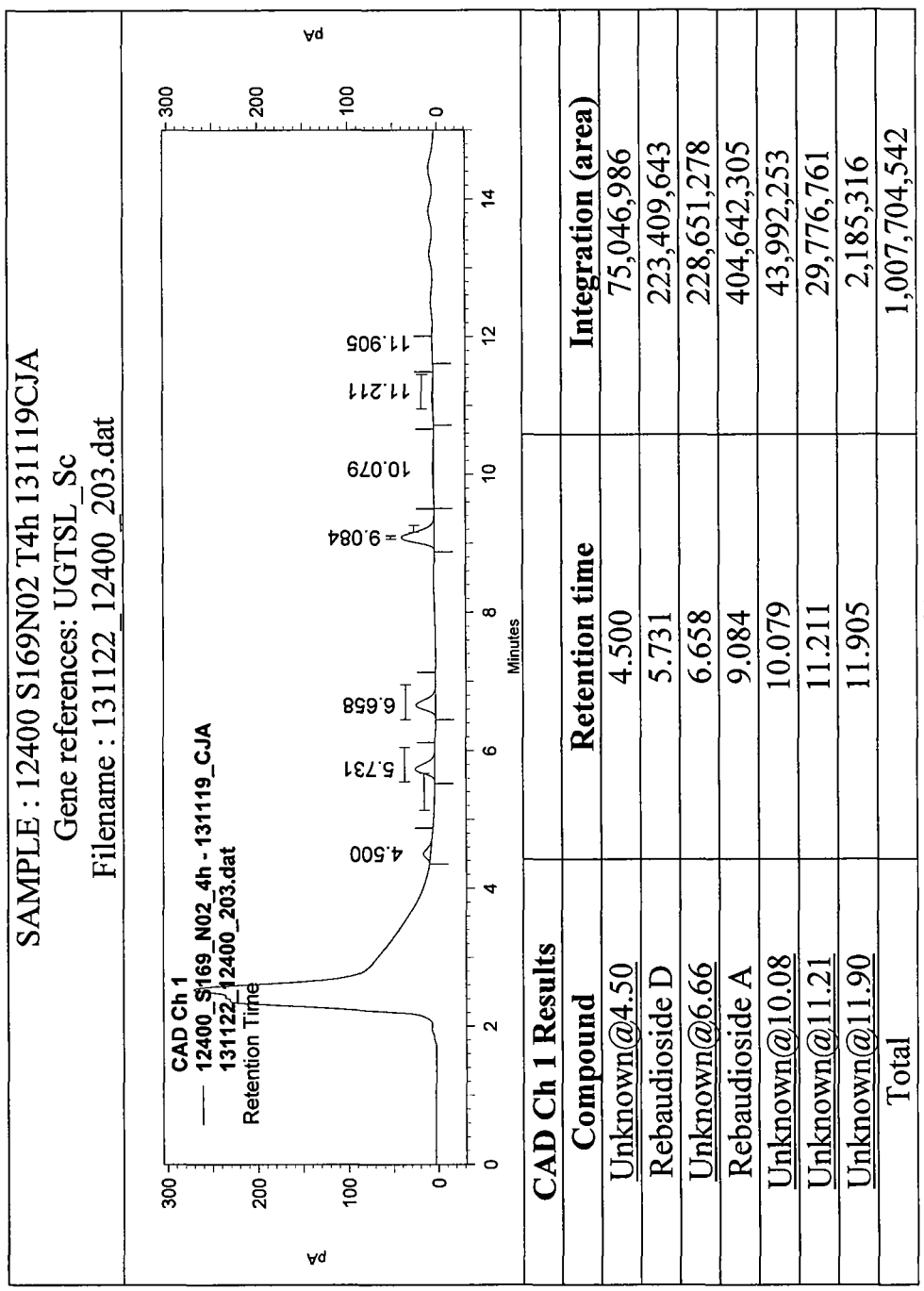
FIG. 65 shows an HPLC chromatogram showing the HPLC assay results for Example 37

Determination of Activity of UGTSL_Sc for the Conversion of Rebaudioside A to Rebaudioside D UGTSL_Sc was prepared according to EXAMPLE 36. Activity tests were performed at 2 mL scale with 200 μL of lysate for the transformation of Rebaudioside A using 0.5 mM of substrate, 2.5 mM of UDP-Glucose and 3 mM $MgCl_2$ in 50 mM Sodium Phosphate buffer at pH 7.2. Samples were taken and analyzed by HPLC. The corresponding chromatogram is depicted in FIG. 65.

| Enzyme internal reference | Rebaudioside A conv.[1] (reaction time) | Rebaudioside D selectivity[1] |
|---|---|---|
| UGTSL_Sc | 46% (4 h) | 42% |

Note:
[1]Based on initial concentration of Rebaudioside A

Example 38

Isolation of Rebaudioside M

The amount of the product mixture of Example 14 was not large enough to separate via preparative HPLC methods. Accordingly, analytical HPLC with a series of injections was used to separate the components of the mixture. Separation was conducted according to the method described above in Example 14 to provide two fractions corresponding to the two main peaks in the HPLC trace of FIG. 5: Fraction A (retention time 24.165 minutes) and Fraction B (retention time 31.325 minutes).

The retention time of Fraction A was consistent with reb D, indicating unreacted starting material from the biotransformation reaction.

Figure 6:
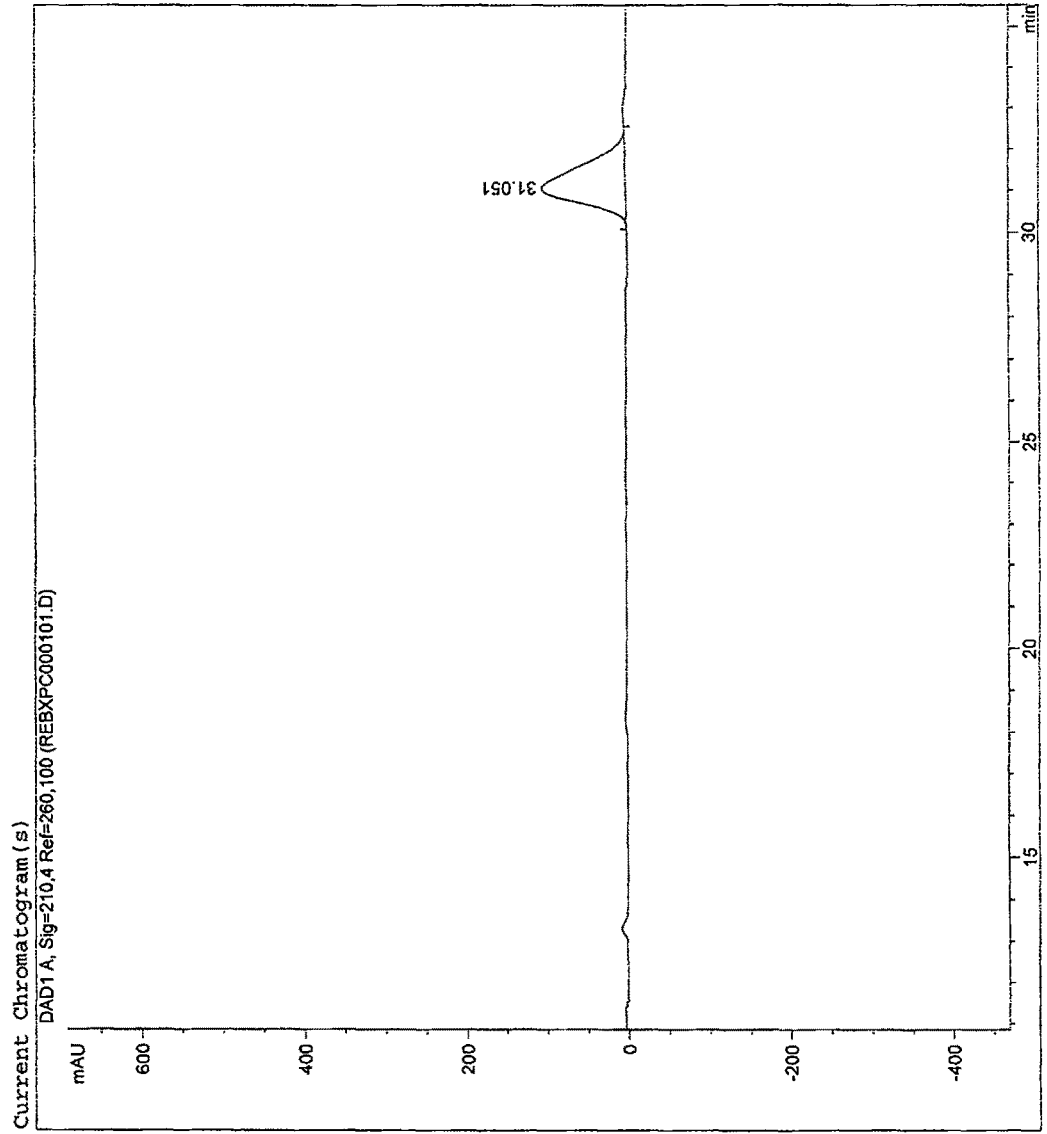
FIG. 6. shows the HPLC chromatogram of purified reb M produced by biocatalysis from reb D.
Figure 7:
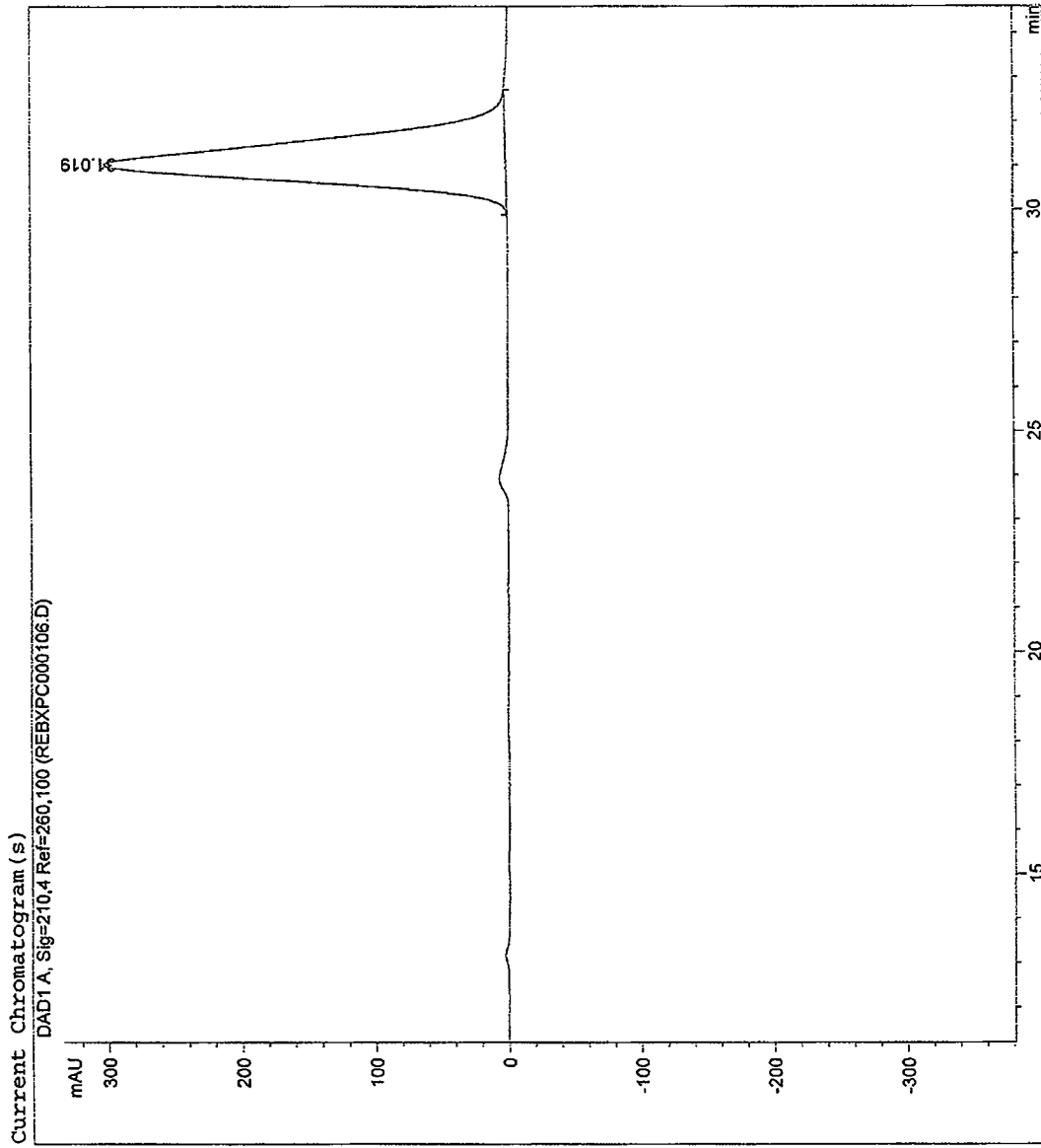
FIG. 7 shows the HPLC chromatogram of a reb M standard.
Figure 8:
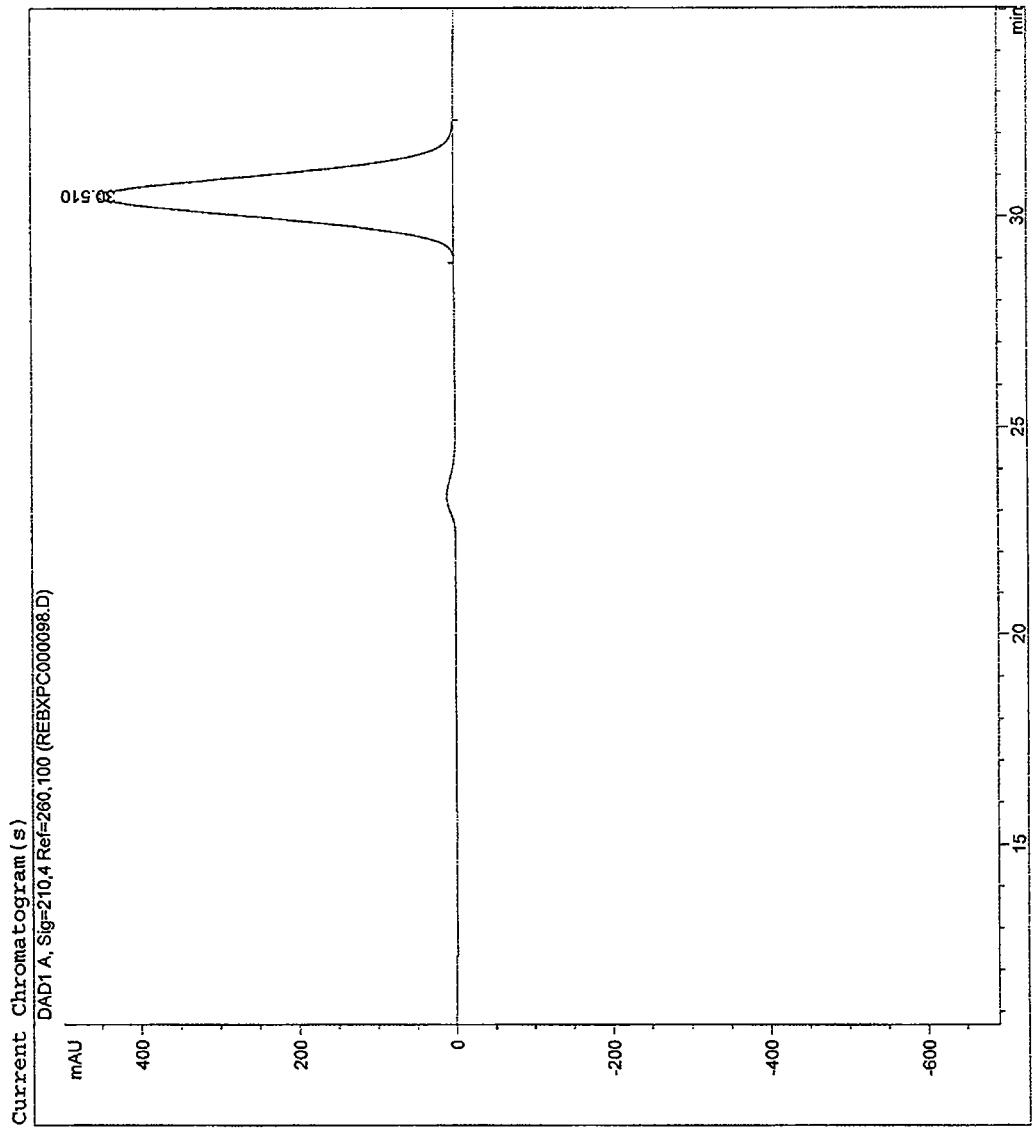
FIG. 8 shows the HPLC chromatogram of co-injection of a reb M standard and reb M purified from biotransformation from reb D.

The retention time of purified Fraction B (FIG. 6) was consistent with reb M, indicating successful biotransformation from reb D. The identity of the material collected in Fraction B as reb M was confirmed by co-injection of purified Fraction B with a reb M standard (available from PureCircle, HPLC trace of reb M standard shown in FIG. 7). Both Fraction B and the reb M standard were found to elute at the same retention time (FIG. 8), indicating Fraction B was reb M.

The identity of Fraction B as reb M was also separately confirmed by NMR and HRMS. For sampling, Fraction B was concentrated under rotary evaporator, freeze dried and dried for 40 h at 40° C.

Figure 9:
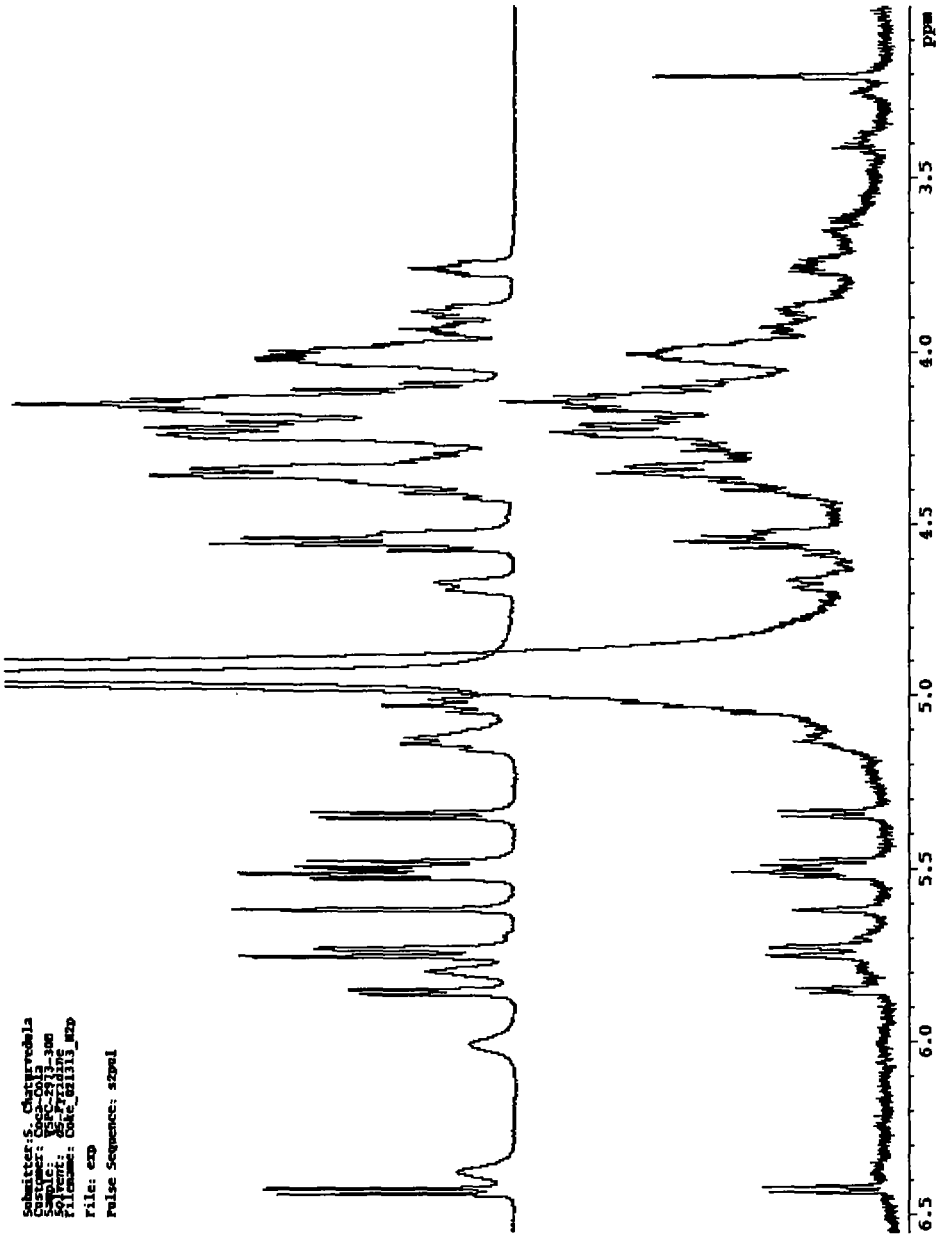
FIG. 9 shows an overlay of the $^1$H NMR spectra of a reb M standard and reb M purified following biosynthesis from reb D.

The NMR sample was dissolved in deuterated pyridine ($C_5D_5N$) and spectra were acquired on a Varian Unity Plus 600 MHz instrument using standard pulse sequences. The NMR spectra of Fraction B was compared to the NMR spectra of reb M. An overlay of the two spectra (FIG. 9) showed consistency of peaks of Fraction B with reb M. A table of the NMR assignments for reb M is shown below:

| $^{1}$H and $^{13}$C NMR spectral data for Rebaudioside M in $C_5D_5N^{a-c}$. | | |
|---|---|---|
| Position | $^{13}$C NMR | $^{1}$H NMR |
| 1 | 40.3 | 0.75 t (13.2) |
|  |  | 1.76 m |
| 2 | 19.6 | 1.35 m |
|  |  | 2.24 m |
| 3 | 38.4 | 1.01 m |
|  |  | 2.30 d (13.3) |
| 4 | 44.3 | — |
| 5 | 57.4 | 1.06 d (12.8) |
| 6 | 23.5 | 2.23 m |
|  |  | 2.41 q (13.2) |
| 7 | 42.6 | 1.41 m |
|  |  | 1.80 m |
| 8 | 41.2 | — |
| 9 | 54.3 | 0.91 d (7.7) |
| 10 | 39.7 | — |
| 11 | 20.2 | 1.65 m |
|  |  | 1.75 m |
| 12 | 38.5 | 1.86 m |
|  |  | 2.73 m |
| 13 | 87.6 | — |
| 14 | 43.3 | 2.02 m |
|  |  | 2.74 m |
| 15 | 46.5 | 1.88 d (16.4) |
|  |  | 2.03 m |
| 16 | 153.3 | — |
| 17 | 104.9 | 4.90 s |
|  |  | 5.69 s |
| 18 | 28.2 | 1.32 s |
| 19 | 176.9 | — |
| 20 | 16.8 | 1.38 s |
| 1' | 94.9 | 6.39 d (8.2) |
| 2' | 76.9 | 4.51 t (8.5) |
| 3' | 88.6 | 5.09 t (8.5) |
| 4' | 70.1 | 4.18 m |
| 5' | 78.4 | 4.13 m |
| 6' | 61.8 | 4.20 m |
|  |  | 4.31 m |
| 1'' | 96.2 | 5.46 d (7.1) |
| 2'' | 81.4 | 4.13 m |
| 3'' | 87.9 | 4.98 t (8.5) |
| 4'' | 70.4 | 4.07 t (9.6) |
| 5'' | 77.7 | 3.94 m |
| 6'' | 62.6 | 4.19 m |
|  |  | 4.32 m |
| 1''' | 104.8 | 5.48 d (7.7) |
| 2''' | 75.8 | 4.15 m |
| 3''' | 78.6 | 4.13 m |
| 4''' | 73.2 | 3.98 m |
| 5''' | 77.6 | 3.74 ddd (2.8, 6.4, 9.9) |
| 6''' | 64.0 | 4.27 m |
|  |  | 4.51 m |
| 1'''' | 103.9 | 5.45 d (7.5) |
| 2'''' | 75.6 | 3.98 m |
| 3'''' | 77.8 | 4.50 t (7.8) |
| 4'''' | 71.3 | 4.14 m |
| 5'''' | 78.0 | 3.99 m |
| 6'''' | 62.1 | 4.20 m |
|  |  | 4.32 m |
| 1''''' | 104.2 | 5.81 d (7.2) |
| 2''''' | 75.5 | 4.20 m |
| 3''''' | 78.4 | 4.20 m |
| 4''''' | 73.6 | 4.10 m |
| 5''''' | 77.8 | 3.90 ddd (2.8, 6.4, 9.9) |
| 6''''' | 64.0 | 4.32 m |
|  |  | 4.64 d (10.3) |
| 1'''''' | 104.1 | 5.31 d (8.0) |
| 2'''''' | 75.5 | 3.95 m |
| 3'''''' | 78.0 | 4.37 t (9.1) |
| 4'''''' | 71.1 | 4.10 m |
| 5'''''' | 78.1 | 3.85 ddd (1.7, 6.1, 9.9) |
| 6'''''' | 62.1 | 4.10 m |
|  |  | 4.32 m |

$^a$assignments made on the basis of COSY, HMQC and HMBC correlations;
$^b$Chemical shift values are in δ (ppm);
$^c$Coupling constants are in Hz.

Figure 10:
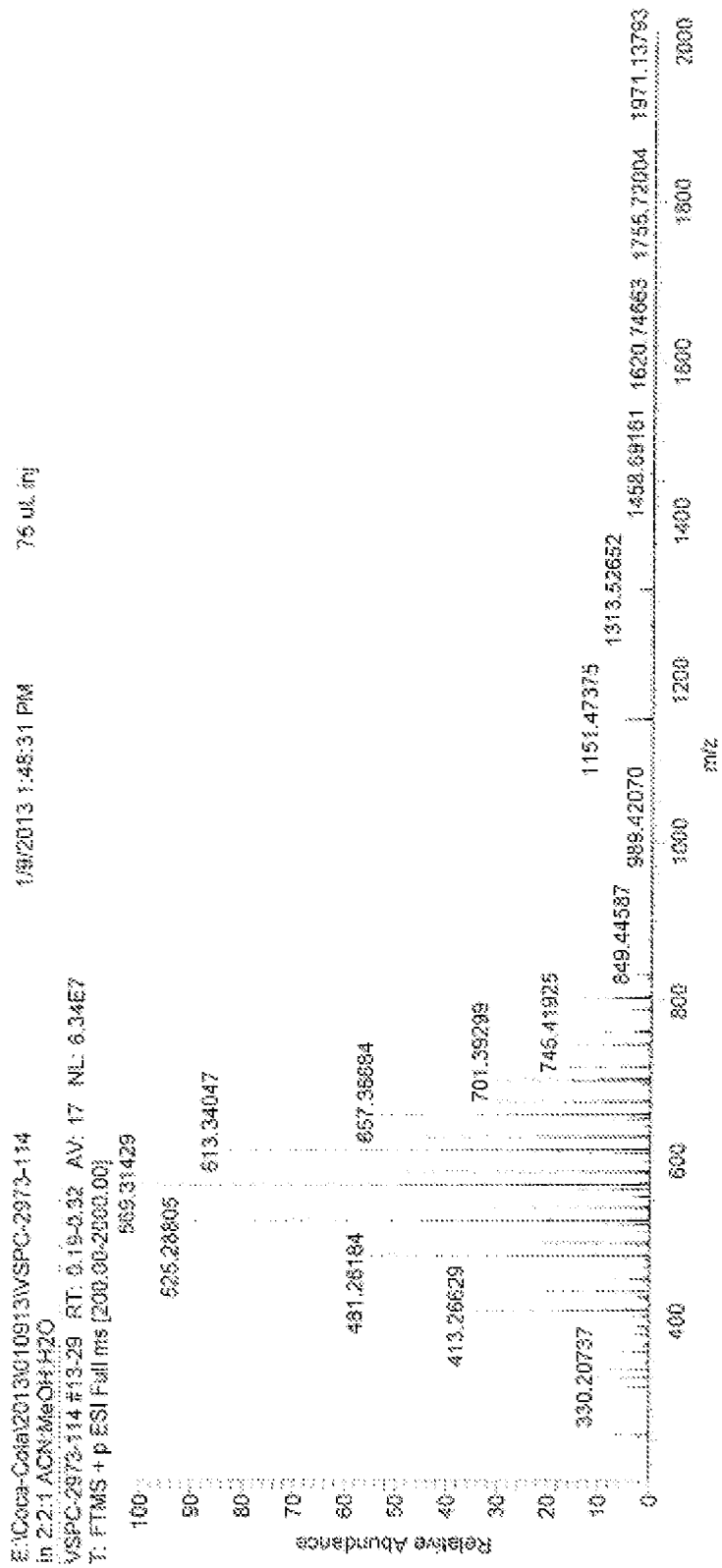
FIG. 10 shows the HRMS spectrum of reb M purified following biocatalytic production from reb D.

HRMS (FIG. 10) was generated with a Waters Premier Quadropole Time-of-Flight (Q-TOF) mass spectrometer equipped with an electrospray ionization source operated in the positive-ion mode. The sample was dissolved in methanol and eluted in 2:2:1 methanol: acetonitrile: water and introduced via infusion using the onboard syringe pump. The presence of reb M was confirmed by a $[M+Na]^+$ adduct at m/z 1313.5265, which corresponds to a molecular formula of $C_{56}H_{90}O_{33}$

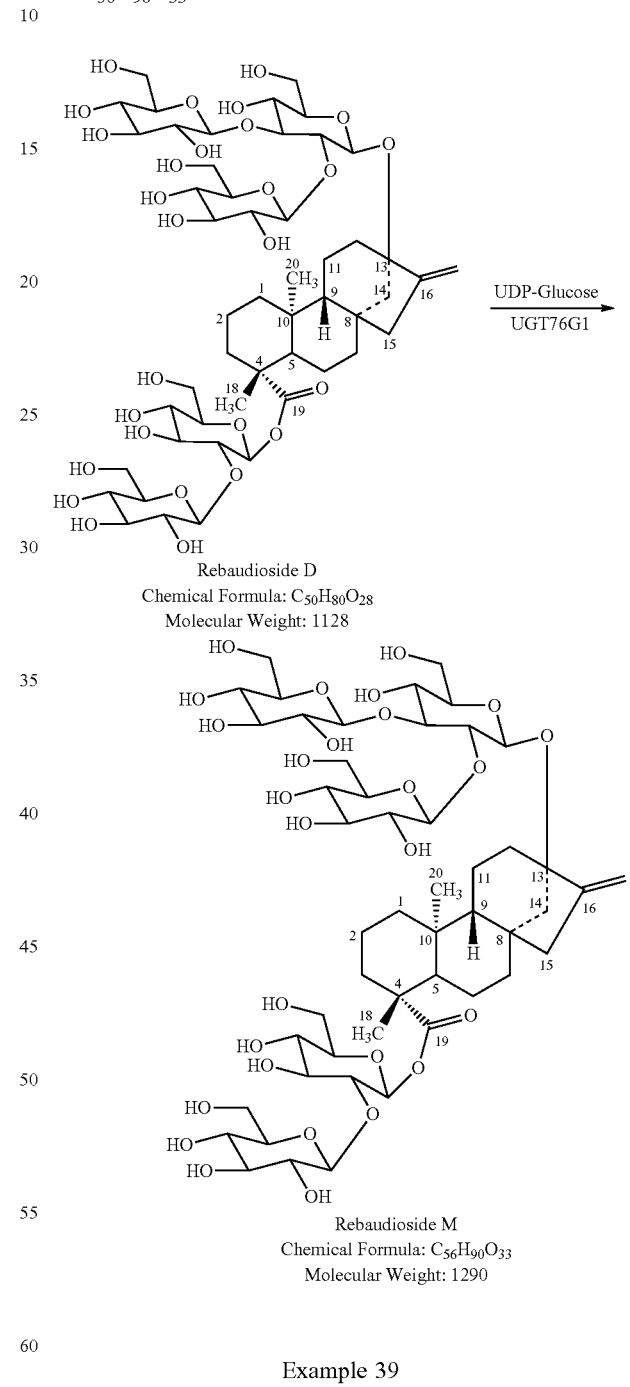

Rebaudioside D
Chemical Formula: $C_{50}H_{80}O_{28}$
Molecular Weight: 1128

Rebaudioside M
Chemical Formula: $C_{56}H_{90}O_{33}$
Molecular Weight: 1290

Example 39

Isolation and Characterization of Reb D2
Crude Reaction Sample.
The sample, Lot CB-2977-106, used for isolation, was prepared according to Example 22 with UGTSL (GI #460409128).

HPLC Analysis.

Preliminary HPLC analyses of samples were performed using a Waters 2695 Alliance System with the following method: Phenomenex Synergi Hydro-RP, 4.6×250 mm, 4 μm (p/n 00G-4375-E0); Column Temp: 55° C.; Mobile Phase A: 0.0284% ammonium acetate (NH$_4$OAc) and 0.0116% acetic acid (HOAc) in water; Mobile Phase B: Acetonitrile (MeCN); Flow Rate: 1.0 mL/min; Injection volume: 10 μL. Detection was by UV (210 nm) and CAD.

Gradient:

| Time (min) | % A | % B |
|---|---|---|
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31-37 | 30 | 70 |
| 38 | 75 | 25 |

Analyses of semi-preparative purification fractions were performed with the following method: Waters Atlantis dC18, 4.6×100 mm, 5 μm (p/n 186001340); Mobile Phase A: 25% MeCN in water; Mobile Phase B: 30% MeCN in water; Flow Rate: 1.0 mL/min; Injection volume: 10 μL. Detection was by CAD.

Gradient:

| Time (min) | % A | % B |
|---|---|---|
| 0.0-5.0 | 100 | 0 |
| 20 | 20 | 80 |
| 25 | 20 | 80 |
| 30 | 100 | 0 |

LC-MS.

Preliminary analysis of the semi-synthetic steviol glycoside mixture was carried out on a Waters AutoPurification HPLC/MS System with a Waters 3100 Mass Detector operating in negative ion mode. Analysis of the sample was performed using the following method: Phenomenex Synergi Hydro-RP, 4.6×250 mm, 4 μm (p/n 00G-4375-E0); Column Temp: 55° C.; Mobile Phase A: 0.0284% NH$_4$OAc and 0.0116% HOAc in water; Mobile Phase B: Acetonitrile; Flow Rate: 1.0 mL/min; Injection volume: 10 μL. Detection was by UV (210 nm), and MSD (−ESI m/z 500-2000). Gradient conditions were as listed above.

Isolation by HPLC.

The purification was performed in two steps. The first method used for the semi-preparative purification is summarized below. Column: Waters Atlantis dC18, 30×100 mm, 5 μm (p/n 186001375); Mobile Phase A: 25% MeCN in water; Mobile Phase B: 30% MeCN in water; Flow Rate: 45 mL/min; Injection load: 160 mg dissolved in 20 mL of water. Detection was by UV (205 nm).

Gradient:

| Time (min) | % A | % B |
|---|---|---|
| 0.0-5.0 | 100 | 0 |
| 20 | 20 | 80 |
| 25 | 20 | 80 |
| 30 | 100 | 0 |

The secondary purification used the same column and conditions, but isocratic mobile phase: 20% MeCN in water.

Purification from Natural Extracts.

The purification was performed in three steps. The first method used for the preparative purification is summarized below. Primary Process: Waters Symmetry C18, 50×250 mm, 7 μm (p/n WAT248000); Isocratic mobile phase: 50% methanol (MeOH) in water with 0.05% HOAc; Flow Rate: 85 mL/min; Injection load: 6 g crude extract dissolved in 50 mL of mobile phase. Detection was by UV (210 nm). Following the elution of target analytes, the column was flushed with 85% MeOH in water.

Secondary Process: Waters Symmetry Shield RP18, 50×250 mm, 7 μm (p/n WAT248000); Isocratic mobile phase: 20% MeCN in water; Flow Rate: 100 mL/min; Injection load: 0.5 g primary fraction dissolved in 30 mL of water. Detection was by UV (210 nm).

Tertiary Process: Waters Symmetry Shield RP18, 50×250 mm, 7 μm (p/n WAT248000); Isocratic mobile phase: 20% MeCN in water; Flow Rate: 100 mL/min; Injection load: 0.5 g secondary fraction dissolved in 30 mL of water. Detection was by UV (210 nm).

MS and MS/MS.

MS and MS/MS data were generated with a Waters QT of Premier mass spectrometer equipped with an electrospray ionization source. Samples were analyzed by negative ESI. Samples were diluted with H$_2$O:acetonitrile (1:1) by 50 fold and introduced via infusion using the onboard syringe pump. The samples were diluted to yield good s/n which occurred at an approximate concentration of 0.01 mg/mL.

NMR.

The sample was prepared by dissolving 1-2 mg in 150 μL of pyridine-d$_5$ and NMR data were acquired on a Bruker Avance 500 MHz instrument with a 2.5 mm inverse detection probe. The $^1$H NMR spectrum was referenced to the residual solvent signal ($\delta_H$ 8.74 and $\delta_C$ 150.35 for pyridine-d$_5$).

Results and Discussion

Isolation and Purification.

Figure 11:
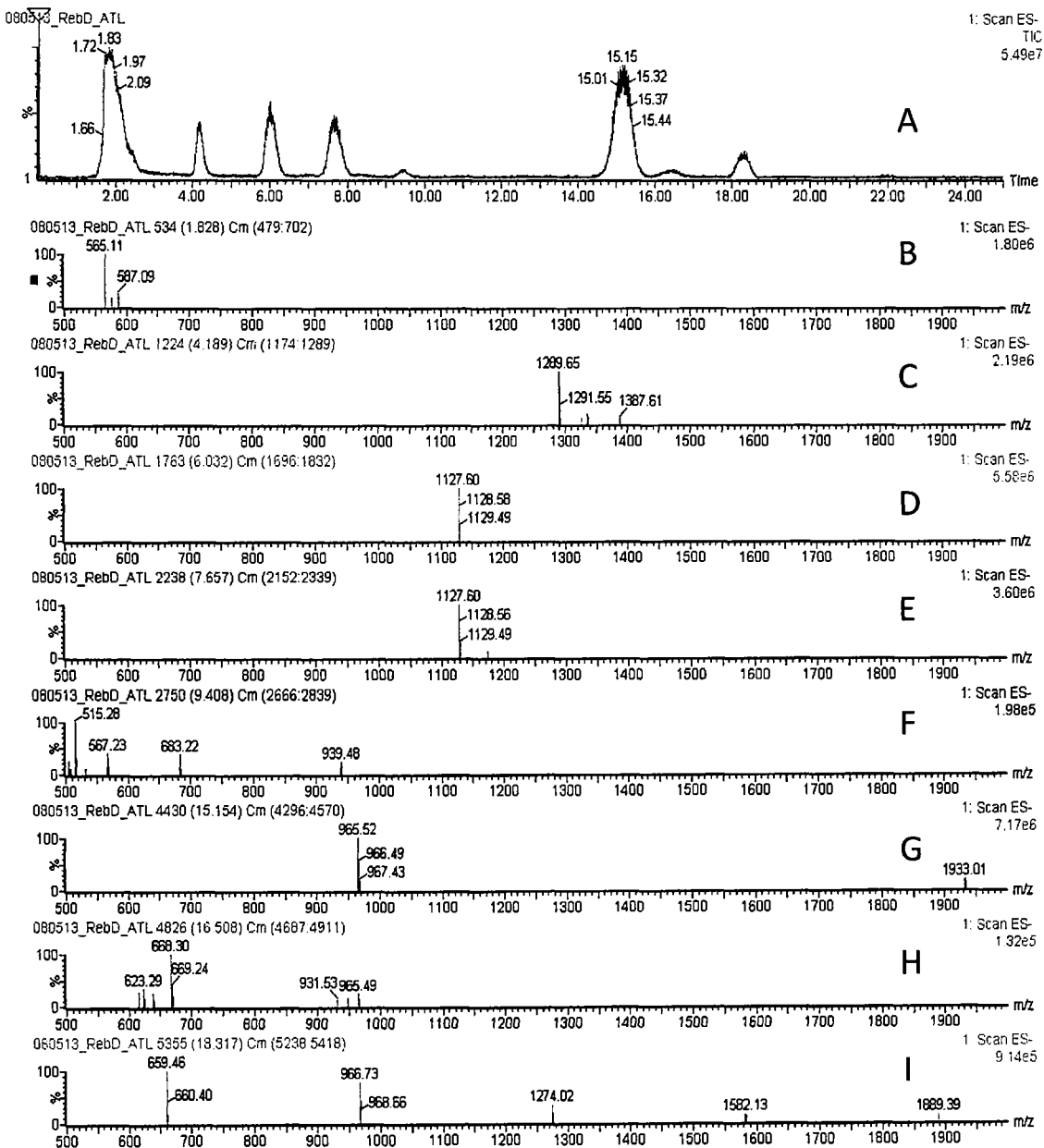
FIG. 11 shows LC-MS analysis of semi-synthetic steviol glycoside mixture, Lot number CB-2977-106, showing TIC (A), MS of peak at 1.8 min (B), MS of reb M2 peak at 4.1 min (C), MS of reb D peak at 6.0 min (D), MS of reb D2 peak at 7.7 min (E), MS of peak at 9.4 min (F), MS of rebaudioside Apeak at 15.2 min (G), MS of peak at 16.5 min (H), and MS of peak at 18.3 min (I).

Isolation was performed on steviol glycoside mixture, Lot number CB-2977-106, prepared according to Example 22 with UGTSL (GI #460409128) The material was analyzed by LC-MS using the method described above and results are provided in FIG. 11. The targeted peak of interest was that at 7.7 min in the TIC chromatogram. The mass spectrum of this peak provided a [M-H]$^-$ ion at m/z 1127.6. The provided sample was preliminarily processed in a single injection (160 mg) using the first method condition provided above. This method fractionated the material into 'polar' and 'non-polar' mixtures of glycosides. The 'polar' mixture was then reprocessed using the second-step conditions above. The semi-preparative HPLC trace is provided in FIG. 12. From this semi-preparative collection, the compound was isolated with a purity >99% (CAD, AUC). The fraction analysis is provided in FIG. 13. Following the purification, the combined fractions were concentrated by rotary evaporation at 35° C. and lyophilized. Approximately 1-2 mg was obtained for characterization.

Mass Spectrometry.

The ESI-TOF mass spectrum acquired by infusing a sample showed a [M-H]$^-$ ion at m/z 1127.4709. The mass of the [M-H]$^-$ ion was in good agreement with the molecular formula $C_{50}H_{80}O_{28}$ (calcd for $C_{50}H_{79}O_{28}$: 1127.4758, error: −4.3 ppm). The MS data confirmed a nominal mass of 1128 Daltons with the molecular formula, $C_{50}H_{80}O_{28}$.

The MS/MS spectrum (selecting the [M-H]$^-$ ion at m/z 1127.5 for fragmentation) indicated the loss of two glucose units and sequential loss of three glucose moieties at m/z 641.3187, 479.2655 and 317.2065.

NMR Spectroscopy.

Figure 14:
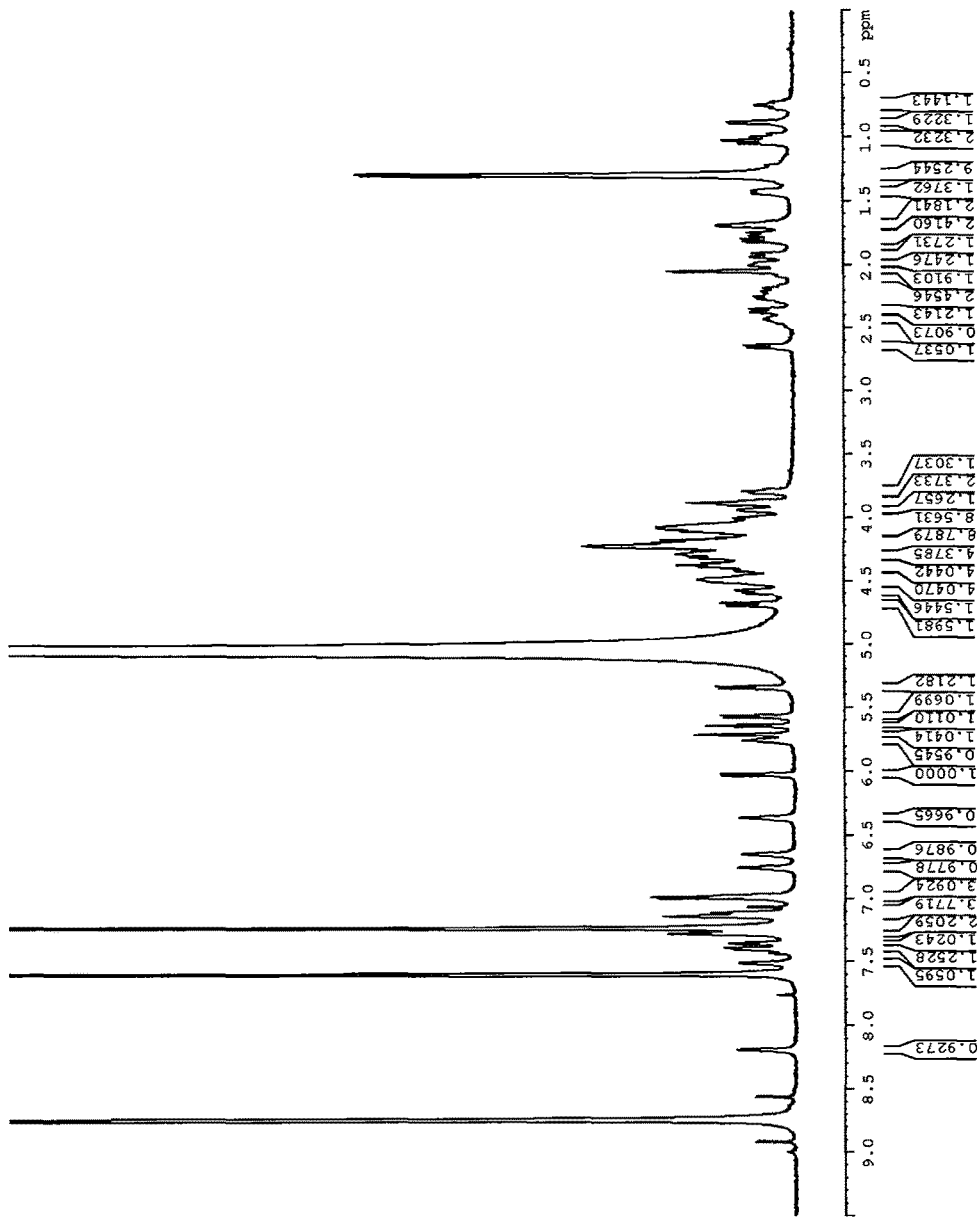
FIG. 14 shows the $^1$H NMR spectrum of reb D2 (500 MHz, pyridine-$d_5$).
Figure 15:
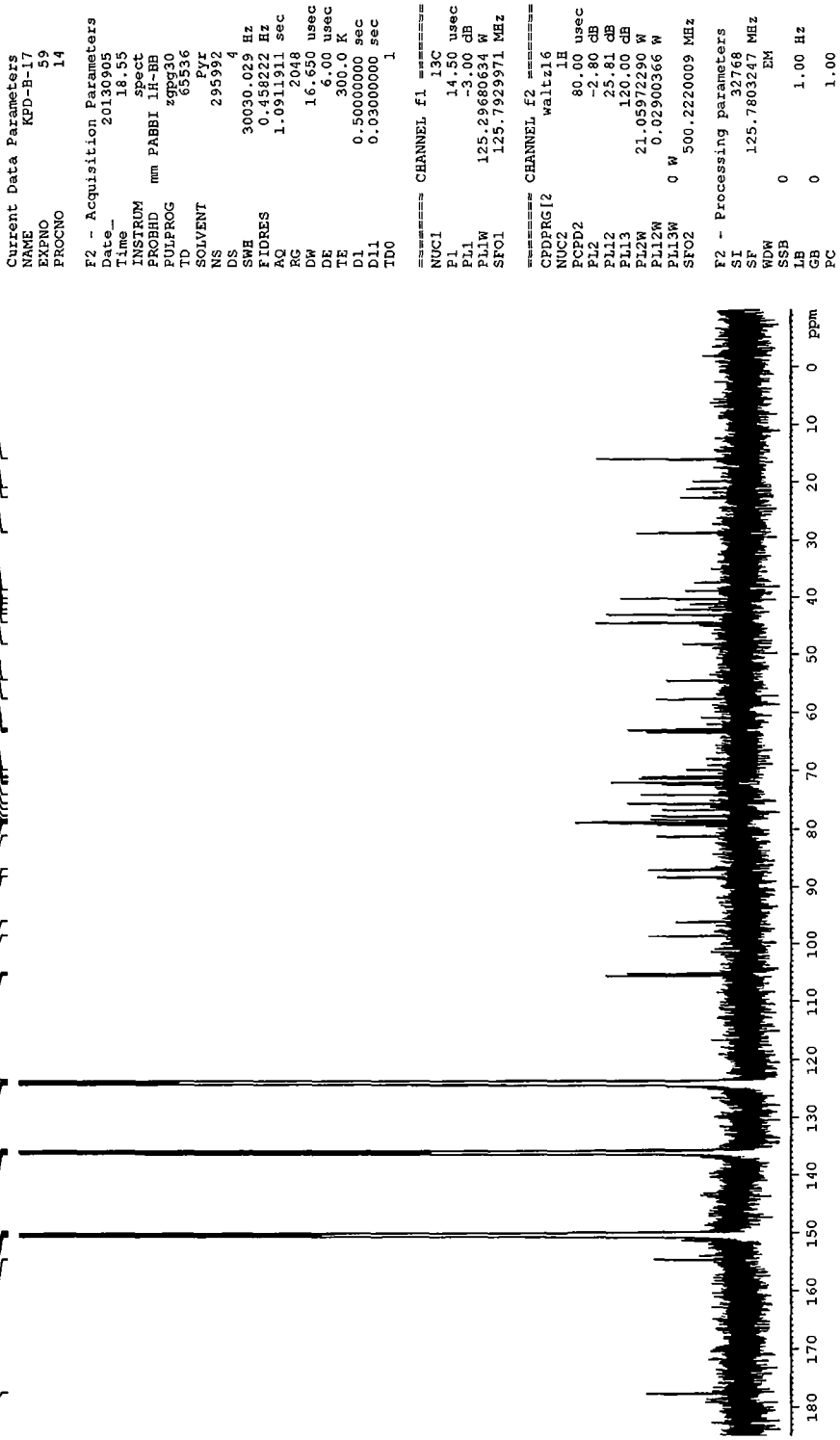
FIG. 15 shows the $^{13}$C NMR spectrum of reb D2 (125 MHz, pyridine-$d_5$).
Figure 16:
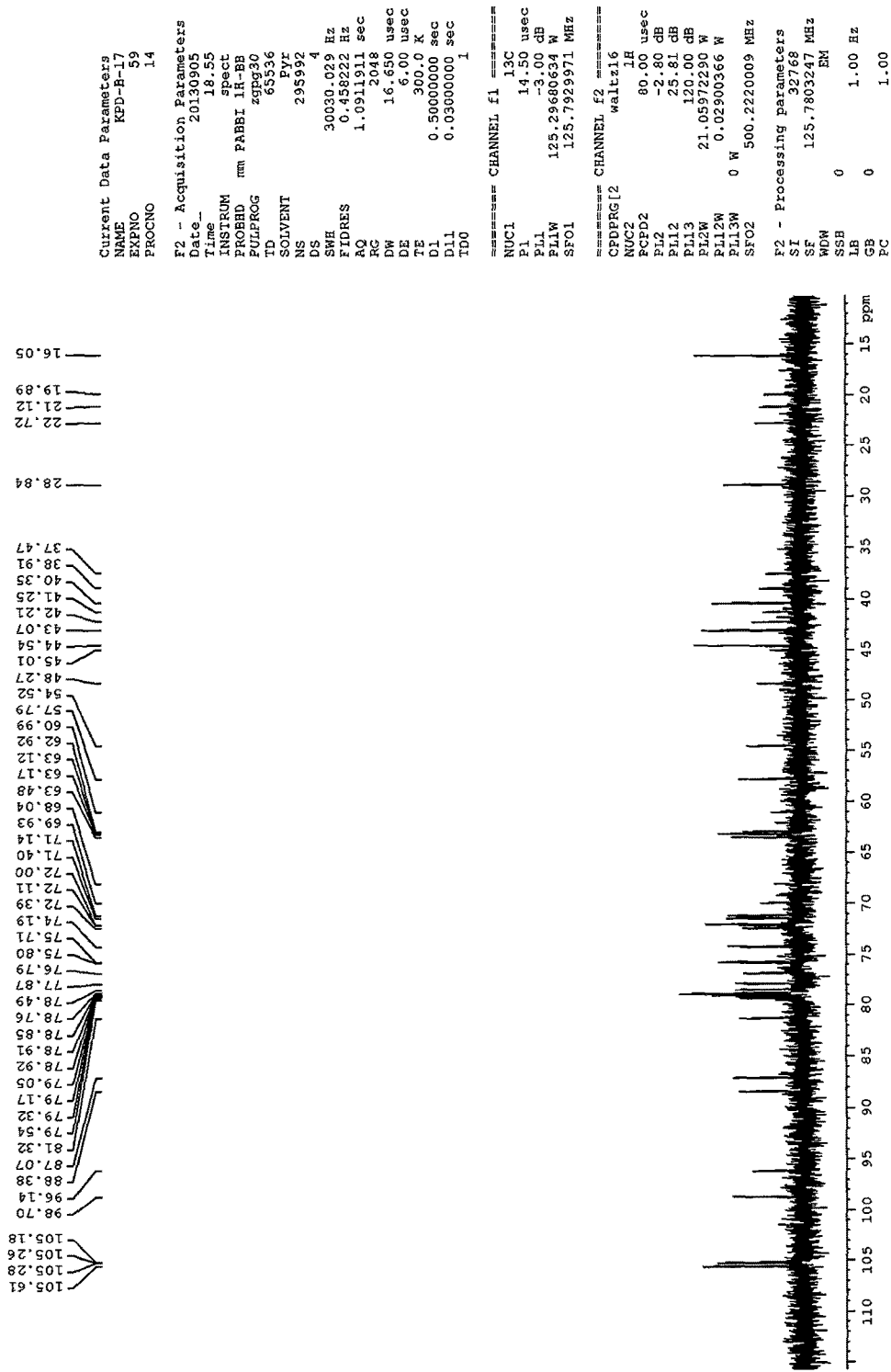
FIG. 16 shows an expansion of the $^{13}$C NMR spectrum of reb D2 (125 MHz, pyridine-$d_5$).
Figure 17:
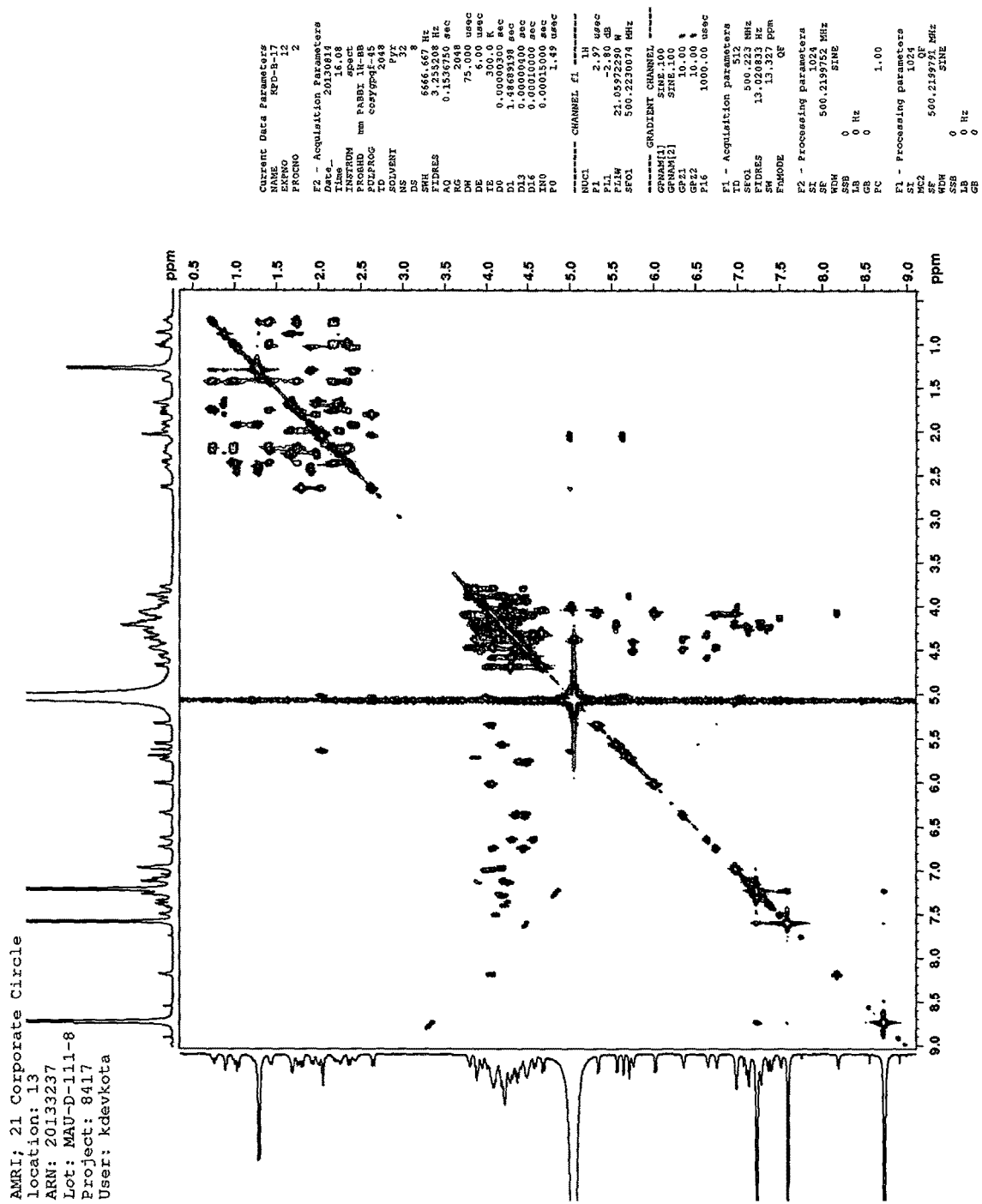
FIG. 17 shows the $^1$H-$^1$H COSY Spectrum of reb D2 (500 MHz, pyridine-$d_5$).
Figure 18:
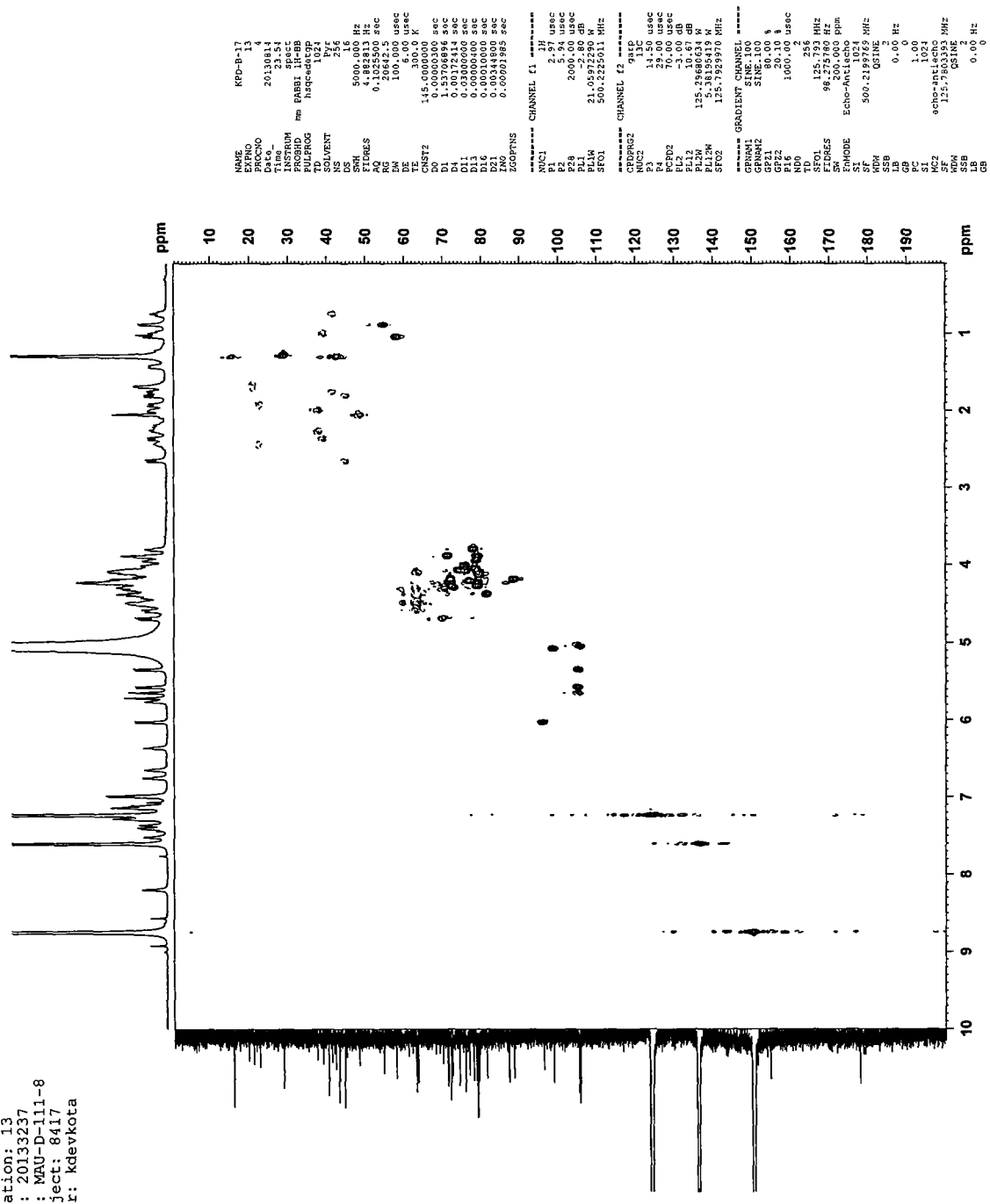
FIG. 18 shows the HSQC-DEPT spectrum of reb D2 (500 MHz, pyridine-$d_5$).
Figure 19:
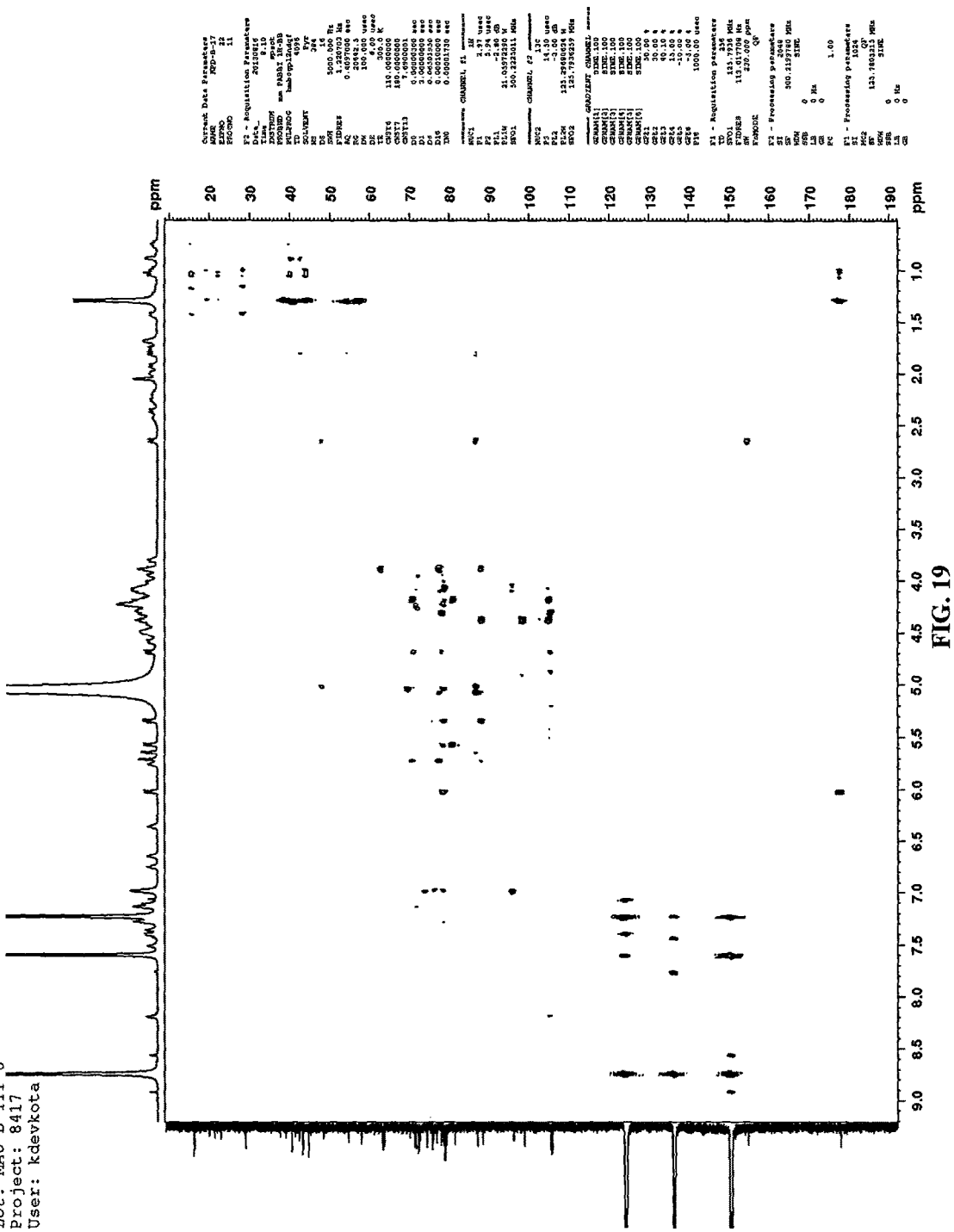
FIG. 19 shows the HMBC spectrum of reb D2.
Figure 20:
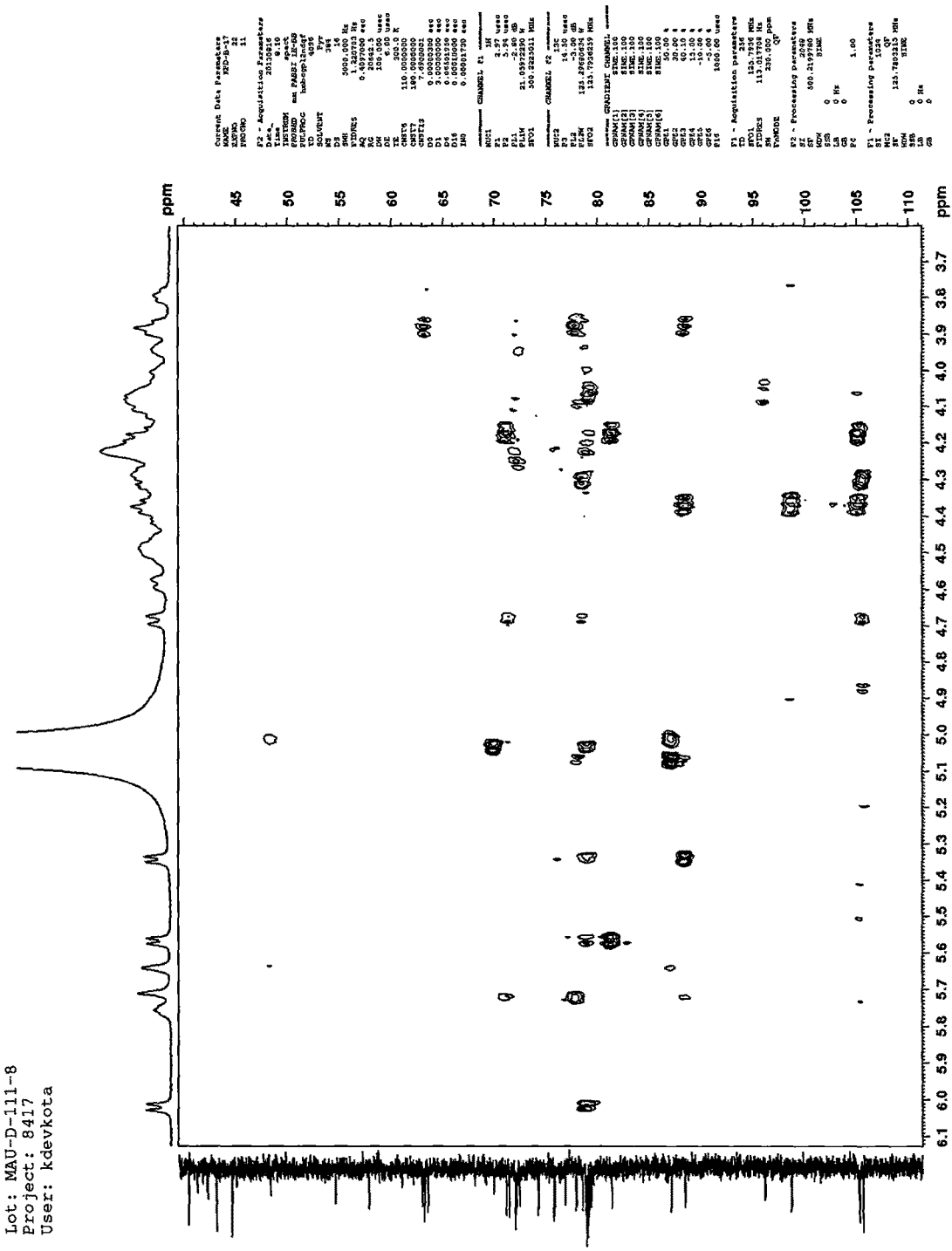
FIG. 20 shows an expansion of HMBC spectrum of reb D2 (500 MHz, pyridine-$d_5$).

A series of NMR experiments including $^1$H NMR (FIG. 14), $^{13}$C NMR (FIGS. 15 and 16), $^1$H-$^1$H COSY (FIG. 17), HSQC-DEPT (FIG. 18), HMBC (FIGS. 19 and 20), and 1D-TOCSY were performed to allow assignment of the compound.

The $^1$H, $^1$H-$^1$H COSY, $^1$H-$^{13}$C HSQC-DEPT and $^1$H-$^{13}$C HMBC NMR data indicated that the central core of the glycoside is a diterpene. The presence of five anomeric protons observed in the $^1$H and $^1$H-$^{13}$C HSQC-DEPT spectra confirm five sugar units in the structure. The methylene $^{13}$C resonance at $\delta_C$ 69.9 in the $^1$H-$^{13}$C HSQC-DEPT spectrum indicated the presence of a 1→6 sugar linkage in the structure. The linkages of sugar units were assigned using $^1$H-$^{13}$C HMBC and 1D-TOCSY correlations.

A HMBC correlation from the methyl protons at $\delta_H$ 1.29 to the carbonyl at $\delta_C$ 177.7 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.9, 45.0, and 57.8 allowed assignment of C-3, C-4, and C-5. Analysis of the $^1$H-$^{13}$C HSQC-DEPT data indicated that the carbon at $\delta_C$ 38.9 was a methylene group and the carbon at $\delta_C$ 57.8 was a methine which were assigned as C-3 and C-5, respectively. This left the carbon at $\delta_C$ 45.0, which did not show a correlation in the HSQC-DEPT spectrum, to be assigned as the quaternary carbon, C-4. The $^1$H chemical shifts for C-3 ($\delta_H$ 0.98 and 2j.36) and C-5 ($\delta_H$ 1.04) were assigned using the HSQC-DEPT data. A COSY correlation between one of the H-3 protons ($\delta_H$ 0.98) and a proton at $\delta_H$ 1.43 allowed assignment of one of the H-2 protons which in turn showed a correlation with a proton at $\delta_H$ 0.75 which was assigned to C-1. The remaining $^1$H and $^{13}$C chemical shifts for C-1 and C-2 were then assigned on the basis of additional COSY and HSQC-DEPT correlations and are summarized in the following table.

| $^1$H and $^{13}$C NMR (500 and 125 MHz, pyridine-d$_5$), Assignments of Reb D2. | | |
|---|---|---|
| | Reb D2 | |
| Position | $^{13}$C | $^1$H |
| 1 | 41.3 | 0.75 t (11.0) |
| | | 1.76 m |
| 2 | 19.9 | 1.43 m |
| | | 2.20 m |
| 3 | 38.9 | 0.98 m |
| | | 2.36 d (12.1) |
| 4 | 45.0 | — |
| 5 | 57.8 | 1.04 d (12.5) |
| 6 | 22.7 | 1.92 m |
| | | 2.43 m |
| 7 | 42.2 | 1.22 m |
| | | 1.30 m |
| 8 | 43.1 | — |
| 9 | 54.5 | 0.88 brs |
| 10 | 40.3 | — |
| 11 | 21.1 | 1.65 m |
| | | 1.69 m |
| 12 | 37.5 | 1.99 m |
| | | 2.25 m |
| 13 | 87.1 | — |
| 14 | 44.5 | 1.80 d (11.7) |
| | | 2.65 d (11.7) |
| 15 | 48.3 | 1.31 m |
| | | 2.04 brs |

-continued

| $^1$H and $^{13}$C NMR (500 and 125 MHz, pyridine-d$_5$), Assignments of Reb D2. | | |
|---|---|---|
| | Reb D2 | |
| Position | $^{13}$C | $^1$H |
| 16 | 154.7 | — |
| 17 | 105.2 | 5.01 s |
| | | 5.64 s |
| 18 | 28.8 | 1.29 s |
| 19 | 177.7 | — |
| 20 | 16.0 | 1.30 s |

The other tertiary methyl singlet, observed at $\delta_H$ 1.30 showed HMBC correlations to C-1 and C-5 and was assigned as C-20. The methyl protons showed additional HMBC correlations to a quaternary carbon ($\delta_C$ 40.3) and a methine carbon ($\delta_C$ 54.5) which were assigned as C-10 and C-9, respectively. COSY correlations between H-5 ($\delta_H$ 1.04) and protons at $\delta_H$ 1.92 and 2.43 then allowed assignment of the H-6 protons which in turn showed correlations to protons at $\delta_H$ 1.22 and 1.30 which were assigned to C-7. The $^{13}$C chemical shifts for C-6 ($\delta_C$ 22.7) and C-7 ($\delta_C$ 42.2) were then determined from the HSQC-DEPT data. COSY correlations between H-9 ($\delta_H$ 0.88) and protons at $\delta_H$ 1.65 and 1.69 allowed assignment of the H-11 protons which in turn showed COSY correlations to protons at $\delta_H$ 1.99 and 2.25 which were assigned as the H-12 protons. The HSQC-DEPT data was then used to assign C-11 ($\delta_C$ 21.1) and C-12 ($\delta_C$ 37.5). HMBC correlations from the H-12 proton ($\delta_H$ 2.25) to carbons at $\delta_C$ 87.1 and 154.7 allowed assignment of C-13 and C-16, respectively. The olefinic protons observed at $\delta_H$ 5.01 and 5.64 showed HMBC correlations to C-13 and were assigned to C-17 ($\delta_C$ 105.2 via HSQC-DEPT). The olefinic protons H-17 and the methine proton H-9 showed HMBC correlations to a carbon at $\delta_C$ 48.3 which was assigned as C-15. An additional HMBC correlation from H-9 to a methylene carbon at $\delta_C$ 44.5 then allowed assignment of C-14. The $^1$H chemical shifts at C-14 ($\delta_H$ 1.80 and 2.65) and C-15 ($\delta_H$ 1.31 and 2.04) were assigned using the HSQC-DEPT data.

The key HMBC and COSY correlations used to assign the aglycone region are provided below:

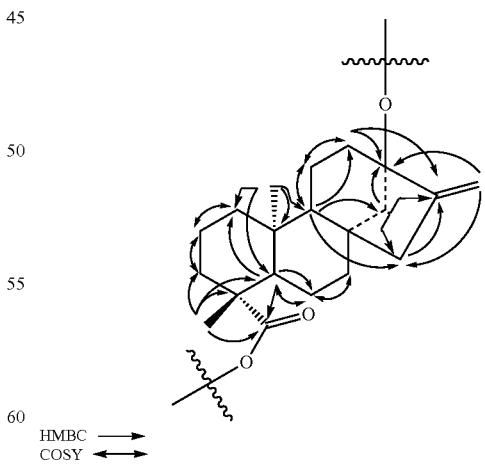

HMBC →
COSY ↔

Analysis of the $^1$H-$^{13}$C HSQC-DEPT data confirmed the presence of five anomeric protons. Three of the anomeric protons were well resolved at $\delta_H$ 6.02 ($\delta_C$ 96.1), 5.57 ($\delta_C$ 105.3), and 5.34 ($\delta_C$ 105.3) in the $^1$H NMR spectrum. The remaining two anomeric protons observed at $\delta_H$ 5.04 ($\delta_C$ 105.6) and 5.07 ($\delta_C$ 98.7) which were obscured by solvent (HOD) resonance in the $^1$H spectrum were identified by $^1$H-$^{13}$C HSQC-DEPT data. The anomeric proton observed at $\delta_H$ 6.02 showed HMBC correlation to C-19 which indicated that it corresponds to the anomeric proton of Glc$_I$. Similarly, the anomeric proton observed at $\delta_H$ 5.07 showed an HMBC correlation to C-13 allowing it to be assigned as the anomeric proton of Glc$_{II}$.

The Glc$_I$ anomeric proton ($\delta_H$ 6.02) showed a COSY correlation to a proton at $\delta_H$ 4.07 was assigned as Glc$_I$ H-2 which in turn showed a COSY correlation to a proton at $\delta_H$ 4.22 (Glc$_I$ H-3) which showed a COSY correlation with a proton at $\delta_H$ 4.12 (Glc$_I$ H-4). Due to data overlap, the COSY spectrum did not allow assignment of H-5 or the H-6 protons. Therefore, a series of 1D-TOCSY experiments were performed using selective irradiation of the Glc$_I$ anomeric proton with several different mixing times. In addition to confirming the assignments for Glc$_I$ H-2 through H-4, the 1D-TOCSY data showed a proton at $\delta_H$ 4.04 assigned as Glc$_I$ H-5 and a proton at $\delta_H$ 4.68 assigned as one of the Glc$_I$ H-6 protons. The latter proton was also used for 1D-TOCSY experiments. The selective irradiation of H-6 with several different mixing times also confirmed the assignment of Glc$_I$ H-1 to H-5 as well as the remaining methylene proton of H-6 ($\delta_H$ 4.30). Assignment of the $^{13}$C chemical shifts for Glc$_I$ C-2 ($\delta_C$ 74.2), C-3 ($\delta_C$ 79.1), C-4 ($\delta_C$ 72.1), C-5 ($\delta_C$ 78.5), and C-6 ($\delta_C$ 69.9) was determined using the $^1$H-$^{13}$C HSQC-DEPT data to complete the assignment of Glc$_I$. Furthermore, the presence of a methylene $^{13}$C resonance at $\delta_C$ 69.9 in the $^1$H-$^{13}$C HSQC-DEPT spectrum indicated a 1→6 sugar linkage of Glc$_I$ in the structure.

Out of four remaining unassigned glucose moieties, one was assigned as a substituent at C-6 of Glc$_I$ on the basis of $^1$H-$^{13}$C HSQC-DEPT, HMBC, and 1D-TOCSY correlations. The relatively downfield shift of a methylene $^{13}$C resonance of Glc$_I$ at $\delta_C$ 69.9 in the HSQC-DEPT spectrum indicated a 1→6 sugar linkage of Glc$_I$. The anomeric proton observed at $\delta_H$ 5.04 showed HMBC correlation to Glc$_I$ C-6 and was assigned as the anomeric proton of Glc$_V$. Similarly, methylene protons of Glc$_I$ showed HMBC correlations to anomeric carbon of Glc$_V$ confirming the presence of a 1→6 sugar linkage between Glc$_I$ and Glc$_V$. The Glc$_V$ anomeric proton showed a COSY correlation to a proton at $\delta_H$ 4.00 which was assigned as Glc$_V$ H-2 which in turn showed a COSY correlation to a proton at $\delta_H$ 4.22 (Glc$_V$ H-3). Due to data overlap, the COSY spectrum did not allow assignment of Glc$_V$ H-4 based on the COSY correlation of Glc$_V$ H-3. However, in the HMBC spectrum, Glc$_V$ H-3 showed a correlation to Glc$_V$ C-5 ($\delta_C$ 78.9). In HSQC-DEPT spectrum, Glc$_V$ C-5 showed a correlation to $\delta_H$ 3.89 (Glc$_V$ H-5). The Glc$_V$ H-5 showed COSY correlations to $\delta_H$ 4.21, 4.37, and 4.48. In the HSQC-DEPT spectrum, $\delta_H$ 4.21 showed a correlation to $\delta_C$ 71.4 (Glc$_V$ H-4), while $\delta_H$ 4.37 and 4.48 showed a correlation to $\delta_C$ 63.1 and were assigned to Glc$_V$ H-6a and H-6b, respectively. Assignment of the $^{13}$C chemical shifts for Glc$_V$ C-2 ($\delta_C$ 75.7) and C-3 ($\delta_C$ 79.1) was determined using the $^1$H-$^{13}$C HSQC-DEPT data to complete the assignment of Glc$_V$.

A summary of the $^1$H and $^{13}$C chemical shifts for the glycoside at C-19 are shown in the following table:

$^1$H and $^{13}$C NMR (500 and 125 MHz, pyridine-d$_5$), Assignments of the reb D2 C-19 glycoside.

| Position | Reb D2 $^{13}$C | Reb D2 $^1$H |
|---|---|---|
| Glc$_I$-1 | 96.1 | 6.02 d (8.1) |
| Glc$_I$-2 | 74.2 | 4.07 m |
| Glc$_I$-3 | 79.1$^\#$ | 4.22 m$^\#$ |
| Glc$_I$-4 | 72.1 | 4.12 m |
| Glc$_I$-5 | 78.5 | 4.04 m |
| Glc$_I$-6 | 69.9 | 4.30 m |
|  |  | 4.68 d (10.7) |
| Glc$_V$-1 | 105.6 | 5.04* |
| Glc$_V$-2 | 75.7 | 4.00 m |
| Glc$_V$-3 | 79.1$^\#$ | 4.22 m$^\#$ |
| Glc$_V$-4 | 71.4 | 4.21 m |
| Glc$_V$-5 | 78.9 | 3.89 m |
| Glc$_V$-6 | 63.1 | 4.37 m |
|  |  | 4.48 m |

*Anomeric proton was obscured by solvent (HDO) resonance. Therefore, the coupling constant value could not be determined.
$^\#$$^1$H and $^{13}$C values can be exchangeable between positions Glc$_I$-3, Glc$_V$-3 and Glc$_{II}$-3.

A summary of the key HMBC, COSY, and 1D-TOCSY correlations used to assign the C-19 glycoside region are provided below.

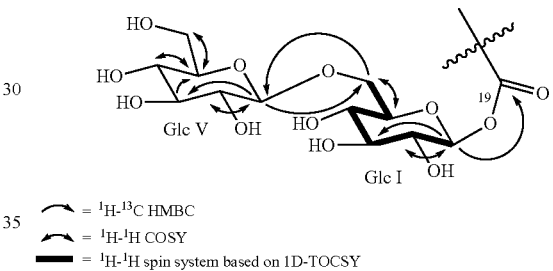

⌒ = $^1$H-$^{13}$C HMBC
⌒ = $^1$H-$^1$H COSY
■ = $^1$H-$^1$H spin system based on 1D-TOCSY Assignment of Glc$_{II}$ was carried out in a similar manner. The Glc$_{II}$ anomeric proton ($\delta_H$ 5.07) showed a COSY correlation to a proton at $\delta_H$ 4.37, assigned as Glc$_{II}$ H-2, which in turn showed a COSY correlation to a proton at $\delta_H$ 4.18 (Glc$_{II}$ H-3). This latter proton showed an additional correlation with a proton at $\delta_H$ 3.88 (Glc$_{II}$ H-4) which also showed a COSY correlation to a proton at $\delta_H$ 3.79 (Glc$_{II}$ H-5). Glc$_{II}$ H-5 also showed a COSY correlation to Glc$_{II}$ H-6 protons ($\delta_H$ 4.08 and 4.46). Assignment of the $^{13}$C chemical shifts for Glc$_{II}$ C-2 ($\delta_C$ 81.3), C-3 ($\delta_C$ 88.4), C-4 ($\delta_C$ 71.1), C-5 ($\delta_C$ 77.9), and C-6 ($\delta_C$ 63.2) was determined using the HSQC-DEPT data. HMBC correlations from Glc$_{II}$ H-3 to C-2 and C-4 and also from Glc$_{II}$ H-4 to C-2 and C-5 confirmed the assignments made above. Additional HMBC correlations of Glc$_{II}$ H-4 to Glc$_{II}$ C-6 further support to complete the assignment of Glc$_{II}$.

Two of the remaining unassigned glucose moieties were assigned as substituents at C-2 and C-3 of Glc$_{II}$ on the basis of HMBC correlations. The anomeric proton observed at $\delta_H$ 5.57 showed a HMBC correlation to Glc$_{II}$ C-2 and was assigned as the anomeric proton of Glc$_{III}$. The anomeric proton observed at $\delta_H$ 5.34 showed a HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ ($\delta_H$ 5.57) showed a COSY correlation with a proton at $\delta_H$ 4.19 which was assigned as Glc$_{III}$ H-2. Due to data overlap, the COSY spectrum did allow assignment of H-3 to H-6 protons. Therefore, a series of 1D-TOCSY experiments were performed using selective irradiation of the Glc$_{III}$ anomeric proton with several different mixing times. In addition to confirming the assignments for Glc$_{III}$ H-2, the 1D-TOCSY data showed protons at $\delta_H$ 4.24 (Glc$_{III}$ H-3), $\delta_H$ 4.27 (Glc$_{III}$ H-4), and $\delta_H$ 3.94 (Glc$_{III}$ H-5). Once H-4 was assigned using 1D-TOCSY data, COSY correlations from H-4 to H-5 and in turn to H-6 were used to assign H-6. In the COSY spectrum, Glc$_{III}$ H-4 showed a correlation to Glc$_{III}$ H-5, which in turn showed COSY correlations to $\delta_H$ 4.41 and 4.50 of Glc$_{III}$ H-6a and H-6b, respectively. The $^{13}$C chemical shifts for Glc$_{III}$ C-2 ($\delta_C$ 76.8), C-3 ($\delta_C$ 78.9), C-4 ($\delta_C$ 72.4), C-5 ($\delta_C$ 78.8), and C-6 ($\delta_C$ 63.5) were then determined using the $^1$H-$^{13}$C HSQC-DEPT correlations to complete the assignment of Glc$_{III}$.

The anomeric proton of Glc$_{IV}$ ($\delta_H$ 5.34) showed a COSY correlation with a proton at $\delta_H$ 4.06 which was assigned as Glc$_{IV}$ H-2. Due to data overlap, the COSY spectrum did not allow assignment of H-3 to H-6 protons. Therefore, a series of 1D-TOCSY experiments were performed using selective irradiation of the Glc$_{IV}$ anomeric proton with several different mixing times. In addition to confirming the assignments for Glc$_{IV}$ H-2, the 1D-TOCSY data showed protons at $\delta_H$ 4.22 (Glc$_{II}$, H-3), $\delta_H$ 4.18 (Glc$_{IV}$ H-4), and $\delta_H$ 4.10 (Glc$_{II}$, H-5). Once H-4 was assigned using 1D-TOCSY data, COSY correlations from H-4 to H-5 and in turn to H-6 were used to assign H-6. In the COSY spectrum, Glc$_{II}$, H-4 showed a correlation to Glc$_{IV}$, H-5, which in turn showed COSY correlations to $\delta_H$ 4.32 and 4.58, Glc$_{IV}$ H-6a and H-6b, respectively. The $^{13}$C chemical shifts for Glc$_{IV}$ C-2 ($\delta_C$ 75.8), C-3 ($\delta_C$ 78.9), C-4 ($\delta_C$ 72.0), C-5 ($\delta_C$ 79.3), and C-6 ($\delta_C$ 62.9) were then determined using the $^1$H-$^{13}$C HSQC-DEPT correlations to complete the assignment of Glc$_{IV}$.

A summary of the $^1$H and $^{13}$C chemical shifts for the glycoside at C-13 are shown in the table below:

| Position | Reb D2 $^{13}$C | Reb D2 $^1$H |
|---|---|---|
| Glc$_{II}$-1 | 98.7 | 5.07* |
| Glc$_{II}$-2 | 81.3 | 4.37 m |
| Glc$_{II}$-3 | 88.4 | 4.18 t (9.0) |
| Glc$_{II}$-4 | 71.1 | 3.88 t (8.6) |
| Glc$_{II}$-5 | 77.9 | 3.79 m |
| Glc$_{II}$-6 | 63.2 | 4.08 m |
| | | 4.46 m |
| Glc$_{III}$-1 | 105.3 | 5.57 d (7.6) |
| Glc$_{III}$-2 | 76.8 | 4.19 m |
| Glc$_{III}$-3 | 78.9 | 4.24 m |
| Glc$_{III}$-4 | 72.4 | 4.27 m |
| Glc$_{III}$-5 | 78.8 | 3.94 m |
| Glc$_{III}$-6 | 63.5 | 4.41 m |
| | | 4.50 m |
| Glc$_{IV}$-1 | 105.3 | 5.34 d (7.9) |
| Glc$_{IV}$-2 | 75.8 | 4.06 m |
| Glc$_{IV}$-3 | 78.9# | 4.22 m# |
| Glc$_{IV}$-4 | 72.0 | 4.18 m |
| Glc$_{IV}$-5 | 79.3 | 4.10 m |
| Glc$_{IV}$-6 | 62.9 | 4.32 m |
| | | 4.58 m |

A summary of the key HMBC, COSY, and 1D-TOCSY correlations used to assign the C-13 glycoside region are provided below:

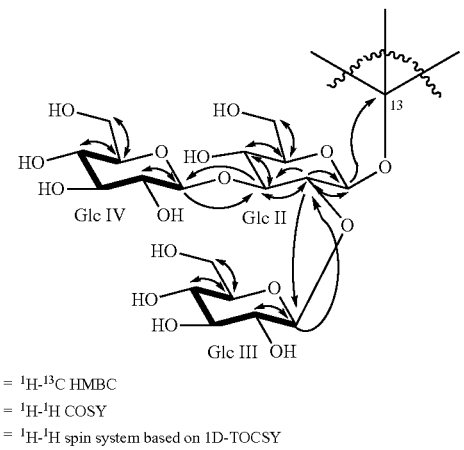

= $^1$H-$^{13}$C HMBC
= $^1$H-$^1$H COSY
= $^1$H-$^1$H spin system based on 1D-TOCSY NMR and MS analyses allowed a full assignment of structure, shown below. The chemical name of the compound is 13-[(2-O-β-D-glucopyranosyl-3-O-β-D-glucopyranosyl-β-D-glucopyranosyl)oxy] ent-kaur-16-en-19-oic acid-[(6-O-β-D-glucopyranosyl-β-D-glucopyranosyl) ester] (rebaudioside D2 or reb D2). The compound is an isomer of rebaudioside D.

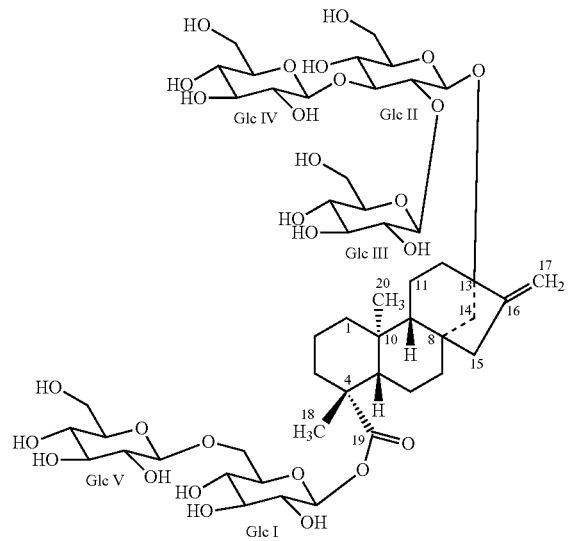

Example 40

Isolation and Characterization of Reb M2

Crude Reaction Sample.

The sample, Lot CB-2977-106, used for isolation was prepared according to Example 22 with UGTSL (GI #460409128).

HPLC Analysis.

Preliminary HPLC analyses was performed using a Waters 2695 Alliance System with the following method: Phenomenex Synergi Hydro-RP, 4.6×250 mm, 4 μm (p/n 00G-4375-E0); Column Temp: 55° C.; Mobile Phase A: 0.0284% NH$_4$OAc and 0.0116% HOAc in water; Mobile Phase B: Acetonitrile (MeCN); Flow Rate: 1.0 mL/min; Injection volume: 10 μL. Detection was by UV (210 nm) and CAD.

Gradient:

| Time (min) | % A | % B |
| --- | --- | --- |
| 0.0-5.0 | 100 | 0 |
| 20 | 20 | 80 |
| 25 | 20 | 80 |
| 30 | 100 | 0 |

Analyses of semi-preparative purification fractions were performed with the following method: Waters Atlantis dC18, 4.6×100 mm, 5 µm (p/n 186001340); Mobile Phase A: 25% MeCN in water; Mobile Phase B: 30% MeCN in water; Flow Rate: 1.0 mL/min; Injection volume: 10 µL. Detection was by CAD.
Gradient:

| Time (min) | % A | % B |
| --- | --- | --- |
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31-37 | 30 | 70 |
| 38 | 75 | 25 |

LC-MS.

Preliminary analysis of the semi-synthetic steviol glycoside mixture was carried out on a Waters AutoPurification HPLC/MS System with a Waters 3100 Mass Detector operating in negative ion mode. Analysis of the sample was performed using the following method: Phenomenex Synergi Hydro-RP, 4.6×250 mm, 4 µm (p/n 00G-4375-E0); Column Temp: 55° C.; Mobile Phase A: 0.0284% NH$_4$OAc and 0.0116% HOAc in water; Mobile Phase B: MeCN; Flow Rate: 1.0 mL/min; Injection volume: 10 µL. Detection was by UV (210 nm), and MSD (−ESI m/z 500-2000). Gradient conditions were as listed above.

Isolation by HPLC.

The purification was performed in two steps. The first method used for the semi-preparative purification is summarized below. Column: Waters Atlantis dC18, 30×100 mm, 5 µm (p/n 186001375); Mobile Phase A: 25% MeCN in water; Mobile Phase B: 30% MeCN in water; Flow Rate: 45 mL/min; Injection load: 160 mg dissolved in 20 mL of water. Detection was by UV (205 nm).
Gradient:

| Time (min) | % A | % B |
| --- | --- | --- |
| 0.0-5.0 | 100 | 0 |
| 20 | 20 | 80 |
| 25 | 20 | 80 |
| 30 | 100 | 0 |

The secondary purification used the same column and conditions, but isocratic mobile phase: 20% MeCN in water.

MS and MS/MS.

MS and MS/MS data were generated with a Waters QT of Premier mass spectrometer equipped with an electrospray ionization source. Samples were analyzed by negative ESI. Samples were diluted with H$_2$O:MeCN (1:1) by 50 fold and introduced via infusion using the onboard syringe pump. The samples were diluted to yield good s/n which occurred at an approximate concentration of 0.01 mg/mL.

NMR.

The sample was prepared by dissolving ~1.0 mg in 150 µL of D$_2$O and NMR data were acquired on a Bruker Avance 500 MHz instrument with a 2.5 mm inverse detection probe. The $^1$H NMR and $^{13}$C NMR spectra were referenced to the residual solvent signal HDO ($\delta_H$ 4.79 ppm) and TSP ($\delta_C$ 0.00 ppm), respectively.

Results and Discussion

Isolation and Purification.

Figure 12:
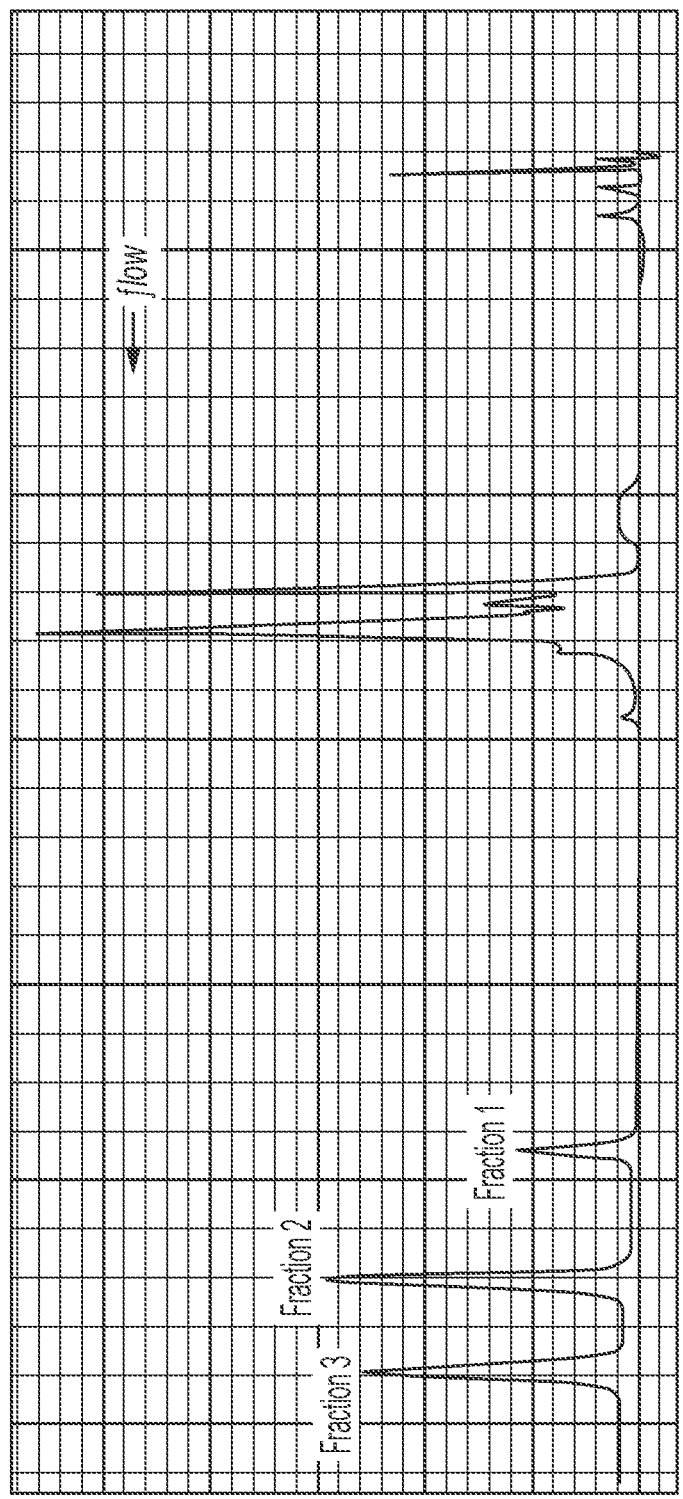
FIG. 12 shows the trace of semi-synthetic steviol glycoside mixture, Lot number CB-2977-106. Chromatogram gridlines are not homogeneous as the detector was re-calibrated 14 min following injection.
Figure 13A:
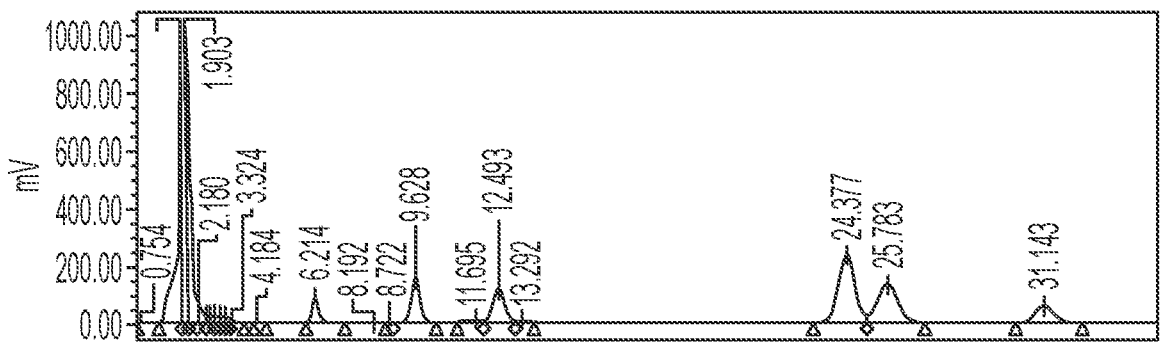
FIG. 13 shows HPLC analysis of semi-synthetic steviol glycoside mixture, Lot number CB-2977-106 (A), Isolated reb M2 (B), isolated reb D (C) and isolated reb D2 (D).
Figure 13B:
Figure 13C:
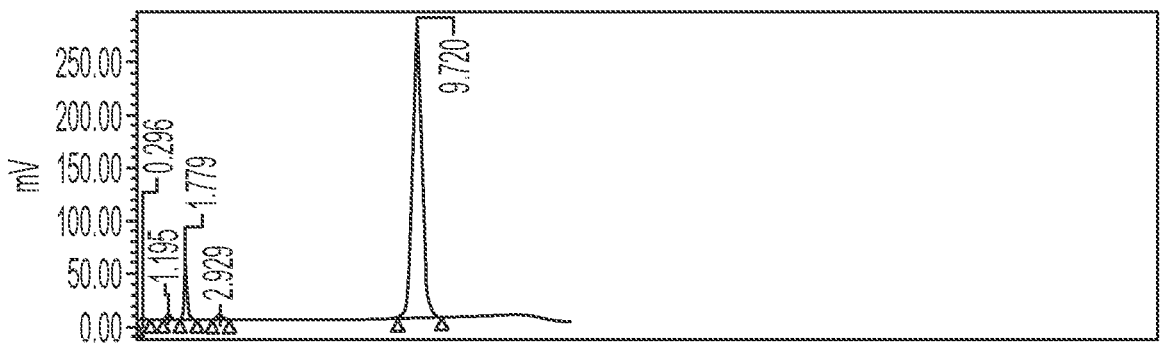
Figure 13D:
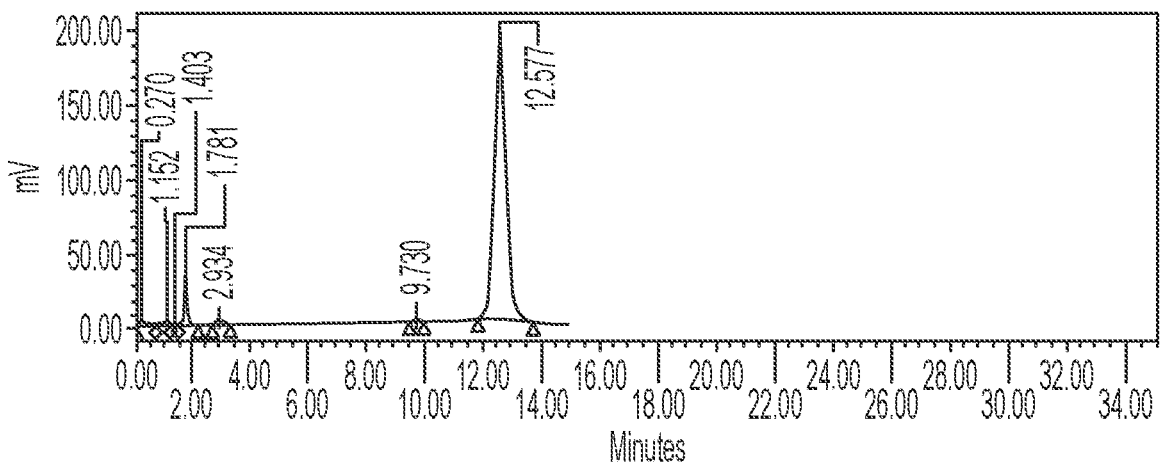

Isolation was performed using on a steviol glycoside mixture, Lot number CB-2977-106, prepared according to Example 22 with UGTSL (GI #460409128). The material was analyzed by LC-MS using the method described above (FIG. 11). The targeted peak of interest was that at 4.1 min in the TIC chromatogram. The mass spectrum of this peak provided a [M-H]$^-$ ion at m/z 1289.7. The provided sample was preliminarily processed in a single injection (160 mg) using the first method condition provided above. This method fractionated the material into 'polar' and 'non-polar' mixtures of glycosides. The 'polar' mixture was then reprocessed using the second-step conditions provided above. The semi-preparative HPLC trace is shown in FIG. 12. From this semi-preparative collection, the peak was isolated with a purity >99% (CAD, AUC). The fraction analysis is provided in FIG. 13. Following the purification, the fractions were concentrated by rotary evaporation at 35° C. and lyophilized. Approximately 1 mg was obtained.

Mass Spectrometry.

The ESI-TOF mass spectrum acquired by infusing a sample of CC-00300 showed a [M-H]$^-$ ion at m/z 1289.5266. The mass of the [M-H]$^-$ ion was in good agreement with the molecular formula C$_{56}$H$_{90}$O$_{33}$ (calcd for C$_{56}$H$_{89}$O$_{33}$: 1289.5286, error: −1.6 ppm) expected for reb M2. The MS data confirmed that CC-00300 has a nominal mass of 1290 Daltons with the molecular formula, C$_{56}$H$_{90}$O$_{33}$.

The MS/MS spectrum (selecting the [M-H]$^-$ ion at m/z 1289.5 for fragmentation) indicated the loss of three glucose units at m/z 803.3688 and sequential loss of three glucose moieties at m/z 641.3165, 479.2633 and 317.2082.

NMR Spectroscopy.

Figure 21:
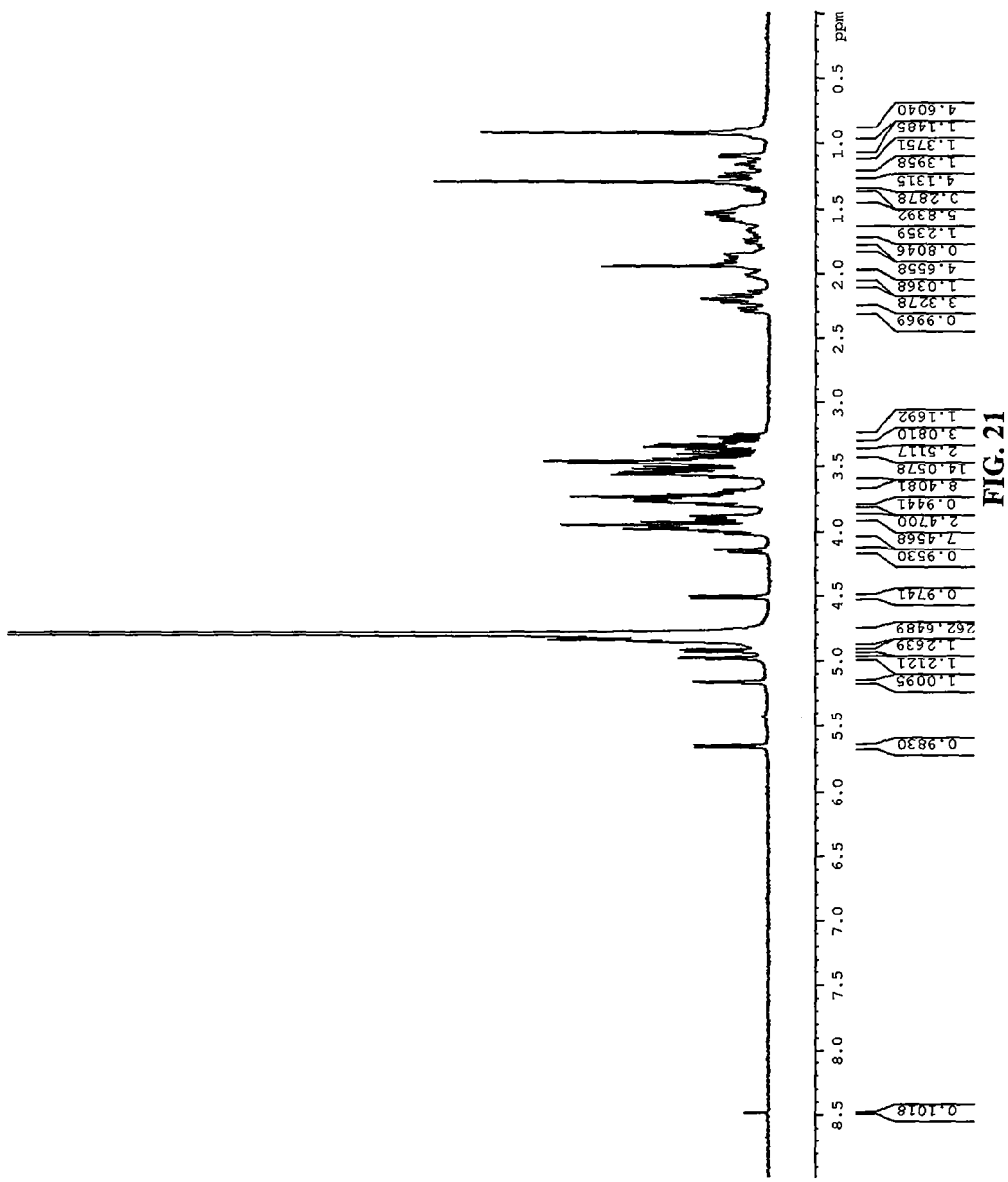
FIG. 21 shows the $^1$H NMR spectrum of reb M2 (500 MHz, D$_2$O).
Figure 22:
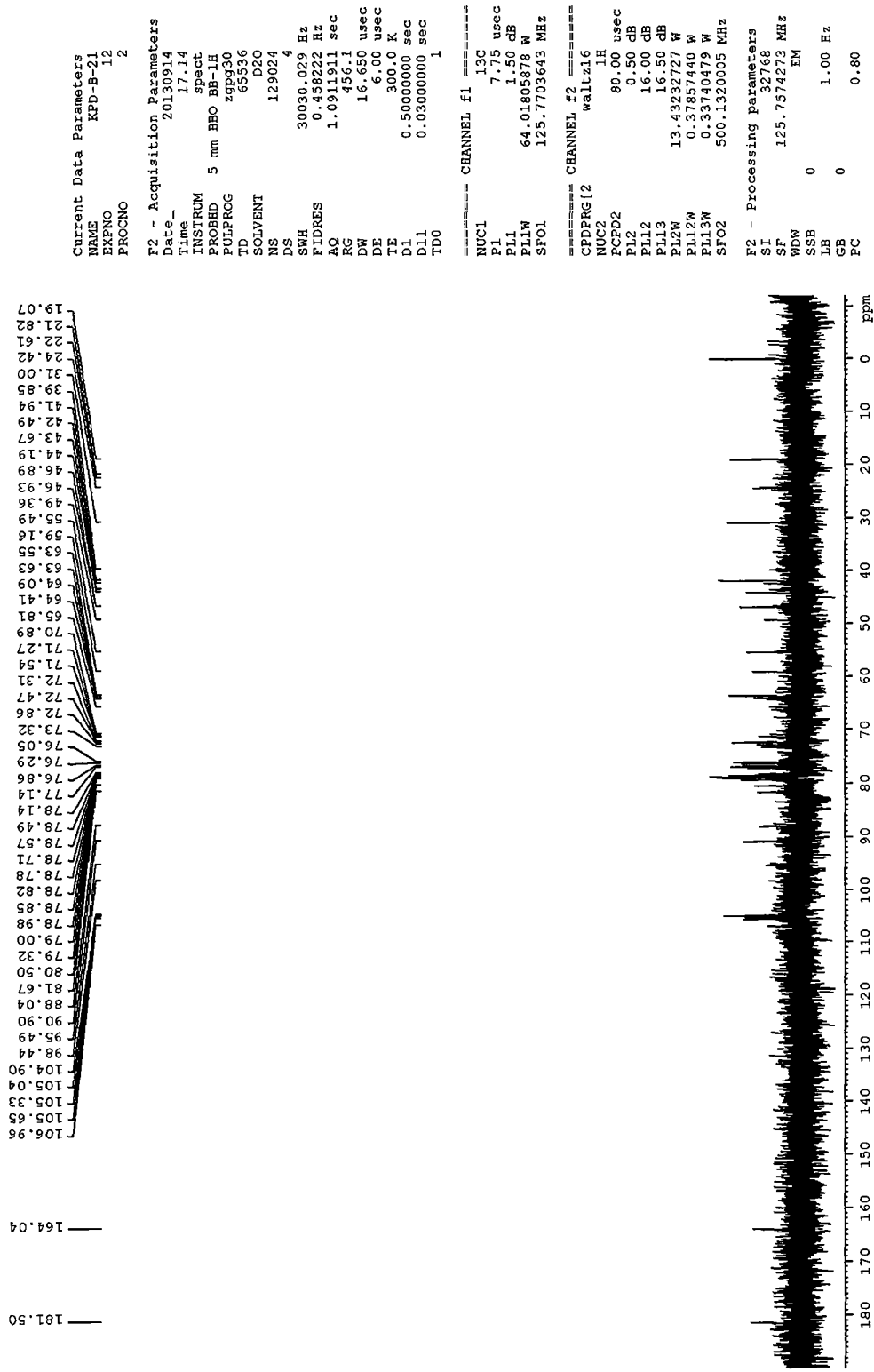
FIG. 22 shows the $^{13}$C NMR spectrum of reb M2 (125 MHz, D$_2$O/TSP).
Figure 23:
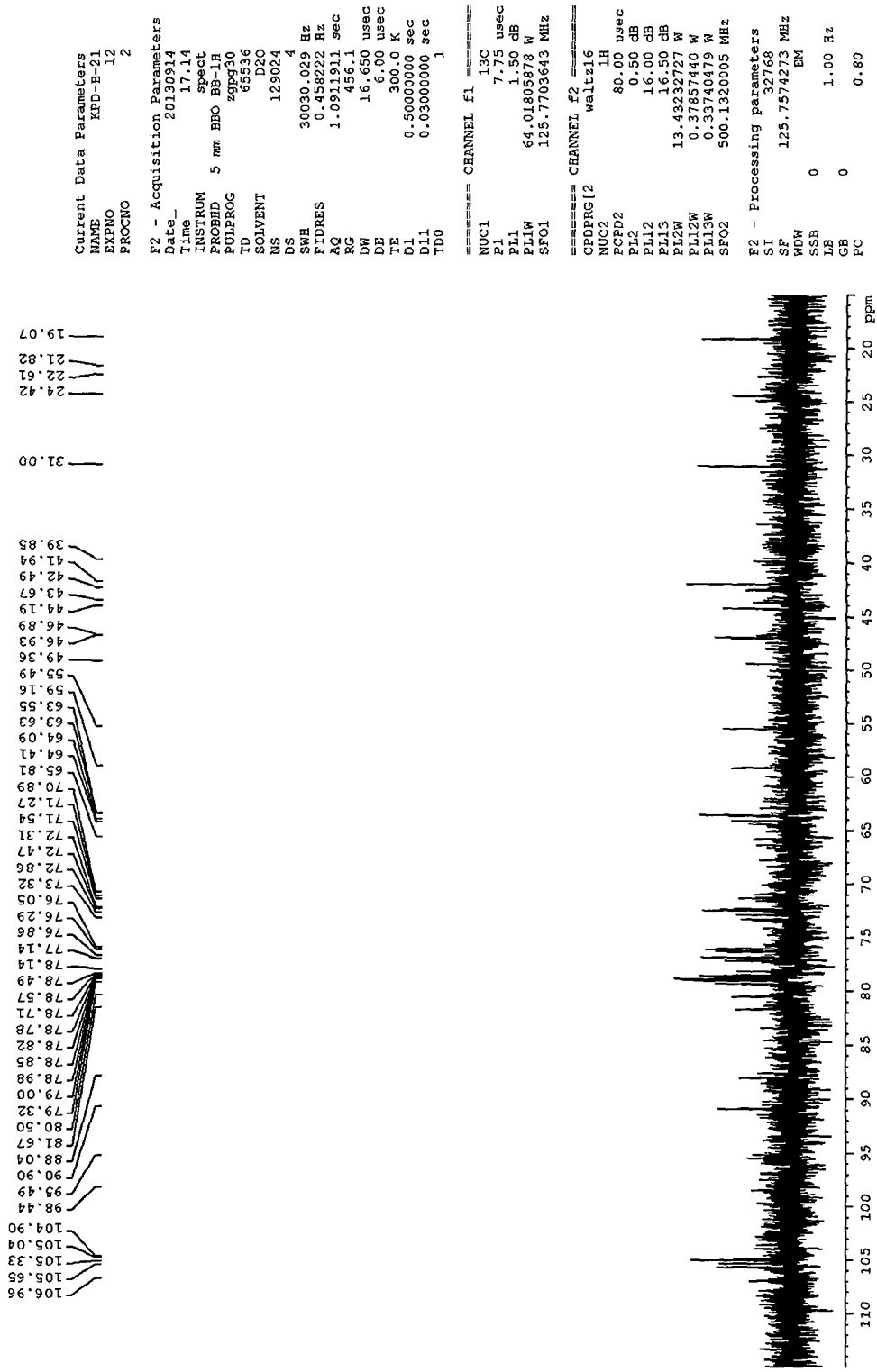
FIG. 23 shows an expansion of the $^{13}$C NMR spectrum of reb M2 (125 MHz, D$_2$O/TSP).
Figure 24:
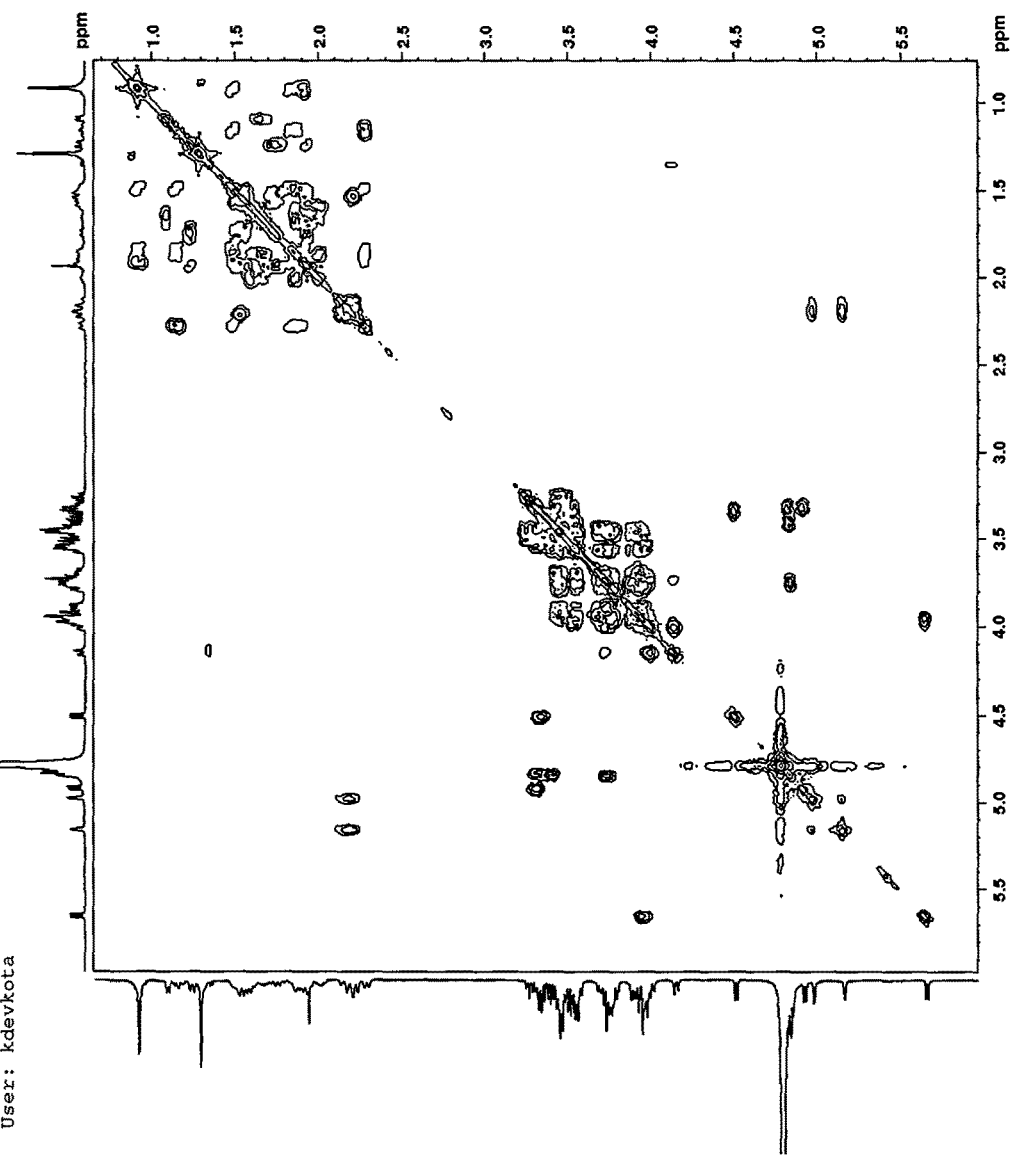
FIG. 24 shows the $^1$H-$^1$H COSY spectrum of reb M2 (500 MHz, D$_2$O).
Figure 25:
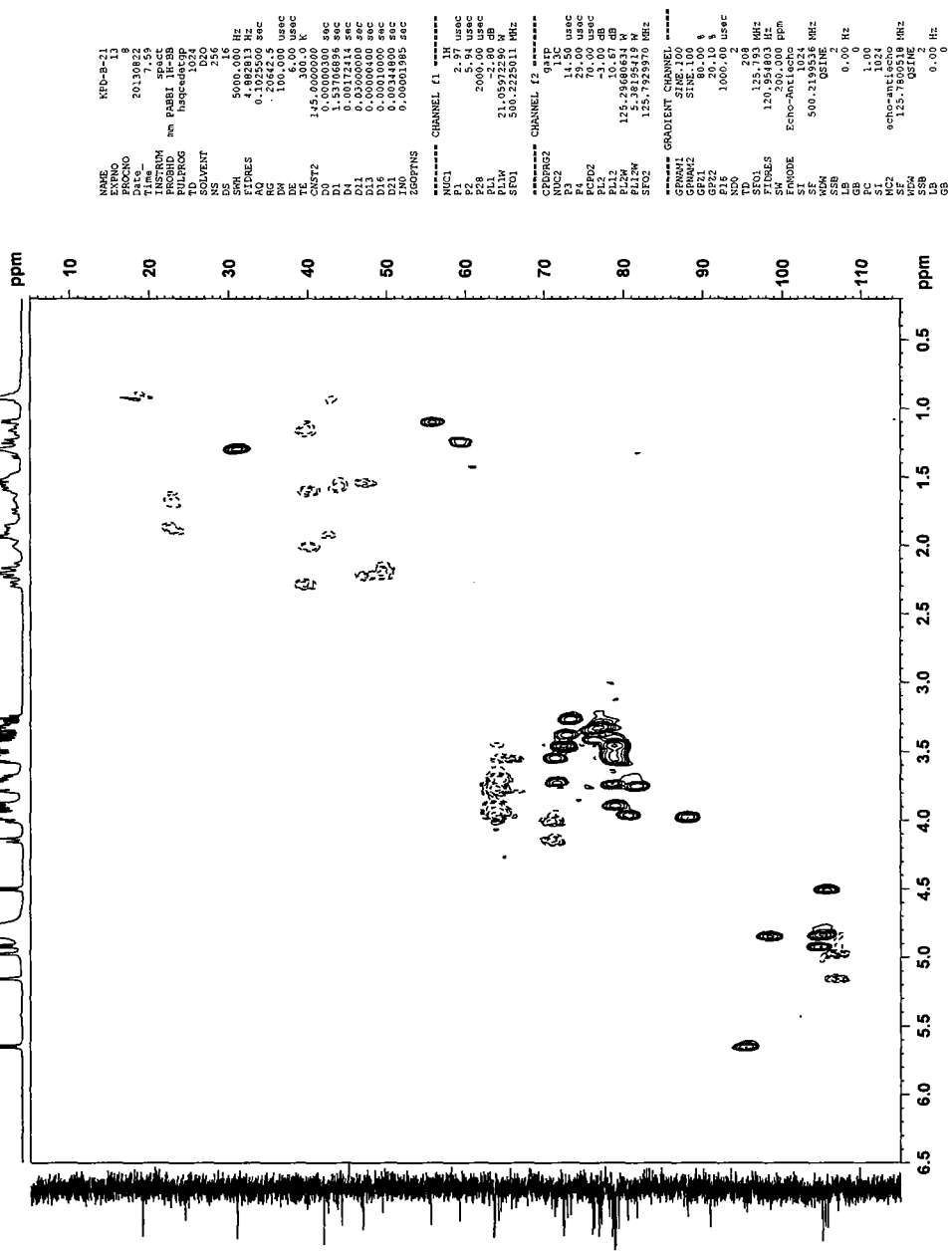
FIG. 25 shows the HSQC-DEPT spectrum of reb M2 (500 MHz, D$_2$O).
Figure 26:
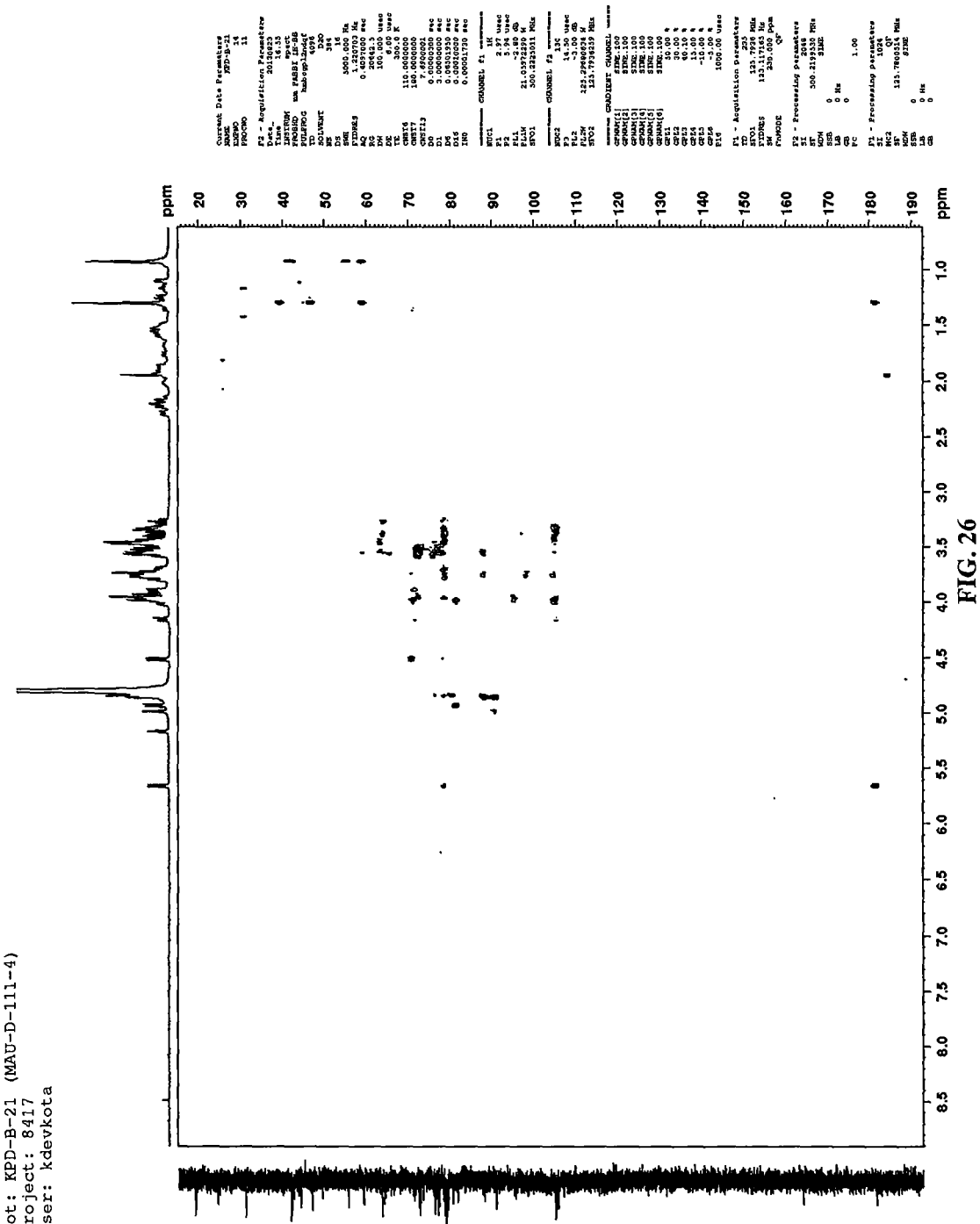
FIG. 26 shows the HMBC spectrum of reb M2 (500 MHz, D$_2$O).
Figure 27:
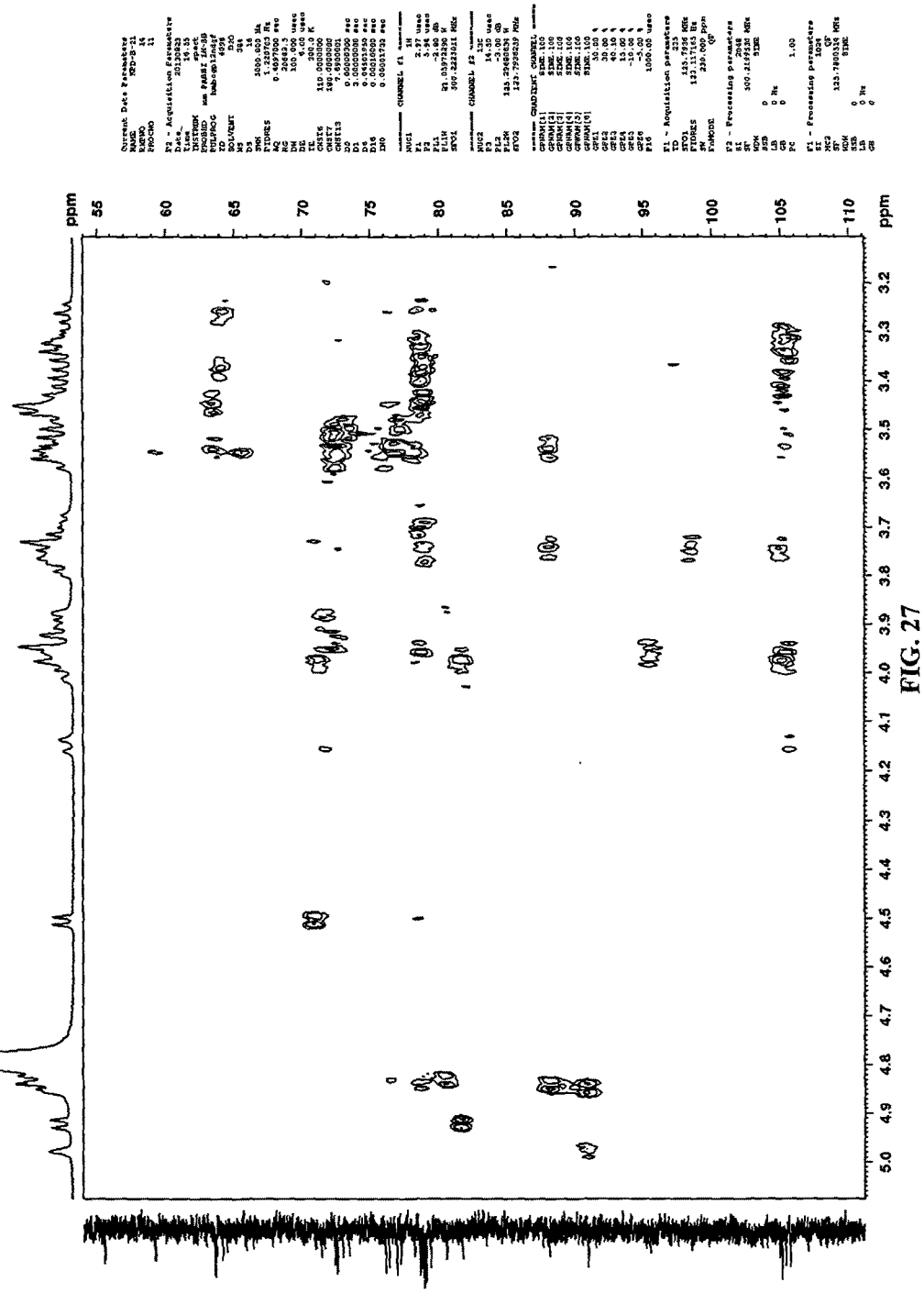
FIG. 27 shows an expansion of HMBC spectrum of reb M2 (500 MHz, D$_2$O).

A series of NMR experiments including $^1$H NMR (FIG. 21), $^{13}$C NMR (FIGS. 22 and 23), $^1$H-$^1$H COSY (FIG. 24), HSQC-DEPT (FIG. 25), HMBC (FIGS. 26 and 27), and 1D-TOCSY were performed to allow assignment of reb M2.

The $^1$H, $^1$H-$^1$H COSY, $^1$H-$^{13}$C HSQC-DEPT and $^1$H-$^{13}$C HMBC NMR data indicated that the central core of the glycoside is a diterpene. The presence of six anomeric protons observed in the $^1$H and $^1$H-$^{13}$C HSQC-DEPT spectra confirm six sugar units in the structure. The methylene $^{13}$C resonance at $\delta_C$ 70.9 in the $^1$H-$^{13}$C HSQC-DEPT spectrum indicated the presence of a 1→6 sugar linkage in the structure. The linkages of sugar units were assigned using $^1$H-$^{13}$C HMBC and 1D-TOCSY correlations.

A HMBC correlation from the methyl protons at $\delta_H$ 1.29 to the carbonyl at $\delta_C$ 181.5 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.8, 43.7, and 59.2 allowed assignment of C3, C4, and C5. Analysis of the $^1$H-$^{13}$C HSQC-DEPT data indicated that the carbon at $\delta_C$ 39.8 was a methylene group and the carbon at $\delta_C$ 59.2 was a methine which were assigned as C-3 and C-5, respectively. This left the carbon at $\delta_C$ 43.7, which did not show a correlation in the HSQC-DEPT spectrum, to be assigned as the quaternary carbon, C-4. The $^1$H chemical shifts for C-3 ($\delta_H$ 1.16 and 2.28) and C-5 ($\delta_H$ 1.24) were assigned using the HSQC- DEPT data. A COSY correlation between one of the H-3 protons $\delta_H$ 1.16) and a proton at $\delta_H$ 1.49 allowed assignment of one of the H-2 protons which in turn showed a correlation with a proton at $\delta_H$ 0.92 which was assigned to C-1. The remaining $^1$H and $^{13}$C chemical shifts for C-1 and C-2 were then assigned on the basis of additional COSY and HSQC-DEPT correlations and are summarized in the table below.

| $^1$H NMR (500 MHz, D$_2$O) and $^{13}$C NMR (125 MHz, D$_2$O/TSP) Assignments of the Reb M2 aglycone. | | |
|---|---|---|
| Position | $^{13}$C | $^1$H |
| 1 | 41.9 | 0.92 m |
| | | 1.93 m |
| 2 | 21.8 | 1.49 m |
| | | 1.86 m |
| 3 | 39.8 | 1.16 m |
| | | 2.28 d (13.4) |
| 4 | 43.7 | — |
| 5 | 59.2 | 1.24 d (12.1) |
| 6 | 24.4 | 1.73 m |
| | | 1.94 m |
| 7 | 44.2 | 1.49 m |
| | | 1.56 m |
| 8 | 46.9 | — |
| 9 | 55.5 | 1.09 d (7.7) |
| 10 | 42.4 | — |
| 11 | 22.6 | 1.66 m |
| | | 1.70 m |
| 12 | 39.9 | 1.60 m |
| | | 2.00 m |
| 13 | 90.9 | — |
| 14 | 46.9 | 1.53 d (12.6) |
| | | 2.21 d (13.6) |
| 15 | 49.4 | 2.15 d (17.2) |
| | | 2.18 d (18.1) |
| 16 | 164.0 | — |
| 17 | 107.0 | 4.98 s |
| | | 5.16 s |
| 18 | 31.0 | 1.29 s |
| 19 | 181.5 | — |
| 20 | 19.1 | 0.92 s |

The other tertiary methyl singlet, observed at $\delta_H$ 0.92 showed HMBC correlations to C-1 and C-5 and was assigned as C-20. The methyl protons showed additional HMBC correlations to a quaternary carbon ($\delta_C$ 42.4) and a methine ($\delta_C$ 55.5) which were assigned as C-10 and C-9, respectively. COSY correlations between H-5 ($\delta_H$ 1.24) and protons at $\delta_H$ 1.73 and 1.94 then allowed assignment of the H-6 protons which in turn showed correlations to protons at $\delta_H$ 1.49 and 1.56 which were assigned to C-7. The $^{13}$C chemical shifts for C-6 ($\delta_C$ 24.4) and C-7 ($\delta_C$ 44.2) were then determined from the HSQC-DEPT data. COSY correlations between H-9 ($\delta_H$ 1.09) and protons at $\delta_H$ 1.66 and 1.70 allowed assignment of the H-11 protons which in turn showed COSY correlations to protons at $\delta_H$ 1.60 and 2.00 which were assigned as the H-12 protons. The HSQC-DEPT data was then used to assign C-11 ($\delta_C$ 22.6) and C-12 ($\delta_C$ 39.9). The olefinic protons observed at $\delta_H$ 4.98 and 5.16 showed HMBC correlations to C-13 ($\delta_C$ 90.9) and were assigned to C-17 ($\delta_C$ 107.0 via HSQC-DEPT). The olefinic protons H-17 showed HMBC correlations to a carbon at $\delta_C$ 49.4 which was assigned as C-15. An additional HMBC correlation from H-9 to a methylene carbon at $\delta_C$ 46.9 then allowed assignment of C-14. The $^1$H chemical shifts at C-14 ($\delta_H$ 1.53 and 2.21) and C-15 ($\delta_H$ 2.15 and 2.18) were assigned using the HSQC-DEPT data.

A summary of the key HMBC and COSY correlations used to assign the aglycone region are provided below:

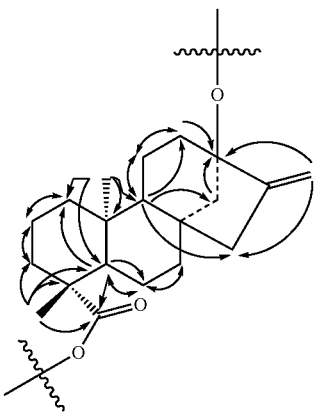

HMBC ⟶
COSY ⟷

Analysis of the $^1$H-$^{13}$C HSQC-DEPT data confirmed the presence of six anomeric protons. Three of the anomeric protons were well resolved at $\delta_H$ 5.65 ($\delta_C$ 95.5), 4.92 ($\delta_C$ 104.9), and 4.50 ($\delta_C$ 105.7) in the $^1$H NMR spectrum. The remaining three anomeric protons observed at $\delta_H$ 4.85 ($\delta_C$ 98.4), 4.84 ($\delta_C$ 105.0), and 4.83 ($\delta_C$ 105.3) were overlapped by the residual solvent resonance in the $^1$H spectrum. The anomeric proton observed at $\delta_H$ 5.65 showed a HMBC correlation to C-19 which indicated that it corresponds to the anomeric proton of Glc$_I$. Similarly, the anomeric proton observed at $\delta_H$ 4.85 showed a HMBC correlation to C-13 allowing it to be assigned as the anomeric proton of Glc$_{II}$.

The Glc$_I$ anomeric proton ($\delta_H$ 5.65) showed a COSY correlation to a proton at $\delta_H$ 3.96 which was assigned as Glc$_I$ H-2 which in turn showed a COSY correlation to a proton at $\delta_H$ 3.89 (Glc$_I$ H-3) which showed a COSY correlation with a proton at $\delta_H$ 3.71 (Glc$_I$ H-4). Due to data overlap, the COSY spectrum did not allow assignment of the H-5 or H-6 protons. Therefore, a series of 1D-TOCSY experiments were performed using selective irradiation of the Glc$_I$ anomeric proton with several different mixing times. In addition to confirming the assignments for Glc$_I$ H-2 through H-4, the 1D-TOCSY data showed a proton at $\delta_H$ 3.73 assigned as Glc$_I$ H-5 and a proton at $\delta_H$ 4.15 assigned as one of the Glc$_I$ H-6 protons. The latter proton was also used for 1D-TOCSY experiments. The selective irradiation of H-6 with several different mixing times also confirmed the assignment of Glc$_I$ H-1 to H-5 as well as the remaining methylene proton of H-6 ($\delta_H$ 4.00). Assignment of the $^{13}$C chemical shifts for Glc$_I$ C-2 ($\delta_C$ 80.5), C-3 ($\delta_C$ 79.0), C-4 ($\delta_C$ 71.5), C-5 ($\delta_C$ 79.0), and C-6 ($\delta_C$ 70.9) was determined using the $^1$H-$^{13}$C HSQC-DEPT data to complete the assignment of Glc$_I$. Furthermore, the presence of a methylene $^{13}$C resonance at $\delta_C$ 70.9 in the $^1$H-$^{13}$C HSQC-DEPT spectrum indicated a 1→6 sugar linkage of Glc$_I$ in the structure.

Two of the unassigned glucose moieties were assigned as substituents at C-2 and C-6 of Glc$_I$ on the basis of HMBC correlations. The anomeric proton observed at $\delta_H$ 4.83 showed an HMBC correlation to Glc$_I$ C-2 and was assigned as the anomeric proton of Glc$_V$. The anomeric proton observed at $\delta_H$ 4.50 showed a HMBC correlation to Glc$_I$ C-6 and was assigned as the anomeric proton of Glc$_{VI}$. The reciprocal HMBC correlations from Glc$_I$ H-2 to the anomeric carbon of Glc$_V$ and from Glc$_I$ H-6 to the anomeric carbon of Glc$_{VI}$ were also observed.

The anomeric proton of Glc$_V$ ($\delta_H$ 4.83) showed a COSY correlation with a proton at $\delta_H$ 3.32 which was assigned as Glc$_V$ H-2. The Glc$_V$ H-2 in turn showed a COSY correlation to a proton at δ$_H$ 3.51 (Glc$_V$ H-3). This latter proton showed an additional correlation with a proton at δ$_H$ 3.38 (Glc$_V$ H-4). H-4 also showed a COSY correlation to a proton at δ$_H$ 3.55 (Glc$_V$ H-5) and Glc$_V$ H-5 in turn showed a COSY correlation to Glc$_V$ H-6 protons (δ$_H$ 3.76 and 3.97). Assignment of the $^{13}$C chemical shifts for Glc$_V$ C-2 (δ$_C$ 78.5), C-3 (δ$_C$ 78.7), C-4 (δ$_C$ 72.9), C-5 (δ$_C$ 78.8), and C-6 (δ$_C$ 63.6) was determined using the HSQC-DEPT data. HMBC correlations from Glc$_V$ H-3 to C-2 and C-4 and also from Glc$_V$ H-4 to C-3 and C-6 confirmed the assignments made above to complete the assignment of Glc$_V$.

Another glucose moiety was assigned as a substituent at C-6 of Glc$_I$ on the basis of $^1$H-$^{13}$C HSQC-DEPT and HMBC correlations. The relatively downfield shift of a methylene $^{13}$C resonance of Glc$_I$ at δ$_C$ 70.9 in the HSQC-DEPT spectrum indicated a 1→6 sugar linkage of Glc$_I$. The anomeric proton observed at δ$_H$ 4.50 showed a HMBC correlation to Glc$_I$ C-6 and was assigned as the anomeric proton of Glc$_{VI}$. Similarly, methylene protons of Glc$_I$ showed HMBC correlations to the anomeric carbon of Glc$_{VI}$ and this confirmed the presence of a 1→6 sugar linkage between Glc$_I$ and Glc$_{VI}$. The Glc$_{VI}$ anomeric proton showed a COSY correlation to a proton at δ$_H$ 3.33 which was assigned as Glc$_{VI}$ H-2 which in turn showed a COSY correlation to a proton at δ$_H$ 3.49 (Glc$_{VI}$ H-3). Due to data overlap, the COSY spectrum did not allow assignment of Glc$_V$ H-4 to H-6 based on the COSY correlations. Therefore, a series of 1D-TOCSY experiments were performed using selective irradiation of the Glc$_{VI}$ anomeric proton with different mixing times. In addition to confirming the assignments for Glc$_{VI}$ H-2 through H-3, the 1D-TOCSY data showed protons at δ$_H$ 3.45 (Glc$_{VI}$ H-4) and δ$_H$ 3.48 (Glc$_{VI}$ H-5) and protons at δ$_H$ 3.92 and 3.94 assigned for Glc$_{VI}$ H-6 protons. Assignment of the $^{13}$C chemical shifts for Glc$_{VI}$ C-2 (δ$_C$ 78.1), C-3 (δ$_C$ 78.6), C-4 (δ$_C$ 72.3), C-5 (δ$_C$ 78.8), and C-6 (δ$_C$ 64.1) was determined using the $^1$H-$^{13}$C HSQC-DEPT data to complete the assignment of Glc$_{VI}$.

A summary of the $^1$H and $^{13}$C chemical shifts for the glycoside at C-19 are found in the table below:

| H NMR (500 MHz, D$_2$O) and $^{13}$C NMR (125 MHz, D$_2$O/TSP) Assignments of the Reb M2 glycoside. | | |
|---|---|---|
| Position | $^{13}$C | $^1$H |
| Glc$_I$-1 | 95.5 | 5.65 d (7.6) |
| Glc$_I$-2 | 80.5 | 3.96 m |
| Glc$_I$-3 | 79.0 | 3.89 m |
| Glc$_I$-4 | 71.5 | 3.71 m |
| Glc$_I$-5 | 79.0 | 3.73 m |
| Glc$_I$-6 | 70.9 | 4.00 m |
| | | 4.15 d (11.7) |
| Glc$_V$-1 | 105.3* | 4.83* d (8.0) |
| Glc$_V$-2 | 78.5 | 3.32 m |
| Glc$_V$-3 | 78.7 | 3.51 m |
| Glc$_V$-4 | 72.9 | 3.38 m |
| Glc$_V$-5 | 78.8 | 3.55 m |
| Glc$_V$-6 | 63.6 | 3.76 m |
| | | 3.97 m |
| Glc$_{VI}$-1 | 105.7 | 4.50 d (7.9) |
| Glc$_{VI}$-2 | 78.1 | 3.33 m |
| Glc$_{VI}$-3 | 78.6 | 3.49 m |
| Glc$_{VI}$-4 | 72.3 | 3.45 m |
| Glc$_{VI}$-5 | 78.8 | 3.48 m |
| Glc$_{VI}$-6 | 64.1 | 3.92 m |
| | | 3.94 m |

*$^1$H and $^{13}$C values can be exchangeable with Glc$_{II}$-1 of the following table.

A summary of the key HMBC, COSY, and 1D-TOCSY correlations used to assign the C-19 glycoside region are provided below:

| $^1$H NMR (500 MHz, D$_2$O) and $^{13}$C NMR (125 MHz, D$_2$O/TSP) Assignments of the Reb M2 glycoside. | | |
|---|---|---|
| Position | $^{13}$C# | $^1$H |
| Glc$_{II}$-1 | 98.4 | 4.85 d (7.8) |
| Glc$_{II}$-2 | 81.7 | 3.75 m |
| Glc$_{II}$-3 | 88.0 | 3.98 m |
| Glc$_{II}$-4 | 71.3 | 3.54 m |
| Glc$_{II}$-5 | 80.5 | 3.96 m |
| Glc$_{II}$-6 | 63.6 | 3.45 m |
| | | 3.77 m |
| Glc$_{III}$-1 | 104.9 | 4.92 d (7.9) |
| Glc$_{III}$-2 | 76.3 | 3.32 m |
| Glc$_{III}$-3 | 78.8 | 3.51 m |
| Glc$_{III}$-4 | 73.3 | 3.26 t (9.5) |
| Glc$_{III}$-5 | 78.8 | 3.44 m |
| Glc$_{III}$-6 | 64.4 | 3.75 m |
| | | 3.94 m |
| Glc$_{IV}$-1 | 105.0 | 4.84 d (7.8) |
| Glc$_{IV}$-2 | 76.1 | 3.41 m |
| Glc$_{IV}$-3 | 78.8 | 3.46 m |
| Glc$_{IV}$-4 | 72.5 | 3.45 m |
| Glc$_{IV}$-5 | 81.7 | 3.75 m |
| Glc$_{IV}$-6 | 65.8 | 3.55 m |
| | | 3.78 m |

Assignment of Glc$_{II}$ was carried out in a similar manner. The Glc$_{II}$ anomeric proton (δ$_H$ 4.85) showed a COSY correlation to a proton at δ$_H$ 3.75 which was assigned as Glc$_{II}$ H-2 which in turn showed a COSY correlation to a proton at δ$_H$ 3.98 (Glc$_{II}$ H-3). This latter proton showed an additional correlation with a proton at δ$_H$ 3.54 (Glc$_{II}$ H-4). H-4 also showed a COSY correlation to a proton at δ$_H$ 3.96 (Glc$_{II}$ H-5). Glc$_{II}$ H-5 also showed a COSY correlation to Glc$_{II}$ H-6 protons (δ$_H$ 3.77 and 3.45). Assignment of the $^{13}$C chemical shifts for Glc$_{II}$ C-2 (δ$_C$ 81.7), C-3 (δ$_C$ 88.0), C-4 (δ$_C$ 71.3), C-5 (δ$_C$ 80.5), and C-6 (δ$_C$ 63.6) was determined using the HSQC-DEPT data. HMBC correlations from Glc$_{II}$ H-3 to C-2 and C-4 and also from Glc$_{II}$ H-4 to C-3 and C-6 confirmed the assignments made above to complete the assignment of Glc$_{II}$.

Two of the remaining unassigned glucose moieties were assigned as substituents at C-2 and C-3 of Glc$_{II}$ on the basis of HMBC correlations. The anomeric proton observed at δ$_H$ 4.92 showed a HMBC correlation to Glc$_{II}$ C-2 and was assigned as the anomeric proton of Glc$_{III}$. The anomeric proton observed at δ$_H$ 4.84 showed a HMBC correlation to Glc$_{II}$ C-3 and was assigned as the anomeric proton of Glc$_{IV}$. The reciprocal HMBC correlations between Glc$_{II}$ H-2 and the anomeric carbon of Glc$_{III}$ and between Glc$_{II}$ H-3 and the anomeric carbon of Glc$_{IV}$ were also observed.

The anomeric proton of Glc$_{III}$ (δ$_H$ 4.92) showed a COSY correlation with a proton at δ$_H$ 3.32 which was assigned as Glc$_{III}$ H-2. Due to data overlap, the COSY spectrum did not allow assignment of H-3 to H-6 protons. Therefore, a series of 1D-TOCSY experiments were performed using selective irradiation of the Glc$_{III}$ anomeric proton with different mixing times. In addition to confirming the assignments for Glc$_{III}$ H-2, the 1D-TOCSY data showed protons at δ$_H$ 3.51 (Glc$_{III}$ H-3), δ$_H$ 3.26 (Glc$_{III}$ H-4), and δ$_H$ 3.44 (Glc$_{III}$ H-5). Once H-4 was assigned using 1D-TOCSY data, COSY correlations from H-4 to H-5 and in turn to H-6 were used to assign H-6. In the COSY spectrum, Glc$_{III}$ H-4 showed a correlation to Glc$_{III}$ H-5, which in turn showed COSY correlations to δ$_H$ 3.94 and 3.75 of Glc$_{III}$ H-6a and H-6b, respectively. The $^{13}$C chemical shifts for Glc$_{III}$ C-2 ($\delta_C$ 76.3), C-3 ($\delta_C$ 78.8), C-4 ($\delta_C$ 73.3), C-5 ($\delta_C$ 78.8), and C-6 ($\delta_C$ 64.4) were then determined using the $^1$H-$^{13}$C HSQC-DEPT correlations to complete the assignment of Glc$_{III}$.

The anomeric proton of Glc$_{IV}$ ($\delta_H$ 4.84) which showed a COSY correlation to a proton at $\delta_H$ 3.41 was assigned as Glc$_{II}$/H-2 which in turn showed a COSY correlation to a proton at $\delta_H$ 3.46 (Glc$_{IV}$ H-3). This latter proton showed an additional correlation with a proton at $\delta_H$ 3.45 (Glc$_{II}$ H-4) which also showed a COSY correlation to a proton at $\delta_H$ 3.75 (Glc$_{IV}$ H-5). Glc$_{IV}$ H-5 also showed a COSY correlation to Glc$_{IV}$ H-6 protons ($\delta_H$ 3.55 and 3.78). Assignment of the $^{13}$C chemical shifts for Glc$_{IV}$ C-2 ($\delta_C$ 76.1), C-3 ($\delta_C$ 78.8), C-4 ($\delta_C$ 72.5), C-5 ($\delta_C$ 81.7), and C-6 ($\delta_C$ 65.8) was determined using the HSQC-DEPT data. HMBC correlations from Glc$_{IV}$ H-3 to C-4 and C-5 and also from Glc$_{II}$, H-4 to C-3 and C-6 confirmed the assignments made above to complete the assignment of Glc$_{IV}$.

A summary of the $^1$H and $^{13}$C chemical shifts for the glycoside at C-13 are found in the following table:

$^1$H NMR (500 MHz, D$_2$O) and $^{13}$C NMR (125 MHz, D$_2$O/TSP) Assignments of the Reb M2 glycoside.

| Position | $^{13}$C# | $^1$H |
|---|---|---|
| Glc$_{II}$-1 | 98.4 | 4.85 d (7.8) |
| Glc$_{II}$-2 | 81.7 | 3.75 m |
| Glc$_{II}$-3 | 88.0 | 3.98 m |
| Glc$_{II}$-4 | 71.3 | 3.54 m |
| Glc$_{II}$-5 | 80.5 | 3.96 m |
| Glc$_{II}$-6 | 63.6 | 3.45 m |
|  |  | 3.77 m |
| Glc$_{III}$-1 | 104.9 | 4.92 d (7.9) |
| Glc$_{III}$-2 | 76.3 | 3.32 m |
| Glc$_{III}$-3 | 78.8 | 3.51 m |
| Glc$_{III}$-4 | 73.3 | 3.26 t (9.5) |
| Glc$_{III}$-5 | 78.8 | 3.44 m |
| Glc$_{III}$-6 | 64.4 | 3.75 m |
|  |  | 3.94 m |
| Glc$_{IV}$-1 | 105.0 | 4.84 d (7.8) |
| Glc$_{IV}$-2 | 76.1 | 3.41 m |
| Glc$_{IV}$-3 | 78.8 | 3.46 m |
| Glc$_{IV}$-4 | 72.5 | 3.45 m |
| Glc$_{IV}$-5 | 81.7 | 3.75 m |
| Glc$_{IV}$-6 | 65.8 | 3.55 m |
|  |  | 3.78 m |

A summary of the key HMBC, COSY, and 1D-TOCSY correlations used to assign the C-13 glycoside region are provided below:

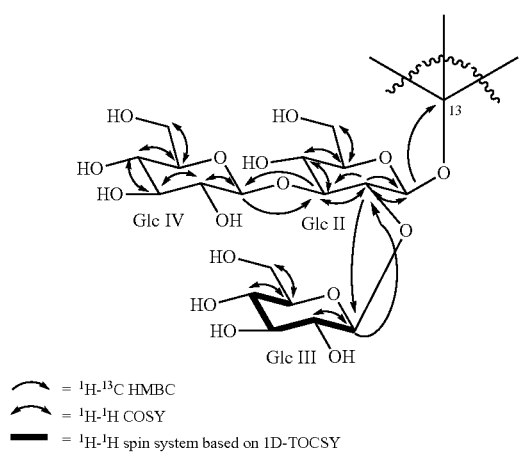

= $^1$H-$^{13}$C HMBC
= $^1$H-$^1$H COSY
= $^1$H-$^1$H spin system based on 1D-TOCSY NMR and MS analyses allowed a full assignment of its structure, shown below. The chemical name of the compound is 13-[(2-O-β-D-glucopyranosyl-3-O-β-D-glucopyranosyl-β-D-glucopyranosyl)oxy] ent-kaur-16-en-19-oic acid-[(2-O-β-D-glucopyranosyl-6-O-β-D-glucopyranosyl-β-D-glucopyranosyl) ester] (rebaudioside M2 or reb M2). The compound is an isomer of rebaudioside M.

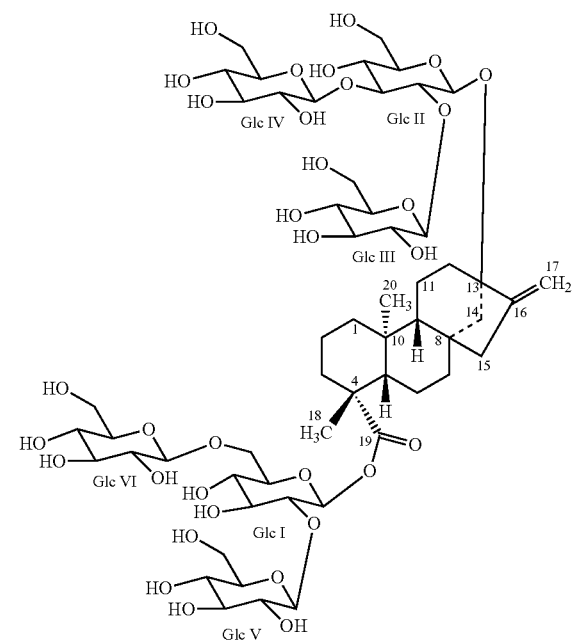

Example 41

Directed Evolution of UGT76G1 for the Conversion of Rebaudioside D to Rebaudioside X (Round 2)

The most active clone from the first round of directed evolution of UGT76G1 (see EXAMPLE 26 UGT76G1var94 containing mutations: Q266E_P272A_R334K_G348P_L379G) was chosen as baseline clone for round 2. A list of 53 mutations was established containing different identified positive mutations from the first round and new mutations obtained by DNA2.0 ProteinGPStm strategy. This list of mutations was subsequently used to design 92 variant genes that contained each 3 different mutations. After codon-optimized for expression in E. coli the genes were synthesized, subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 μL aliquots were stored at −20° C. and at −80° C.

These storage aliquots of E. coli BL21(DE3) containing the pET30a+_UGT76G1var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 μL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 μL of fresh lysate that was added to a solution of Rebaudioside D (final concentration 0.5 mM), $MgCl_2$ (final concentration 3 mM) and UDP-Glucose (final concentration 2.5 mM) in 50 mM phosphate buffer pH 7.2.

The reaction was allowed to run at 30° C. and samples were taken after 2, 4, 7 and 24 h. to determine conversion and initial rate by HPLC (CAD detection) using the analytical method that was described above for the transformation of Rebaudioside D to Rebaudioside X. In parallel the experiments were performed with baseline clone, Round1-Var94. The conversion after 22 h. and initial rate for this baseline clone was defined as 100% and the normalized conversions and initial rates for the round 2 clones are depicted in the following table:

| Clone | Mutations* | Normalized conversion Reb D to Reb X after 22 h. | Normalized initial rate (0-4 h) |
|---|---|---|---|
| Round1-Var94 | UGT76G1 (Q266E_P272A_R334K_G348P_L379G) baseline clone | 100% | 100% |
| Round2-Var1 | Round1-Var94 (A213N_P348G_I411V) | 70% | 86% |
| Round2-Var2 | Round1-Var94 (K303G_I423M_Q425E) | 120% | 134% |
| Round2-Var3 | Round1-Var94 (V20L_N138K_S147G) | 14% | 15% |
| Round2-Var4 | Round1-Var94 (I16V_V133A_L299I) | 37% | 43% |
| Round2-Var5 | Round1-Var94 (S241V_S274G_Q432E) | 75% | 72% |
| Round2-Var6 | Round1-Var94 (I16V_L139V_I218V) | 62% | 68% |
| Round2-Var7 | Round1-Var94 (K334R_N409K_Q432E) | 104% | 92% |
| Round2-Var8 | Round1-Var94 (I15L_R141T_I407V) | 17% | 26% |
| Round2-Var9 | Round1-Var94 (R141T_K303G_G379L) | 31% | 42% |
| Round2-Var10 | Round1-Var94 (I190L_K303G_P348G) | 131% | 149% |
| Round2-Var11 | Round1-Var94 (E266Q_F314S_N409R) | 106% | 132% |
| Round2-Var12 | Round1-Var94 (V133A_I295V_K303G) | 43% | 49% |
| Round2-Var13 | Round1-Var94 (I16V_S241V_N409R) | 80% | 79% |
| Round2-Var14 | Round1-Var94 (A239V_K334R_G379L) | 58% | 55% |
| Round2-Var15 | Round1-Var94 (I190L_K393R_V396L) | 118% | 126% |
| Round2-Var16 | Round1-Var94 (L101F_I295M_K393R) | 84% | 89% |
| Round2-Var17 | Round1-Var94 (A239V_E266Q_Q425E) | 96% | 101% |
| Round2-Var18 | Round1-Var94 (V20L_I190L_I423M) | 98% | 98% |
| Round2-Var19 | Round1-Var94 (V20L_G379L_S456L) | 84% | 81% |
| Round2-Var20 | Round1-Var94 (K334R_P348G_N409R) | 73% | 73% |
| Round2-Var21 | Round1-Var94 (E231A_S241V_E449D) | 53% | 50% |
| Round2-Var22 | Round1-Var94 (K188R_L299I_V394I) | 56% | 59% |
| Round2-Var23 | Round1-Var94 (E231A_S274G_V394I) | 110% | 124% |
| Round2-Var24 | Round1-Var94 (S42A_I295V_Q432E) | 71% | 78% |
| Round2-Var25 | Round1-Var94 (A213N_A272P_K334R) | 95% | 80% |
| Round2-Var26 | Round1-Var94 (L158Y_S274K_N409K) | 80% | 50% |
| Round2-Var27 | Round1-Var94 (K188R_I295M_Q425E) | 132% | 116% |
| Round2-Var28 | Round1-Var94 (I15L_I295M_V394I) | 53% | 36% |
| Round2-Var29 | Round1-Var94 (V133A_A239V_V394I) | 47% | 30% |
| Round2-Var30 | Round1-Var94 (L158Y_F314S_K316R) | 107% | 72% |
| Round2-Var31 | Round1-Var94 (L158Y_A239V_A272P) | 54% | 30% |
| Round2-Var32 | Round1-Var94 (F46I_D301N_V396L) | 109% | 101% |
| Round2-Var33 | Round1-Var94 (L101F_I218V_Q432E) | 78% | 54% |
| Round2-Var34 | Round1-Var94 (I16V_F46I_I295M) | 110% | 95% |
| Round2-Var35 | Round1-Var94 (A213N_E266S_I407V) | 98% | 79% |
| Round2-Var36 | Round1-Var94 (A239V_S274K_I295M) | 102% | 89% |
| Round2-Var37 | Round1-Var94 (A239V_F314S_S450K) | 105% | 99% |
| Round2-Var38 | Round1-Var94 (L139V_K188R_D301N) | 66% | 51% |
| Round2-Var39 | Round1-Var94 (I45V_I218V_S274K) | 87% | 58% |
| Round2-Var40 | Round1-Var94 (S241V_K303G_V394I) | 78% | 57% |
| Round2-Var41 | Round1-Var94 (R141T_S274G_K334R) | 41% | 28% |
| Round2-Var42 | Round1-Var94 (V217L_S274G_L299I) | 47% | 34% |
| Round2-Var43 | Round1-Var94 (S274G_D301N_P348G) | 98% | 91% |
| Round2-Var44 | Round1-Var94 (E231A_N409R_S450K) | 87% | 65% |
| Round2-Var45 | Round1-Var94 (R64H_E231A_K316R) | 88% | 64% |
| Round2-Var46 | Round1-Var94 (V394I_N409K_I411V) | 110% | 100% |
| Round2-Var47 | Round1-Var94 (I45V_I295M_K303G) | 113% | 88% |
| Round2-Var48 | Round1-Var94 (L101F_V396L_L398V) | 46% | 43% |
| Round2-Var49 | Round1-Var94 (N27S_L101F_S447A) | 54% | 37% |
| Round2-Var50 | Round1-Var94 (S274G_F314S_L398V) | 129% | 156% |
| Round2-Var51 | Round1-Var94 (E266Q_L299I_K393R) | 70% | 51% |
| Round2-Var52 | Round1-Var94 (V217L_E266S_V394I) | 62% | 48% |
| Round2-Var53 | Round1-Var94 (N138K_A272P_N409R) | 118% | 102% |
| Round2-Var54 | Round1-Var94 (E266S_F314S_Q432E) | 124% | 146% |
| Round2-Var55 | Round1-Var94 (D301N_G379L_L398V) | 56% | 45% |
| Round2-Var56 | Round1-Var94 (F46I_E266S_K334R) | 123% | 142% |
| Round2-Var57 | Round1-Var94 (A272P_V394I_Q432E) | 133% | 142% |
| Round2-Var58 | Round1-Var94 (V394I_I407V_S456L) | 118% | 114% |
| Round2-Var59 | Round1-Var94 (I218V_E266Q_I423M) | 106% | 98% |

-continued

| Clone | Mutations* | Normalized conversion Reb D to Reb X after 22 h. | Normalized initial rate (0-4 h) |
|---|---|---|---|
| Round2-Var60 | Round1-Var94 (A272P_G379L_I407V) | 80% | 63% |
| Round2-Var61 | Round1-Var94 (E231A_K303G_S456L) | 113% | 110% |
| Round2-Var62 | Round1-Var94 (I190L_E266Q_I407V) | 150% | 167% |
| Round2-Var63 | Round1-Var94 (N27S_L139V_I295V) | 43% | 25% |
| Round2-Var64 | Round1-Var94 (V217L_I423M_S447A) | 67% | 51% |
| Round2-Var65 | Round1-Var94 (L158Y_E266S_E449D) | 68% | 43% |
| Round2-Var66 | Round1-Var94 (S42A_F46I_I407V) | 160% | 203% |
| Round2-Var67 | Round1-Var94 (N138K_E231A_D301N) | 118% | 93% |
| Round2-Var68 | Round1-Var94 (K188R_G379L_N409R) | 52% | 35% |
| Round2-Var69 | Round1-Var94 (I15L_E231A_V396L) | 38% | 22% |
| Round2-Var70 | Round1-Var94 (E231A_Q425E_Q432E) | 115% | 119% |
| Round2-Var71 | Round1-Var94 (D301N_K316R_Q425E) | 126% | 121% |
| Round2-Var72 | Round1-Var94 (L139V_I295M_F314S) | 76% | 91% |
| Round2-Var73 | Round1-Var94 (S147G_E266S_D301N) | 30% | 18% |
| Round2-Var74 | Round1-Var94 (R64H_S147G_S447A) | 23% | 12% |
| Round2-Var75 | Round1-Var94 (S42A_K303G_L398V) | 95% | 110% |
| Round2-Var76 | Round1-Var94 (I45V_D301N_E449D) | 62% | 60% |
| Round2-Var77 | Round1-Var94 (V133A_E266S_I411V) | 37% | 28% |
| Round2-Var78 | Round1-Var94 (I45V_N409R_Q425E) | 63% | 59% |
| Round2-Var79 | Round1-Var94 (R141T_A272P_F314S) | 23% | 10% |
| Round2-Var80 | Round1-Var94 (E266S_S274G_N409R) | 81% | 91% |
| Round2-Var81 | Round1-Var94 (N409K_Q425E_S450K) | 81% | 84% |
| Round2-Var82 | Round1-Var94 (N27S_R64H_K393R) | 47% | 37% |
| Round2-Var83 | Round1-Var94 (S42A_A213N_V217L) | 62% | 46% |
| Round2-Var84 | Round1-Var94 (N27S_S274K_I407V) | 49% | 44% |
| Round2-Var85 | Round1-Var94 (I411V_Q425E_S456L) | 75% | 81% |
| Round2-Var86 | Round1-Var94 (A239V_K316R_E449D) | 83% | 72% |
| Round2-Var87 | Round1-Var94 (S147G_A239V_P348G) | 18% | 7% |
| Round2-Var88 | Round1-Var94 (V20L_S274G_S450K) | 71% | 68% |
| Round2-Var89 | Round1-Var94 (F314S_V394I_S447A) | 88% | 123% |
| Round2-Var90 | Round1-Var94 (R64H_E266Q_I295M) | 45% | 47% |
| Round2-Var91 | Round1-Var94 (N138K_I295V_I407V) | 50% | 51% |
| Round2-Var92 | Round1-Var94 (I15L_P348G_Q432E) | 18% | 13% |

*Mutations are noted as follows: reference gene-original amino acid-position-new amino acid: For example the mutation of an alanine at position 33 to a glycine for variant 94 from the first round of directed evolution of UGT76G1 is noted as Round1-Var94 (A33G)

Modeling of these results allowed to obtain a ranking of the effect of each mutation. The following mutations were determined as being beneficial for activity: S42A, F46I, I190L, S274G, I295M, K303G, F314S, K316R, K393R, V394I, I407V, N409K, N409R, Q425E, Q432E, S447A, S456L.

Example 42

In Vivo Production of AtSUS
AtSUS
>gi|79328294|ref|NP_001031915.1| sucrose synthase 1 [*Arabidopsis thaliana*]
SEQ ID NO:13:

```
MANAERMITRVHSQRERLNETLVSERNEVLALLSRVEAKGKGILQQNQII
AEFEALPEQTRKKLEGGPFFDLLKSTQEAIVLPPWVALAVRPRPGVWEYL
RVNLHALVVEELQPAEFLHFKEELVDGVKNGNFTLELDFEPFNASIPRPT
LHKYIGNGVDFLNRHLSAKLFHDKESLLPLLKFLRLHSHQGKNLMLSEKI
QNLNTLQHTLRKAEEYLAELKSETLYEEFEAKFEEIGLERGWGDNAERVL
DMIRLLLDLLEAPDPCTLETFLGRVPMVFNVVILSPHGYFAQDNVLGYPD
TGGQVVYILDQVRALEIEMLQRIKQQGLNIKPRILILTRLLPDAVGTICG
ERLERVYDSEYCDILRVPFRTEKGIVRKWISRFEVWPYLETYTEDAAVEL
SKELNGKPDLIIGNYSDGNLVASLLAHKLGVTQCTIAHALEKTKYPDSDI
YWKKLDDKYHFSCQFTADIFAMNHTDFIITSTFQEIAGSKETVGQYESHT
AFTLPGLYRVVHGIDVFDPKFNIVSPGADMSIYFPYTEEKRRLTKFHSEI
EELLYSDVENKEHLCVLKDKKKPILFTMARLDRVKNLSGLVEWYGKNTRL
RELANLVVVGGDRRKESKDNEEKAEMKKMYDLIEEYKLNGQFRWISSQMD
RVRNGELYRYICDTKGAFVQPALYEAFGLTVVEAMTCGLPTFATCKGGPA
EIIVHGKSGFHIDPYHGDQAADTLADFFTKCKEDPSHWDEISKGGLQRIE
EKYTWQIYSQRLLTLTGVYGFWKHVSNLDRLEARRYLEMFYALKYRPLAQ
AVPLAQDD
```

The synthetic gene of AtSuS that was codon optimized for expression in *E. coli* and subcloned in the pET30a+ plasmid using the NdeI and XhoI restriction sites. The pET30A+ vector containing the AtSUS gene was used to transform electrocompetent *E. coli* Bl21(DE3) cells. The obtained cells were grown in petri-dishes in the presence of Kanamycin and suitable colonies were selected and allowed to grow in liquid LB medium (erlenmeyer flasks). Glycerol was added to the suspension as cryoprotectant and 400 µL, aliquots were stored at −20° C. and at −80° C.

The storage aliquots of *E. coli* BL21(DE3) containing the pET30A+_AtSUS plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake at 135 rpm at 30° C. for 8 h.

The production medium contained 60 g/L of overnight express instant TB medium (Novagen), 10 g/L of glycerol and 50 mg/L of Kanamycine. The preculture was added to 800 mL of this medium and the solution was allowed to stir at 20° C. while taking samples to measure the OD and pH. The culture gave significant growth and a good OD was obtained. After 40 h, the cells were harvested by centrifugation and frozen to obtain 30.1 g of cell wet weight.

Lysis was performed by Fastprep (MP Biomedicals, Lysing matrix B, speed 6.0, 3×40 sec) with a cell suspension of 200 mg of cells in 1.0 mL of 50 mM Tris buffer pH 7.5. The lysate was recovered by centrifugation and used fresh.

Example 43

Figure 66:
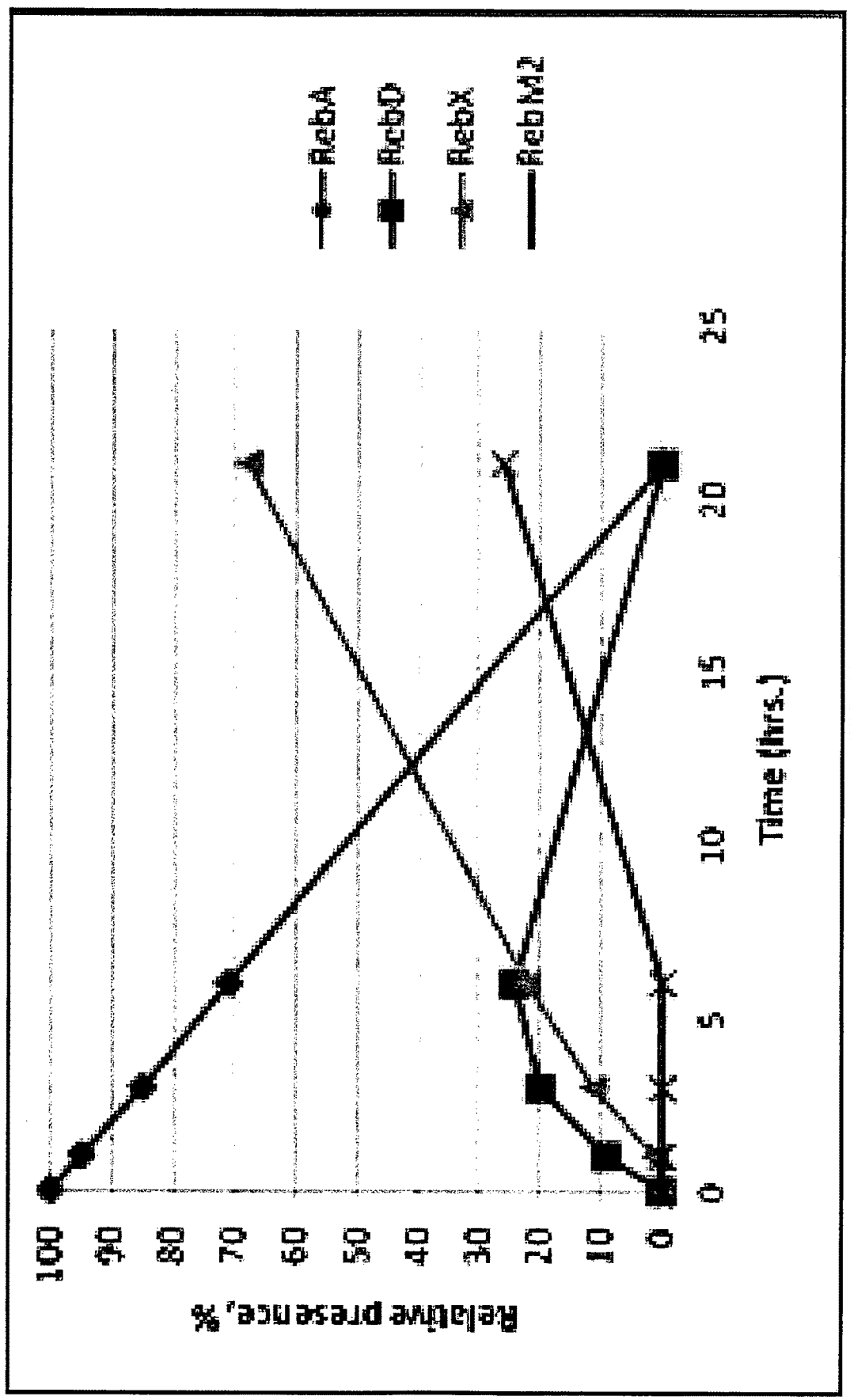
FIG. 66 shows a graph showing the HPLC results for Example 43.

Conversion of Rebaudioside A to Rebaudioside X with In Situ Prepared UDP-Glucose using UGTSL2, UGT76G1-R1-F12 and AtSUS The reaction was performed at 1 mL scale using 100 mM of sucrose, 3 mM of $MgCl_2$, 0.25 mM of UDP and 0.5 mM of Rebaudioside A in potassium phosphate buffer (50 mM final concentration, pH 7.5). The reaction was started by adding 15 μL of UGTSL2 (see EXAMPLE 27) lysate (2 U/mL), 150 μL of UGT76G1var94 (see EXAMPLE 26) (2.5 U/mL) and 15 μL of AtSUS (see EXAMPLE 42) (400 U/mL). The reaction was followed by HPLC after quenching 125 μL samples with 10 μL of 2 N $H_2SO_4$ and 115 μL of 60% methanol. 68% of Rebaudioside X and 26% of Rebaudioside M2 was obtained after 21 h of reaction time, as shown in FIG. 66.

Example 44

Directed Evolution of UGT76G1 for the Conversion of Rebaudioside D to Rebaudioside X (Round 3)

The most active clone from the second round of directed evolution of UGT76G1 (see EXAMPLE 41 round2_UGT76G1var66 containing mutations: S42A_F46I_I407V) was chosen as baseline clone for round 3. A list of 56 mutations was established containing different identified positive mutations from the second round and 30 new mutations obtained by DNA2.0 ProteinGPStm strategy. This list of mutations was subsequently used to design 92 variant genes that contained each 3 or 4 different mutations.

After codon-optimized for expression in E. coli the genes were synthesized, subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 μL aliquots were stored at −20° C. and at −80° C.

These storage aliquots of E. coli BL21(DE3) containing the pET30a+_UGT76G1var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 μL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 μL of fresh lysate that was added to a solution of Rebaudioside D (final concentration 0.5 mM), $MgCl_2$ (final concentration 3 mM) and UDP-Glucose (final concentration 2.5 mM) in 50 mM phosphate buffer pH 7.2.

The reaction was allowed to run at 30° C. and samples were taken after 1, 2, 4, 6 and 22 h. to determine conversion and initial rate by HPLC (CAD detection) using the analytical method that was described above for the transformation of Rebaudioside D to Rebaudioside X. In parallel the experiments were performed with baseline clone, Round2-Var66. The conversion after 22 h. and initial rate for this baseline clone was defined as 100% and the normalized conversions and initial rates for the round 3 clones are depicted in the following table:

| Clone | Mutations* | Normalized conversion Reb D to Reb X after 22 h. | Normalized initial rate (0-4 h) |
|---|---|---|---|
| Round2-Var66 | UGT76G1 (S42A_F46I_Q266E_P272A_R334K_G348P_L379G_I407V) Baseline clone | 100% | 100% |
| Round3-Var1 | Round2-Var66 (I46F_L121I_E229A_K393R) | 42% | 96% |
| Round3-Var2 | Round2-Var66 (F18V_A213N_E266S) | 7% | 36% |
| Round3-Var3 | Round2-Var66 (F41L_I190L_A239V_K316R) | 20% | 64% |
| Round3-Var4 | Round2-Var66 (N138K_S274G_Q425E_S456L) | 92% | 104% |
| Round3-Var5 | Round2-Var66 (F22Y_E229S_V407I_N409R) | 15% | 66% |
| Round3-Var6 | Round2-Var66 (F150A_G216A_T355S_S447A) | 15% | 50% |
| Round3-Var7 | Round2-Var66 (V394I_N409R_Q425E_S447A) | 72% | 97% |
| Round3-Var8 | Round2-Var66 (Y37H_F41L_N409R_Q425E) | 6% | 37% |
| Round3-Var9 | Round2-Var66 (L121V_F182L_K303G_E331G) | 75% | 95% |
| Round3-Var10 | Round2-Var66 (S274G_K303G_N409R_Q432E) | 99% | 106% |
| Round3-Var11 | Round2-Var66 (F41L_K303G_F314S) | 26% | 67% |
| Round3-Var12 | Round2-Var66 (F22Y_R141S_T284V) | 3% | 15% |
| Round3-Var13 | Round2-Var66 (I190L_E229A_T284V) | 31% | 70% |
| Round3-Var14 | Round2-Var66 (K303G_Q425E_S447A) | 109% | 114% |
| Round3-Var15 | Round2-Var66 (K316R_L383V_V394I) | 107% | 117% |
| Round3-Var16 | Round2-Var66 (I190L_K303G_S447A_S456L) | 112% | 110% |
| Round3-Var17 | Round2-Var66 (N138G_V264C_A352G_S447A) | 102% | 107% |
| Round3-Var18 | Round2-Var66 (S274K_V407I_Q425E) | 91% | 107% |
| Round3-Var19 | Round2-Var66 (I190L_S274G_K393R_V394I) | 120% | 108% |
| Round3-Var20 | Round2-Var66 (A213N_L277I_Q425E_E449D) | 79% | 101% |
| Round3-Var21 | Round2-Var66 (I46L_K303G_K393R) | 147% | 117% |
| Round3-Var22 | Round2-Var66 (S221T_S274G_S375Q) | 19% | 65% |
| Round3-Var23 | Round2-Var66 (Y37H_L383V_S456L) | 67% | 99% |

| Clone | Mutations* | Normalized conversion Reb D to Reb X after 22 h. | Normalized initial rate (0-4 h) |
|---|---|---|---|
| Round3-Var24 | Round2-Var66 (N138G_I190L_I295T_N409R) | 45% | 84% |
| Round3-Var25 | Round2-Var66 (A42S_S119A_K303G_V407I) | 92% | 99% |
| Round3-Var26 | Round2-Var66 (F22Y_I46F_I190L_V394I) | 76% | 95% |
| Round3-Var27 | Round2-Var66 (N138K_A213N_F314S) | 83% | 92% |
| Round3-Var28 | Round2-Var66 (D301N_F314S_V394I_N409R) | 76% | 86% |
| Round3-Var29 | Round2-Var66 (G216A_E266S_Q432E) | 70% | 88% |
| Round3-Var30 | Round2-Var66 (N138K_A239V_P382R_K393R) | 42% | 76% |
| Round3-Var31 | Round2-Var66 (I46L_S274G_K316R_S456L) | 149% | 109% |
| Round3-Var32 | Round2-Var66 (F18V_I190L_S375Q_S456L) | 1% | 2% |
| Round3-Var33 | Round2-Var66 (N138K_R141S_S274G) | 18% | 57% |
| Round3-Var34 | Round2-Var66 (N138K_K393R_N409R_S447A) | 59% | 82% |
| Round3-Var35 | Round2-Var66 (I295T_K303G_P382R_V394I) | 31% | 70% |
| Round3-Var36 | Round2-Var66 (N138K_I218V_S456L) | 54% | 81% |
| Round3-Var37 | Round2-Var66 (M145R_S274K_L383V) | 1% | 1% |
| Round3-Var38 | Round2-Var66 (F182L_A352G_V394I) | 86% | 96% |
| Round3-Var39 | Round2-Var66 (A42S_N138G_E229A_S456L) | 21% | 77% |
| Round3-Var40 | Round2-Var66 (R141S_I190L_E331G_Q425E) | 6% | 35% |
| Round3-Var41 | Round2-Var66 (E229S_K316R_T355S) | 32% | 81% |
| Round3-Var42 | Round2-Var66 (I46F_N138K_F292L_N409R) | 30% | 83% |
| Round3-Var43 | Round2-Var66 (A42S_F182L_L277I_T355S) | 40% | 89% |
| Round3-Var44 | Round2-Var66 (S274G_T284V_Q425E) | 85% | 93% |
| Round3-Var45 | Round2-Var66 (A272P_E331G_V394I_S447A) | 88% | 96% |
| Round3-Var46 | Round2-Var66 (S274G_F314S_Q432E_S447A) | 112% | 104% |
| Round3-Var47 | Round2-Var66 (L121I_K316R_S375Q_N409R) | 24% | 76% |
| Round3-Var48 | Round2-Var66 (L121I_N138G_F150A_K303G) | 40% | 83% |
| Round3-Var49 | Round2-Var66 (I46F_V264C_Q432E) | 61% | 98% |
| Round3-Var50 | Round2-Var66 (F150A_A272P_D301N_K316R) | 44% | 88% |
| Round3-Var51 | Round2-Var66 (I46L_R64V_A239V) | 28% | 71% |
| Round3-Var52 | Round2-Var66 (L121I_I218V_F314S) | 87% | 94% |
| Round3-Var53 | Round2-Var66 (I190L_G216A_E449D) | 49% | 90% |
| Round3-Var54 | Round2-Var66 (S274G_I295M_F314S) | 128% | 106% |
| Round3-Var55 | Round2-Var66 (F22Y_S274G_P382R_Q432E) | 39% | 48% |
| Round3-Var56 | Round2-Var66 (N138K_I190L_K334R) | 93% | 97% |
| Round3-Var57 | Round2-Var66 (N138G_I295M_K303G) | 110% | 100% |
| Round3-Var58 | Round2-Var66 (L121V_G216A_Q425E_S456L) | 28% | 52% |
| Round3-Var59 | Round2-Var66 (F182L_F314S_K393R) | 92% | 97% |
| Round3-Var60 | Round2-Var66 (R64V_K316R_N409K) | 16% | 54% |
| Round3-Var61 | Round2-Var66 (V264C_S274G_K393R) | 102% | 98% |
| Round3-Var62 | Round2-Var66 (F41L_K393R_S456L) | 12% | 49% |
| Round3-Var63 | Round2-Var66 (A42S_S274G_F292L_V394I) | 75% | 87% |
| Round3-Var64 | Round2-Var66 (I190L_S221T_E266S_S447A) | 34% | 71% |
| Round3-Var65 | Round2-Var66 (R64V_E229S_S274K) | 12% | 49% |
| Round3-Var66 | Round2-Var66 (S221T_K334R_K393R_V394I) | 72% | 90% |
| Round3-Var67 | Round2-Var66 (I190L_K393R_Q425E_Q432E) | 101% | 102% |
| Round3-Var68 | Round2-Var66 (F18V_N138K_M145R) | 1% | 1% |
| Round3-Var69 | Round2-Var66 (I218V_F292L_K316R_S447A) | 40% | 79% |
| Round3-Var70 | Round2-Var66 (L121V_E229A_K316R_Q432E) | 19% | 63% |
| Round3-Var71 | Round2-Var66 (Y37H_L121V_D301N) | 35% | 68% |
| Round3-Var72 | Round2-Var66 (N138K_V394I_Q432E_S456L) | 66% | 89% |
| Round3-Var73 | Round2-Var66 (T284V_I295M_A352G_L383V) | 69% | 89% |
| Round3-Var74 | Round2-Var66 (S119A_F150A_V394I_Q425E) | 66% | 88% |
| Round3-Var75 | Round2-Var66 (F18V_A239V_S447A) | 8% | 27% |
| Round3-Var76 | Round2-Var66 (K303G_N409R_Q432E) | 84% | 97% |
| Round3-Var77 | Round2-Var66 (Y37H_A272P_K334R_E449D) | 75% | 89% |
| Round3-Var78 | Round2-Var66 (K303G_F314S_V394I_Q425E) | 121% | 104% |
| Round3-Var79 | Round2-Var66 (R141S_I295T_F314S_Q432E) | 9% | 29% |
| Round3-Var80 | Round2-Var66 (N138K_I190L_F314S_N409R) | 90% | 97% |
| Round3-Var81 | Round2-Var66 (S119A_E331G_S456L) | 87% | 97% |
| Round3-Var82 | Round2-Var66 (K303G_F314S_K393R_S456L) | 100% | 100% |
| Round3-Var83 | Round2-Var66 (N138K_A352G_V407I_Q432E) | 72% | 95% |
| Round3-Var84 | Round2-Var66 (S274G_L277I_I295T) | 34% | 81% |
| Round3-Var85 | Round2-Var66 (R64V_L277I_F314S_S447A) | 34% | 61% |
| Round3-Var86 | Round2-Var66 (S221T_N409K_Q432E) | 39% | 75% |
| Round3-Var87 | Round2-Var66 (N409R_S447A_S456L) | 52% | 86% |
| Round3-Var88 | Round2-Var66 (K393R_Q425E_Q432E) | 102% | 99% |
| Round3-Var89 | Round2-Var66 (I46L_F292L_S375Q_N409K) | 8% | 35% |
| Round3-Var90 | Round2-Var66 (M145R_K393R_N409R) | 1% | 1% |
| Round3-Var91 | Round2-Var66 (S119A_M145R_T355S_P382R) | 0% | 1% |
| Round3-Var92 | Round2-Var66 (I190L_E229S_V264C_F314S) | 64% | 82% |

*Mutations are noted as follows: reference gene-original amino acid-position-new amino acid: For example the mutation of an isoleucine at position 190 to a leucine for variant 66 from the second round of directed evolution of UGT76G1 is noted as Round2-Var66 (I190L)

Modeling of these results allowed to obtain a ranking of the effect of each mutation. The following mutations were determined as being beneficial for activity: I46L, I295M, S119A, S274G, K334R, F314S, K303G, K316R, K393R, I190L, Q425E, Q432E, N138G, V394I, F182L, V407I, A272P, V264$C_{56}$, E449D, A352G.

Example 45

Directed Evolution of UGTSL2 for the Conversion of Rebaudioside A to Rebaudioside D (Round 1)

Starting from native enzyme UGTSL2 (GI_460410132) a list of 60 mutations was established containing different identified positive mutations from the first round and new mutations obtained by DNA2.0 ProteinGPStm strategy. This list of mutations was subsequently used to design 92 variant genes that contained each 3 different mutations. After codon-optimized for expression in E. coli the genes were synthesized, subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 μL aliquots were stored at −20° C. and at −80° C.

These storage aliquots of E. coli BL21(DE3) containing the pET30a+_UGTSL2var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 μL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 μL of fresh lysate that was added to a solution of Rebaudioside D (final concentration 0.5 mM), $MgCl_2$ (final concentration 3 mM) and UDP-Glucose (final concentration 2.5 mM) in 50 mM phosphate buffer pH 7.2.

The reaction was allowed to run at 30° C. and samples were taken after 2, 4, 6 and 22 h. to determine the initial rate by HPLC (CAD detection) using the analytical method that was described above for the transformation of Rebaudioside A to Rebaudioside D. In parallel the experiments were performed with baseline clone, UGTSL2. The initial rate for this baseline clone was defined as 100%. As an indication of the specificity of the clones, Rebaudioside M2 content was determined at 100% UDP-Glucose conversion and Rebaudioside D2 content was determined at 50% UDP-Glucose conversion. Wherein UDP glucose conversion is defined as: $([Reb\ D]/[Reb\ A]_0)+([Reb\ D2]/[Reb\ A]_0)+2*([Reb\ M2]/[Reb\ A]_0)$.

The normalized initial rate, Rebaudioside M2 content at 100% UDP-glucose conversion and Rebaudioside D2 content at 50% UDP-glucose conversion are depicted in the following table

| Clone | Mutations* | Normalized initial rate (0-4 h) | Reb M2 content at 100% UDP-Glc conversion | Reb D2 content at 50% UDP-Glc conversion |
|---|---|---|---|---|
| UGTSL2 | baseline clone | 100% | 100% | 12.5% |
| Round1-Var1 | UGTSL2 (L276A_N278G_T329V) | 220% | 98% | 8.5% |
| Round1-Var2 | UGTSL2 (S19I_E259G_V270L) | 0% | 0% | |
| Round1-Var3 | UGTSL2 (I323V_S334T_V368E) | 0% | 0% | |
| Round1-Var4 | UGTSL2 (V125I_E259G_L393V) | 0% | 0% | |
| Round1-Var5 | UGTSL2 (Q27R_H247P_I333L) | 185% | 134% | 15.0% |
| Round1-Var6 | UGTSL2 (Q27R_N325S_G387E_T392A) | 148% | 116% | 17.0% |
| Round1-Var7 | UGTSL2 (F253Y_N325A_K365V_G371K) | 0% | 0% | |
| Round1-Var8 | UGTSL2 (T245R_N325A_G331A_S334T) | 8% | 17% | |
| Round1-Var9 | UGTSL2 (G331A_N339S_G371K) | 2% | 3% | |
| Round1-Var10 | UGTSL2 (R6H_F272L_I323V) | 3% | 6% | |
| Round1-Var11 | UGTSL2 (R6H_F21L_T329I) | 0% | 0% | |
| Round1-Var12 | UGTSL2 (F21L_N280P_I282L) | 0% | 0% | |
| Round1-Var13 | UGTSL2 (T245R_V254L_I333V) | 0% | 1% | |
| Round1-Var14 | UGTSL2 (L276A_I351L_M354L_I389L) | 2% | 2% | |
| Round1-Var15 | UGTSL2 (S19I_I240L_I351M) | 4% | 9% | |
| Round1-Var16 | UGTSL2 (I131V_I333V_S334T) | 3% | 8% | |
| Round1-Var17 | UGTSL2 (S200F_A285V_I351M_P361G) | 0% | 0% | |
| Round1-Var18 | UGTSL2 (R6H_L37F_A285L) | 8% | 21% | |
| Round1-Var19 | UGTSL2 (H247P_N249G_K289P) | 8% | 17% | |
| Round1-Var20 | UGTSL2 (R6H_S19I_N325A) | 50% | 59% | |
| Round1-Var21 | UGTSL2 (N280P_K289P_T329I_V368E) | 0% | 0% | |
| Round1-Var22 | UGTSL2 (I240L_N325S_V368E) | 26% | 43% | |
| Round1-Var23 | UGTSL2 (A205P_T245R_K365V) | 0% | 0% | |
| Round1-Var24 | UGTSL2 (L276A_A341V_T392A) | 255% | 115% | 7.5% |
| Round1-Var25 | UGTSL2 (L37F_I351L_K365V) | 7% | 17% | |
| Round1-Var26 | UGTSL2 (T199S_E259G_T329I) | 80% | 90% | 12.0% |
| Round1-Var27 | UGTSL2 (T245R_S258T_L405V) | 7% | 18% | |
| Round1-Var28 | UGTSL2 (K289S_I352V_P361G) | 9% | 15% | |
| Round1-Var29 | UGTSL2 (L37F_V254L_V270L_I323V) | 0% | 0% | |
| Round1-Var30 | UGTSL2 (I240L_S258T_G387E) | 127% | 107% | 11.0% |
| Round1-Var31 | UGTSL2 (V270I_I282L_T329V_N339S) | 0% | 0% | |
| Round1-Var32 | UGTSL2 (H247P_T329I_I351L) | 0% | 3% | |
| Round1-Var33 | UGTSL2 (N280P_A285L_I352V_G387E) | 37% | 62% | |
| Round1-Var34 | UGTSL2 (S19I_I323V_N325S_P361G) | 0% | 0% | |
| Round1-Var35 | UGTSL2 (L37F_Q65P_F272L) | 14% | 24% | |
| Round1-Var36 | UGTSL2 (H247P_N280R_A285V) | 32% | 54% | |
| Round1-Var37 | UGTSL2 (I240L_N339S_I352V_L405V) | 0% | 0% | |
| Round1-Var38 | UGTSL2 (V125I_N280P_G371K) | 2% | 5% | |

-continued

| Clone | Mutations* | Normalized initial rate (0-4 h) | Reb M2 content at 100% UDP-Glc conversion | Reb D2 content at 50% UDP-Glc conversion |
|---|---|---|---|---|
| Round1-Var39 | UGTSL2 (F253Y_I282L_A285V) | 25% | 45% | |
| Round1-Var40 | UGTSL2 (I282L_R312L_N325S) | 4% | 8% | |
| Round1-Var41 | UGTSL2 (T199S_S258T_N278G) | 0% | 9% | |
| Round1-Var42 | UGTSL2 (I114V_I351M_G387E) | 0% | 0% | |
| Round1-Var43 | UGTSL2 (S255C_S258T_V270L) | 29% | 59% | |
| Round1-Var44 | UGTSL2 (Q27R_R312L_T329V) | 86% | 92% | 12.0% |
| Round1-Var45 | UGTSL2 (V254L_N339S_I345L) | 0% | 0% | 11.0% |
| Round1-Var46 | UGTSL2 (I333V_A341V_M354L) | 84% | 86% | |
| Round1-Var47 | UGTSL2 (F253Y_F272L_T392A) | 125% | 116% | 12.0% |
| Round1-Var48 | UGTSL2 (F253Y_A285V_N339S) | 50% | 70% | |
| Round1-Var49 | UGTSL2 (K289S_I345L_G387E) | 0% | 2% | |
| Round1-Var50 | UGTSL2 (I131V_E259G_V270I) | 0% | 0% | |
| Round1-Var51 | UGTSL2 (F272L_N280R_T329V) | 0% | 4% | |
| Round1-Var52 | UGTSL2 (N278G_R312L_T329I_I333L) | 100% | 100% | 13.0% |
| Round1-Var53 | UGTSL2 (I114V_I131V_N325S) | 10% | 20% | |
| Round1-Var54 | UGTSL2 (A205P_K289P_I333V_G371K) | 0% | 0% | |
| Round1-Var55 | UGTSL2 (S19I_F21L_S200F) | 0% | 0% | |
| Round1-Var56 | UGTSL2 (I131V_H247P_N278G_A285L) | 109% | 120% | 13.0% |
| Round1-Var57 | UGTSL2 (R312L_A341V_M367V) | 14% | 25% | |
| Round1-Var58 | UGTSL2 (N280R_I333L_M354L) | 0% | 1% | |
| Round1-Var59 | UGTSL2 (S258T_E259G_A285V_I333V) | 0% | 0% | |
| Round1-Var60 | UGTSL2 (P361G_I389L_L405V) | 0% | 0% | |
| Round1-Var61 | UGTSL2 (S255C_N280R_I345L_V368E) | 0% | 0% | |
| Round1-Var62 | UGTSL2 (F21L_Q65P_N280R_K289S) | 0% | 0% | |
| Round1-Var63 | UGTSL2 (V270I_M367V_V368E) | 20% | 32% | |
| Round1-Var64 | UGTSL2 (T199S_V254L_A285L) | 0% | 0% | |
| Round1-Var65 | UGTSL2 (S255C_N280P_G331A) | 73% | 82% | 11.5% |
| Round1-Var66 | UGTSL2 (N249G_K365V_M367V_I389L) | 0% | 0% | |
| Round1-Var67 | UGTSL2 (S200F_I333L_I351L) | 0% | 0% | |
| Round1-Var68 | UGTSL2 (N249G_V270L_K289S) | 13% | 24% | |
| Round1-Var69 | UGTSL2 (I114V_V125I_N249G) | 6% | 9% | |
| Round1-Var70 | UGTSL2 (V125I_K289P_N325A) | 0% | 1% | |
| Round1-Var71 | UGTSL2 (N249G_N325A_I352V) | 43% | 76% | 11.5% |
| Round1-Var72 | UGTSL2 (V270I_A285V_M354L) | 196% | 158% | 11.5% |
| Round1-Var73 | UGTSL2 (Q65P_V254L_M367V) | 0% | 0% | |
| Round1-Var74 | UGTSL2 (V270I_K289P_S334T) | 0% | 0% | |
| Round1-Var75 | UGTSL2 (T199S_A205P_L393V) | 0% | 0% | |
| Round1-Var76 | UGTSL2 (V125I_I345L_M367V_T392A) | 8% | 19% | |
| Round1-Var77 | UGTSL2 (A205P_I323V_T392A) | 0% | 0% | |
| Round1-Var78 | UGTSL2 (F21L_L37F_I131V) | 0% | 0% | |
| Round1-Var79 | UGTSL2 (F272L_I282L_A341V_I351L) | 0% | 2% | |
| Round1-Var80 | UGTSL2 (N278G_I352V_I389L) | 95% | 113% | 11.5% |
| Round1-Var81 | UGTSL2 (I114V_G331A_A341V_L405V) | 8% | 20% | |
| Round1-Var82 | UGTSL2 (Q27R_Q65P_I351M) | 0% | 0% | |
| Round1-Var83 | UGTSL2 (R6H_T329V_M354L_L393V) | 77% | 100% | 10.5% |
| Round1-Var84 | UGTSL2 (S200F_G331A_L393V) | 0% | 0% | |
| Round1-Var85 | UGTSL2 (T199S_K289S_R312L_I351M) | 0% | 0% | |
| Round1-Var86 | UGTSL2 (Q65P_A205P_L405V) | 0% | 0% | |
| Round1-Var87 | UGTSL2 (V270L_I345L_K365V) | 0% | 0% | |
| Round1-Var88 | UGTSL2 (S200F_F253Y_S255C) | 0% | 0% | |
| Round1-Var89 | UGTSL2 (I114V_G371K_I389L) | 0% | 3% | |
| Round1-Var90 | UGTSL2 (L276A_I333L_S334T_L393V) | 75% | 94% | 11.5% |
| Round1-Var91 | UGTSL2 (I240L_S255C_P361G) | 5% | 13% | |
| Round1-Var92 | UGTSL2 (Q27R_T245R_L276A) | 51% | 81% | 12.0% |

*Mutations are noted as follows: reference gene-original amino acid-position-new amino acid: For example the mutation of an isoleucine at position 240 to a Leucine for UGTSL2 is noted as UGTSL2 (I240L)

Modeling of these results allowed to obtain a ranking of the effect of each mutation. The following mutations were determined as being beneficial for activity: L276A, T392A, Q27R, N278G, T329V, A341V, I333L, G387E, H247P, M354L, A285V, V270I, N325S, I240L, F253Y, A285L, I352V.

The following mutations were determined as being beneficial for lower Rebaudioside M2 formation:

Q27R, N325S, G387E, I333L, H247P, T329I, R312L, T199S, E259G, S334T, I131V, A285L, I389L, L393V, V254L, N339S, I345L, T245R.

Example 46

Conversion of Rebaudioside A to Rebaudioside I using UGT76G1

The reaction was conducted using UGT76G1-R1-F12 (also known as UGT76G1 var94 (see EXAMPLE 26))

The total volume of the reaction was 40 mL with the following composition: 50 mM potassium phosphate buffer pH 7.5, 3 mM $MgCl_2$, 2.5 mM UDP-glucose, 0.5 mM Rebaudioside A and 4 mL of UGT76G1-R1-F12 lysate (2.5 U/mL). The reaction was run at 30° C. on an orbitary shaker at 135 rpm. For sampling 125 μL of the reaction mixture was quenched with 10 μL of 2N $H_2SO_4$ and 115 μL of methanol/water (7/3). The samples were immediately centrifuged and kept at 10° C. before analysis by LC-MS. An Agilent 1200 series HPLC system, equipped with binary pump (G1312B), autosampler (G1367D), thermostatted column compartment (G1316B), DAD detector (G1315C), connected with Agilent 6110A MSD, and interfaced with "LC/MSD Chemstation" software, was used.

Instrument Conditions

| Column | Phenomenex Kinetex 2.6u C18 100A, 4.6 mm × 150 mm, 2.6 μm |
|---|---|
| Column Temperature | 55° C. |
| Detection | DAD at 210 nm bw 360 nm |
| | MSD (Scan and SIM mode) |
| | Mode: ES-API, Negative Polarity |
| | Drying gas flow: 13.0 L/min |
| | Nebulizer pressure: 30 psig |
| | Drying gas temperature: 270° C. |
| Analysis duration | 20 min |
| Injected volume | 2 μL |
| Flow rate | 0.8 mL/min |

Mobile Phase Gradient Program

| Time (min) | A (%): Formic acid 0.1% | B (%): Acetonitrile |
|---|---|---|
| 0 | 76 | 24 |
| 8.5 | 76 | 24 |
| 10.0 | 71 | 29 |
| 16.5 | 70 | 30 |

Figure 67A:
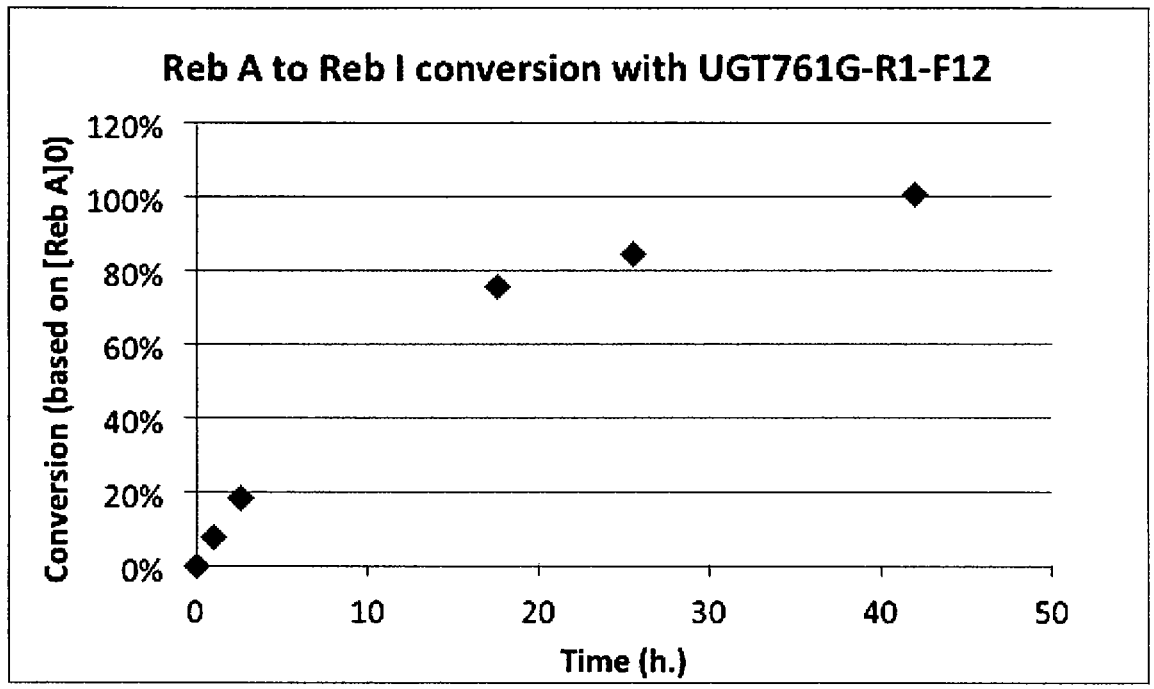
FIG. 67 shows a graph showing the reaction profile for Example 46.

The reaction profile shown in FIG. 67a was obtained:

After 42 h. of reaction, 20 mL of the reaction mixture was quenched with 20 mL of ethanol and used for structure elucidation.

Figure 67B:
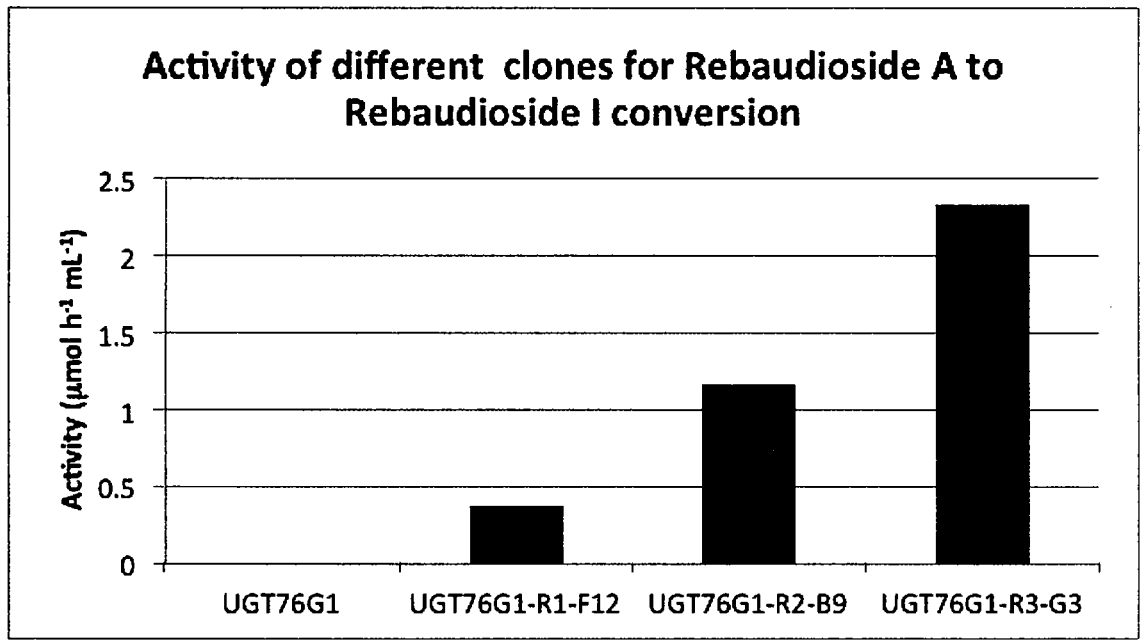
Figure 68A:
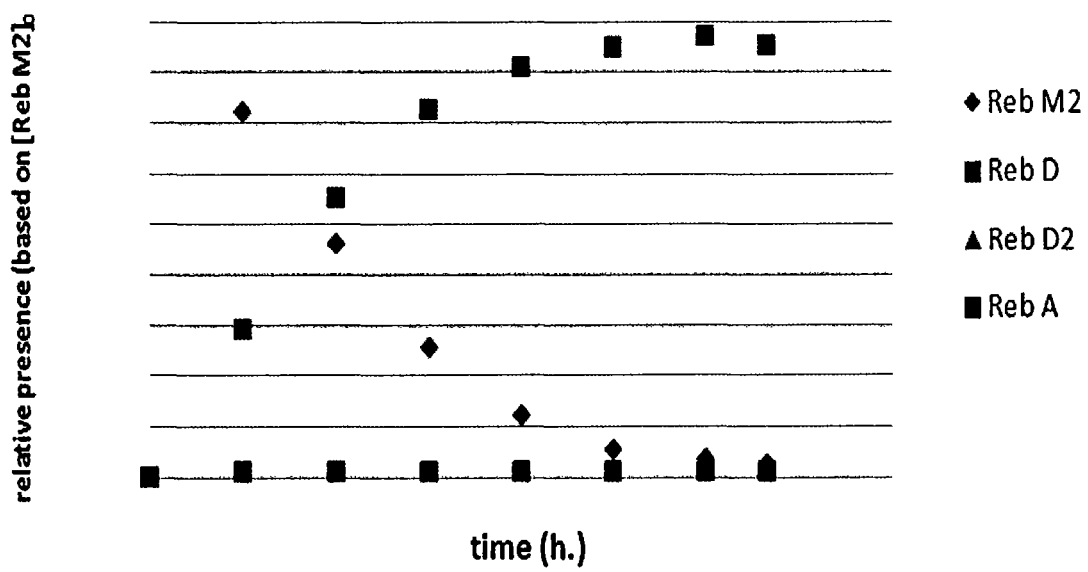
FIG. 68a-f show reaction profiles for Example 49.
Figure 68B:
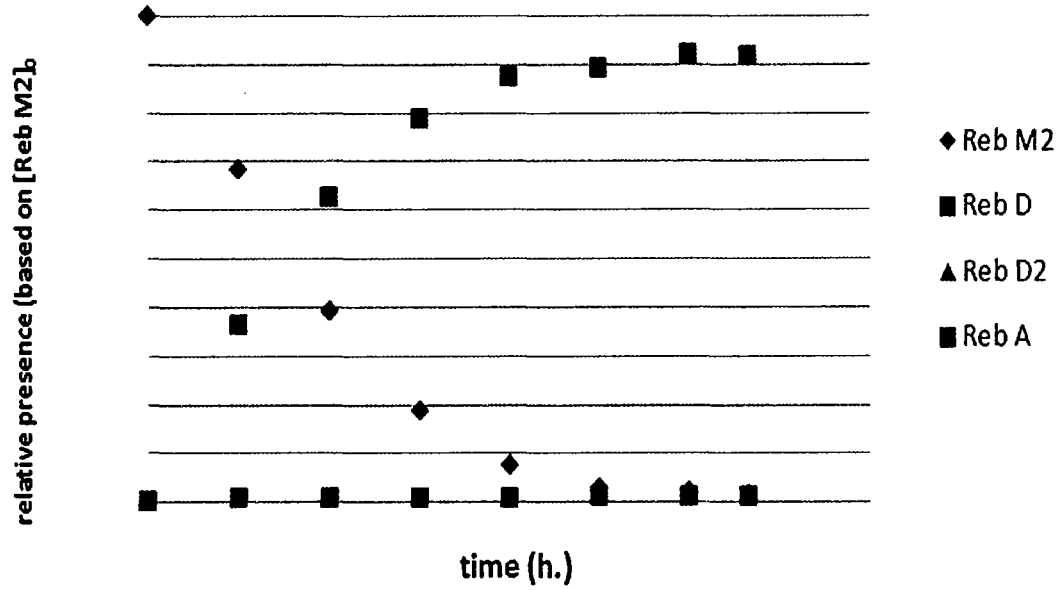
Figure 68C:
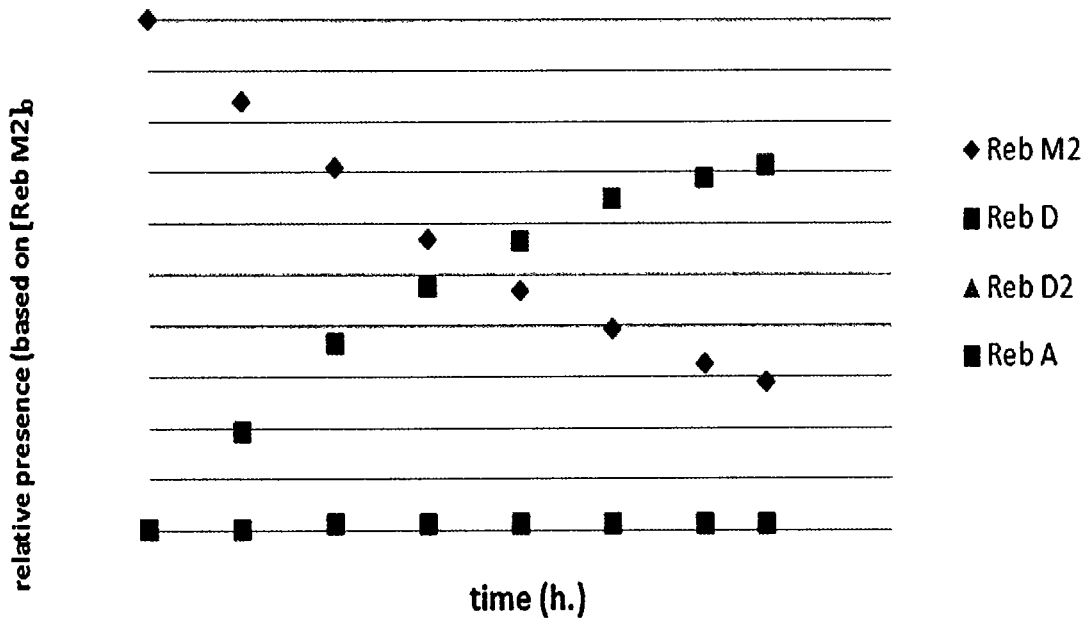
Figure 68D:
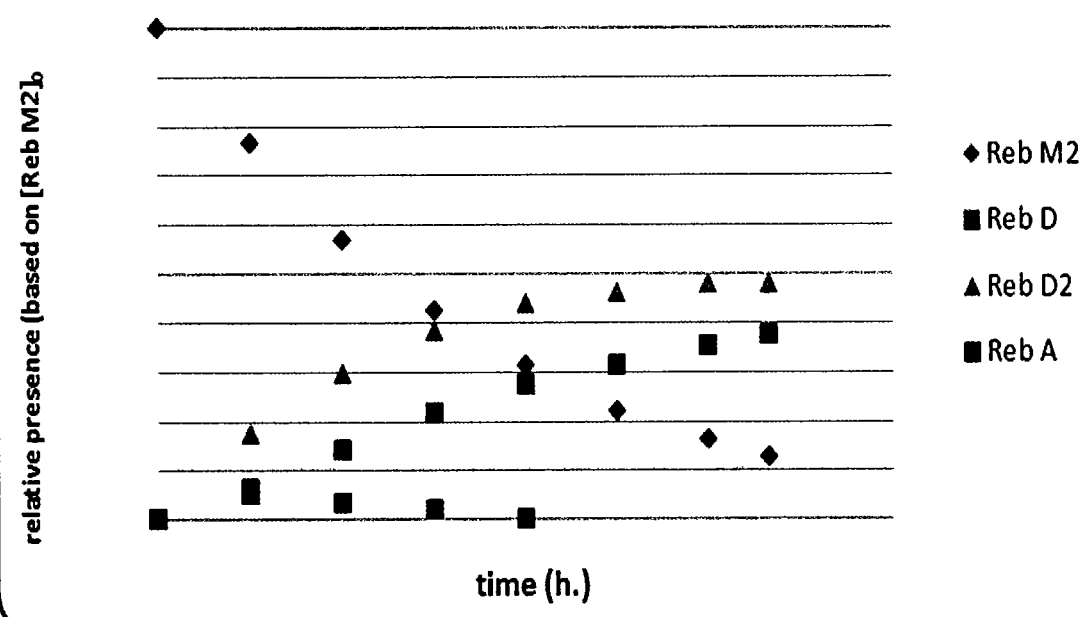
Figure 68E:
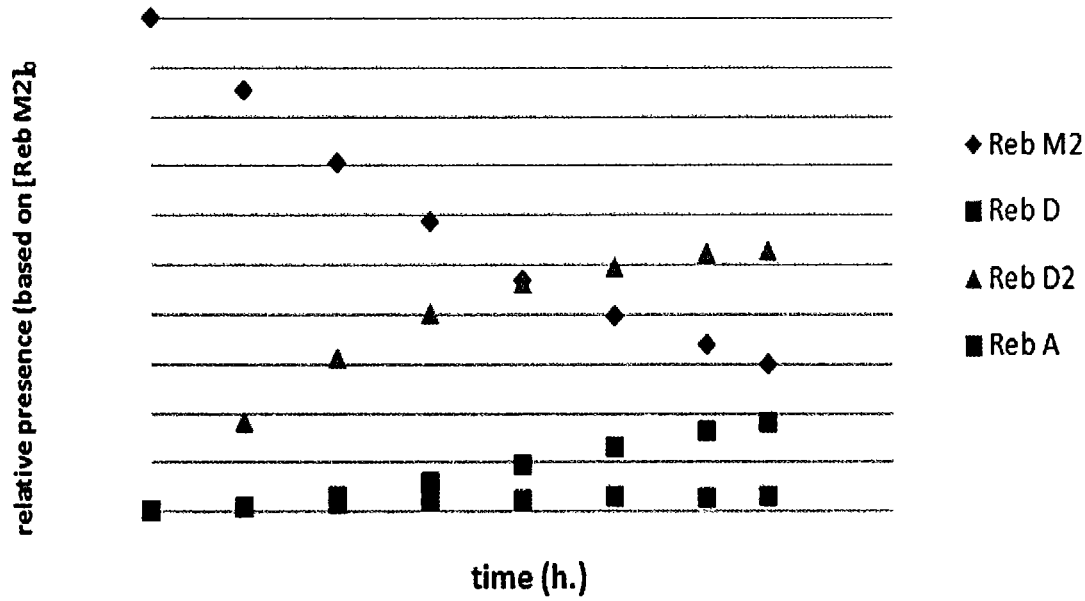
Figure 68F:
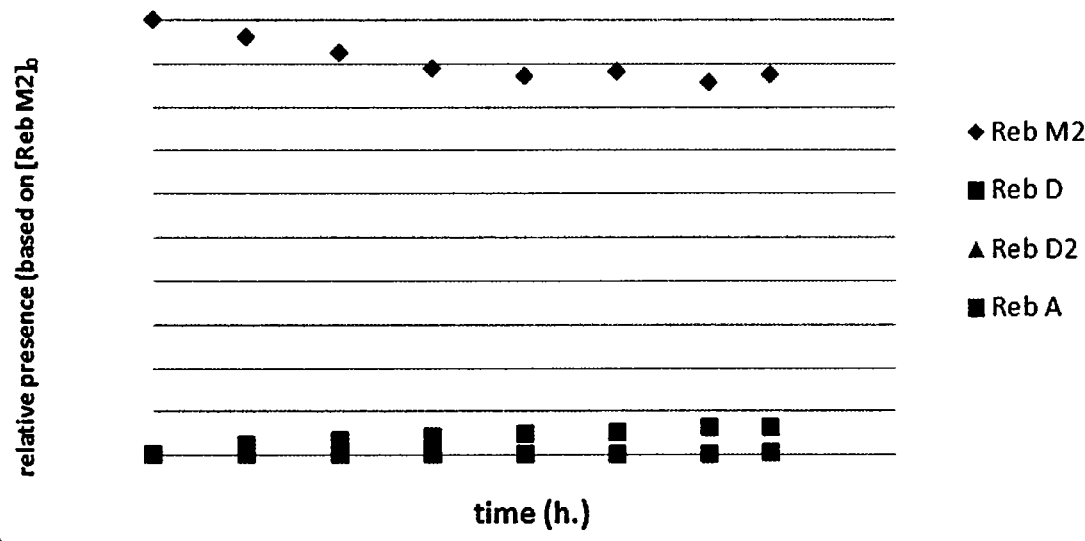
Figure 69A:
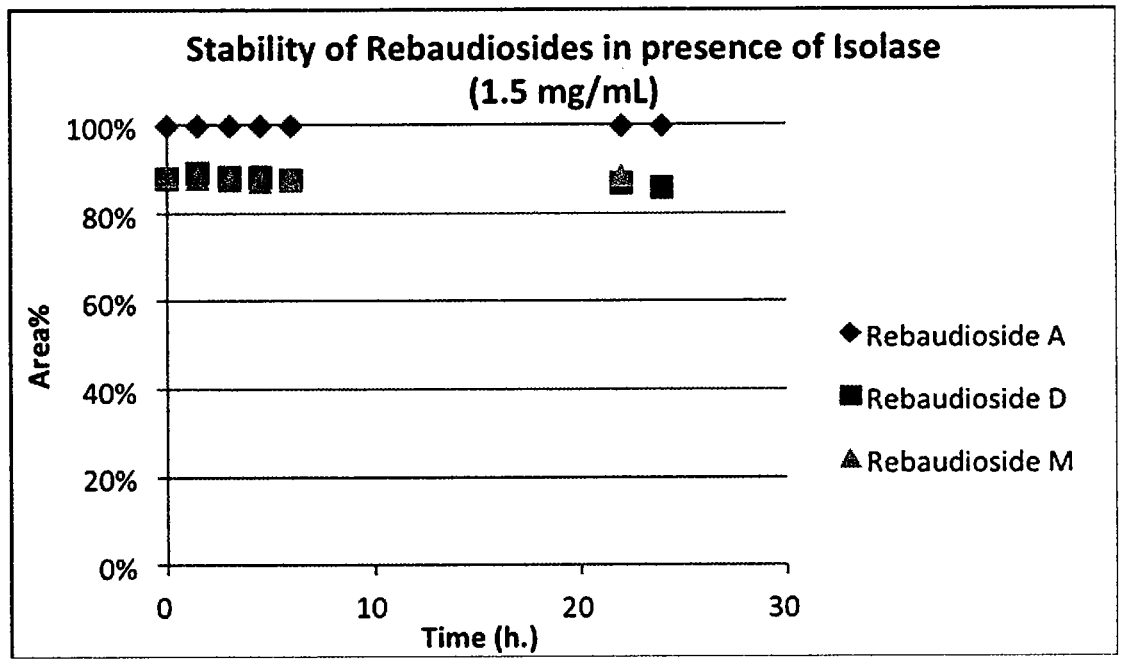
FIG. 69a-c show graphs showing the HPLC results for Example 50.
Figure 69B:
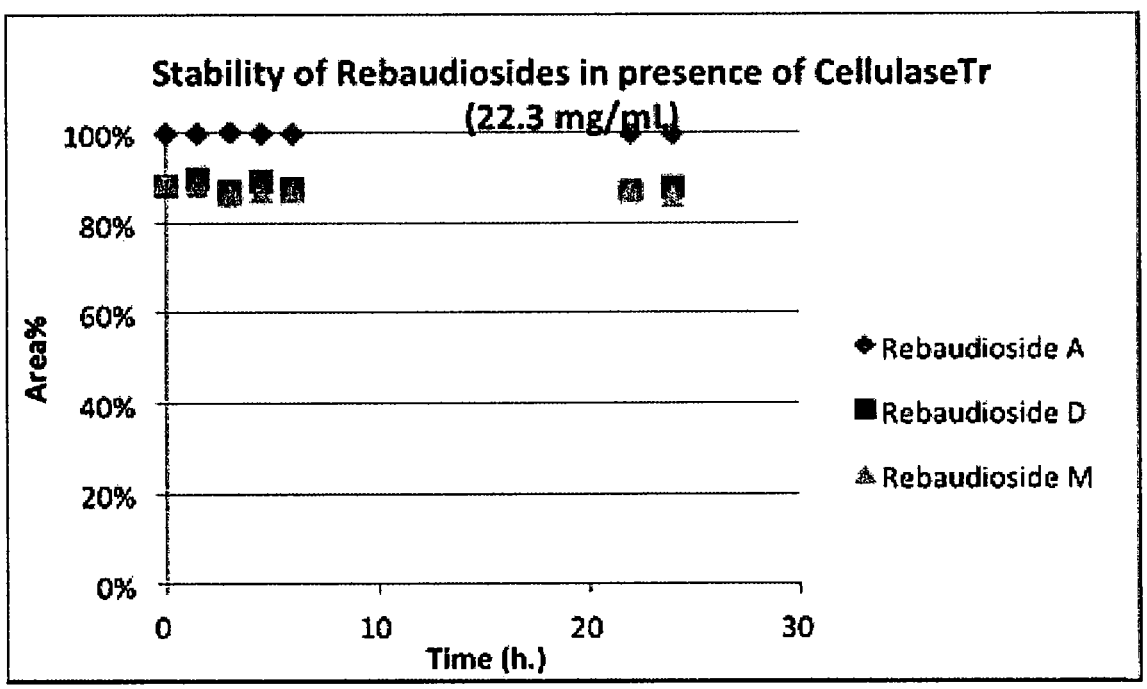
Figure 69C:
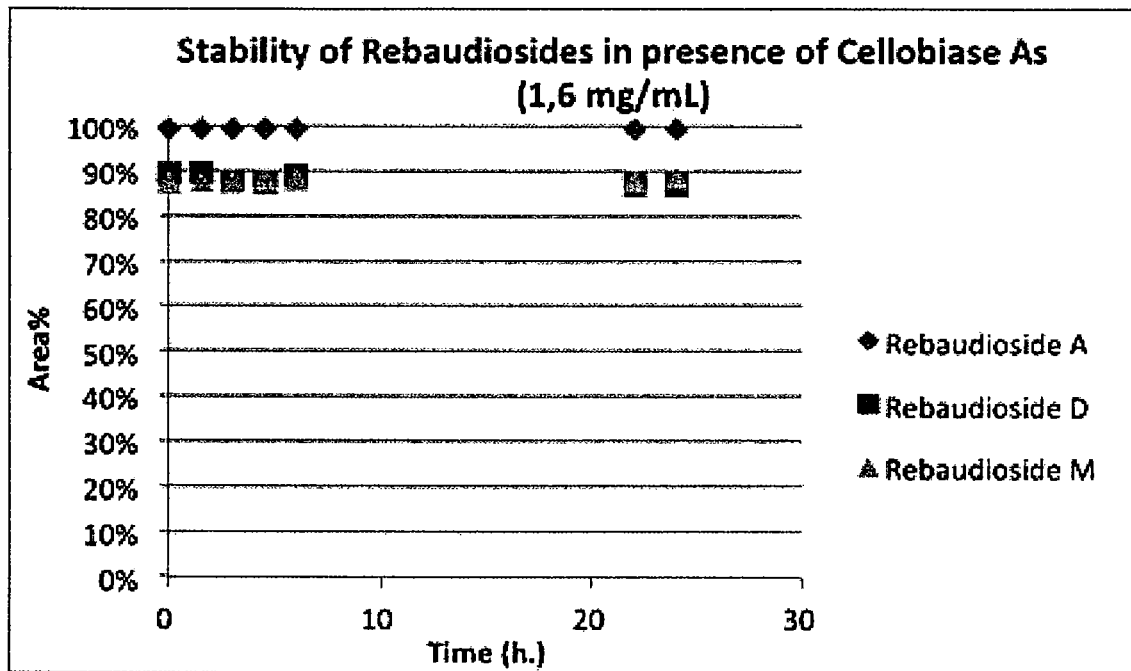
Figure 70A:
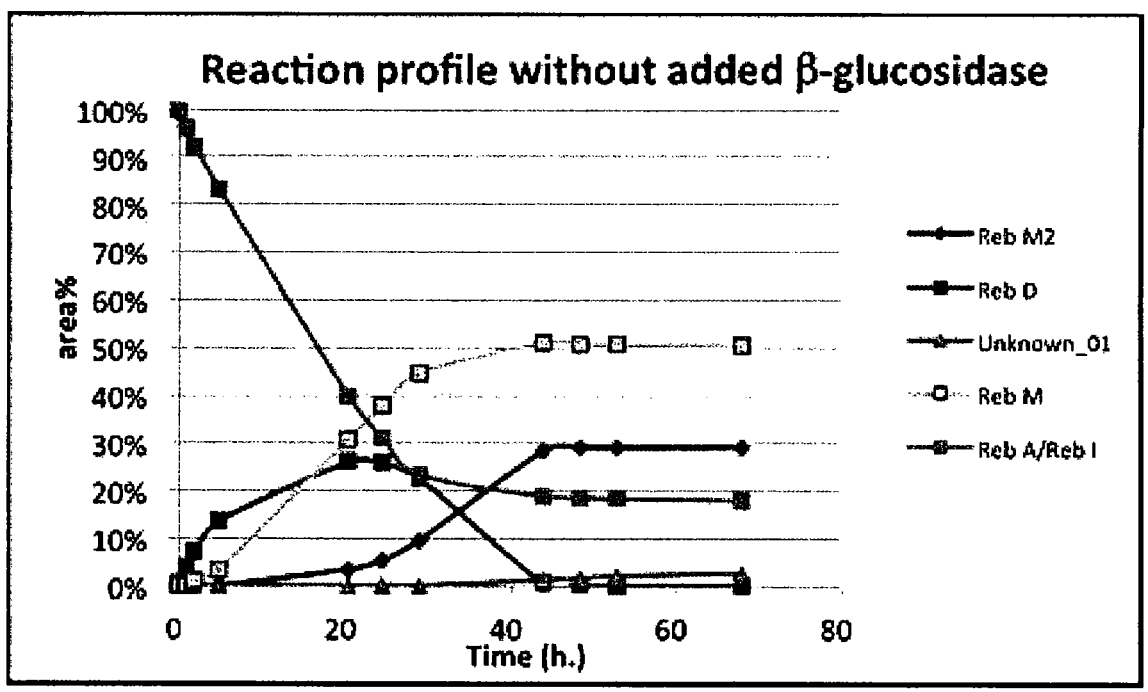
FIG. 70a-d show reaction profile graphs for Example 51.
Figure 70B:
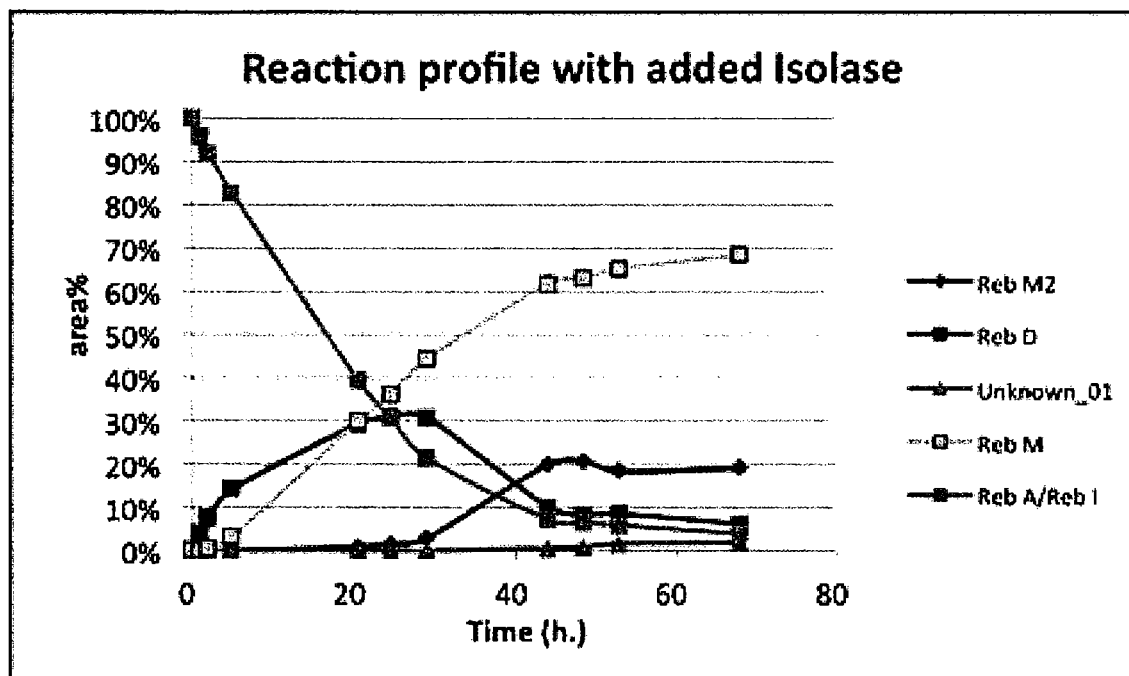
Figure 70C:
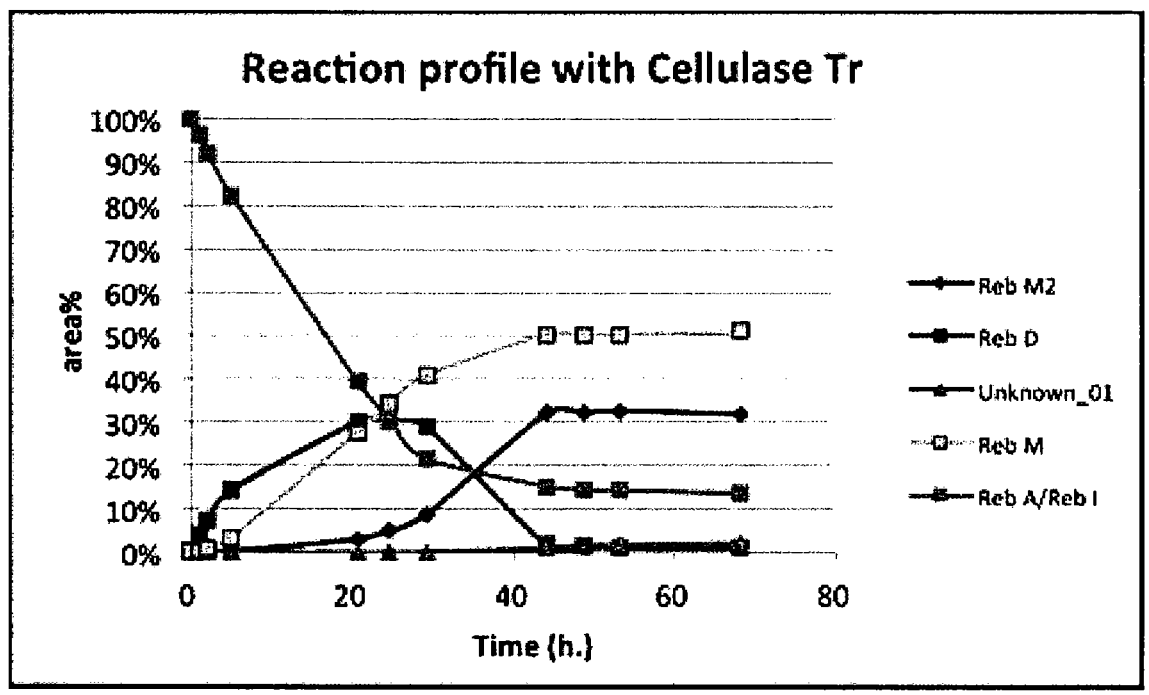
Figure 70D:
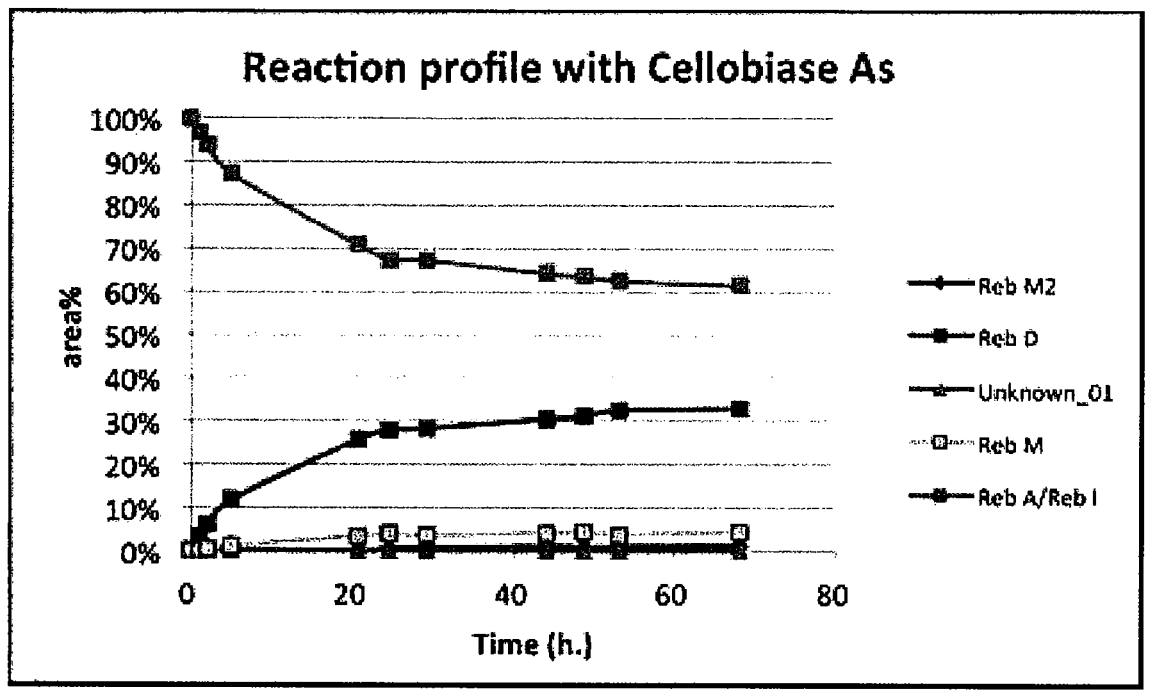

In similar manner the best clones of UGT76G1 directed evolution round 2 (UGT76G1-R2-B9 identified above as "Round2-Var66", see EXAMPLE 41) and round 3 (UGT76G1-R3-G3 identified above as "Round3-Var21", see EXAMPLE 44) and native UGT76G1 (see EXAMPLE 26) were tested for the conversion of Rebaudioside A to Rebaudioside I and the activities shown in FIG. 67b were determined.

Example 47

Isolation and Characterization of Reb I
Crude Reaction Sample.

The sample, Lot Crude CB-2977-198, used for isolation, was prepared according to Example 46 with UGT76G1.
HPLC Analysis.

Preliminary HPLC analyses of samples were performed using a Waters 2695 Alliance System with the following method: Phenomenex Synergi Hydro-RP, 4.6×250 mm, 4 μm (p/n 00G-4375-E0); Column Temp: 55° C.; Mobile Phase A: 0.0284% NH$_4$OAc and 0.0116% HOAc in water; Mobile Phase B: Acetonitrile (MeCN); Flow Rate: 1.0 mL/min; Injection volume: 10 μL. Detection was by UV (210 nm) and CAD Gradient:

| Time (min) | % A | % B |
|---|---|---|
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |

-continued

| Time (min) | % A | % B |
|---|---|---|
| 31-37 | 30 | 70 |
| 38 | 75 | 25 |

Isolation by HPLC.

The purification was performed using a Waters Atlantis dC18 (30×100 mm, 5 μm, p/n 186001375) column with isocratic mobile phase conditions of 80:20 water/MeCN. Flow rate was maintained at 45 mL/min and injection load was 180 mg. Detector wavelength was set at 210 nm.

The analyses of fractions were performed using a Waters Atlantis dC18 (4.6×150 mm, 5 μm, p/n 186001342) column; Mobile Phase A: water; Mobile Phase B: MeCN; Flow Rate: 1 mL/min; Isocratic mobile phase conditions: 75:25 AB for 30 min.

MS and MS/MS.

MS and MS/MS data were generated with a Waters QT of Micro mass spectrometer equipped with an electrospray ionization source. The sample was analyzed by negative ESI. The sample was diluted to a concentration of 0.25 mg/mL with H$_2$O:MeCN (1:1) and introduced via flow injection for MS data acquisition. The sample was diluted further to 0.01 mg/mL to yield good s/n to tune for MS/MS and acquired by direct infusion. The collision energy was set to 60 V in order to acquire MS/MS data with increased fragment ion peaks due to the nature of the molecule

NMR.

The sample was prepared by dissolving ~1.0 mg in 180 μL of pyridine-d$_5$+TMS, and NMR data were acquired on a Bruker Avance 500 MHz instrument with either a 2.5 mm inverse probe or a 5 mm broad band probe. The 13C and HMBC NMR data were acquired at Rensselaer Polytechnic Institute using their Bruker Avance 600 MHz and 800 MHz instruments with 5 mm cryo-probe, respectively. The $^1$H and $^{13}$C NMR spectra were referenced to the TMS resonance ($\delta_H$ 0.00 ppm and $\delta_C$ 0.0 ppm).

Figure 28:
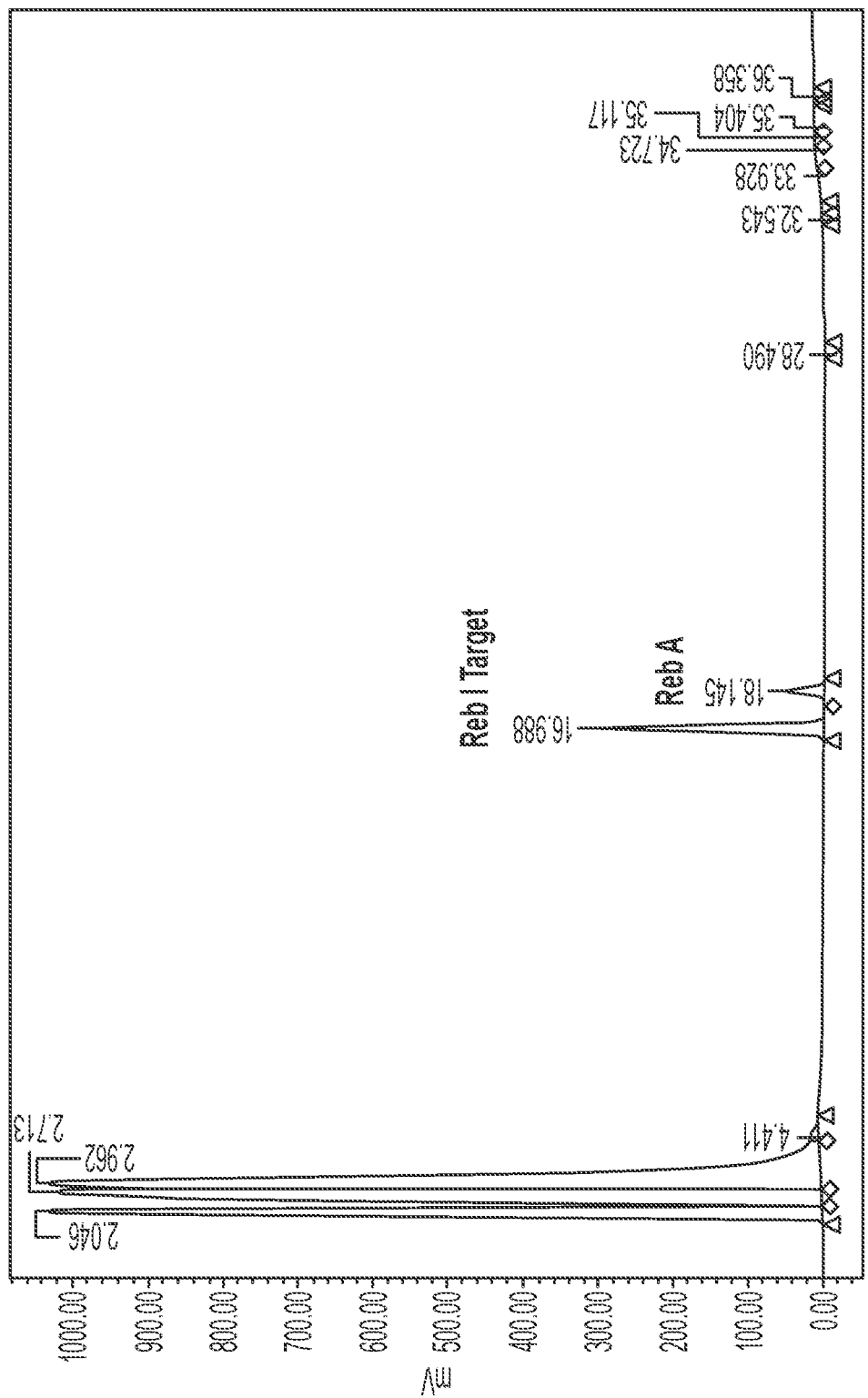
FIG. 28 shows an HPLC chromatogram for the analysis done in Example 47.

Isolation of Reb I was performed using a semi-synthetic steviol glycoside mixture, Lot number CB-2977-198. The material was analyzed by HPLC as described above. The Reb I peak was observed at a retention time ($t_R$) of approximately 17 min as shown in FIG. 28.

Results and Discussion

Figure 29:
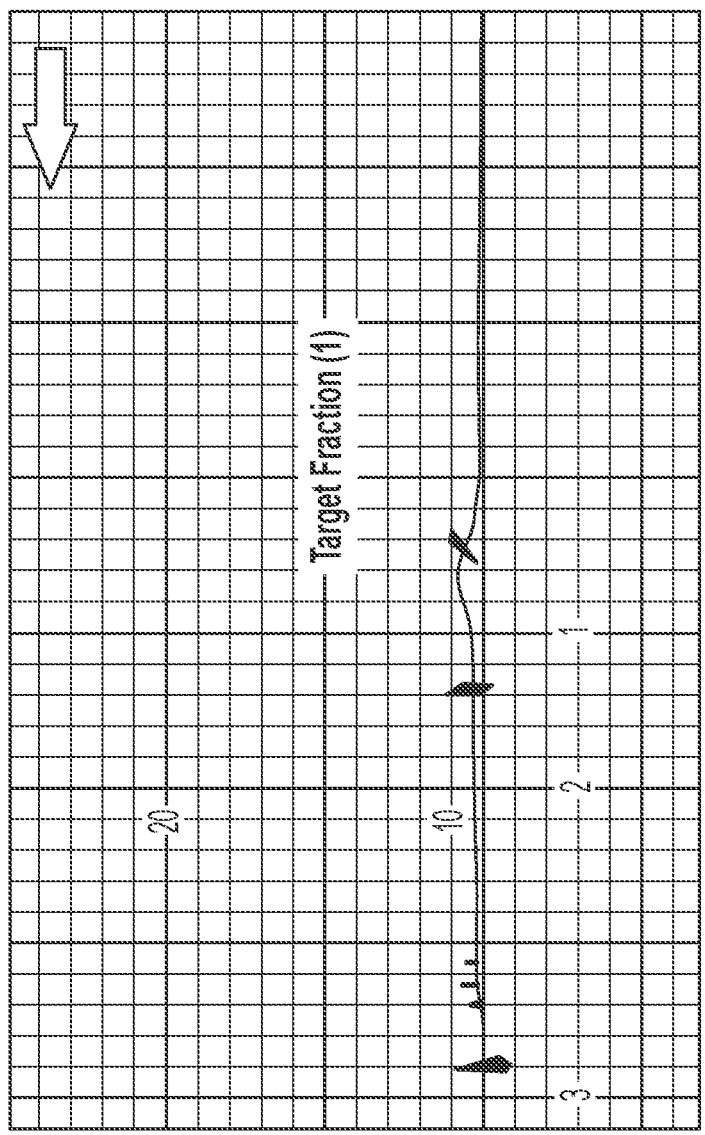
FIG. 29 shows an HPLC chromatogram for the analysis done in Example 47.
Figure 30:
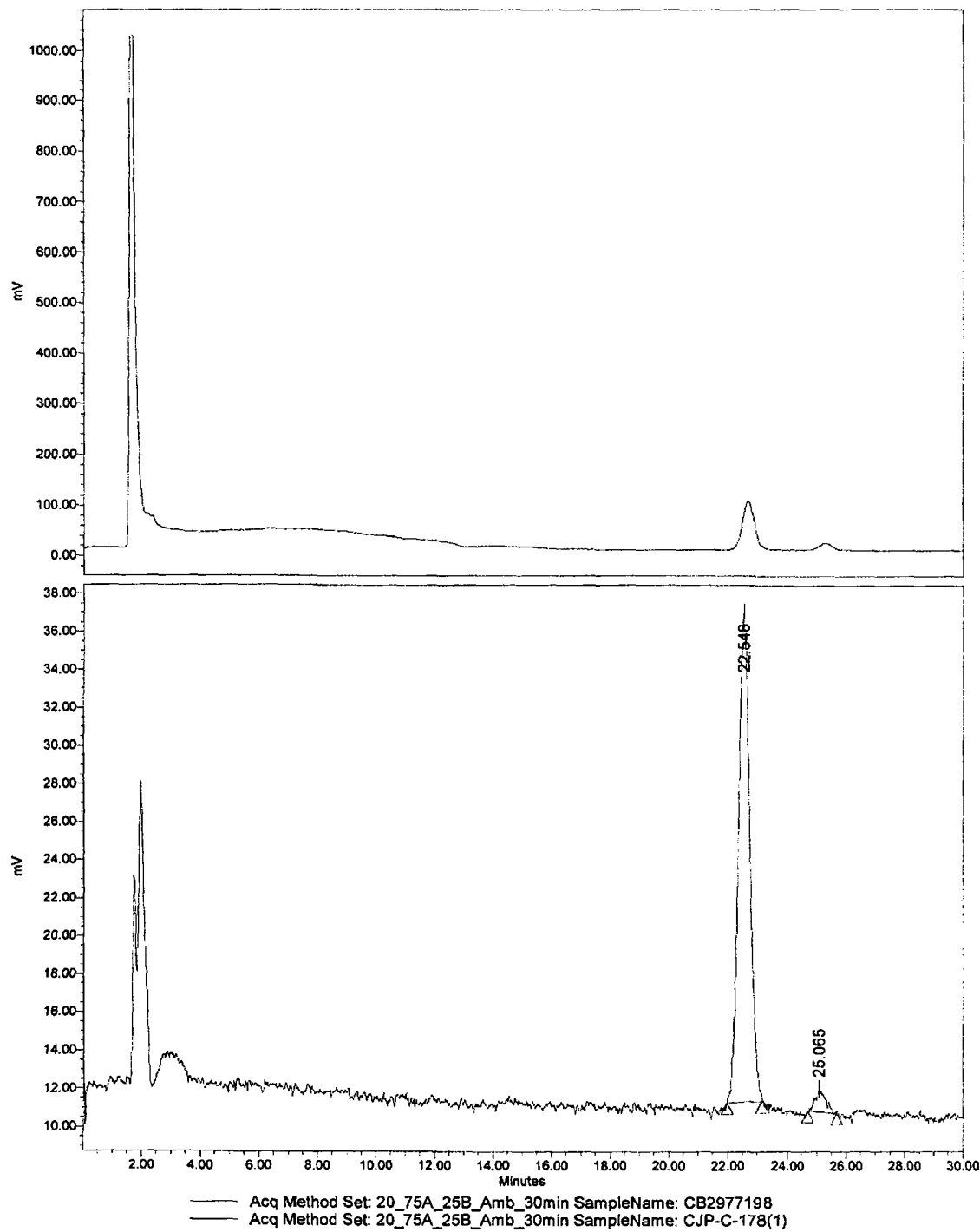
FIG. 30 shows an LC-CAD analysis done in Example 47.

The reb I peak was isolated from the reaction crude as described above and shown in FIG. 29. The isolated fraction was pooled and lyophilized. Purity of the final product was 91% as confirmed by LC-CAD using the method described above (FIG. 30). Approximately 1 mg of Reb I was provided for spectroscopic and spectrometric analyses.

Mass Spectrometry.

Figure 31:
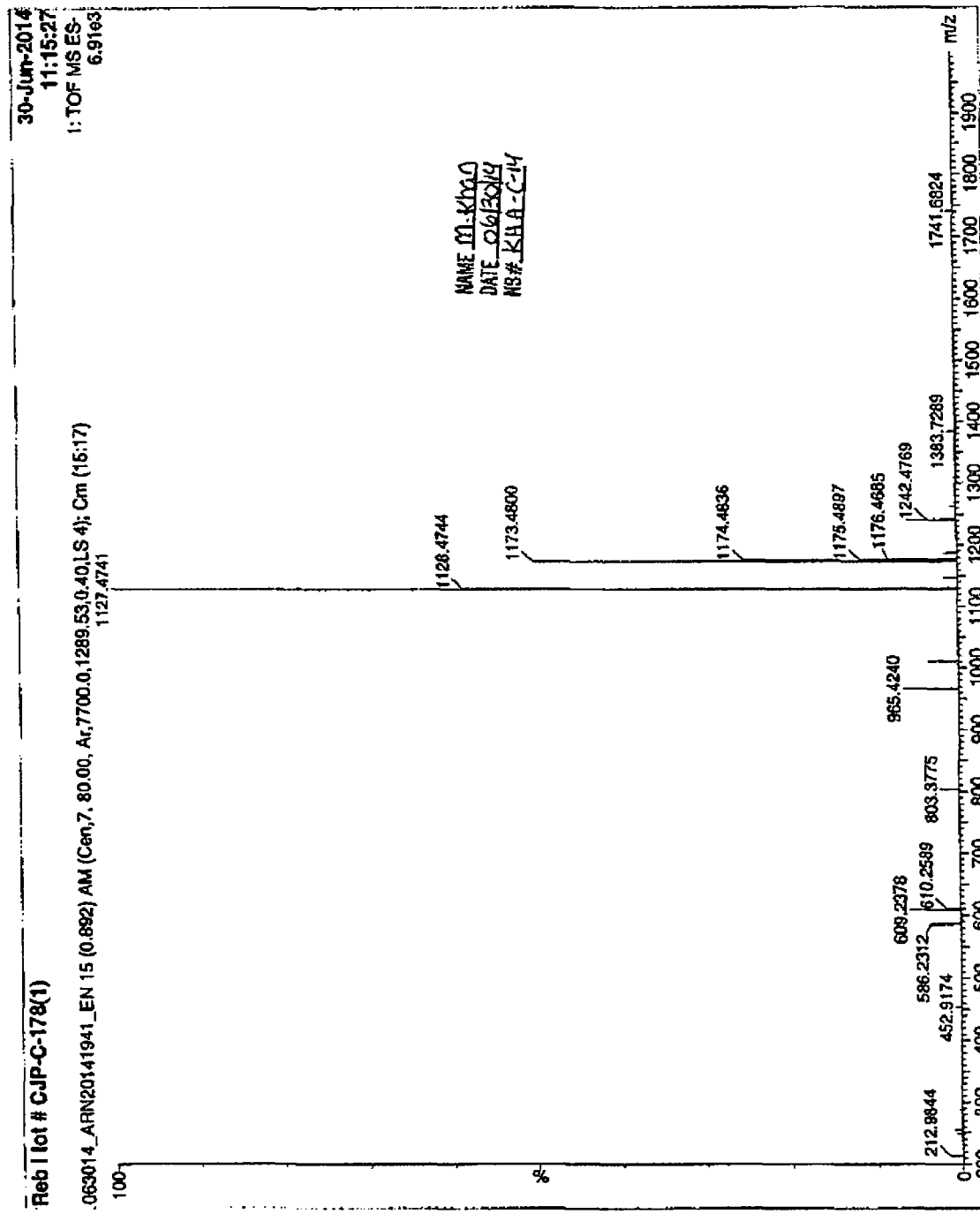
FIG. 31 shows an ESI-TOF mass spectrogram as described in Example 47.
Figure 32:
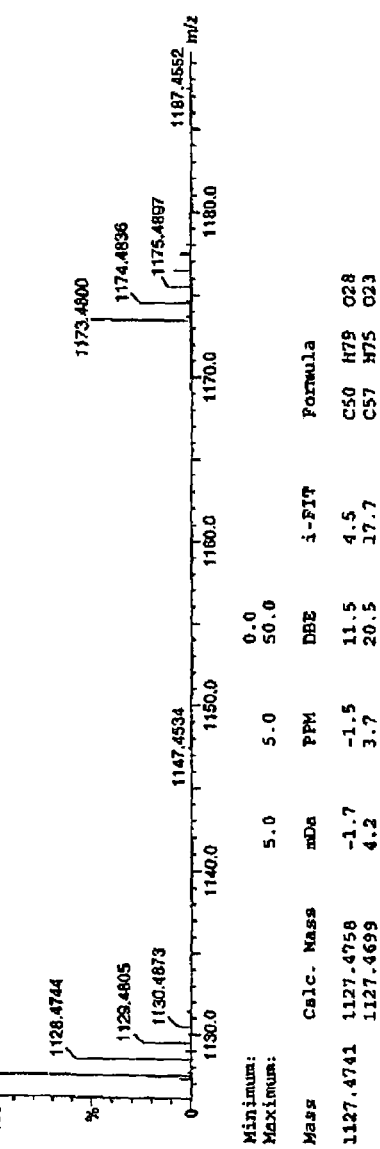
FIG. 32 shows a mass spectrogram as described in Example 47.

The ESI-TOF mass spectrum acquired by infusing a sample of reb I showed a [M-H]$^-$ ion at m/z 1127.4741 (FIG. 31). The mass of the [M-H]$^-$ ion was in good agreement with the molecular formula $C_{50}H_{79}O_{28}$ (calcd for $C_{50}H_{79}O_{28}$: 1127.4758, error: −1.5 ppm) expected for reb I (FIG. 32). The MS data confirmed that reb I has a nominal mass of 1128 Daltons with the molecular formula, $C_{50}H_{80}O_{28}$.

Figure 33:
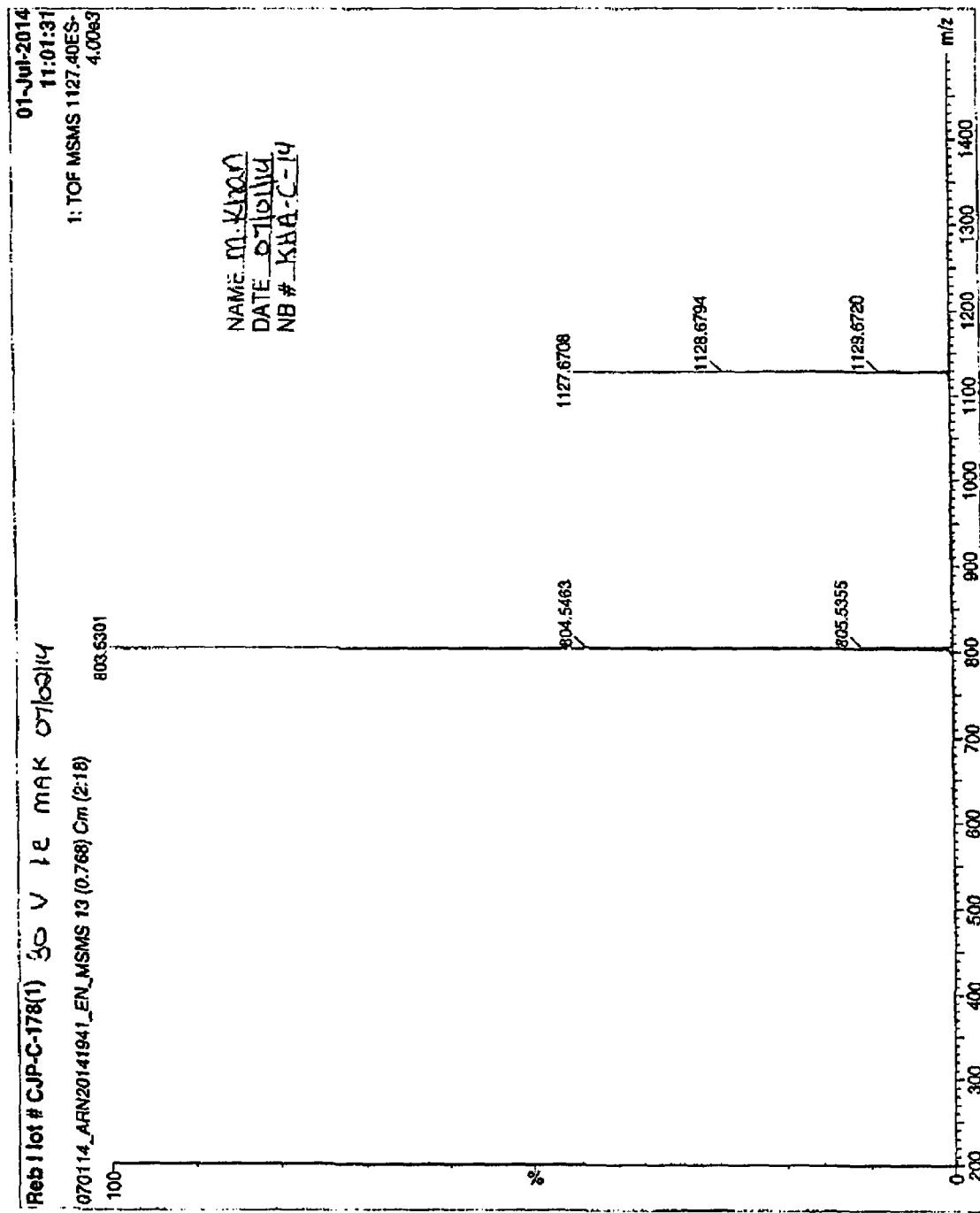
FIG. 33 shows an MS/MS spectrogram as described in Example 47.
Figure 34:
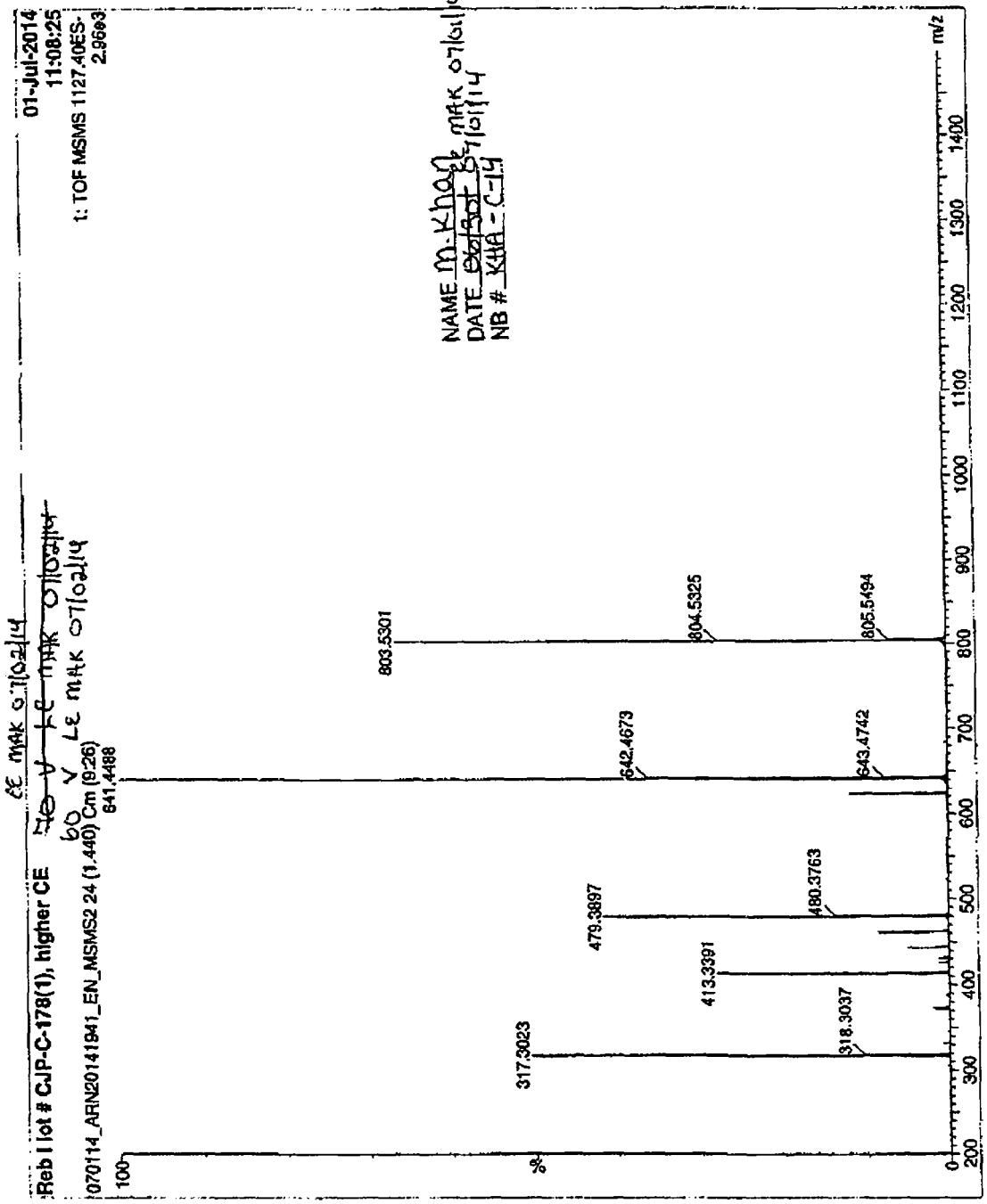
FIG. 34 shows an MS/MS spectrogram as described in Example 47.

The MS/MS spectrum of reb I, selecting the [M-H]$^-$ ion at m/z 1127.4 for fragmentation, indicated loss of two sugar units at m/z 803.5301, however did not show additional fragmentation with collision energy of 30 V (FIG. 33). When higher collision energy was applied (60 V) (FIG. 34), the parent ion was not observed but sequential loss of three sugar units at m/z 641.4488, 479.3897, and 317.3023 were observed from m/z 803.5301

NMR Spectroscopy.

Figure 35:
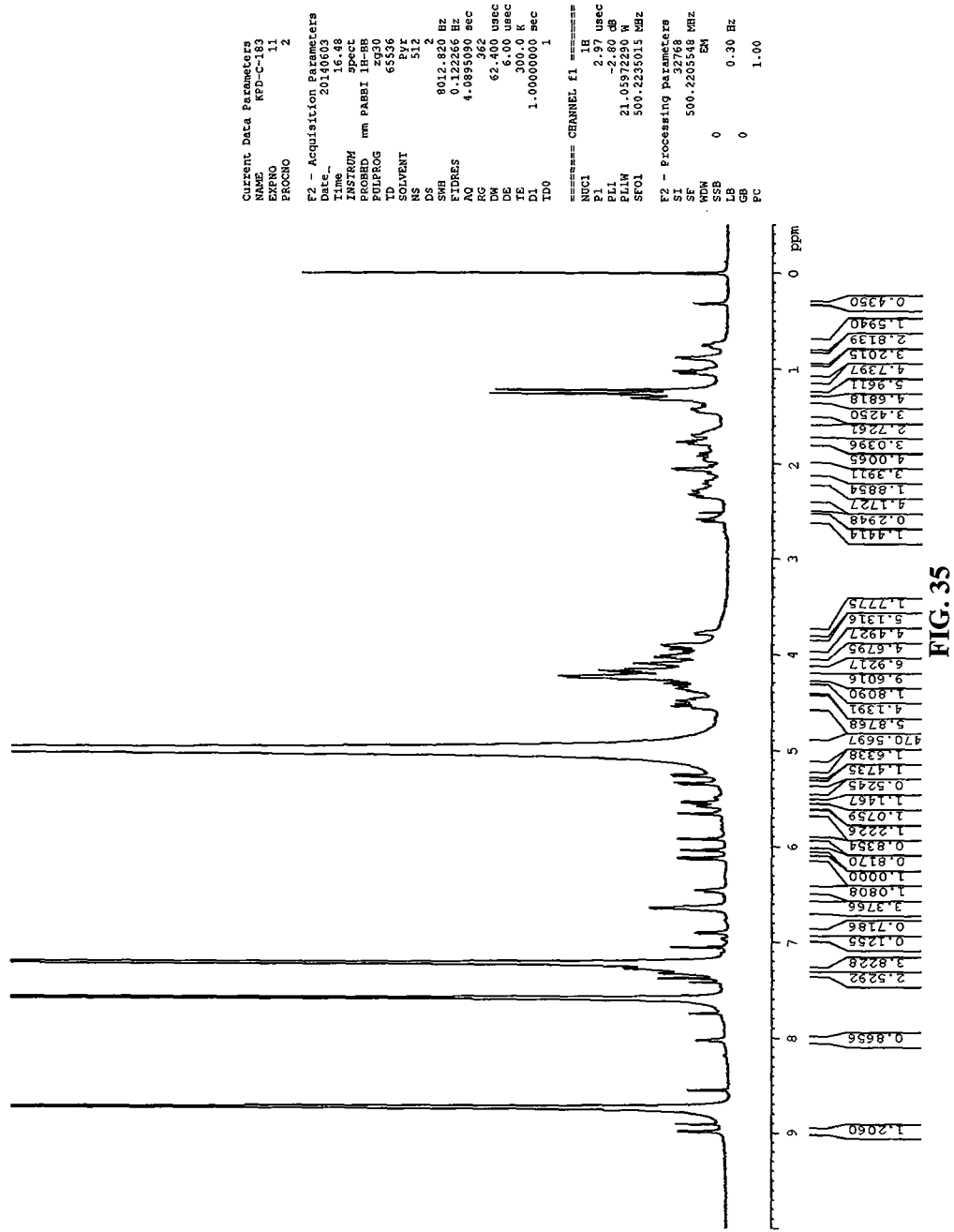
FIG. 35 shows the results of $^1$H NMR as described in Example 47.
Figure 38:
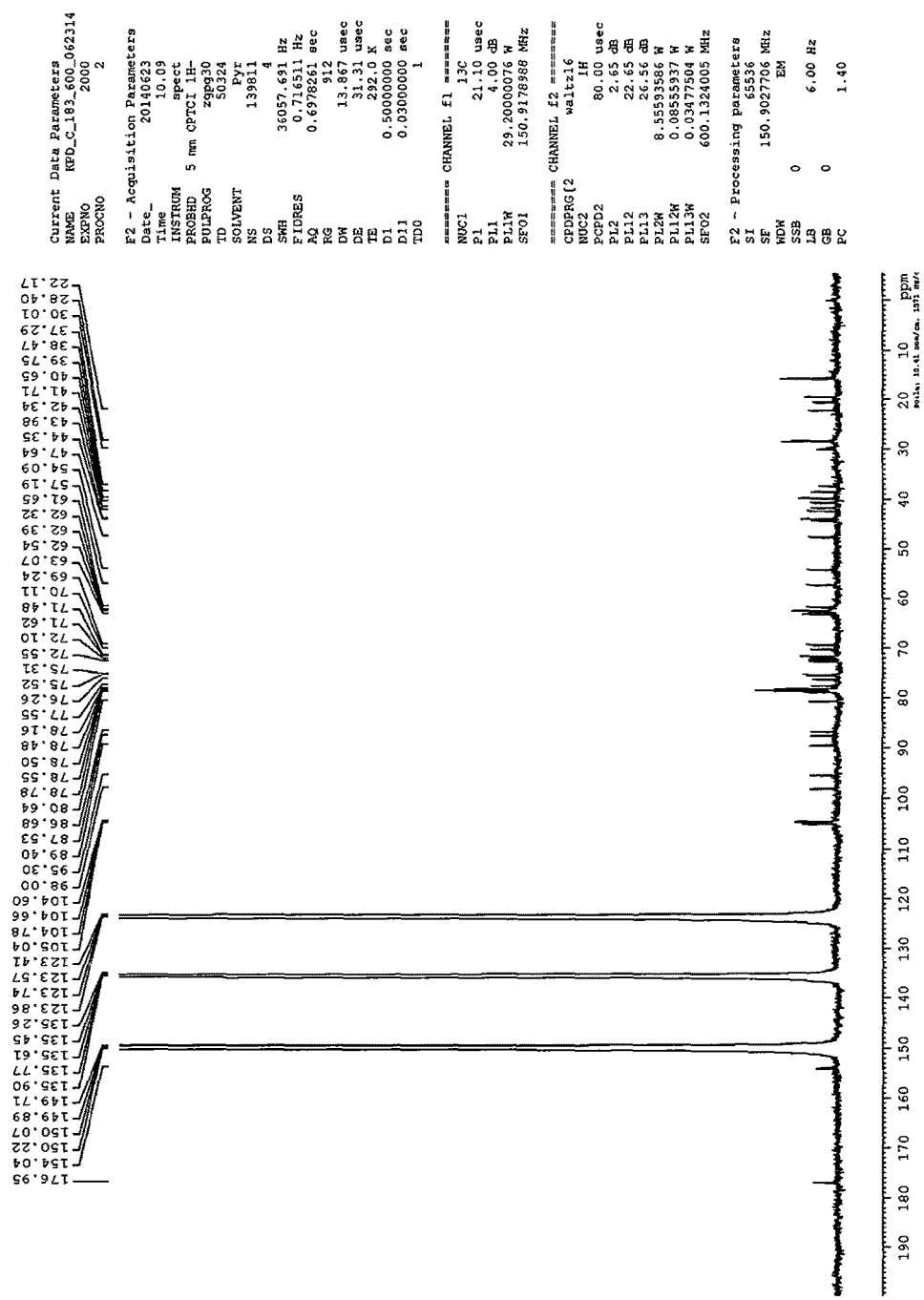
FIG. 38 shows the results of $^{13}$C NMR as described in Example 47.
Figure 39:
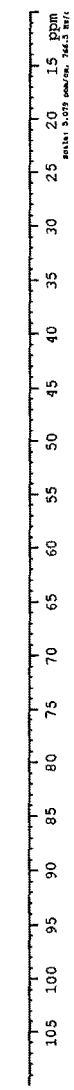
FIG. 39 shows the results of $^{13}$C NMR as described in Example 47.
Figure 40:
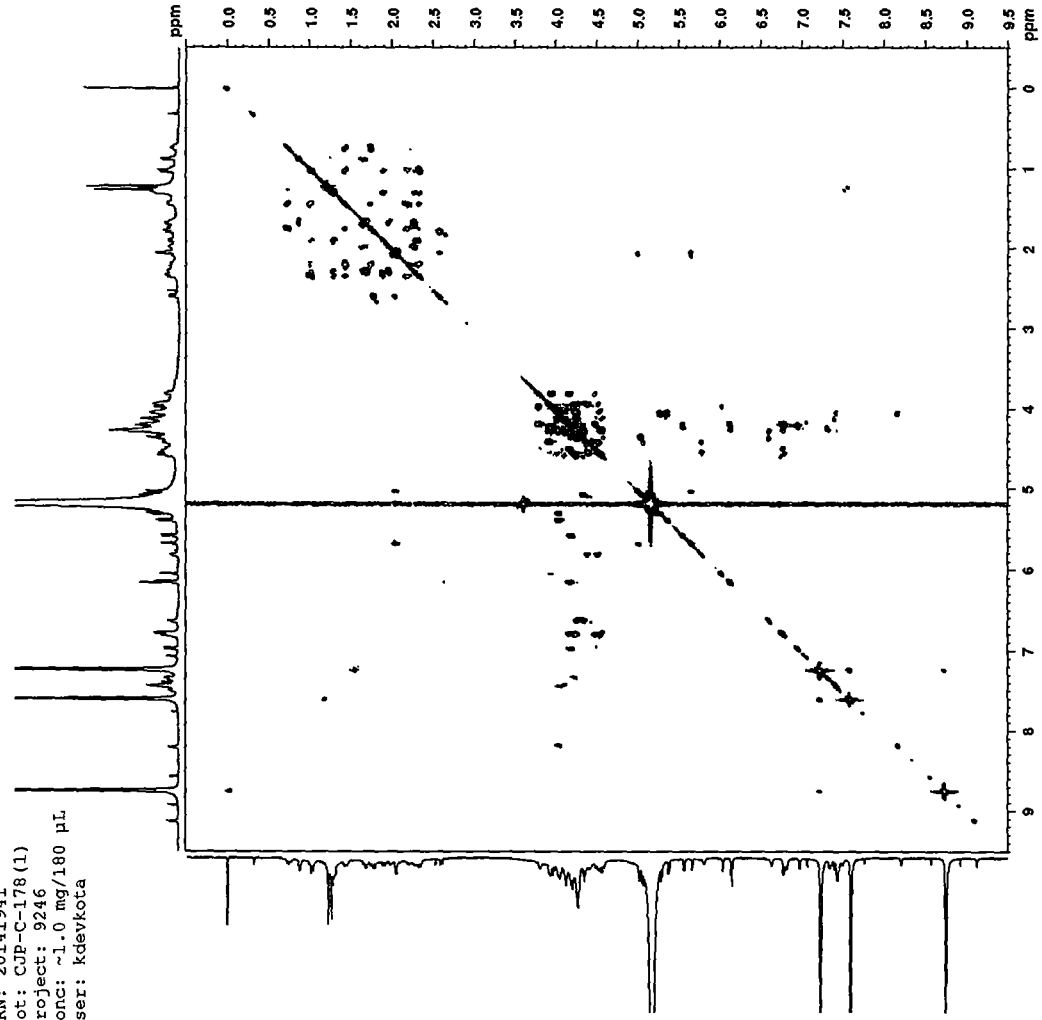
FIG. 40 shows the results of $^1$H-$^1$H COSY as described in Example 47.
Figure 41:
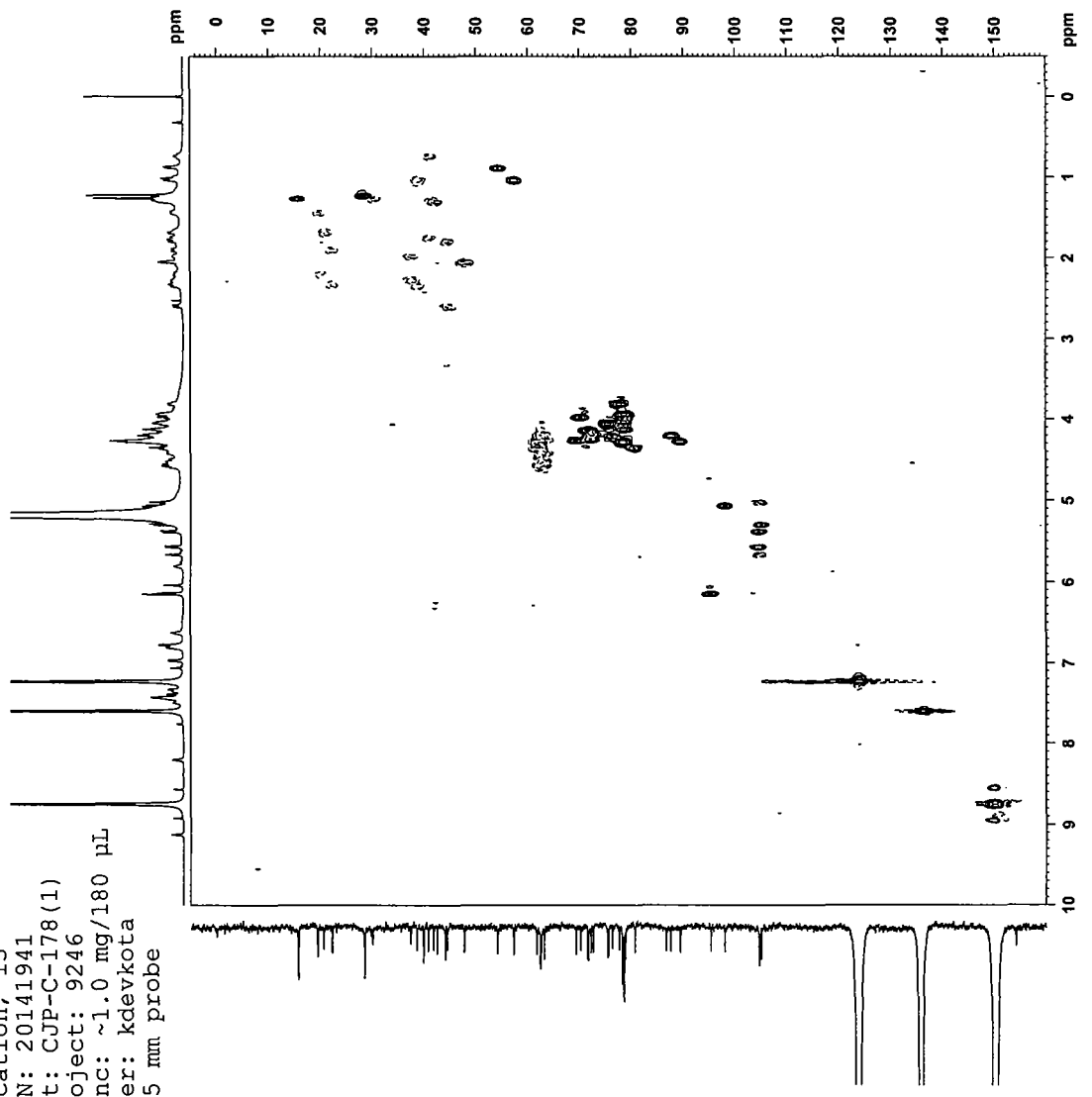
FIG. 41 shows the results of HSQC-DEPT as described in Example 47.
Figure 42:
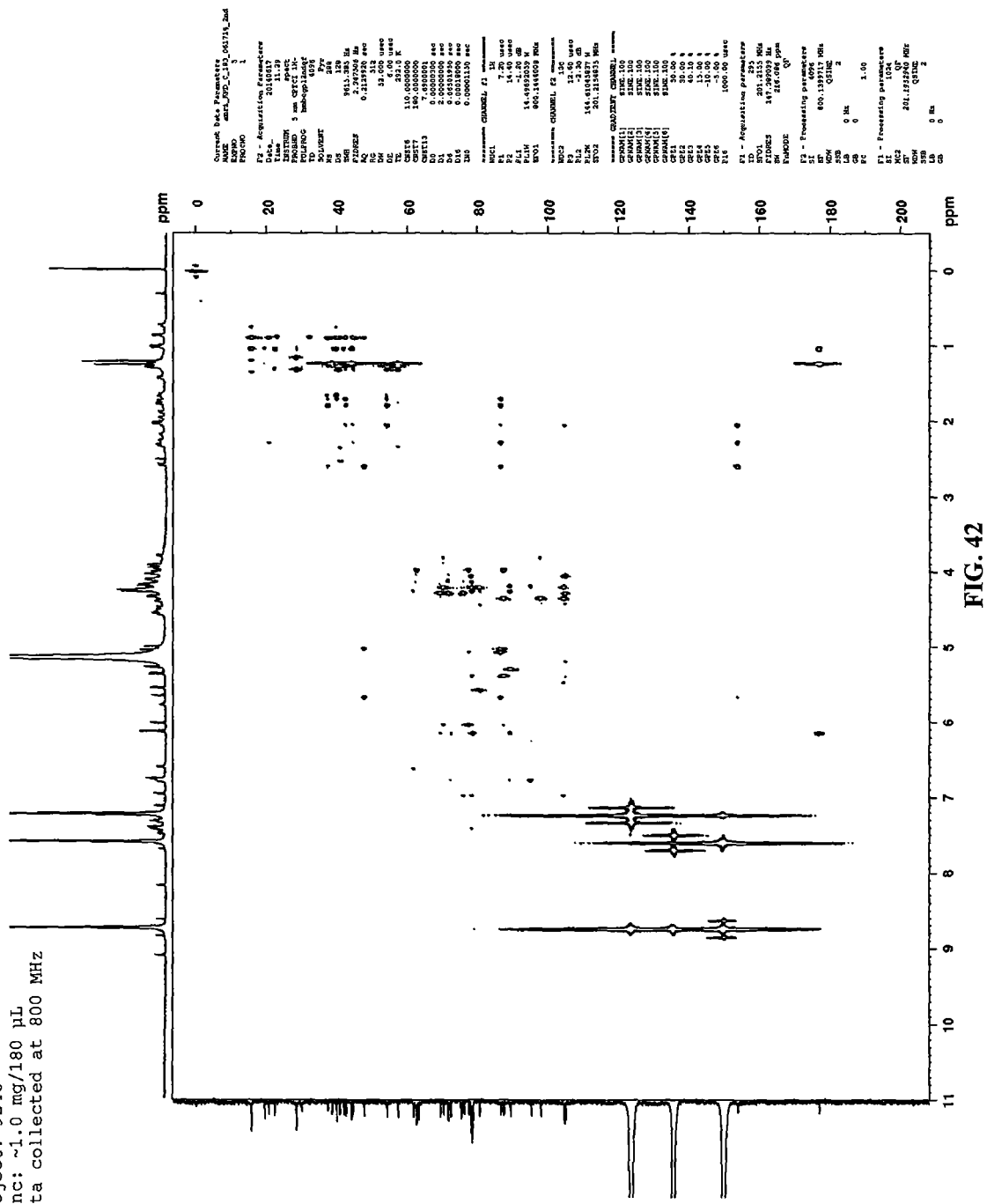
FIG. 42 shows the results of HMBC as described in Example 47.
Figure 43:
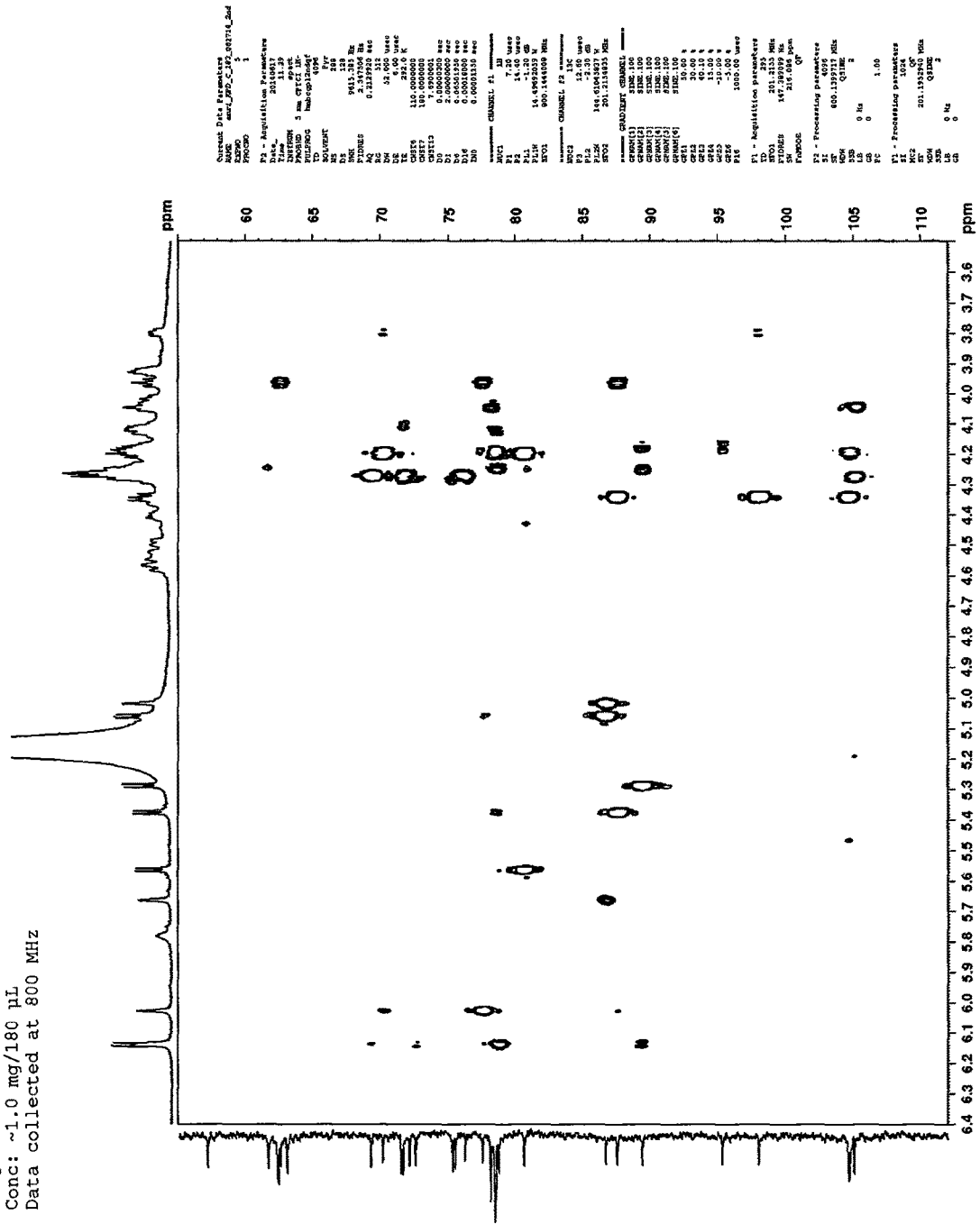
FIG. 43 shows the results of HMBC as described in Example 47.
Figure 44:
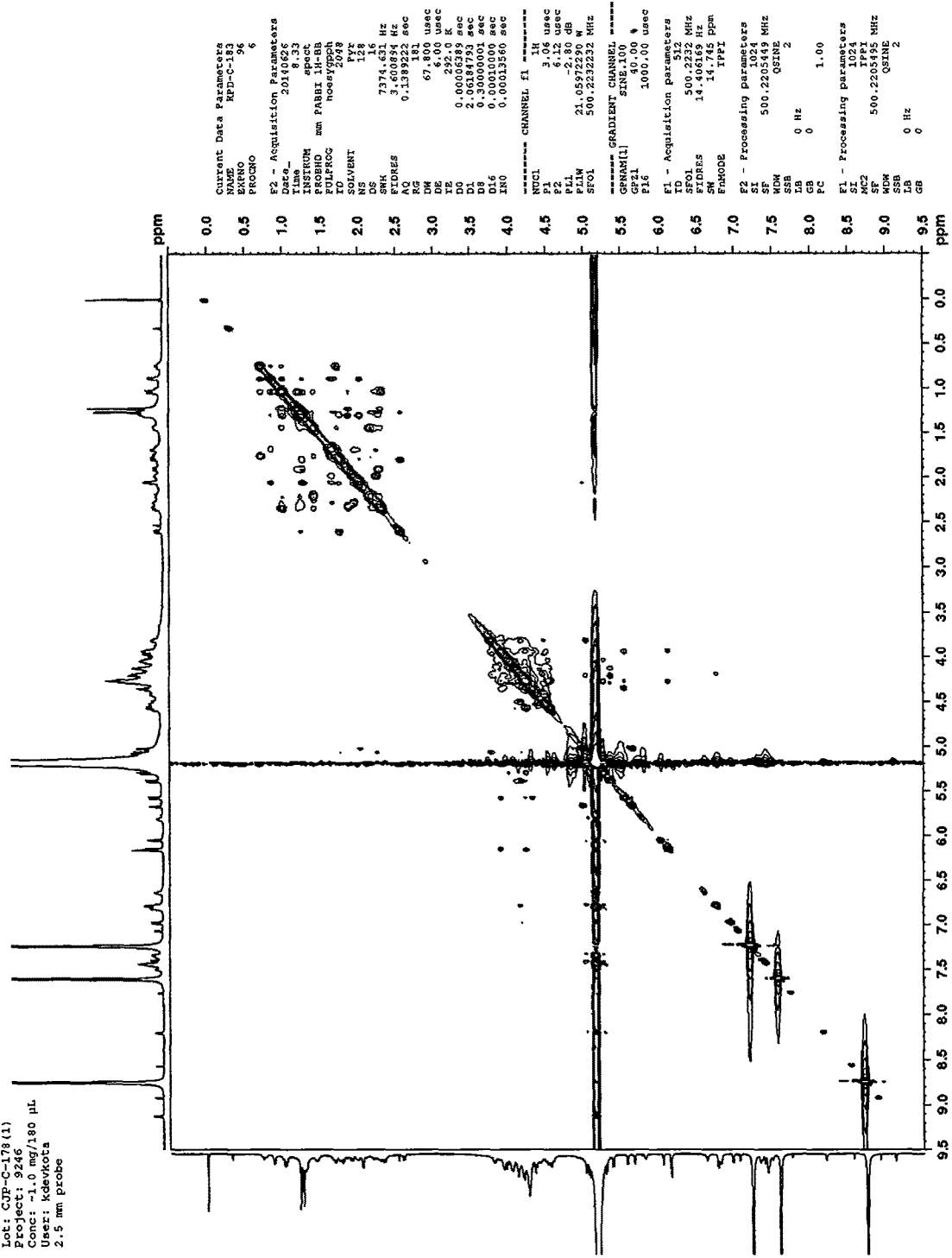
FIG. 44 shows the results of NOESY as described Example 47.
Figure 45:
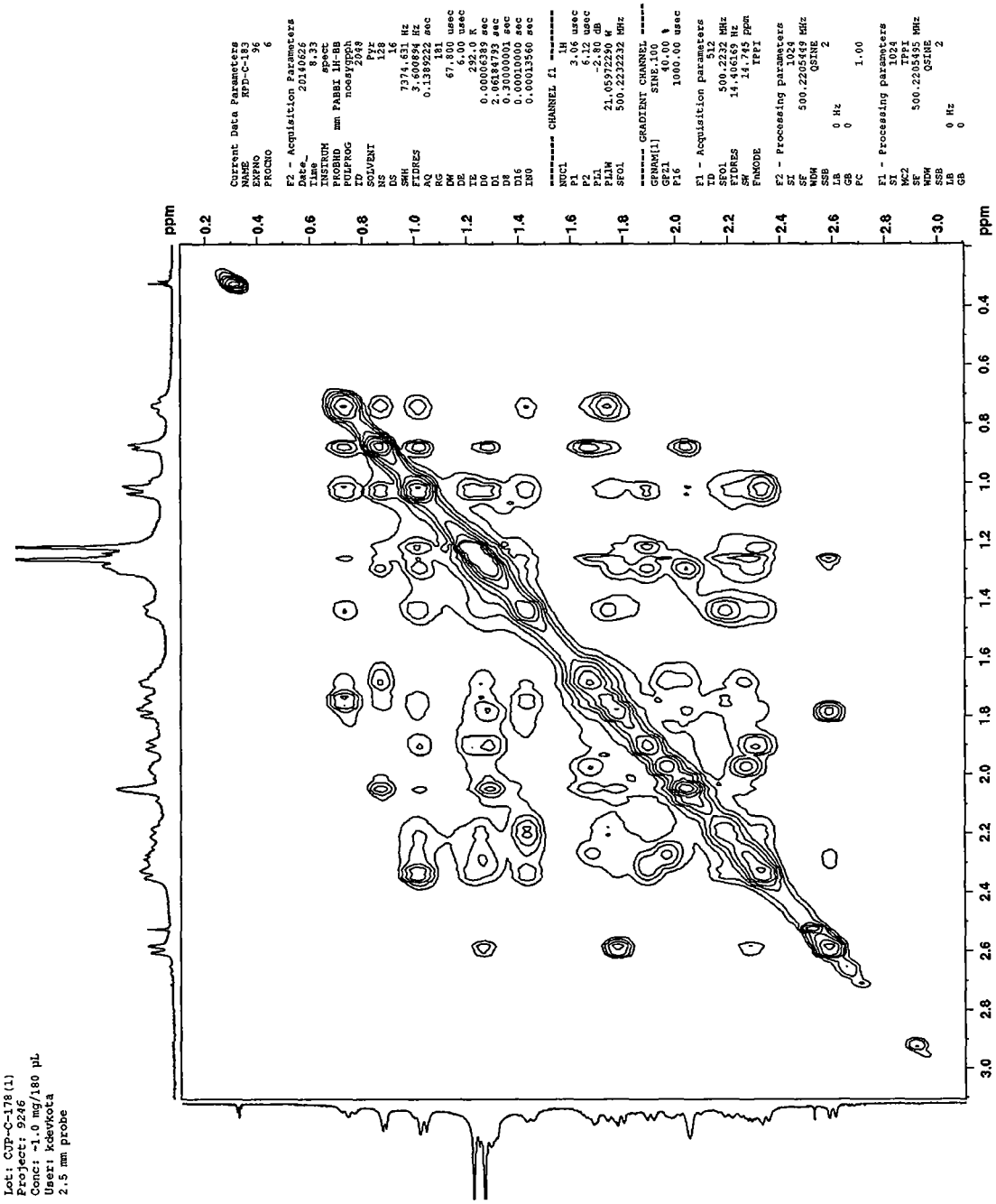
FIG. 45 shows the results of NOESY as described Example 47.

A series of NMR experiments including $^1$H NMR (FIGS. 35-37), $^{13}$C NMR (FIGS. 38-39), $^1$H-$^1$H COSY (FIG. 40), HSQC-DEPT (FIG. 41), HMBC (FIGS. 42-43), NOESY (FIGS. 44-45), and 1D TOCSY (FIGS. 46-50) were performed to allow assignment of reb I.

Figure 36:
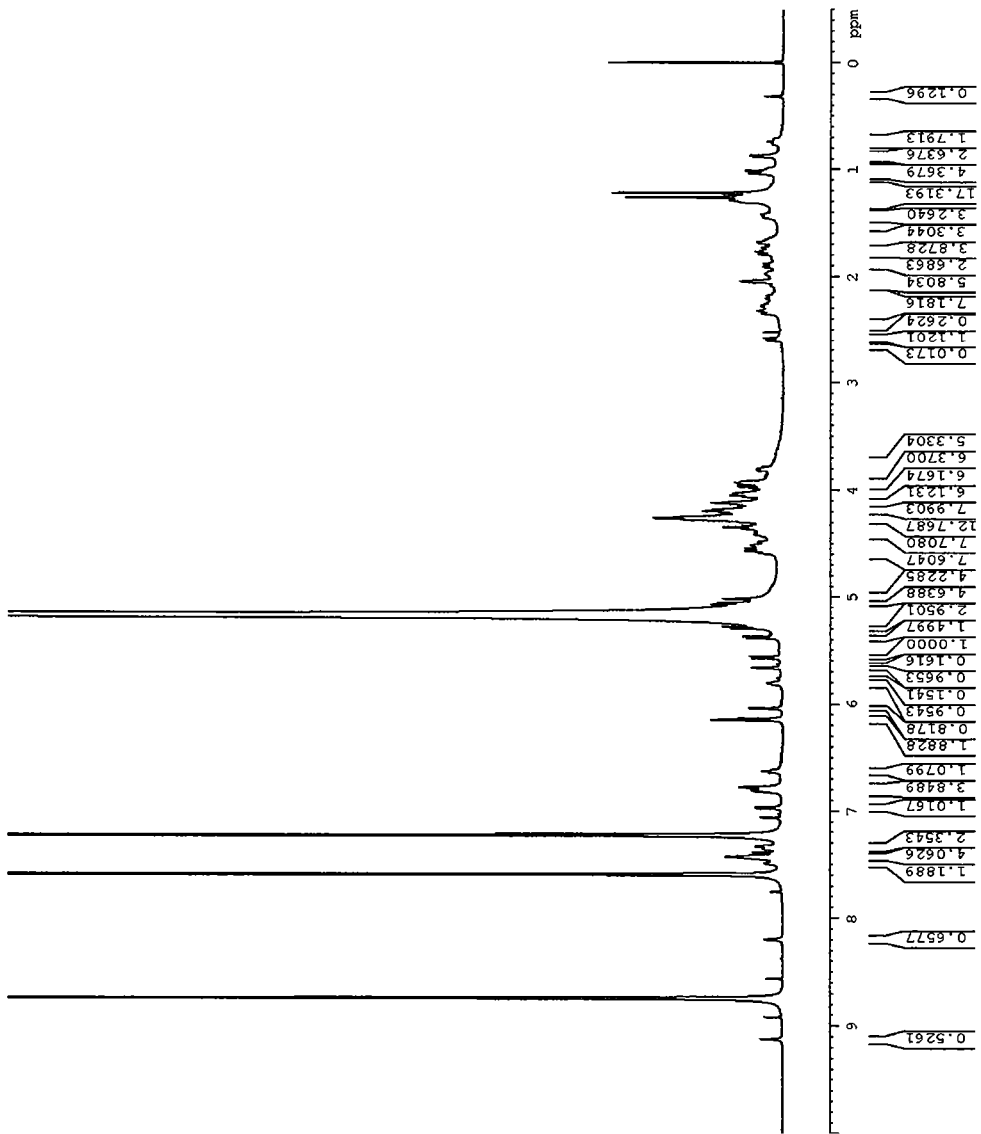
FIG. 36 shows the results of $^1$H NMR as described in Example 47.
Figure 37:
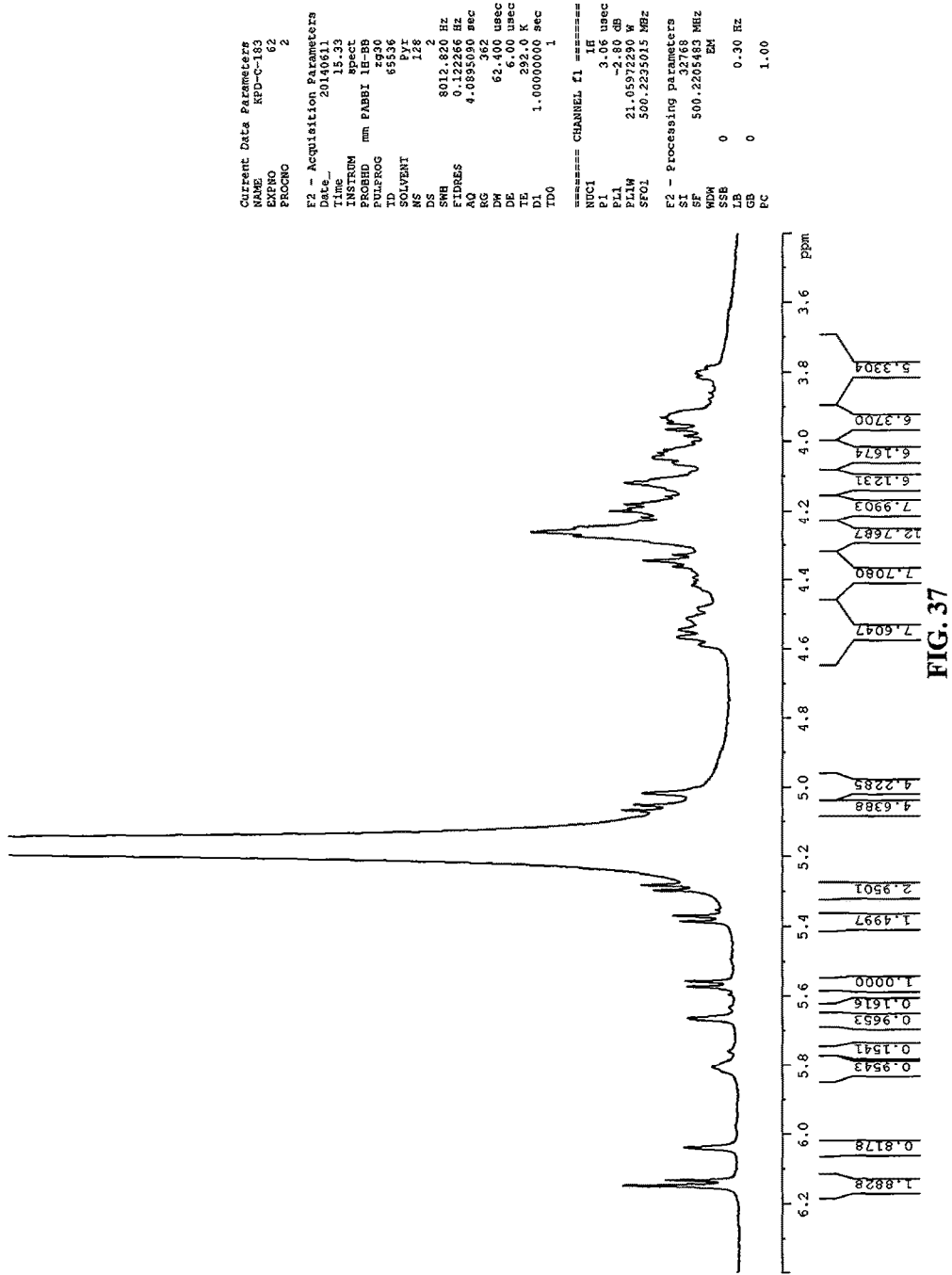
FIG. 37 shows the results of $^1$H NMR as described in Example 47.

In the $^1$H NMR spectrum of reb I acquired at 300 K (FIG. 35), one of the anomeric protons was completely obscured by the water resonance. Therefore, $^1$H NMR spectrum of the sample was acquired at lower temperature (292 K), to shift out the water resonance, and at this temperature anomeric proton was sufficiently resolved (FIGS. 36-37). Thus, all other NMR data of reb I was acquired at 292 K.

The 1D and 2D NMR data indicated that the central core of the glycoside is a diterpene. An HMBC correlation from the methyl protons at $\delta_H$ 1.22 to the carbonyl at $\delta_C$ 176.9 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.5, 44.0, and 57.2 allowed assignment of C-3, C-4, and C-5. Analysis of the $^1$H-$^{13}$C HSQC-DEPT data indicated that the carbon at $\delta_C$ 38.5 was a methylene group and the carbon at $\delta_C$ 57.2 was a methine which were assigned as C-3 and C-5, respectively. This left the carbon at $\delta_C$ 44.0, which did not show a correlation in the HSQC-DEPT spectrum, to be assigned as the quaternary carbon, C-4. The $^1$H chemical shifts for C-3 ($\delta_H$ 1.02 and 2.35) and C-5 ($\delta_H$ 1.03) were assigned using the HSQC-DEPT data. A COSY correlation between one of the H-3 protons ($\delta_H$ 1.02) and a proton at $\delta_H$ 1.44 allowed assignment of one of the H-2 protons which in turn showed a correlation with a proton at $\delta_H$ 0.74 which was assigned to H-1. The remaining $^1$H and $^{13}$C chemical shifts for C-1 and C-2 were then assigned on the basis of additional COSY and HSQC-DEPT correlations and are summarized in the table below.

$^1$H and $^{13}$C NMR (500 and 150 MHz, pyridine-d$_5$), assignments of the Rebaudioside I aglycone.

| Position | $^{13}$C | $^1$H |
|---|---|---|
| 1 | 40.7 | 0.74 t (11.6) |
|   |      | 1.75 m |
| 2 | 19.4 | 1.44 m |
|   |      | 2.20 m |
| 3 | 38.5 | 1.02 m |
|   |      | 2.35 m |
| 4 | 44.0 | — |
| 5 | 57.2 | 1.03 m |
| 6 | 22.2 | 1.90 m |
|   |      | 2.33 m |
| 7 | 41.7 | 1.29 m |
|   |      | 1.31 m |
| 8 | 42.3 | — |
| 9 | 54.1 | 0.88 d (6.3) |
| 10 | 39.8 | — |
| 11 | 20.5 | 1.67 m |
|    |      | 1.70 m |
| 12 | 37.3 | 1.98 m |
|    |      | 2.28 m |
| 13 | 86.7 | — |
| 14 | 44.3 | 1.78 m |
|    |      | 2.59 d (11.9) |
| 15 | 47.6 | 2.04 brs |
| 16 | 154.0 | — |
| 17 | 104.8 | 5.02 s |
|    |       | 5.67 s |
| 18 | 28.4 | 1.22 s |
| 19 | 176.9 | — |
| 20 | 15.7 | 1.26 s |

The other tertiary methyl singlet, observed at $\delta_H$ 1.26, showed HMBC correlations to C-1 and C-5 and was assigned as H-20. The methyl protons showed additional HMBC correlations to a quaternary carbon ($\delta_C$ 39.8) and a methine carbon ($\delta_C$ 54.1) which were assigned as C-10 and C-9, respectively. COSY correlations between H-5 ($\delta_H$ 1.03) and protons at $\delta_H$ 1.90 and 2.33 then allowed assignment of the H-6 protons which in turn showed correlations to protons at $\delta_H$ 1.29 and 1.31 which were assigned to H-7. The $^{13}$C chemical shifts for C-6 ($\delta_C$ 22.2) and C-7 ($\delta_C$ 41.7) were then determined from the HSQC-DEPT data. COSY correlations between H-9 ($\delta_H$ 0.88) and protons at $\delta_H$ 1.67 and 1.70 allowed assignment of the H-11 protons which in turn showed COSY correlations to protons at $\delta_H$ 1.98 and 2.28 which were assigned as the H-12 protons. The HSQC-DEPT data was then used to assign C-11 ($\delta_C$ 20.5) and C-12 ($\delta_C$ 37.3). The olefinic protons observed at $\delta_H$ 5.02 and 5.67 showed HMBC correlations to a quaternary carbon at $\delta_C$ 86.7 (C-13) and thus were assigned to H-17 ($\delta_C$ 104.8 via HSQC-DEPT). The methine proton H-9 showed HMBC correlations to carbons at $\delta_C$ 42.3, 44.3 and 47.6 which were assigned as C-8, C-14 and C-15, respectively. The $^1$H chemical shifts at C-14 ($\delta_H$ 1.78 and 2.59) and C-15 ($\delta_H$ 2.04) were assigned using the HSQC-DEPT data. Additional HMBC correlations from H-9 to C-11 and H-12 to C-9 further confirmed the assignments made above. HMBC correlations observed from H-14 to a quaternary carbon at $\delta_C$ 154.0 allowed the assignment of C-16 to complete the assignment of the central core.

Correlations observed in the NOESY spectrum were used to assign the relative stereochemistry of the central diterpene core. In the NOESY spectrum, NOE correlations were observed between H-14 and H-20 indicating that H-14 and H-20 are on the same face of the rings. Similarly, NOE correlations were observed between H-9 and H-5 as well as H-5 and H-18. NOE correlations between H-9 and H-14 were not observed. The NOESY data thus indicate that H-5, H-9 and H-18 were on the opposite face of the rings compared to H-14 and H-20 as presented in the figure below. These data thus indicate that the relative stereochemistry in the central core was retained during the glycosylation step.

Analysis of the $^1$H-$^{13}$C HSQC-DEPT data for reb I confirmed the presence of five anomeric protons. All five anomeric protons were resolved in the spectra acquired at 292 K at $\delta_H$ 6.14 ($\delta_C$ 95.3), 5.57 ($\delta_C$ 104.6), 5.38 ($\delta_C$ 104.7), 5.29 ($\delta_C$ 105.0), and 5.06 ($\delta_C$ 98.0). Additionally, all five anomeric protons had large couplings (7.7 Hz-8.2 Hz) indicating that they had n-configurations. The anomeric proton observed at $\delta_H$ 6.14 showed an HMBC correlation to C-19 which indicated that it corresponds to the anomeric proton of Glc$_I$. Similarly, the anomeric proton observed at $\delta_H$ 5.06 showed an HMBC correlation to C-13 allowing it to be assigned as the anomeric proton of Glc$_{II}$.

Figure 46:
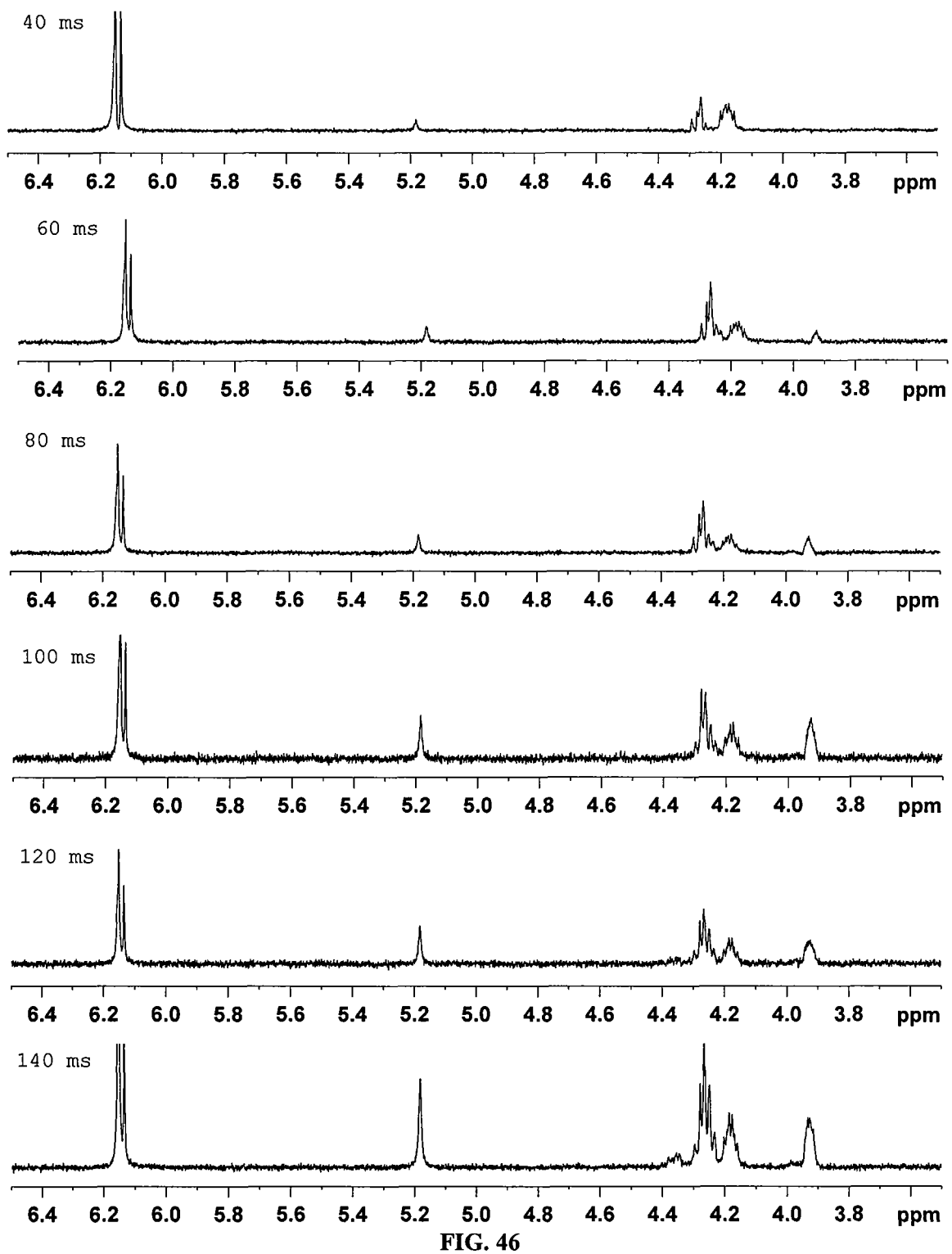
FIG. 46 shows the results of 1D TOCSY as described in Example 47.

The Glc$_I$ anomeric proton ($\delta_H$ 6.14) showed a COSY correlation to a proton at $\delta_H$ 4.18 which was assigned as Glc$_I$ H-2. Due to data overlap the COSY spectrum did not allow assignment of H-3 or H-4. Therefore, a series of 1D TOCSY experiments were performed using selective irradiation of the Glc$_I$ anomeric proton with several different mixing times (FIG. 46). In addition to confirming the assignment for Glc$_I$ H-2, the TOCSY data showed protons at $\delta_H$ 4.27, 4.25, and 3.93 which were assigned as H-3, H-4 and H-5, respectively. The proton observed at $\delta_H$ 4.37 in the TOCSY spectrum was assigned to one of the Glc$_I$ H-6 protons. The other H-6 methylene proton at $\delta_H$ 4.27 was assigned based on COSY correlation from H-5 to $\delta_H$ 4.27. The $^{13}$C chemical shifts for Glc$_I$ C-2 ($\delta_C$ 72.5), C-3 ($\delta_C$ 89.4), C-4 ($\delta_C$ 69.2), C-5 ($\delta_C$ 78.2-78.8) and C-6 ($\delta_C$ 61.7) were assigned using the HSQC-DEPT data. HMBC correlations from H-1 to C-3 and H-4 to C-6 further confirmed the assignments made above to complete the assignment of $Glc_I$.

Of the four remaining unassigned glucose moieties one was assigned as a substituent at C-3 of $Glc_I$ on the basis of HMBC correlations. The anomeric proton observed at $\delta_H$ 5.29 showed an HMBC correlation to $Glc_I$ C-3 and was assigned as the anomeric proton of $Glc_V$. The reciprocal HMBC correlation from $Glc_I$ H-3 to the anomeric carbon of $Glc_V$ was also observed.

A summary of the $^1H$ and $^{13}C$ chemical shifts for the glycoside at C-19 are shown in the following table:

| $^1H$ and $^{13}C$ NMR (500 and 150 MHz, pyridine-$d_5$) assignments of Rebaudioside I C-19 glycoside. | | |
|---|---|---|
| Position | $^{13}C$ | $^1H$ |
| $Glc_I$-1 | 95.3 | 6.14 d (8.2) |
| $Glc_I$-2 | 72.5 | 4.18 m |
| $Glc_I$-3 | 89.4 | 4.27 m |
| $Glc_I$-4 | 69.2 | 4.25 m |
| $Glc_I$-5 | 78.2-78.8† | 3.93 m |
| $Glc_I$-6 | 61.7 | 4.27 m, 4.37 m |
| $Glc_V$-1 | 105.0 | 5.29 d (7.9) |
| $Glc_V$-2 | 75.3 or 75.5 | 4.04 m |
| $Glc_V$-3 | 78.2-78.6† | 4.27 m |
| $Glc_V$-4 | 71.5 or 71.6 | 4.12 m |
| $Glc_V$-5 | 78.5 or 78.6† | 4.05 m |
| $Glc_V$-6 | 62.3 or 62.4 | 4.26 m, 4.56 m |

†Five carbon resonances in the range of 78.2-78.8 (78.16, 78.47, 78.50, 78.55, and 78.77), hence chemical shift could not be unequivocally assigned.

A summary of key HMBC and COSY correlations used to assign the C-19 glycoside region are provided below.

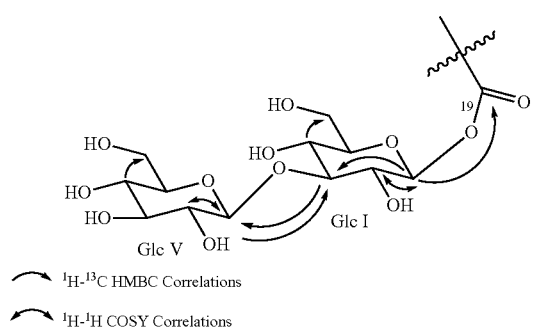

⌒ $^1H$-$^{13}C$ HMBC Correlations

⌒ $^1H$-$^1H$ COSY Correlations

Figure 47:
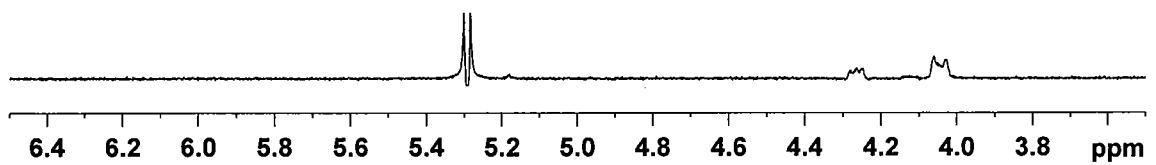
FIG. 47 shows the results of 1D TOCSY as described in Example 47.
Figure 47:
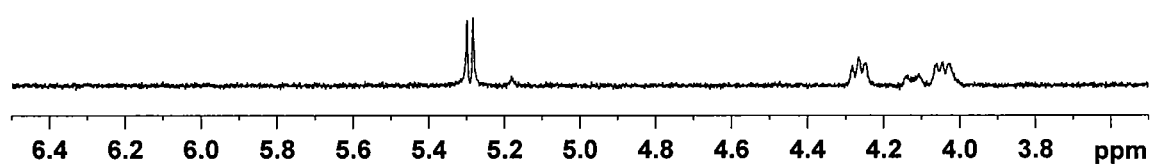
Figure 47:
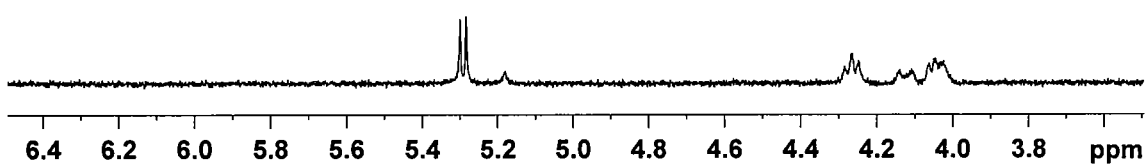
Figure 47:
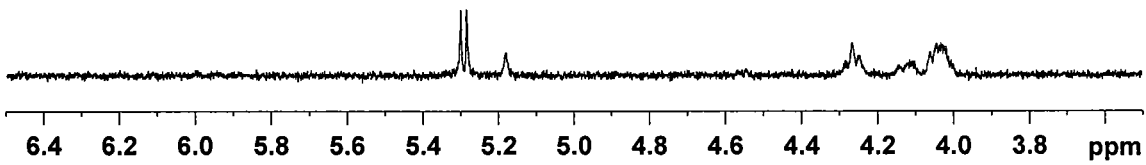
Figure 47:
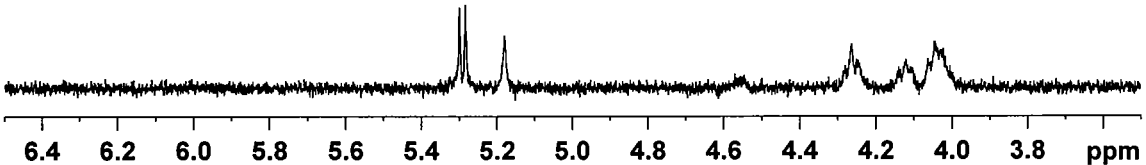
Figure 47:
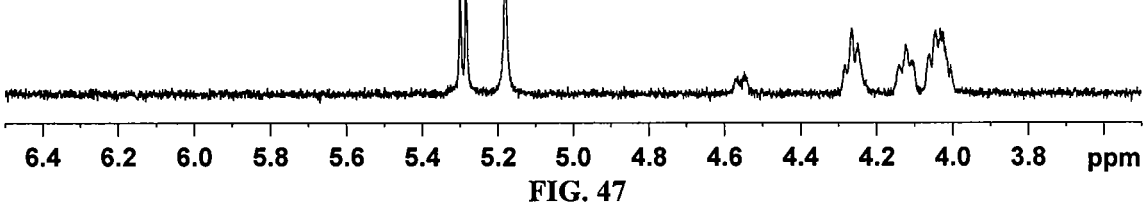

The anomeric proton of $Glc_V$ ($\delta_H$ 5.29) showed a COSY correlation with a proton at $\delta_H$ 4.04 which was assigned as $Glc_V$ H-2. $Glc_V$ C-2 ($\delta_C$ 75.3 or 75.5) was then assigned using the HSQC-DEPT data. Due to overlap in the data the COSY spectrum did not allow assignment of the remaining protons. Therefore, a series of 1D TOCSY experiments were performed using selective irradiation of the $Glc_V$ anomeric proton with several different mixing times (FIG. 47). In addition to confirming the assignments for $Glc_V$ H-2, the TOCSY data allowed assignment of $Glc_V$ H-3 ($\delta_H$ 4.27), H-4 ($\delta_H$ 4.12), and H-5 ($\delta_H$ 4.05). The proton observed at $\delta_H$ 4.56 in the TOCSY spectrum was assigned to one of the $Glc_V$ H-6 protons. The other H-6 methylene proton at $\delta_H$ 4.26 was assigned based on COSY correlation from H-5 to $\delta_H$ 4.26. The $^{13}C$ chemical shifts for $Glc_V$ C-3 ($\delta_C$ 78.2-78.6), C-4 ($\delta_C$ 71.5 or 71.6), C-5 ($\delta_C$ 78.5 or 78.6) and C-6 ($\delta_C$ 62.3 or 62.4) were assigned using the HSQC-DEPT data to complete the assignment of $Glc_V$.

Figure 48:
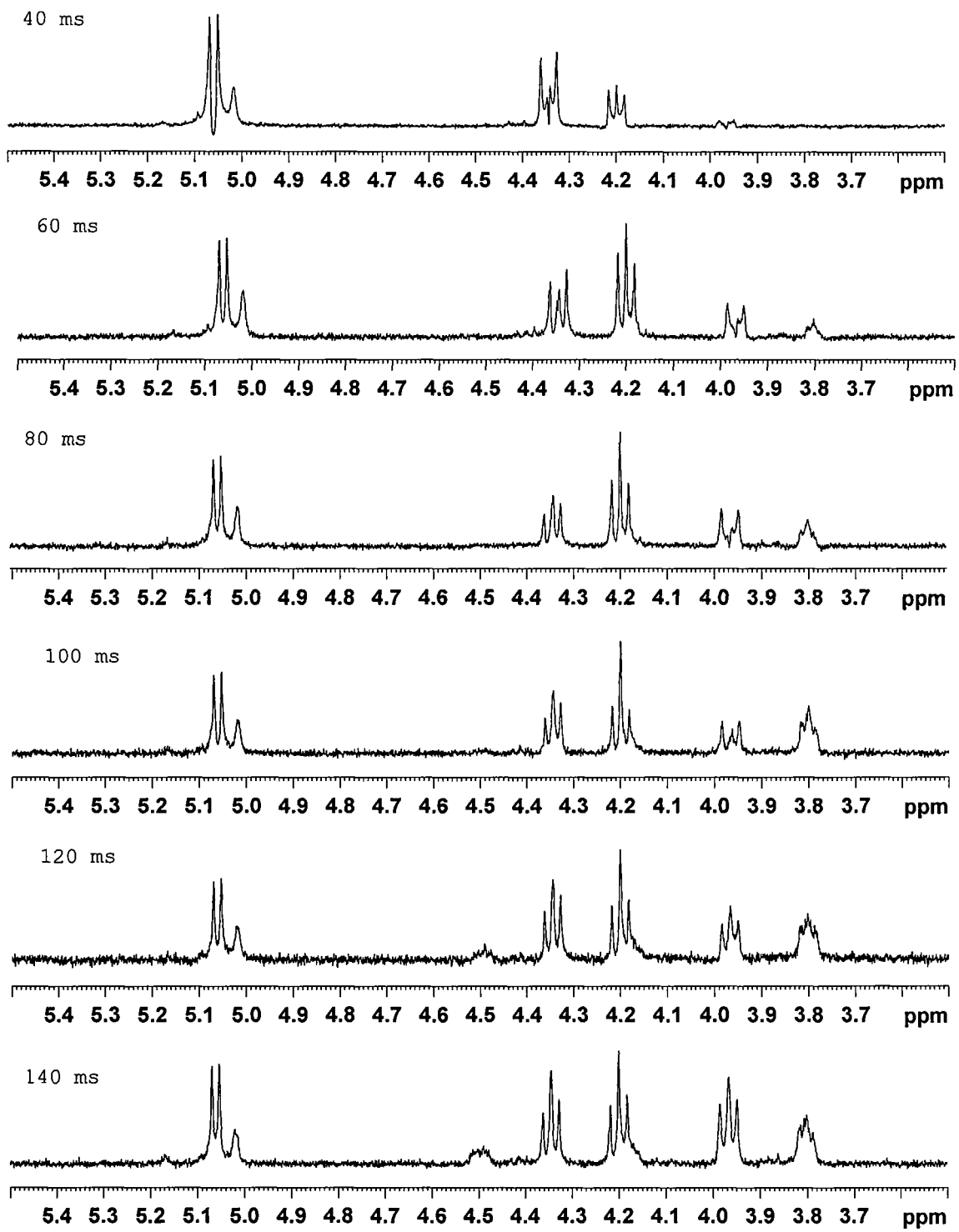
FIG. 48 shows the results of 1D TOCSY as described in Example 47.

Assignment of $Glc_{II}$ was carried out in a similar manner. The $Glc_{II}$ anomeric proton ($\delta_H$ 5.06) showed a COSY correlation to a proton at $\delta_H$ 4.34 which was assigned as $Glc_{II}$ H-2 and in turn showed a COSY correlation to a proton at $\delta_H$ 4.20 ($Glc_{II}$ H-3) which showed an additional correlation with a proton at $\delta_H$ 3.97 ($Glc_{II}$ H-4) which also showed a COSY correlation to a proton at $\delta_H$ 3.80 ($Glc_{II}$ H-5). H-5 showed additional COSY correlations to protons at $\delta_H$ 4.18 and 4.49 which were assigned to H-6. A series of 1D TOCSY experiments were also performed using selective irradiation of the $Glc_{II}$ anomeric proton with several different mixing times (FIG. 48). The TOCSY data confirmed the above proton assignments. Assignment of the $^{13}C$ chemical shifts for $Glc_{II}$ C-2 ($\delta_C$ 80.2), C-3 ($\delta_C$ 87.5), C-4 ($\delta_C$ 70.1), C-5 ($\delta_C$ 77.6) and C-6 ($\delta_C$ 62.5) was based on HSQC-DEPT data. HMBC correlations from $Glc_{II}$ H-3 to C-2 and C-4 and also from $Glc_{II}$ H-4 to C-3, C-5 and C-6 confirmed the assignments made above to complete the assignment of $Glc_{II}$.

The remaining two unassigned glucose moieties were assigned as substituents at C-2 and C-3 of $Glc_{II}$ on the basis of HMBC correlations. The anomeric proton observed at $\delta_H$ 5.57 showed an HMBC correlation to $Glc_{II}$ C-2 and was assigned as the anomeric proton of $Glc_{III}$. The anomeric proton observed at $\delta_H$ 5.38 showed an HMBC correlation to $Glc_{II}$ C-3 and was assigned as the anomeric proton of $Glc_{IV}$. The reciprocal HMBC correlations from $Glc_{II}$ H-2 to the anomeric carbon of $Glc_{III}$ and from $Glc_{II}$ H-3 to the anomeric carbon of $Glc_{IV}$ were also observed.

Figure 49:
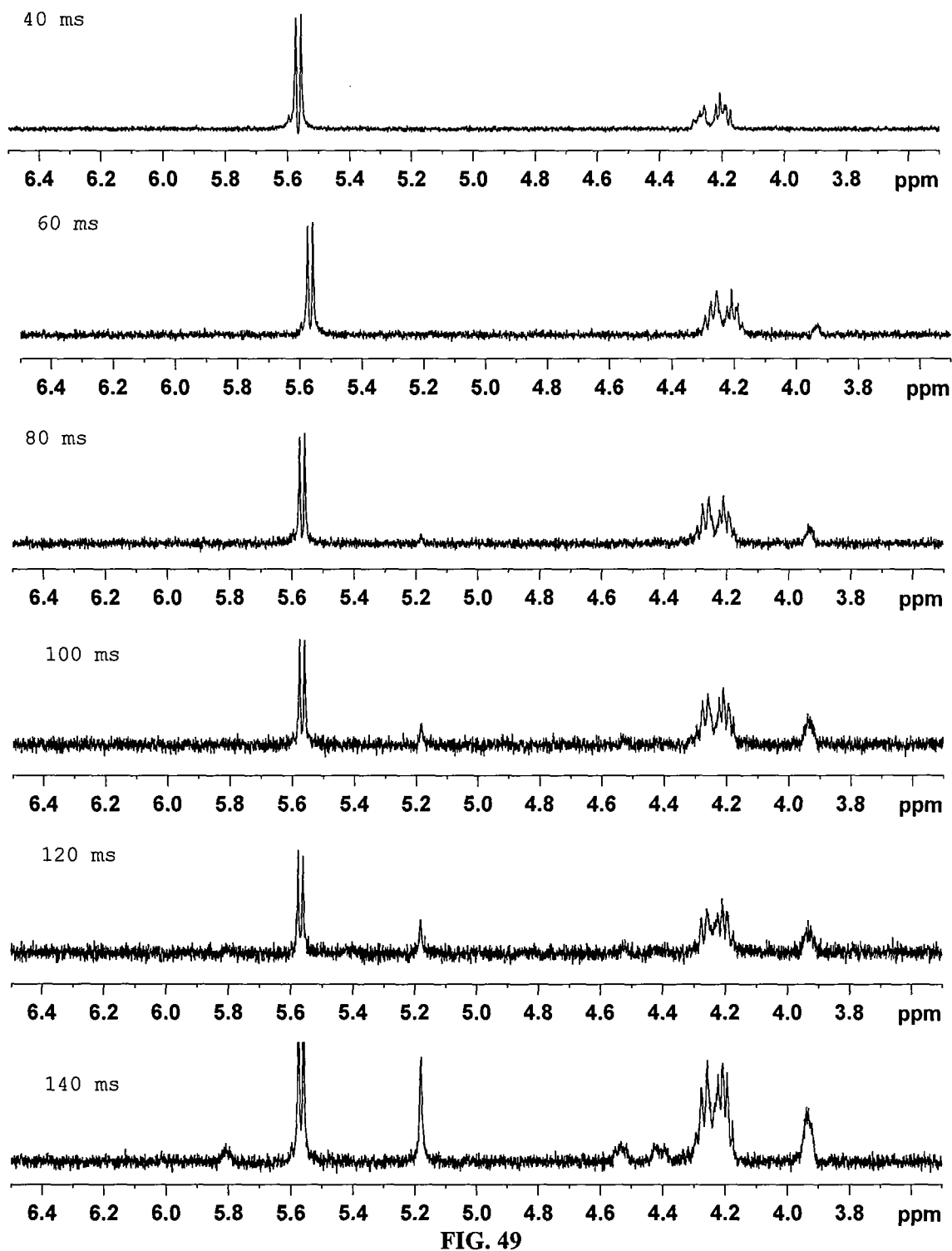
FIG. 49 shows the results of 1D TOCSY as described in Example 47.

The anomeric proton of $Glc_{III}$ ($\delta_H$ 5.57) showed a COSY correlation with a proton at $\delta_H$ 4.21 which was assigned as $Glc_{III}$ H-2. $Glc_{III}$ C-2 ($\delta_C$ 76.3) was then assigned using the HSQC-DEPT data. Due to data overlap the COSY spectrum did not allow assignment of the remaining protons. Therefore, a series of 1D TOCSY experiments were performed using selective irradiation of the $Glc_{III}$ anomeric proton with several different mixing times (FIG. 49). In addition to confirming the assignments for $Glc_{III}$ H-2, the TOCSY data allowed assignment of $Glc_{III}$ H-3 ($\delta_H$ 4.27), H-4 ($\delta_H$ 4.25) and H-5 ($\delta_H$ 3.94). The protons observed at $\delta_H$ 4.41 and $\delta_H$ 4.53 in the TOCSY spectrum were assigned as the $Glc_{III}$ H-6 protons. The $^{13}C$ chemical shifts for C-3 ($\delta_C$ 78.2-78.6), C-4 ($\delta_C$ 72.1), C-5 ($\delta_C$ 78.2-78.8) and C-6 ($\delta_C$ 63.1) were assigned using the HSQC-DEPT data. HMBC correlations from H-5 to a carbon at $\delta_C$ 63.1 further confirmed the assignment of $Glc_{III}$ C-6 to complete the assignment of $Glc_{II}$'.

Figure 50:
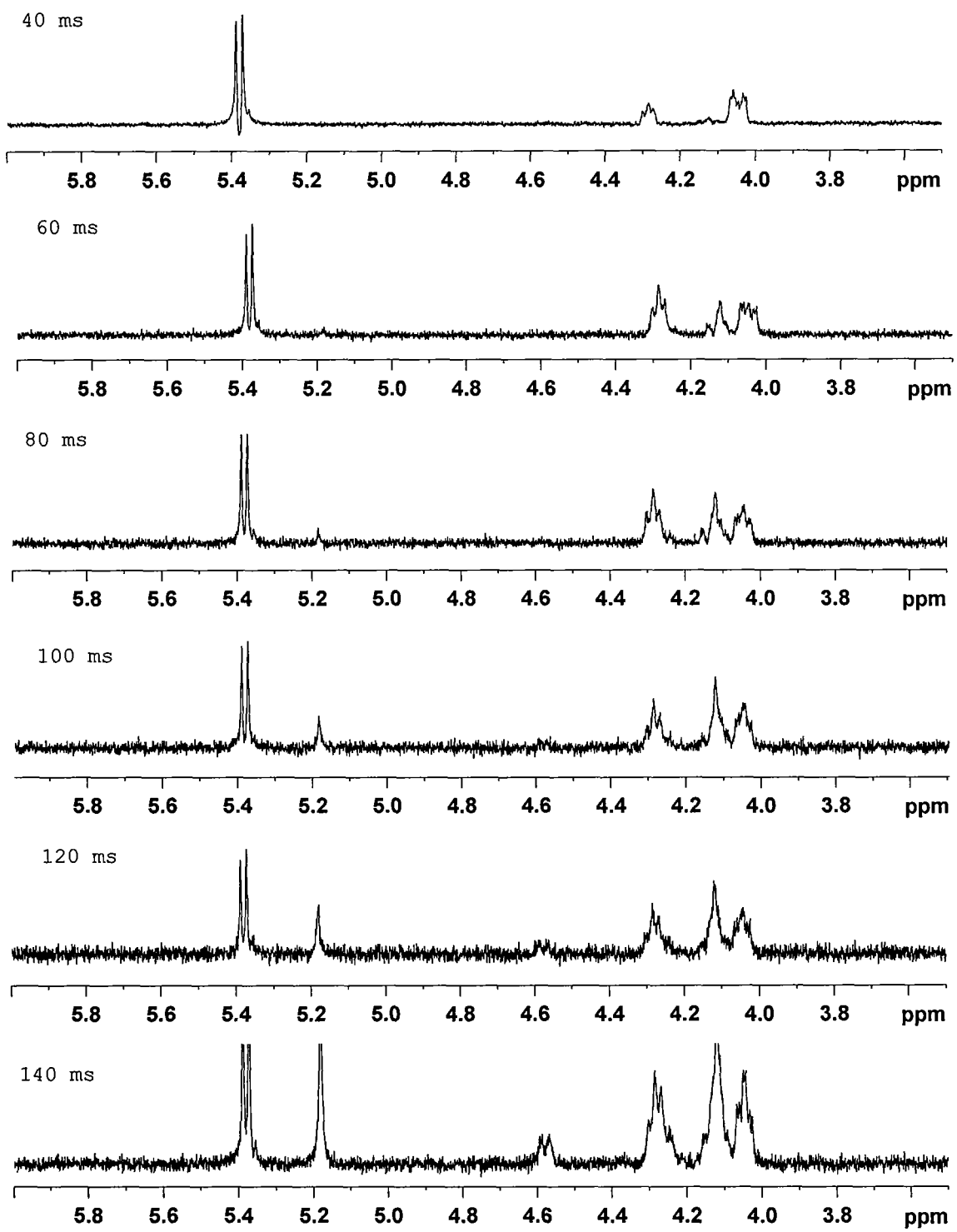
FIG. 50 shows the results of 1D TOCSY as described in Example 47.

The anomeric proton of $Glc_{IV}$ ($\delta_H$ 5.38) showed a COSY correlation with a proton at $\delta_H$ 4.01 which was assigned as $Glc_{II}$/H-2. $Glc_{II}$, C-2 ($\delta_C$ 75.3 or 75.5) was then assigned using the HSQC-DEPT data. Due to data overlap the COSY spectrum did not allow assignment of the remaining protons. Therefore a series of 1D TOCSY experiments were performed using selective irradiation of the $Glc_{IV}$ anomeric proton with several different mixing times (FIG. 50). In addition to confirming the assignments for $Glc_{IV}$ H-2, the 1D TOCSY data allowed assignment of H-3 ($\delta_H$ 4.28), H-4 ($\delta_H$ 4.11), H-5 ($\delta_H$ 4.13) and H-6 ($\delta_H$ 4.25 and 4.58). The proton at $\delta_H$ 4.25 also showed COSY correlation with $\delta_H$ 4.58 further confirmed that these protons belong to H-6. The $^{13}$C chemical shifts for C-3 ($\delta_C$ 78.2-78.6), C-4 ($\delta_C$ 72.1), C-5 ($\delta_C$ 78.2-78.6) and C-6 ($\delta_C$ 62.3 or 62.4) were assigned using the HSQC-DEPT data. HMBC correlations from H-4 to C-6 and H-5 to C-1 further confirmed the assignment of $Glc_{II}$, C-6 to complete the assignment of $Glc_{IV}$.

A summary of the $^1$H and $^{13}$C chemical shifts for the glycoside at C-13 are found are shown below:

| Position | $^{13}$C | $^1$H |
|---|---|---|
| $Glc_{II}$-1 | 98.0 | 5.06 d (7.9) |
| $Glc_{II}$-2 | 80.6 | 4.34 m |
| $Glc_{II}$-3 | 87.5 | 4.20 m |
| $Glc_{II}$-4 | 70.1 | 3.97 m |
| $Glc_{II}$-5 | 77.6 | 3.80 m |
| $Glc_{II}$-6 | 62.5 | 4.18 m, 4.49 m |
| $Glc_{III}$-1 | 104.6 | 5.57 d (7.7) |
| $Glc_{III}$-2 | 76.3 | 4.21 m |
| $Glc_{III}$-3 | 78.2-78.6† | 4.27 m |
| $Glc_{III}$-4 | 72.1 | 4.25 m |
| $Glc_{III}$-5 | 78.2-78.8† | 3.94 m |
| $Glc_{III}$-6 | 63.1 | 4.41 m, 4.53 m |
| $Glc_{IV}$-1 | 104.7 | 5.38 d (7.9) |
| $Glc_{IV}$-2 | 75.3 or 75.5 | 4.01 m |
| $Glc_{IV}$-3 | 78.2-78.6† | 4.28 m |
| $Glc_{IV}$-4 | 72.1 | 4.11 m |
| $Glc_{IV}$-5 | 78.2-78.6† | 4.13 m |
| $Glc_{IV}$-6 | 62.3 or 62.4 | 4.25 m, 4.58 m |

†Five carbon resonances in the range of 78.2-78.8 (78.16, 78.47, 78.50, 78.55, and 78.77), hence chemical shift could not be unequivocally assigned.

A summary of key HMBC and COSY correlations used to assign the C-13 glycoside region are provided below.

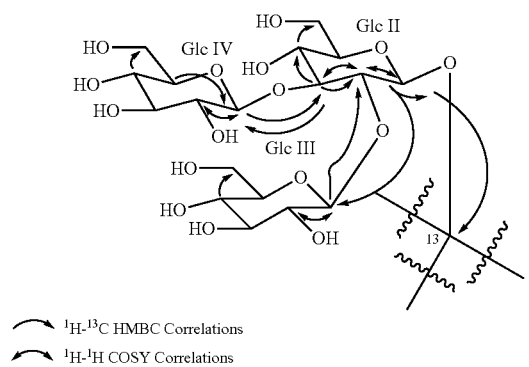

$^1$H-$^{13}$C HMBC Correlations
$^1$H-$^1$H COSY Correlations

NMR and MS analyses of rebaudioside I, reb I, allowed the full assignment of structure, shown below. The name of the chemical compound is (13-[(2-O-β-D-glucopyranosyl-3-O-β-D-glucopyranosyl)-β-D-glucopyranosyl)oxy] ent-kaur-16-en-19-oic acid-(3-O-β-D-glucopyranosyl)-β-D-glucopyranosyl) ester].

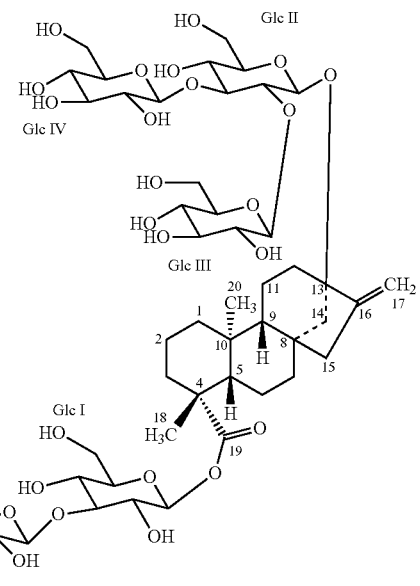

Example 48

Directed Evolution of UGTSL2 for the Conversion of Rebaudioside A to Rebaudioside D (Round 2)

Taking the native enzyme UGTSL2 (GI_460410132) as baseline, a list of 23 mutations was established containing different identified positive mutations for activity from the first round (EXAMPLE 45) and new mutations obtained by DNA2.0 ProteinGPS™ strategy. This list of mutations was subsequently used to design 46 variant genes that contained each 3 different mutations. After codon-optimized for expression in E. coli the genes were synthesized, subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of E. coli BL21(DE3) containing the pET30a+_UGTSL2var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysates were recovered by centrifugation.

In order to measure the activity of the variants for the transformation of Rebaudioside A to Rebaudioside D, 100 µL of fresh lysate was added to a solution of Rebaudioside A (final concentration 0.5 mM), $MgCl_2$ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the initial rates after HPLC analysis (CAD detection) using the analytical method that was described above for the transformation of Rebaudioside A to Rebaudioside D.

In parallel for the most active clones, 100 μL of fresh lysate was added to a solution of Rebaudioside D (final concentration 0.5 mM), MgCl$_2$ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the initial rates for Rebaudioside D conversion after HPLC analysis (CAD detection).

Apart from the new variants, both experiments were also performed with baseline clone, UGTSL2. The initial rates for the conversion of Rebaudioside A or Rebaudioside D for this baseline clone were defined as 100%.

Activity of each clone was defined as normalized activity compared to baseline clone UGTSL2 whereas specificity of each clone was expressed as the ratio between the initial rates for the conversion of Rebaudioside A and Rebaudioside D.

The normalized initial rate for the conversion of Rebaudioside A and the ratio between the initial rates for the conversion of Rebaudioside A and Rebaudioside D are depicted in the following table.

| Clone | Mutations* | Normalized initial rate for conversion of Rebaudioside A | Ratio between initial rates for the conversion of Rebaudioside A and Rebaudioside D |
|---|---|---|---|
| UGTSL2 | Baseline clone | 100% | 1.67 |
| Round2-var1 | UGTSL2 (Q27R_V270I_A285V) | 188% | 1.21 |
| Round2-var2 | UGTSL2 (F253Y_S255C_M354L) | 5% | Nd |
| Round2-var3 | UGTSL2_S255C_I352V_L393V | 28% | Nd |
| Round2-var4 | UGTSL2_R6H_N278G_T329I | 7% | Nd |
| Round2-var5 | UGTSL2_H247P_V270I_A285L | 75% | 1.27 |
| Round2-var6 | UGTSL2_I240L_T392A_L393V | 114% | 1.85 |
| Round2-var7 | UGTSL2_A285L_R312L_T392A | 135% | 1.66 |
| Round2-var8 | UGTSL2_Q27R_G387E_T392A | 164% | 1.65 |
| Round2-var9 | UGTSL2_Q27R_N278G_A341V | 178% | 3.13 |
| Round2-var10 | UGTSL2_I240L_A285L_N325S | 9% | Nd |
| Round2-var11 | UGTSL2_S255C_S258T_N325S | 26% | Nd |
| Round2-var12 | UGTSL2_Q27R_N325S_I352V | 6% | Nd |
| Round2-var13 | UGTSL2_N325S_A341V_M354L | 116% | 1.89 |
| Round2-var14 | UGTSL2_S255C_A285V_T392A | 98% | 2.63 |
| Round2-var15 | UGTSL2_A285L_A341V_I352V | 26% | Nd |
| Round2-var16 | UGTSL2_F253Y_G387E_L393V | 88% | 1.69 |
| Round2-var17 | UGTSL2_V270I_T329I_L393V | 88% | 2.16 |
| Round2-var18 | UGTSL2_H247P_I333L_L393V | 197% | 1.75 |
| Round2-var19 | UGTSL2_L276A_R312L_N325S | 53% | 1.72 |
| Round2-var20 | UGTSL2_V270I_T329V_M354L | 30% | Nd |
| Round2-var21 | UGTSL2_A285V_I352V_G387E | 30% | Nd |
| Round2-var22 | UGTSL2_I240L_H247P_L276A | 76% | 2.00 |
| Round2-var23 | UGTSL2_A285V_R312L_T329I | 4% | Nd |
| Round2-var24 | UGTSL2_I240L_M354L_G387E | 8% | Nd |
| Round2-var25 | UGTSL2_N278G_R312L_I333L | 50% | 1.57 |
| Round2-var26 | UGTSL2_L276A_T329I_I352V | 0% | Nd |
| Round2-var27 | UGTSL2_L276A_T329V_G387E | 73% | Nd |
| Round2-var28 | UGTSL2_R6H_Q27R_L393V | 9% | Nd |
| Round2-var29 | UGTSL2_H247P_S258T_T329I | 129% | 1.21 |
| Round2-var30 | UGTSL2_N278G_N325S_T392A | 206% | 2.06 |
| Round2-var31 | UGTSL2_S255C_V270I_I333L | 81% | 2.87 |
| Round2-var32 | UGTSL2_R6H_H247P_A341V | 119% | 2.05 |
| Round2-var33 | UGTSL2_H247P_R312L_G387E | 67% | Nd |
| Round2-var34 | UGTSL2_R6H_I240L_T329V | 0% | Nd |
| Round2-var35 | UGTSL2_S258T_V270I_T392A | 146% | 1.71 |
| Round2-var36 | UGTSL2_F253Y_T329I_I333L | 76% | 1.69 |
| Round2-var37 | UGTSL2_S258T_A285V_A341V | 187% | 2.32 |
| Round2-var38 | UGTSL2_L276A_A285L_M354L | 12% | Nd |
| Round2-var39 | UGTSL2_Q27R_F253Y_T329V | 35% | Nd |
| Round2-var40 | UGTSL2_R6H_S258T_L276A | 36% | Nd |
| Round2-var41 | UGTSL2_S258T_N278G_M354L | 88% | 0.96 |
| Round2-var42 | UGTSL2_R6H_F253Y_A285L | 72% | 1.40 |
| Round2-var43 | UGTSL2_F253Y_R312L_I352V | 8% | Nd |
| Round2-var44 | UGTSL2_I240L_A285V_I333L | 43% | 1.06 |
| Round2-var45 | UGTSL2_S255C_N278G_T329V | 45% | 2.51 |

*Mutations are noted as follows: reference gene-original amino acid-position-new amino acid: For example the mutation of an isoleucine at position 240 to a Leucine for UGTSL2 is noted as UGTSL2 (I240L).
Nd means Not determined.

Modeling of these results allowed to obtain a ranking of the effect of each mutation. The following mutations were determined as being beneficial for activity:

N325S, G387E, A285V, I333L, V270I, Q27R, N278G, L393V, S258T, A341V, H247P and T392A.

The following mutations were determined as being beneficial for an improved ratio between initial rate for the conversion of Rebaudioside A and Rebaudioside D:

V270I, T392A, T329V, L276A, L393V, A341V and S255C$_{56}$.

Example 49

Use of β-Glucosidases for the Conversion of Rebaudioside M2 to Rebaudioside D Different β-glucosidases were tested for the hydrolysis of Rebaudioside M2. The goal was to selectively hydrolyze the (1→6) glucoside bond in order to obtain Rebaudioside D. The desired general reaction scheme is as follows:

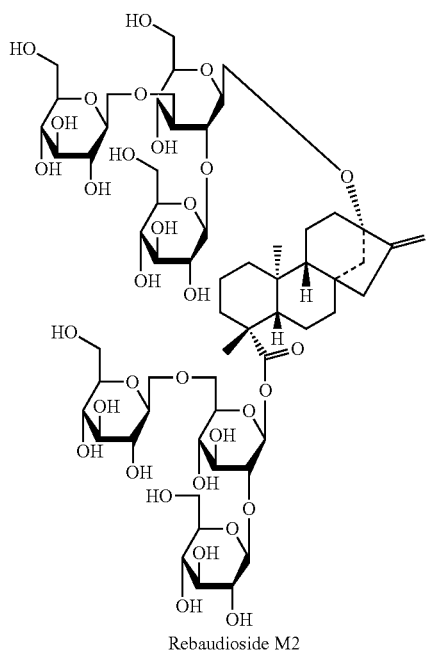

Rebaudioside M2

β-glucosidase →

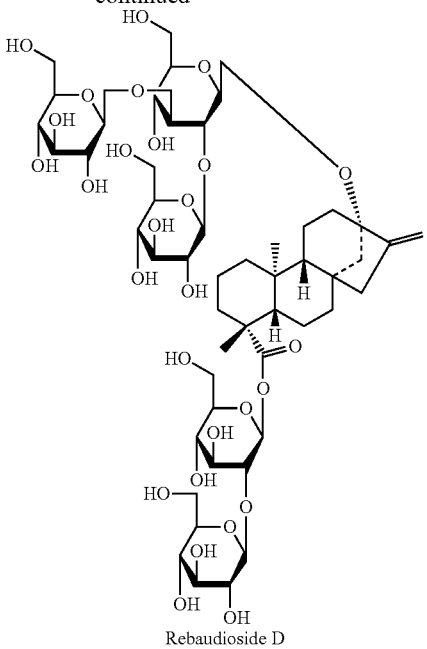

Rebaudioside D

First the selected β-glucosidases were tested on reference substrate 4-nitrophenyl-β-D-glucopyranoside to determine the activity. Based on the determined activities, the used quantities of enzyme were calculated as units for use in the hydrolysis of Rebaudioside M2.

The tested β-glucosidases are depicted in the following table:

| β-glucosidase | Manufacturer* | Activity enzyme using 4-nitrophenyl-β-D-glucopyranoside (mmol · min$^{-1}$ · mg$^{-1}$) | Quantity of enzyme used (mg/mL of reaction mixture)/(U/mL) |
|---|---|---|---|
| Isolase | NEC | 0.29 | 1.50/0.44 |
| Aromase | Amano | 0.030 | 11.3/0.35 |
| Naringinase | Amano | 0.017 | 13.5/0.23 |
| Cellulase Tr (Celluclast ®1.5L) | Novozyme | 0.026 | 20.4/0.53 |
| Cellobiase As (Novozyme 188) | Novozyme | 0.26 | 1.50/0.39 |
| CWD (Viscozyme ®L) | Novozyme | 0.0062 | 132/0.82 |

*Isolase (011410; National Enzyme Company, USA); Aromase (GLY0151441; Amano Enzyme, Japan); Naringinase (NAH0550102; Amano Enzyme, Japan), Cellulase from *Trichoderma reesei* ATCC 26921 (Sigma C2730); Cellobiase from *Aspergillus niger* (Sigma C6105); Viscozyme L (Sigma V2010)

The assay conditions were as follows:

Reactions were performed at 30° C. at a total volume of 10 mL containing 15 mM of sodium acetate buffer (pH 4.5) and 1 mM Rebaudioside M2. The reaction was started by the addition of enzyme.

625 µL of reaction mixture was sampled after 0, 0.5, 1, 1.5, 2, 2.5, 3 and 3.3 hrs and quenched with a mixture of 575 µL of 80% methanol and 50 µL of 2N $H_2SO_4$. The samples were analyzed by HPLC analysis (CAD detection) using the analytical method that was described above.

The reaction profiles of these reactions with different β-glucosidases are shown in FIGS. 68a-f.

It can be concluded that Naringinase and CWD catalyzed the formation of Rebaudioside D2 and Rebaudioside A which indicates a (1→2) bond glucolysis and (1→6) bond glucolysis respectively. These enzymes can be considered as non-selective for the conversion of Rebaudioside M2.

Isolase, Cellulase Tr and Cellobiase As possess a clear-cut selectivity for the conversion of Rebaudioside M2 to Rebaudioside D (hydrolysis of (1→6) glucoside bond), whereas Aromase possessed low overall activity for the conversion of Rebaudioside M2.

Example 50

Stability of Rebaudiosides in the Presence of Isolase, Cellulase Tr and Cellobiase as In order to assess the selectivity of Isolase, Cellulase Tr and Cellobiase As for Rebaudioside M2, Rebaudioside A, Rebaudioside D and Rebaudioside M were tested as substrates under the following conditions:

Reactions were performed over 24 h. at 30° C. at a total volume of 10 mL containing 15 mM of sodium acetate buffer (pH 4.5) and 1 mM of Rebaudioside A, Rebaudioside D or Rebaudioside M. The reaction was started by the addition of enzyme.

625 µL of reaction mixture was sampled after 0, 0.5, 1, 1.5, 2, 2.5, 3 and 3.3 hrs and quenched with a mixture of 575 µL of 80% methanol and 50 µL of 2N $H_2SO_4$. The samples were analyzed by HPLC.

The results shown in FIGS.>69a-c were obtained. It can be observed that no significant conversion of Rebaudioside A, Rebaudioside D and Rebaudioside M can be observed in the presence of Isolase, Cellulase Tr and Cellobiase As.

Example 51

Four-Enzyme Reaction for the Conversion of Rebaudioside A to Rebaudioside M

The influence of adding Isolase, Cellulase Tr or Cellobiase As to the one-pot reaction of Rebaudioside A to Rebaudioside M with UGTSL2, UGT76G1-1R-F12 and AtSUS was studied. The following reaction conditions were used:

| Compound | Assay conc (mM) |
| --- | --- |
| Rebaudioside A | 2 |
| UDP | 0.25 |
| $MgCl_2$ | 3 |
| Phosphate buffer pH 7.0 | 50 |
| Sucrose | 100 |
| UGTSL2 lysate (2.1 U/mL) | 25 µL/mL (0.053 U/mL) |
| UGT76G1-R1-F12 lysate (2.5 U/mL) | 170 µL/mL (0.425 U/mL) |
| AtSUS (130 U/mL) | 25 µL/mL (3.25 U/mL) |
| Isolase | 0.3 mg/mL |
| Cellulase Tr | 0.3 mg/mL |
| Cellobiase As | 4.0 mg/mL |

The results for the experiments without and with added β-glucosidase are shown in FIGS. 70a-d. It can be seen that addition of Cellobiase As is blocking the reaction and that addition of Cellulase Tr does not have an influence on the reaction profile. However, addition of Isolase to the reaction mixture has a positive effect on the quantity of Rebaudioside M that is formed in the reaction. An increase of almost 20% is observed when Isolase is added. The Rebaudioside M2 content is approximately 10% lower and Rebaudioside I content is approximately 15% lower when Isolase is added to the reaction mixture compared to the reaction without added β-glucosidase.

Further improvement Reb M yield and reduction of Reb M2 and Reb I content can be achieved through optimization of the reaction parameters and amount of Isolase.

Example 52

Use of β-Glucosidases for the Conversion of Rebaudioside I to Rebaudioside A

Three β-glucosidases were tested for the hydrolysis of Rebaudioside I to Rebaudioside A. The goal was to selectively hydrolyze the (1→6) glucoside bond in order to obtain Rebaudioside D. The desired general reaction scheme is as follows:

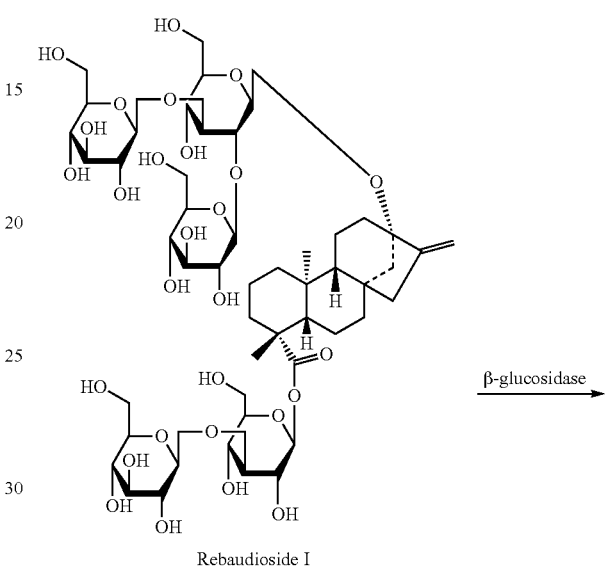

Rebaudioside I

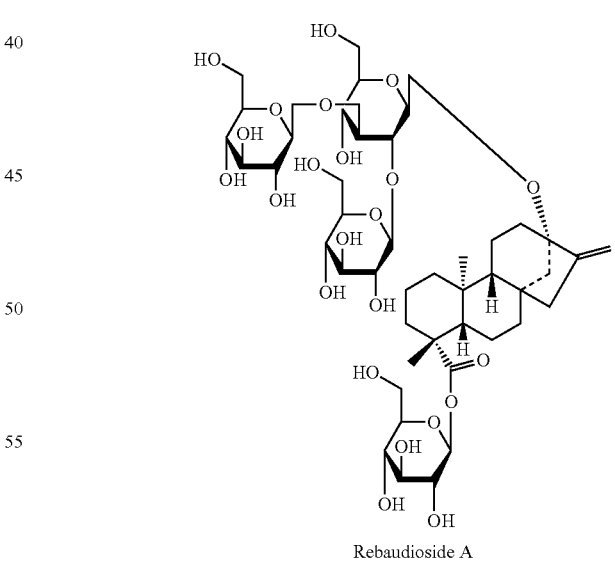

Rebaudioside A

The selected β-glucosidases were tested on reference substrate 4-nitrophenyl-β-D-glucopyranoside to determine the activity. Based on the determined activities, the used quantities of enzyme were calculated as units for use in the hydrolysis of Rebaudioside I. The tested β-glucosidases are depicted in the following table:

| β-glucosidase | Manufacturer* | Activity enzyme using 4-nitrophenyl-β-D-glucopyranoside (mmol · min$^{-1}$ · mg$^{-1}$) | Quantity of enzyme used (mg/mL of reaction mixture)/(U/mL) |
|---|---|---|---|
| Isolase | NEC (011410) | 0.29 | 1.50/0.44 |
| Cellulase Tr (Celluclast ®1.5L) | Novozymes* | 0.026 | 22.3/0.58 |
| Cellobiase As (Novozyme 188) | Novozymes* | 0.26 | 1.60/0.42 |

*Isolase (011410; National Enzyme Company, USA); Cellulase from *Trichoderma reesei* ATCC 26921 (Sigma C2730); Cellobiase from *Aspergillus niger* (Sigma C6105)

The assay conditions were as follows. Reactions were performed at 30° C. at a total volume of 2 mL containing 15 mM of sodium acetate buffer (pH 4.5) and 1 mM Rebaudioside I. The reaction was started by the addition of enzyme.

Figure 71:
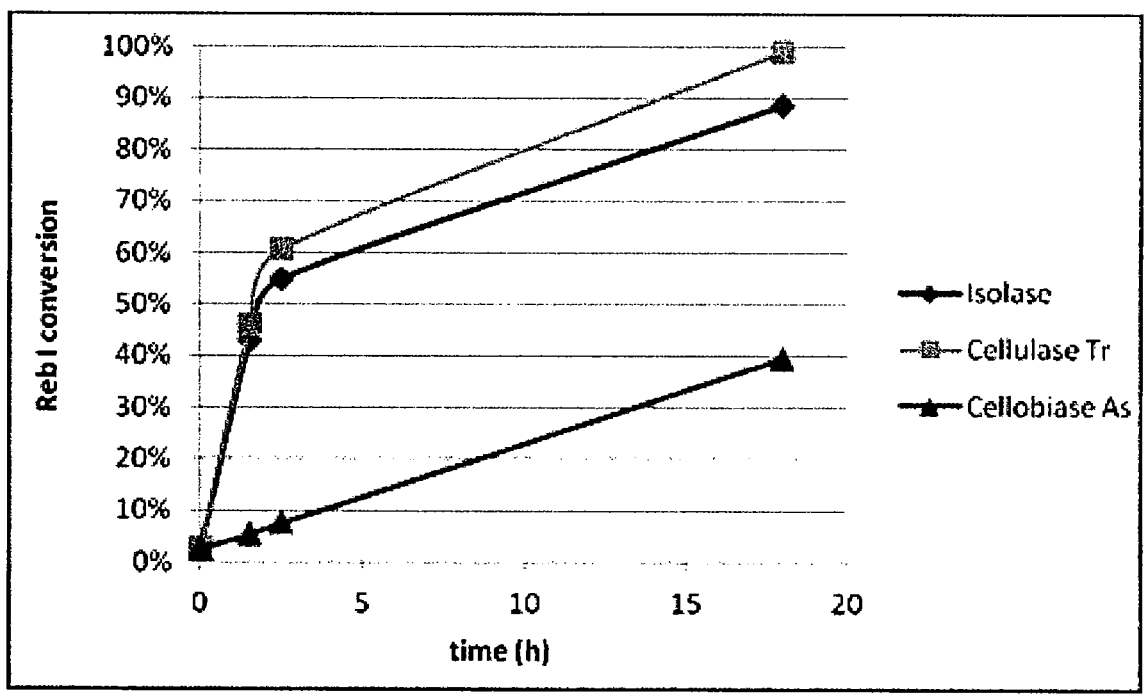
FIG. 71 shows a reaction profile graph for Example 52.

125 μL of reaction mixture was sampled after 0, 1.5, 2.5 and 18 h. and quenched with a mixture of 115 μL of 80% methanol and 10 μL of 2N $H_2SO_4$. The samples were analyzed by HPLC analysis (CAD detection) using the analytical method that was described above. The reaction profiles of the different β-glucosidases with Rebaudioside I are depicted in the graph shown in FIG. 71.

It can be observed that all three tested β-glucosidases converted Rebaudioside I. The sole product was Rebaudioside A.

Example 53

Directed Evolution of UGTSL2 for the Conversion of Rebaudioside A to Rebaudioside D (Round 3)

Taking the native enzyme UGTSL2 (GI_460410132) as baseline, a list of 13 mutations that were identified during round 2 (EXAMPLE 48) and another list of 12 new mutations that were obtained by DNA2.0 ProteinGPS™ strategy were prepared. This list of mutations was subsequently used to design 46 variant genes that contained each 1 to 8 different mutations. After codon-optimized for expression in *E. coli* the genes were synthesized, subcloned in the pET30a+ plasmid and used for transformation of *E. coli* BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 μL aliquots were stored at −20° C. and at −80° C.

These storage aliquots of *E. coli* BL21(DE3) containing the pET30a+_UGTSL2var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycin). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 μL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysates were recovered by centrifugation.

In order to measure the activity of the variants for the transformation of Rebaudioside A to Rebaudioside D, 100 μL of fresh lysate was added to a solution of Rebaudioside A (final concentration 0.5 mM), $MgCl_2$ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the initial rates after HPLC analysis (CAD detection) using the analytical method that was described above for the transformation of Rebaudioside A to Rebaudioside D.

In parallel 100 μL of fresh lysate was added to a solution of Rebaudioside D (final concentration 0.5 mM), $MgCl_2$ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the initial rates for Rebaudioside D conversion after HPLC analysis (CAD detection).

Apart from the new variants for this round, both experiments were also performed with baseline clone, UGTSL2. The initial rates for the conversion of Rebaudioside A or Rebaudioside D for this baseline clone were defined as 100%.

Activity of each clone was defined as normalized activity compared to baseline clone UGTSL2 whereas specificity of each clone was expressed as the ratio between the initial rates for the conversion of Rebaudioside A and Rebaudioside D.

The normalized initial rate for the conversion of Rebaudioside A and the ratio between the initial rates for the conversion of Rebaudioside A and Rebaudioside D are depicted in the following table.

| Clone | Mutations* | Normalized initial rate for conversion of Rebaudioside A | Ratio between initial rates for the conversion of Rebaudioside A and Rebaudioside D |
|---|---|---|---|
| UGTSL2 | Baseline clone | 100% | 1.67 |
| Round3-var1 | UGTSL2_S255C_A285V_V349L_L393V | 13% | 1.86 |
| Round3-var2 | UGTSL2_N130G_S255C_N339G_T392A | 264% | 3.09 |
| Round3-var3 | UGTSL2_S255C_V270I_L276A_A285V | 10% | 4.50 |
| Round3-var4 | UGTSL2_S255C_A285I_T329V_H357Y_T392A | 70% | 4.87 |

-continued

| Clone | Mutations* | Normalized initial rate for conversion of Rebaudioside A | Ratio between initial rates for the conversion of Rebaudioside A and Rebaudioside D |
|---|---|---|---|
| Round3-var5 | UGTSL2_S255C_A341V_T392A_I412M | 359% | 4.34 |
| Round3-var6 | UGTSL2_S255C_A285V_K301E_A341V_T392A_L393V | 104% | 4.34 |
| Round3-var7 | UGTSL2_S255C_L276A_K301E_T392A | 79% | 4.51 |
| Round3-var8 | UGTSL2_S255C_T392A_L393V_I412L | 46% | 2.12 |
| Round3-var9 | UGTSL2_F226V_S255C_V270I_T392A | 226% | 2.67 |
| Round3-var10 | UGTSL2_S255C_L276A_A285V_T329V_T392A_I412L | 5% | 8.57 |
| Round3-var11 | UGTSL2_S255C_H357Y_T392A_K408R | 0% | Nd |
| Round3-var12 | UGTSL2_S255C_V270I_A285V_A341V_T392A_I412L | 403% | 7.83 |
| Round3-var13 | UGTSL2_S255C_A285V_T329V_N339G_A341V_V349L_T392A | 0% | Nd |
| Round3-var14 | UGTSL2_N130G_A285V_A341V_T392A_K408R | 475% | 2.69 |
| Round3-var15 | UGTSL2_T329V | 122% | 2.62 |
| Round3-var16 | UGTSL2_P225L_F226V_S255C_A285V_T329V_T392A_L393V | 14% | 3.03 |
| Round3-var17 | UGTSL2_I203L_P225L_S255C_V349L_T392A | 0% | Nd |
| Round3-var18 | UGTSL2_V270I_A285I_K301E_T392A | 390% | 1.40 |
| Round3-var19 | UGTSL2_I203L_S255C_V270I_A285V_N339G_T392A_L393V | 12% | 1.81 |
| Round3-var20 | UGTSL2_N130G_S255C_L276A_A285I_T392A_L393V | 262% | 3.35 |
| Round3-var21 | UGTSL2_S255C_V270I_A285V_T329V_T392A_K408R_I412M | 67% | 3.33 |
| Round3-var22 | UGTSL2_I203L_F226V_S255C_L276A_A285V_T392A_I412M | 0% | Nd |
| Round3-var23 | UGTSL2_P225L_S255C_L276A_A285V_A341V_H357Y_T392A | 1% | Nd |
| Round3-var24 | UGTSL2_S258T_K408R | 58% | 3.12 |
| Round3-var25 | UGTSL2_F226V_H247P_S258T_A341V | 85% | 2.47 |
| Round3-var26 | UGTSL2_S258T_V270I_A341V_V349L | 5% | 1.74 |
| Round3-var27 | UGTSL2_S258T_L276A_A285V_K301E_A341V_L393V | 297% | 2.26 |
| Round3-var28 | UGTSL2_P225L_S258T_L276A_A341V | 22% | 1.08 |
| Round3-var29 | UGTSL2_S258T_L276A_N339G_A341V | 18% | 1.08 |
| Round3-var30 | UGTSL2_S258T_V270I_N278G_A285V_A341V_T392A | 313% | 2.29 |
| Round3-var31 | UGTSL2_F253Y_A341V_L393V | 105% | 3.88 |
| Round3-var32 | UGTSL2_N130G_S258T_N278G_A341V_H357Y | 13% | 1.66 |
| Round3-var33 | UGTSL2_H247P_S258T_N278G_A285V_A341V_L393V_K408R | 286% | 3.29 |
| Round3-var34 | UGTSL2_F253Y_S258T_V270I_L276A_A285I_A341V | 362% | 1.90 |
| Round3-var35 | UGTSL2_F253Y_S255C_S258T_A341V_T392A | 24% | 3.28 |
| Round3-var36 | UGTSL2_S255C_S258T_L276A_N278G_A285V_I333L_A341V | 121% | 3.36 |
| Round3-var37 | UGTSL2_F226V_S258T_I333L | 5% | 1.20 |
| Round3-var38 | UGTSL2_S255C_S258T_V270I_A285V_T329V | 139% | 2.59 |
| Round3-var39 | UGTSL2_S258T_L276A_A285V_H357Y_T392A | 94% | 1.98 |
| Round3-var40 | UGTSL2_S258T_N278G_K301E_T329V_A341V_I412L | 179% | 2.82 |
| Round3-var41 | UGTSL2_P225L_S258T_A285I_L393V_I412L | 1% | 0.59 |
| Round3-var42 | UGTSL2_I203L_N278G_A285V_I412M | 3% | 2.68 |
| Round3-var43 | UGTSL2_I203L_S258T_V270I_I333L_A341V_L393V | 44% | 6.27 |
| Round3-var44 | UGTSL2_S258T_A285V_T329V_N339G_A341V_V349L_T392A_L393V | 0% | Nd |
| Round3-var45 | UGTSL2_N130G_H247P_V270I_A285V_A341V_T392A | 869% | 2.69 |
| Round3-var46 | UGTSL2_S258T_A341V_T392A_I412M | 132% | 3.27 |

*Mutations are noted as follows: reference gene-original amino acid-position-new amino acid: For example the mutation of an isoleucine at position 240 to a Leucine for UGTSL2 is noted as UGTSL2 (I240L).
Nd means Not determined.

Modeling of these results allowed to obtain a ranking of the effect of each mutation. The following mutations were determined as being beneficial for activity:

N130G, H247P, F253Y, V270I, L276A, A285I, A285V, K301E, A341V, T392A, K408R, I412L.

The following mutations were determined as being beneficial for an improved ratio between initial rate for the conversion of Rebaudioside A and Rebaudioside D:

I203L, S255C$_{56}$, I333L, A341V, H357Y, L393V, K408R, I412L.

Example 54

One-Pot, Four-Enzyme Conversion of Rebaudioside A to Rebaudioside M 10 mL of a reaction mixture containing 5.0 mM of Rebaudioside A, 0.25 mM of UDP, 2 mM of MgCl$_2$, 100 mM of sucrose, 50 mM of potassium phosphate buffer pH 7.5, 2.5 U of UGTSL2-R3-D2 (UGTSL2-Round3-var12, see EXAMPLE 53), 25 U of UGT76G1-R3-G3 (UGT76G1-Round3-var21, see EXAMPLE 44), 25 U of AtSUS and 5 U of Isolase® was filtered through a 0.2 μm filter in a sterile flask. The resulting reaction mixture was gently shaken at 30° C. for 65 h.

Samples were taken under sterile conditions at regular intervals by taking 125 μL, of reaction mixture and quenching it with 10 μL of 2 N H$_2$SO$_4$ and 765 μL, of 50% methanol. After centrifugation, 200 μL of the supernatant was analyzed by HPLC.

Figure 72A:
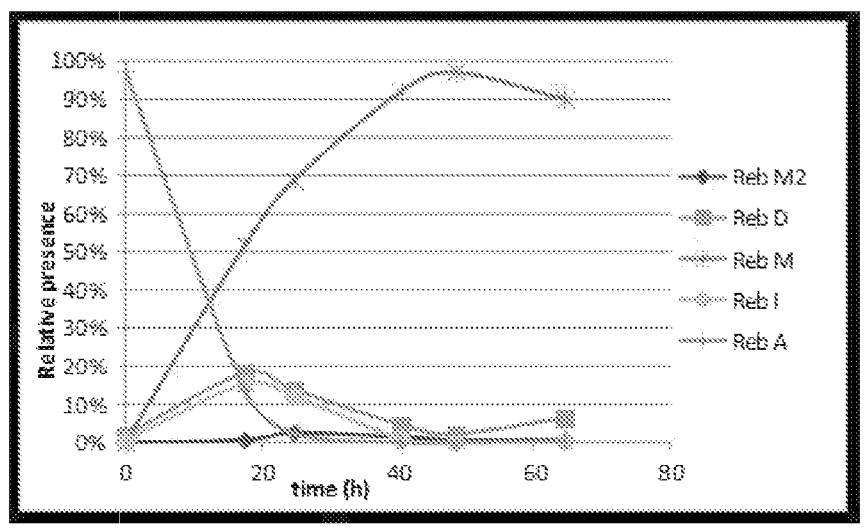
FIG. 72a shows a reaction profile graph for Example 54.
Figure 72B:
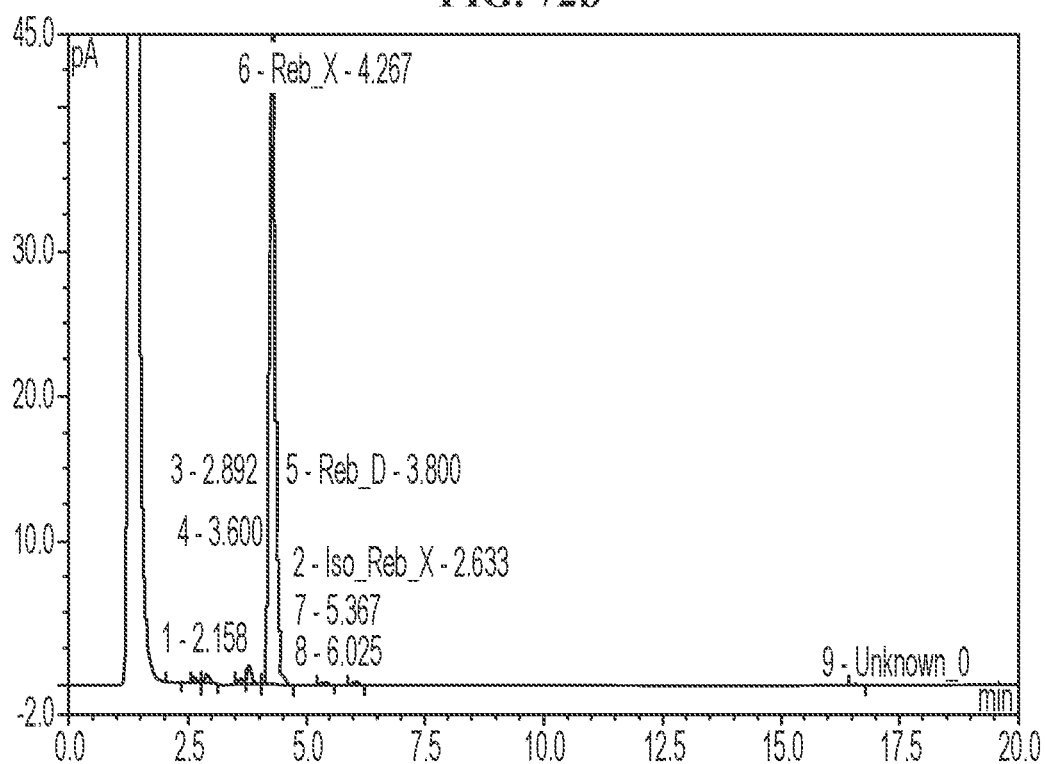
FIG. 72b shows an HPLC chromatogram showing the HPLC analysis for Example 54.

The reaction profile shown in FIG. 72a was obtained. The HPLC analysis after 48 h of reaction is shown in FIG. 72b.

Example 55

One-Pot, Four-Enzyme Conversion of Rebaudioside A to Rebaudioside M 10 mL of a reaction mixture containing 10.0 mM of Rebaudioside A, 0.50 mM of UDP, 3 mM of MgCl$_2$, 100 mM of sucrose, 50 mM of potassium phosphate buffer pH 7.5, 5.0 U of UGTSL2-R3-D2 (UGTSL2-Round3-var12, see EXAMPLE 53), 50 U of UGT76G1-R3-G3 (UGT76G1-Round3-var21, see EXAMPLE 44), 50 U of AtSUS and 10

U of Isolase® was filtered through a 0.2 µm filter in a sterile flask. The resulting reaction mixture was gently shaken at 30° C. for 66 h.

Samples were taken under sterile conditions at regular intervals by taking 125 µL of reaction mixture and quenching it with 10 µL of 2N $H_2SO_4$ and 765 µL of 50% methanol. After centrifugation, 200 µL of the supernatant was analyzed by HPLC.

Figure 73A:
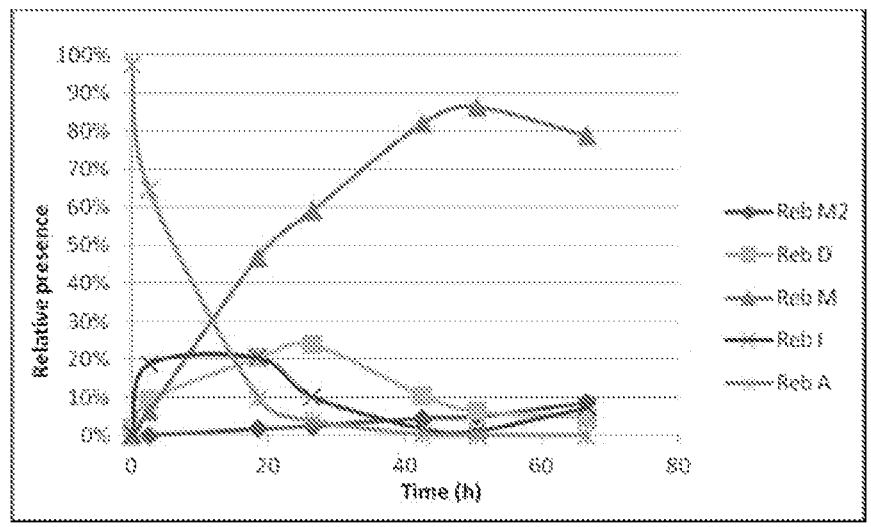
FIG. 73a shows a reaction profile graph for Example 55.
Figure 73B:
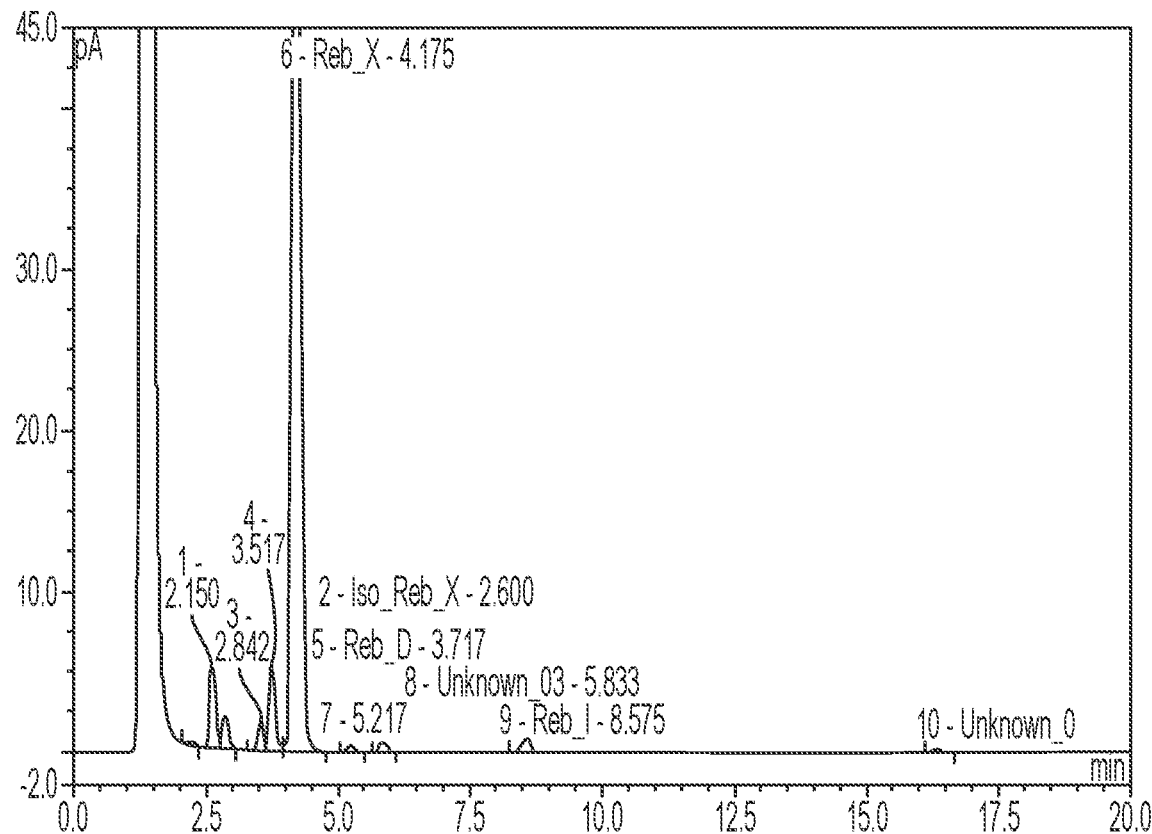
FIG. 73b shows an HPLC chromatogram showing the HPLC analysis for Example 55.

The reaction profile shown in FIG. 73a was obtained. The HPLC analysis after 48 h of reaction is shown in FIG. 73b.

Example 56

One-Pot, Four-Enzyme Conversion of Rebaudioside A to Rebaudioside M 50 mL of a reaction mixture containing 10.0 mM of Rebaudioside A, 0.5 mM of UDP, 4 mM of $MgCl_2$, 100 mM of sucrose, 50 mM of potassium phosphate buffer pH 7.5, 25 U of UGTSL2-R3-D2 (UGTSL2-Round3-var12, see EXAMPLE 53), 250 U of UGT76G1-R3-G3 (UGT76G1-Round3-var21, see EXAMPLE 44), 250 U of AtSUS and 50 U of Isolase® was filtered through a 0.2 µm filter in a sterile flask. The resulting reaction mixture was gently shaken at 35° C. for 95 hrs.

Samples were taken under sterile conditions at regular intervals by taking 125 µL of reaction mixture and quenching it with 10 µL of 2 $N_2SO_4$ and 765 µL of 50% methanol. After centrifugation, 200 µL of the supernatant was analyzed by HPLC.

At the end of the reaction, the reaction mixture became a fine suspension. Filtration of the suspension and HPLC analysis of the residue and filtrate showed that the Reb M content in the filtrate was 79% and that the Reb M content in the solid was 97%.

Figure 74A:
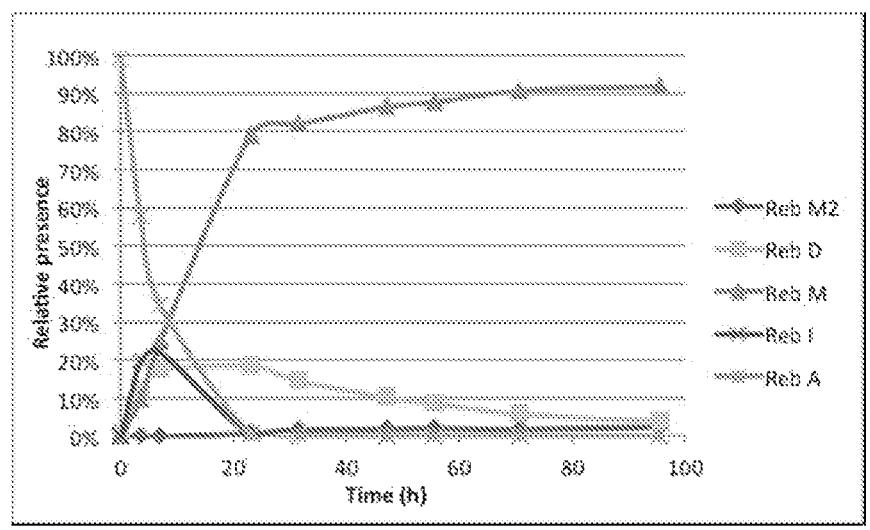
FIG. 74a shows a reaction profile graph for Example 56.
Figure 74B:
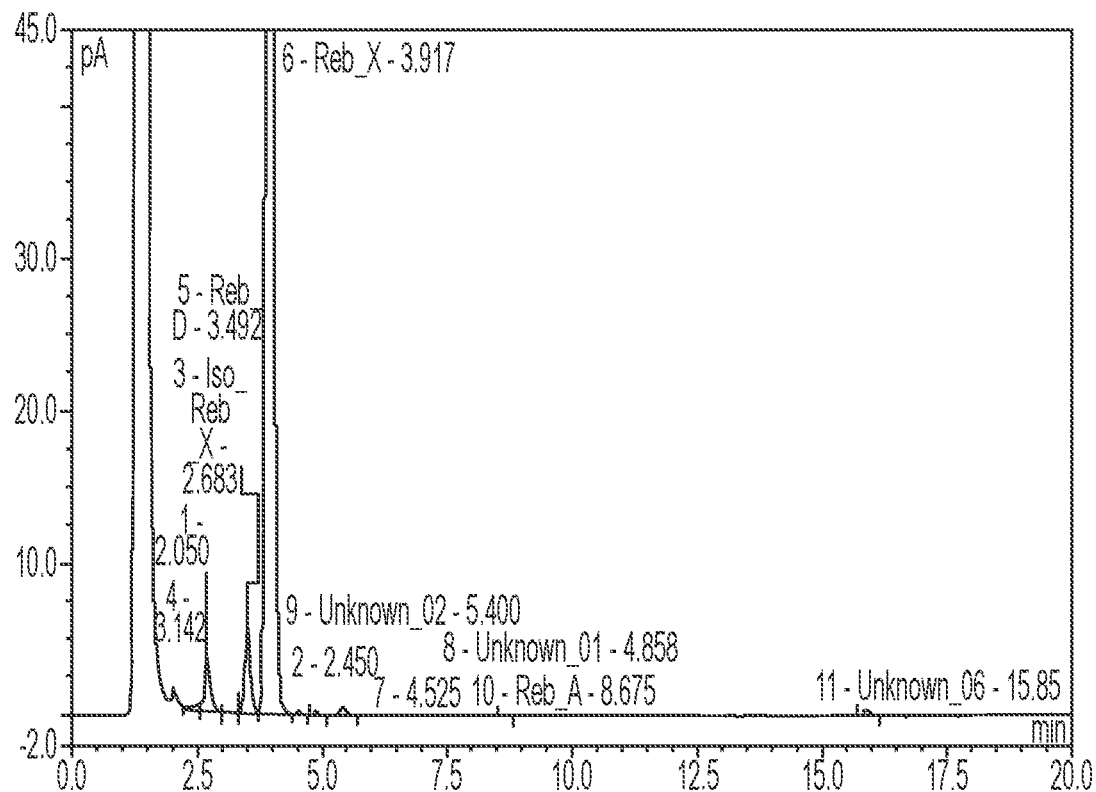
FIG. 74b shows an HPLC chromatogram showing the HPLC analysis for Example 56.

The reaction profile shown in FIG. 74a was obtained. The HPLC of the reaction mixture after 95 hrs is shown in FIG. 74b.

Example 57

One-Pot, Four-Enzyme Conversion of Rebaudioside A to Rebaudioside M (Addition of UGT76G1 and Isolase after 6.5 h)

A reaction mixture containing Rebaudioside A, UDP, $MgCl_2$, sucrose, potassium phosphate buffer pH 7.5, UGTSL2-R3-D2 (UGTSL2-Round3-var12, see EXAMPLE 53) and AtSUS was filtered through a 0.2 µm filter in a sterile flask. The resulting reaction mixture was gently shaken at 35° C. for 6.5 h. UGT76G1-R3-G3 (UGT76G1-Round3-var21, see EXAMPLE 44) and Isolase® were added and the reaction mixture was filtered through a 0.2 µm filter in a sterile flask and gently shaken for another 89 h at 35° C. The final volume of the reaction mixture was 50 mL and final concentrations of reagents and enzymes were as follows: 10.0 mM of Rebaudioside A, 0.5 mM of UDP, 4 mM of $MgCl_2$, 100 mM of sucrose, 50 mM of potassium phosphate buffer pH 7.5, 25 U of UGTSL2-R3-D2, 250 U of UGT76G1-R3-G3, 250 U of AtSUS and 50 U of Isolase®

Samples were taken under sterile conditions at regular intervals by taking 125 µL of reaction mixture and quenching it with 10 µL of 2 N $H_2SO_4$ and 765 µL of 50% methanol. After centrifugation, 200 µL of the supernatant was analyzed by HPLC.

Figure 75A:
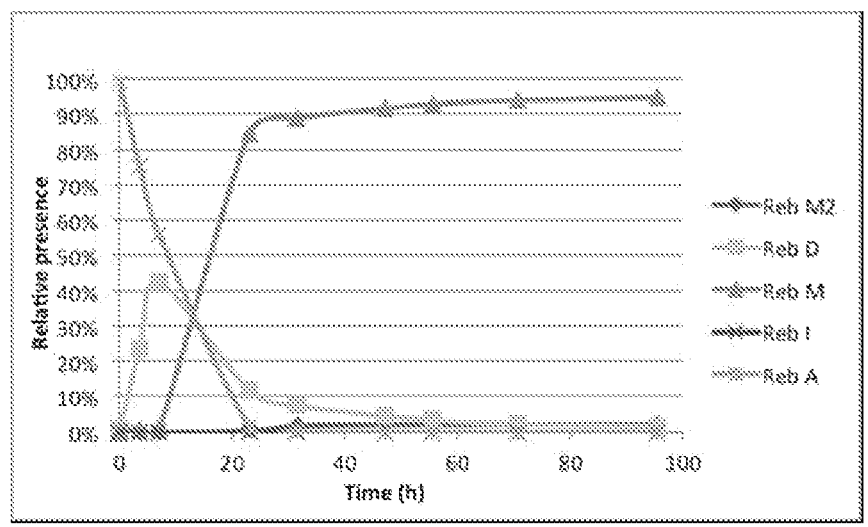
FIG. 75a shows a reaction profile graph for Example 57.
Figure 75B:
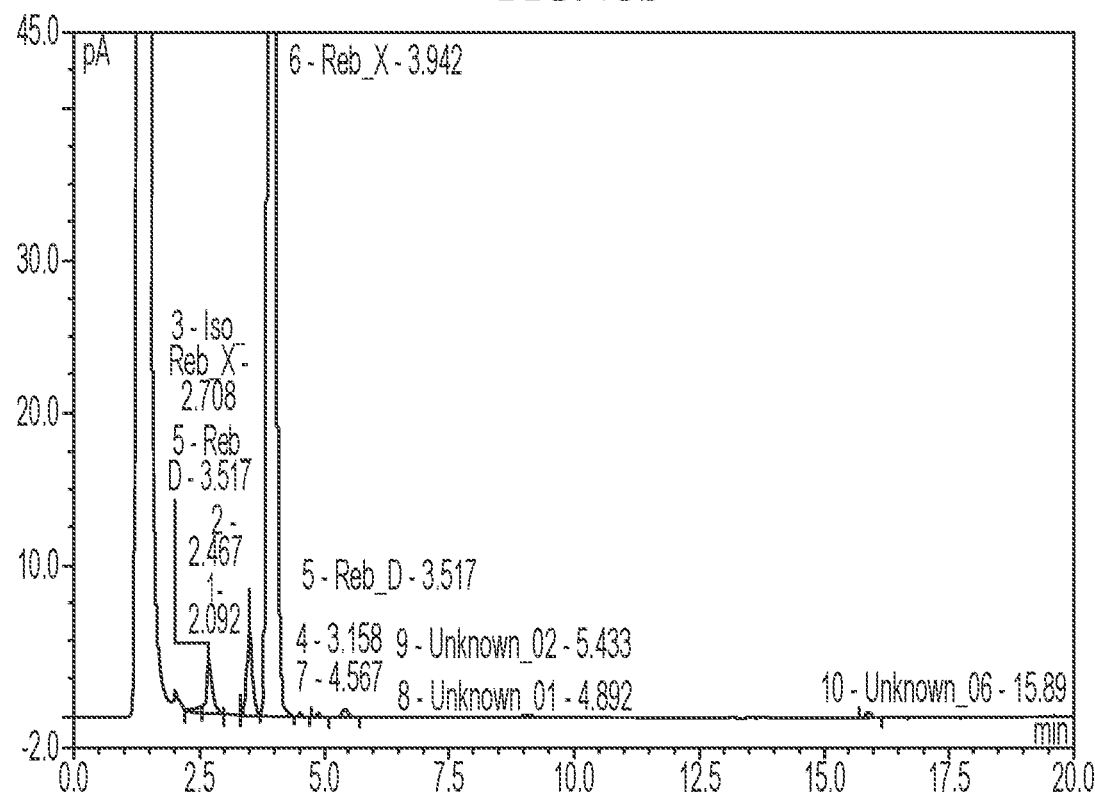
FIG. 75b shows an HPLC chromatogram showing the HPLC analysis for Example 57.

The reaction profile shown in FIG. 75a was obtained. The HPLC of the reaction mixture after 95 h is shown in FIG. 75b.

Example 58

One-Pot, Four-Enzyme Conversion of Rebaudioside A to Rebaudioside M (Addition of UGT76G1 and Isolase after 6.5 h)

A reaction mixture containing Rebaudioside A, UDP, $MgCl_2$, sucrose, potassium phosphate buffer pH 7.5, UGTSL2-R3-D2 (UGTSL2-Round3-var12, see EXAMPLE 53) and AtSUS was filtered through a 0.2 µm filter in a sterile flask. The resulting reaction mixture was gently shaken at 35° C. for 6.5 h. UGT76G1-R3-G3 (UGT76G1-Round3-var21, see EXAMPLE 44) and Isolase® were added and the reaction mixture was filtered through a 0.2 µm filter in a sterile flask and gently shaken for another 89 h at 35° C. The final volume of the reaction mixture was 50 mL and the final concentrations of reagents and enzymes were as follows: 10.0 mM of Rebaudioside A, 0.5 mM of UDP, 4 mM of $MgCl_2$, 100 mM of sucrose, 50 mM of potassium phosphate buffer pH 7.5, 25 U of UGTSL2-R3-D2, 250 U of UGT76G1-R3-G3, 250 U of AtSUS and 25 U of Isolase®.

Samples were taken under sterile conditions at regular intervals by taking 125 µL of reaction mixture and quenching it with 10 µL of 2 N $H_2SO_4$ and 765 µL of 50% methanol. After centrifugation, 200 µL of the supernatant was analyzed by HPLC.

At the end of the reaction, the reaction mixture became a fine suspension. Filtration of the suspension and HPLC analysis of the residue and filtrate showed that the Reb M content in the filtrate was 81% and that the Reb M content in the solid was 98%.

Figure 76A:
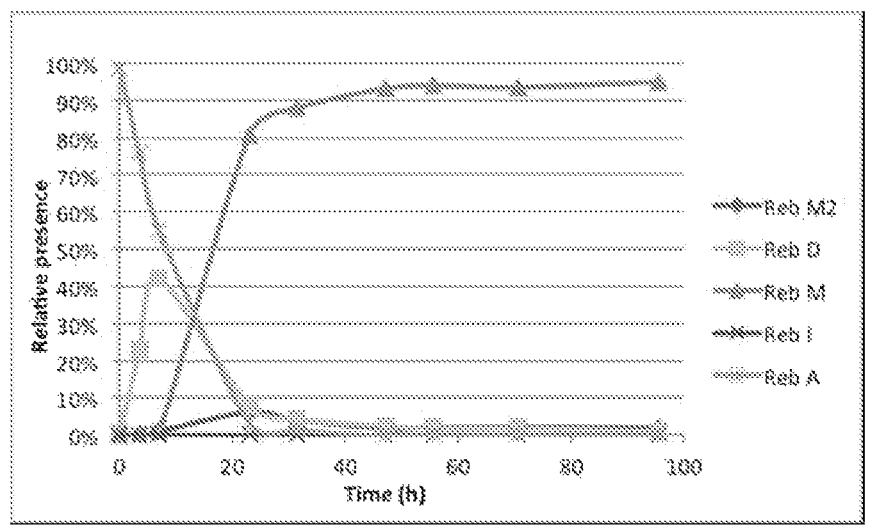
FIG. 76a shows a reaction profile graph for Example 58.
Figure 76B:
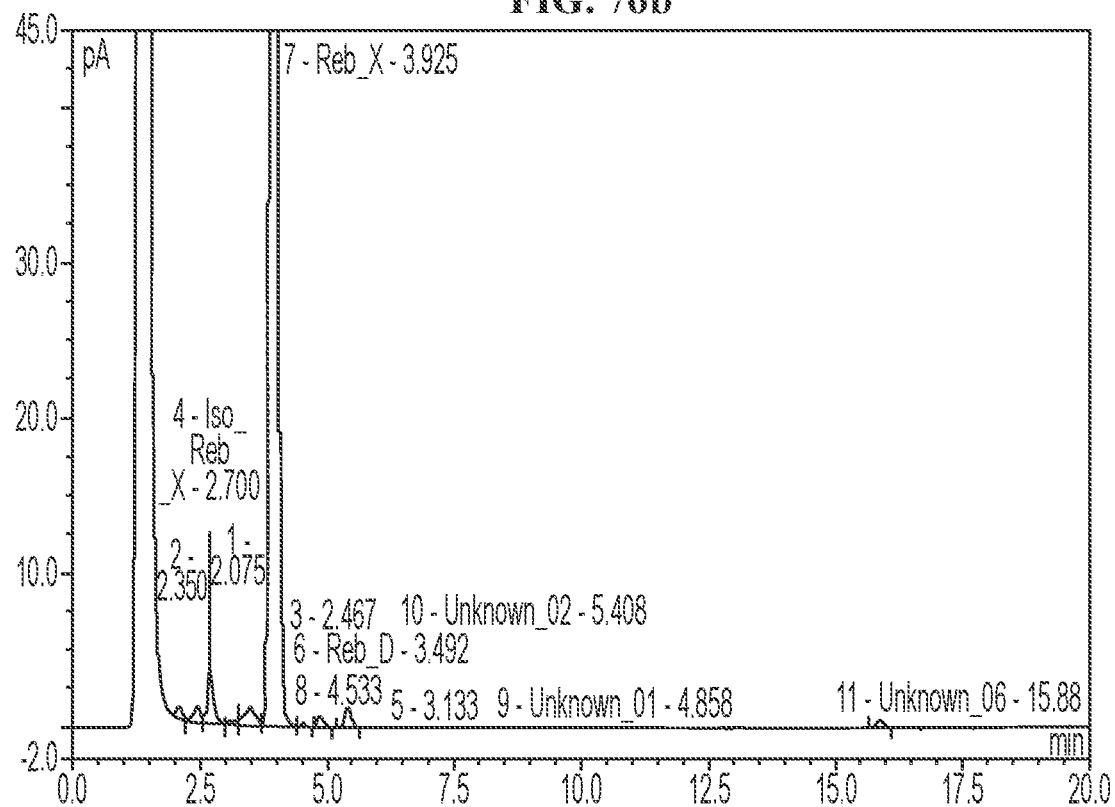
FIG. 76b shows an HPLC chromatogram showing the HPLC analysis for Example 58.

The reaction profile shown in FIG. 76a was obtained. The HPLC of the reaction mixture after 95 h is shown in FIG. 76b.

Example 59

Directed Evolution of UGTSL2 for the Conversion of Rebaudioside A to Rebaudioside D (Round 4)

The most active enzyme from the third round (see EXAMPLE 53) UGTSL2_round3-var45 was taken as starting point. The five best mutations for activity from round 3 were used to create a set of 10 variants containing each two of these mutations. After codon-optimized for expression in E. coli the genes were synthesized, subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of E. coli BL21(DE3) containing the pET30a+_UGTSL2var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h. 3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysates were recovered by centrifugation. Lysates were diluted five-fold with water before activity testing.

In order to measure the activity of the variants for the transformation of Rebaudioside A to Rebaudioside D, 100 µL of fresh lysate was added to a solution of Rebaudioside A (final concentration 0.5 mM), MgCl$_2$ (final concentration 3 mM) and UDP-Glucose (final concentration 2.5 mM) in 50 mM phosphate buffer pH 7.2. The reaction was allowed to run at 30° C. and samples were taken after 2, 4, 6 and 22 h. to determine the activities after HPLC analysis (CAD detection) using the analytical method that was described above for the transformation of Rebaudioside A to Rebaudioside D.

Selectivity of each clone was determined by measuring the amount of Rebaudioside M2 that was formed at 100% UDP-Glc conversion (defined as (2*[Reb M2]+[Reb D])/ ([Reb A]+[Reb D]+[Reb M2]).

In parallel the experiments were performed with baseline clone, UGTSL2-Round3-Var45. The initial rate for this baseline clone was defined as 100%. The relative initial rates and the amounts of Rebaudioside M2 that are formed at 100% UDP-Glc conversion for the round 4 clones are depicted in the following table:

LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of E. coli BL21(DE3) containing the pET30a+_UGT76G1var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h. 3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysate was

| Clone | Mutations* | Normalized initial rate for conversion of Rebaudioside A | Rebaudioside M2 content at 100% UDP-Glc conversion |
|---|---|---|---|
| Round3-var45 | UGTSL2 (N130G_H247P_V270I_A285V_A341V_T392A) | 100% | 15.80% |
| Round4-var1 | UGTSL2-Round3-var45 (K301E_V285I) | 96% | 15.90% |
| Round4-var2 | UGTSL2-Round3-var45 (K301E_I412L) | 90% | 15.30% |
| Round4-var3 | UGTSL2-Round3-var45 (K301E_L276A) | 135% | 16.80% |
| Round4-var4 | UGTSL2-Round3-var45 (K301E_K408R) | 90% | 14.90% |
| Round4-var5 | UGTSL2-Round3-var45 (V285I_I412L) | 77% | 15.60% |
| Round4-var6 | UGTSL2-Round3-var45 (V285I_L276A) | 124% | 16.60% |
| Round4-var7 | UGTSL2-Round3-var45 (V285I_K408R) | 98% | 16.50% |
| Round4-var8 | UGTSL2-Round3-var45 (I412L_L276A) | 88% | 15.10% |
| Round4-var9 | UGTSL2-Round3-var45 (I412L_K408R) | 82% | 15.00% |
| Round4-var10 | UGTSL2-Round3-var45 (L276A_K408R) | 93% | 15.40% |

*Mutations are noted as follows: reference gene-original amino acid-position-new amino acid: For example the mutation of an isoleucine at position 240 to a Leucine for UGTSL2 is noted as UGTSL2 (I240L).

Example 60

Directed Evolution of UGT76G1 for the Conversion of Rebaudioside D to Rebaudioside X (Round 4)

The most active clone from the third round of directed evolution of UGT76G1 (see EXAMPLE 44 round3_UGT76G1var21 containing mutations: I46L_K303G_K393R) was chosen as baseline clone for round 4. The best identified mutations from round 3 (S119A, 274G, I295M, F314S and K334R) were used to create a set of 10 variants that contained each 2 of these mutations. After codon-optimized for expression in E. coli the genes were synthesized, subcloned in the pET30a+ plasmid and used for transformation of E. coli BL21 (DE3) chemically competent cells. The obtained cells were grown in Petri-dishes on solid recovered by centrifugation. Activity tests were performed with 100 µL of fresh lysate that was added to a solution of Rebaudioside D (final concentration 0.5 mM), MgCl2 (final concentration 3 mM) and UDP-Glucose (final concentration 2.5 mM) in 50 mM phosphate buffer pH 7.2.

The reaction was allowed to run at 30° C. and samples were taken after 1, 2, 4, 6 and 22 h. to determine conversion and initial rate by HPLC (CAD detection) using the analytical method that was described above for the transformation of Rebaudioside D to Rebaudioside X. In parallel the experiments were performed with baseline clone, Round3-Var21. The conversion after 22 h. and initial rate for this baseline clone was defined as 100% and the normalized conversions and initial rates for the round 4 clones are depicted in the following table:

| Clone | Mutations* | Normalized conversion Reb D to Reb X after 22 h. | Normalized initial rate (0-4 h) |
|---|---|---|---|
| Round3-Var21 | UGT76G1 (S42A_F46L_Q266E_P272A_K303G_R334K_G348P_L379G_K393R_I407V) | 100% | 100% |
| Round4-Var1 | Round3-Var21 (S119A_S274G) | 99.5% | 100% |
| Round4-Var2 | Round3-Var21 (S119A_I295M) | 95.4% | 93% |
| Round4-Var3 | Round3-Var21 (S119A_F314S) | 87.5% | 77% |
| Round4-Var4 | Round3-Var21 (S119A_K334R) | 94.0% | 81% |
| Round4-Var5 | Round3-Var21 (S274G_I295M) | 88.8% | 77% |
| Round4-Var6 | Round3-Var21 (S274G_F314S) | 86.7% | 75% |
| Round4-Var7 | Round3-Var21 (S274G_K334R) | 89.8% | 74% |
| Round4-Var8 | Round3-Var21 (I295M_F314S) | 84.3% | 72% |
| Round4-Var9 | Round3-Var21 (I295M_K334R) | 81.2% | 60% |
| Round4-Var10 | Round3-Var21 (F314S_K334R) | 85.6% | 74% |

*Mutations are noted as follows: reference gene-original amino acid-position-new amino acid: For example the mutation of Serine at position 119 to Alanine for variant 1 from the fourth round of directed evolution of UGT76G1 is noted as Round3-Var21 (S119A)

It is to be understood that the foregoing descriptions and specific embodiments have fully disclosed, illustrated and enabled the best mode of the invention and the principles thereof, and that modifications and additions may be made by those skilled in the art without departing from the spirit and scope of the invention, which is limited only by the scope of the appended claims.

The invention claimed is:

1. A method for producing a highly purified target steviol glycoside composition, comprising the steps of:
   (a) providing a starting composition comprising steviol glycosides;
   (b) providing a recombinant microorganism *E. coli*, the recombinant microorganism containing uridine diphosphate glycosyltransferases (UDP-glycosyltransferases), wherein the UDP-glycosyltransferase comprises an amino acid sequence selected from the group consisting of the amino acid sequence set forth in SEQ ID NO: 11 ("UGT76G1"), an amino acid sequence having greater than 95% amino-acid sequence identity with the amino acid sequence set forth in SEQ ID NO: 11, the amino acid sequence set forth in SEQ ID NO: 9 ("UGTSL2") and an amino acid sequence having greater than 95% amino-acid sequence identity with the amino acid sequence set forth in SEQ ID NO: 9, and further providing an enzyme with β-glucosidase activity from *Trichoderma reesei* or *Aspergillus niger*;
   (c) contacting the recombinant microorganism and the enzyme with β-glucosidase activity with a medium comprising the starting composition to produce a composition comprising a target steviol glycoside, wherein the target steviol glycoside is selected from the group consisting of rebaudioside A ("reb A"), rebaudioside D ("reb D"), rebaudioside D2 ("reb D2"), rebaudioside M ("reb M'), rebaudioside M2 ("reb M2"), rebaudioside I ("reb'"), and combinations thereof; and
   (d) separating the target steviol glycoside from the medium to provide a highly purified target steviol glycoside composition.

2. The method of claim 1, wherein the enzyme with β-glucosidase activity is for the hydrolysis of reb D2 and/or reb M2.

3. The method of claim 1, wherein the target steviol glycoside is separated from the medium using crystallization, separation by membranes, centrifugation, extraction, chromatographic separation or a combination of such methods.

4. The method of claim 1, wherein the highly purified target steviol glycoside composition comprises the target steviol glycoside in an amount greater than 95% by weight on a dry weight basis.

5. The method of claim 1, wherein the recombinant microorganism further comprises UDP glucose recycling enzymes.

* * * * *